US012800574B2

(12) United States Patent
Samuels et al.

(10) Patent No.: US 12,800,574 B2
(45) **Date of Patent: *Nov. 17, 2026**

(54) COMPOSITIONS AND METHODS FOR MOLECULAR LABELING

(71) Applicant: Bio-Rad Laboratories, Inc., Hercules, CA (US)

(72) Inventors: Michael L. Samuels, Windham, NH (US); Jeffrey Charles Olson, Chelmsford, MA (US); Andrew Watson, Bedford, MA (US); Keith Brown, Carlsbad, CA (US); Darren R. Link, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/085,379

(22) Filed: Mar. 20, 2025

(65) Prior Publication Data

US 2025/0216383 A1 Jul. 3, 2025

Related U.S. Application Data

(63) Continuation of application No. 18/178,121, filed on Mar. 3, 2023, which is a continuation of application No. 14/874,553, filed on Oct. 5, 2015, now Pat. No. 11,965,877, which is a continuation of application No. 13/398,677, filed on Feb. 16, 2012, now Pat. No. 9,150,852.

(60) Provisional application No. 61/476,714, filed on Apr. 18, 2011, provisional application No. 61/444,612, filed on Feb. 18, 2011.

(51) Int. Cl.

| | |
|---|---|
| ***G01N 33/53*** | (2006.01) |
| ***C12N 15/10*** | (2006.01) |
| ***C12Q 1/6804*** | (2018.01) |
| ***C12Q 1/6806*** | (2018.01) |
| ***C12Q 1/6874*** | (2018.01) |
| ***C40B 50/08*** | (2006.01) |
| ***G01N 33/532*** | (2006.01) |
| ***G01N 33/543*** | (2006.01) |
| ***G01N 33/58*** | (2006.01) |

(52) U.S. Cl.

CPC ......... *G01N 33/53* (2013.01); *C12N 15/1075* (2013.01); *C12Q 1/6804* (2013.01); *C12Q 1/6806* (2013.01); *C12Q 1/6874* (2013.01); *C40B 50/08* (2013.01); *G01N 33/532* (2013.01); *G01N 33/5436* (2013.01); *G01N 33/58* (2013.01); *C12Q 2521/10* (2013.01); *C12Q 2563/179* (2013.01); *C12Q 2565/30* (2013.01); *G01N 2458/10* (2013.01)

(58) Field of Classification Search

None

See application file for complete search history.

(56) References Cited

U.S. PATENT DOCUMENTS

| | | | | |
|---|---|---|---|---|
| 5,665,539 | A | 9/1997 | Sano | |
| 5,854,033 | A | 12/1998 | Lizardi | |
| 5,985,548 | A | 11/1999 | Collier | |
| 6,087,103 | A | 7/2000 | Burmer | |
| 6,143,495 | A | 11/2000 | Lizardi et al. | |
| 6,210,884 | B1 | 4/2001 | Lizardi | |
| 6,261,797 | B1 | 7/2001 | Sorge et al. | |
| 8,383,061 | B2 | 2/2013 | Prakash | |
| 9,562,897 | B2 | 2/2017 | Samuels et al. | |
| 9,714,937 | B2 | 7/2017 | Dunaway | |
| 10,030,261 | B2 | 7/2018 | Frisen et al. | |
| 10,138,509 | B2 | 11/2018 | Church et al. | |
| 10,144,950 | B2 * | 12/2018 | Nolan | C12Q 1/6806 |
| 10,227,639 | B2 | 3/2019 | Levner et al. | |
| 10,472,669 | B2 | 11/2019 | Chee | |
| 10,480,022 | B2 | 11/2019 | Chee | |
| 10,494,667 | B2 | 12/2019 | Chee | |
| 10,612,079 | B2 | 4/2020 | Chee | |
| 10,619,196 | B1 | 4/2020 | Chee | |
| 10,626,442 | B2 | 4/2020 | Nolan | |
| 10,662,468 | B2 | 5/2020 | Chee | |
| 10,761,090 | B2 | 9/2020 | Samuels et al. | |
| 10,787,701 | B2 | 9/2020 | Chee | |
| 10,837,883 | B2 | 11/2020 | Kleinschmidt et al. | |
| 10,914,730 | B2 | 2/2021 | Chee | |

(Continued)

FOREIGN PATENT DOCUMENTS

| | | | |
|---|---|---|---|
| EP | 2794928 | B1 | 2/2019 |
| EP | 2697391 | B1 | 10/2019 |

(Continued)

OTHER PUBLICATIONS

Huang, 2007, Counting low-copy number proteins in a single cell, Science 315:81-84.

Yang, 2002, Construction and selection of bead-bound combinatorial oligonucleoside phosphorothioate and phosphorodithioate aptamer libraries designed for rapid PCR-based sequencing, Nucl Acids Res 30(23):e132.

(Continued)

*Primary Examiner* — Kaijiang Zhang

(74) *Attorney, Agent, or Firm* — Thomas C. Meyers; Sullivan & Worcester LLP

(57) ABSTRACT

The invention provides barcode libraries and methods of making and using them including obtaining a plurality of nucleic acid constructs in which each construct comprises a unique N-mer and a functional N-mer and segregating the constructs into a fluid compartments such that each compartment contains one or more copies of a unique construct. The invention further provides methods for digital PCR and for use of barcode libraries in digital PCR.

18 Claims, 134 Drawing Sheets

Specification includes a Sequence Listing.

(56) References Cited

U.S. PATENT DOCUMENTS

| | | | |
|---|---|---|---|
| 10,961,566 | B2 | 3/2021 | Chee |
| 10,962,532 | B2 | 3/2021 | Chee |
| 10,982,268 | B2 | 4/2021 | Chee |
| 10,983,113 | B2 | 4/2021 | Chee |
| 10,996,219 | B2 | 5/2021 | Chee |
| 11,001,878 | B1 | 5/2021 | Chee |
| 11,001,879 | B1 | 5/2021 | Chee |
| 11,008,607 | B2 | 5/2021 | Chee |
| 11,021,737 | B2 | 6/2021 | Church et al. |
| 11,067,567 | B2 | 7/2021 | Chee |
| 11,078,520 | B2 | 8/2021 | Church et al. |
| 11,111,521 | B2 | 9/2021 | Church et al. |
| 11,156,603 | B2 | 10/2021 | Chee |
| 11,208,684 | B2 | 12/2021 | Chee |
| 11,293,051 | B2 | 4/2022 | Church et al. |
| 11,293,052 | B2 | 4/2022 | Church et al. |
| 11,293,054 | B2 | 4/2022 | Levner et al. |
| 11,293,917 | B2 | 4/2022 | Chee |
| 11,299,767 | B2 | 4/2022 | Church et al. |
| 11,313,856 | B2 | 4/2022 | Chee |
| 11,352,659 | B2 | 6/2022 | Frisen et al. |
| 11,365,442 | B2 | 6/2022 | Chee |
| 11,371,086 | B2 | 6/2022 | Chee |
| 11,384,386 | B2 | 7/2022 | Chee |
| 11,401,545 | B2 | 8/2022 | Chee |
| 11,479,809 | B2 | 10/2022 | Frisen et al. |
| 11,479,810 | B1 | 10/2022 | Chee |
| 11,519,022 | B2 | 12/2022 | Chee |
| 11,542,543 | B2 | 1/2023 | Chee |
| 11,549,136 | B2 | 1/2023 | Church et al. |
| 11,549,138 | B2 | 1/2023 | Chee |
| 11,560,587 | B2 | 1/2023 | Chee |
| 11,566,276 | B2 | 1/2023 | Church et al. |
| 11,566,277 | B2 | 1/2023 | Church et al. |
| 11,634,756 | B2 | 4/2023 | Chee |
| 11,635,427 | B2 | 4/2023 | Samuels et al. |
| 11,639,518 | B2 | 5/2023 | Church et al. |
| 11,732,292 | B2 | 8/2023 | Chee |
| 11,733,238 | B2 | 8/2023 | Chee |
| 11,747,327 | B2 | 9/2023 | Samuels et al. |
| 11,761,030 | B2 | 9/2023 | Chee |
| 11,767,550 | B2 | 9/2023 | Chee |
| 11,768,198 | B2 | 9/2023 | Samuels et al. |
| 11,788,122 | B2 | 10/2023 | Frisen et al. |
| 11,795,498 | B2 | 10/2023 | Frisen et al. |
| 11,866,770 | B2 | 1/2024 | Chee |
| 11,976,318 | B2 | 5/2024 | Church et al. |
| 12,140,590 | B2 | 11/2024 | Samuels et al. |
| 12,140,591 | B2 | 11/2024 | Samuels et al. |
| 12,234,505 | B2 | 2/2025 | Chee |
| 12,264,358 | B2 | 4/2025 | Church et al. |
| 12,292,440 | B2 | 5/2025 | Samuels et al. |
| 12,297,487 | B2 | 5/2025 | Chee |
| 12,297,488 | B2 | 5/2025 | Chee |
| 12,391,979 | B2 | 8/2025 | Chee |
| 12,391,980 | B2 | 8/2025 | Chee |
| 2003/0148335 | A1 | 8/2003 | Shen |
| 2004/0023271 | A1 | 2/2004 | Kurn |
| 2005/0079520 | A1 | 4/2005 | Wu |
| 2006/0257893 | A1 | 11/2006 | Takahashi et al. |
| 2007/0275415 | A1 | 11/2007 | Srinivasan et al. |
| 2008/0269068 | A1 | 10/2008 | Church et al. |
| 2009/0092603 | A1 | 4/2009 | Bamdad |
| 2010/0015626 | A1 | 1/2010 | Oliphant et al. |
| 2010/0041046 | A1 | 2/2010 | Chiu et al. |
| 2010/0075436 | A1 | 3/2010 | Urdea et al. |
| 2012/0220494 | A1 | 8/2012 | Samuels |
| 2013/0143749 | A1 | 6/2013 | Ghadessy et al. |
| 2015/0132743 | A1 | 5/2015 | Egidio |
| 2017/0009278 | A1 | 1/2017 | Soderberg |
| 2021/0230681 | A1 | 7/2021 | Patterson et al. |
| 2022/0064711 | A1 | 3/2022 | Samuels et al. |
| 2022/0220532 | A1 | 7/2022 | Samuels et al. |
| 2022/0251628 | A1 | 8/2022 | Samuels |
| 2023/0220447 | A1 | 7/2023 | Samuels et al. |
| 2023/0280337 | A1 | 9/2023 | Samuels et al. |
| 2023/0417765 | A1 | 12/2023 | Agresti |
| 2024/0011974 | A1 | 1/2024 | Samuels et al. |
| 2025/0216383 | A1 | 7/2025 | Samuels et al. |
| 2026/0036574 | A1 | 2/2026 | Samuels et al. |
| 2026/0036577 | A1 | 2/2026 | Samuels et al. |

FOREIGN PATENT DOCUMENTS

| | | | |
|---|---|---|---|
| WO | 2011005221 | A1 | 1/2011 |
| WO | 2012106385 | A2 | 8/2012 |
| WO | 2015058052 | A1 | 4/2015 |
| WO | 2015103339 | A1 | 7/2015 |

OTHER PUBLICATIONS

Hendrickson, 1995, High sensitivity multianalyte immunoassay using covalent DNA-labeled antibodies and polymerase chain reaction, Nucl Acids Res 23(3):522-529.

Adler, 2008, Sensitivity by combination: immuno-PCR and related technologies, The Analyst 133(6):685-824.

Lundberg, 2011, Homogenous antibody-based proximity extension assays provide sensitive and specific detection of low-abundant proteins in human blood, Nuc Acids Res 39(15):e102.

Nam, 2003, Nanoparticle-Based Bio-bar Codes for the Ultrasensitive Detection of Proteins, Science 301:1884-1886.

Niemeyer, 2007, Detecting antigens by quantitative immuno-PCR, Nat Protoc 2(8):1918-1930.

Shendure, 2008, Next-generation DNA sequencing, Nat Biotech 26(10):1135-1145.

Akhras, 2007, PathogenMip assay: a mutliplex pathogen detection assay, PLoSOne 2(2):e223.

Antson, 2000, PCR-generated padlock probes detect single nucleotide variation in genomic DNA, Nucl Ac Res 28(12):e58.

Drmanac, 2010, Human genome sequencing using unchained base reads on self-assembling DNA nanoarrays, Science 327:78-81.

Jarvis, 2006, Digital quantification using amplified single-molecule detection, Nat Meth 3(9):725-727.

Larsson, 2010, In situ detection and genotyping of individusal mRNA molecules, Nat Meth 7(5):395-397.

Sista, 2008, development of a digital microfluidic platform for point of care testing, Lab Chip 8(12):2091-2104.

* cited by examiner

Combining Primary Barcode Library and Secondary Barcode Primers (in series or library)

Combining Forward Barcode Library and Stickey-ended Barcode Primers (in series or library)

Series Mode Shown

Combining Library and Sample for PCR Amplification

Single Molecule Barcoding for Haplotype Phasing: PCR Details

Total #PCR cycles (Droplet PCR + Bulk PCR) can be limited to ~10 cycles, as 150 copies enables robust SNP calls

Universal PCR Barcode Library: Single Molecule DNA Haplotyping 1.2

Combining Universal Barcode Library and Locus-Hybridized Primers

Low number of amplification rounds in droplets enables barcode haplotyping

Additional amplification rounds after droplet release may be performed for sequencing prep (as needed) using Universal ends ( , ).

FIG. 15A Universal Primer Extension Barcode Droplet Library For Haplotyping 2.1
Upfront Bulk Processing of Sample DNA: 3 Target-specific (T) primer pairs targeting 3 loci shown
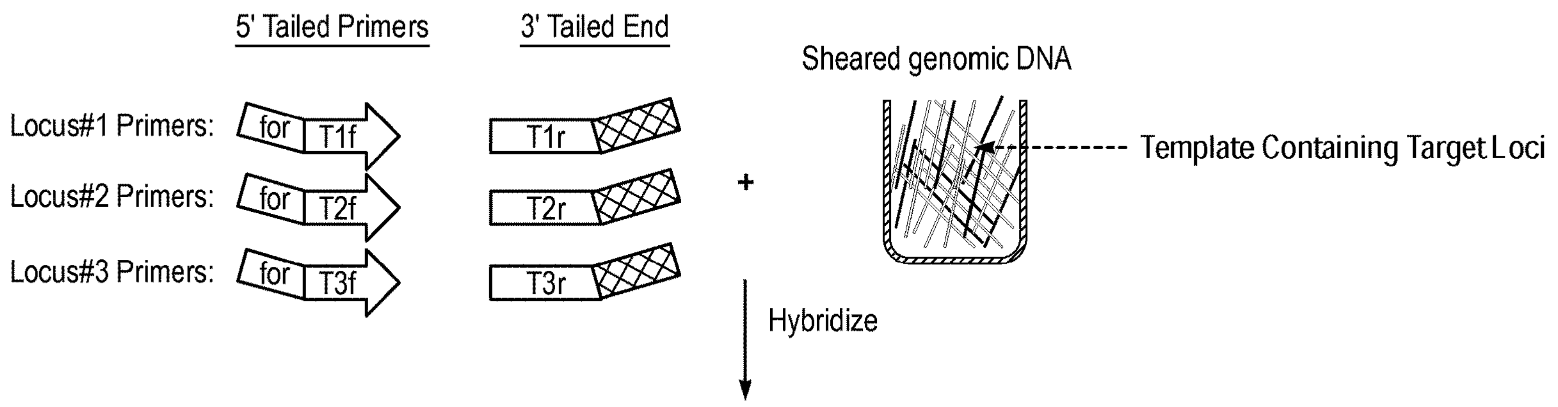

Universal Primer Extension Barcode Droplet Library for Haplotyping 2.2

Combining Universal Barcode Primer Library and Locus-Hybridized Primers

*Phenotypic sorting and barcoded genomic analysis of single cells*

Barcoded Single Cell Genomics: Barcoded Primers

Lysed Cell Droplets Combined with Barcoded Primer Library (& Taq Polymerase)

Loci Sequence from Cell #1 = Barcode 1:1

Barcoded Single Cell Genomics: Universal Barcode Library

Lysed Cell Droplets Generated with Coflow Primers & Taq Polymerase

Loci Sequence from Cell #1 = Barcode 1:1

Droplets for Barcoded Single Cell Transcriptomes

FIG. 26B
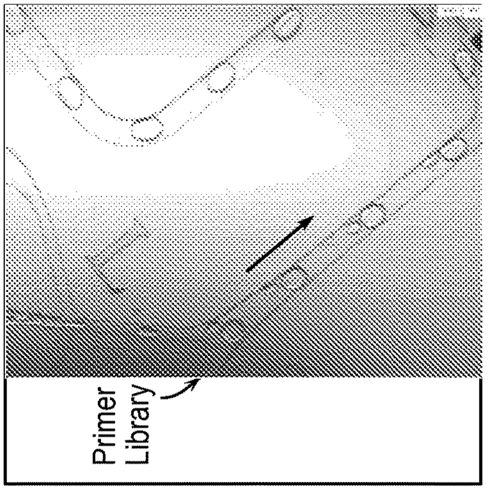
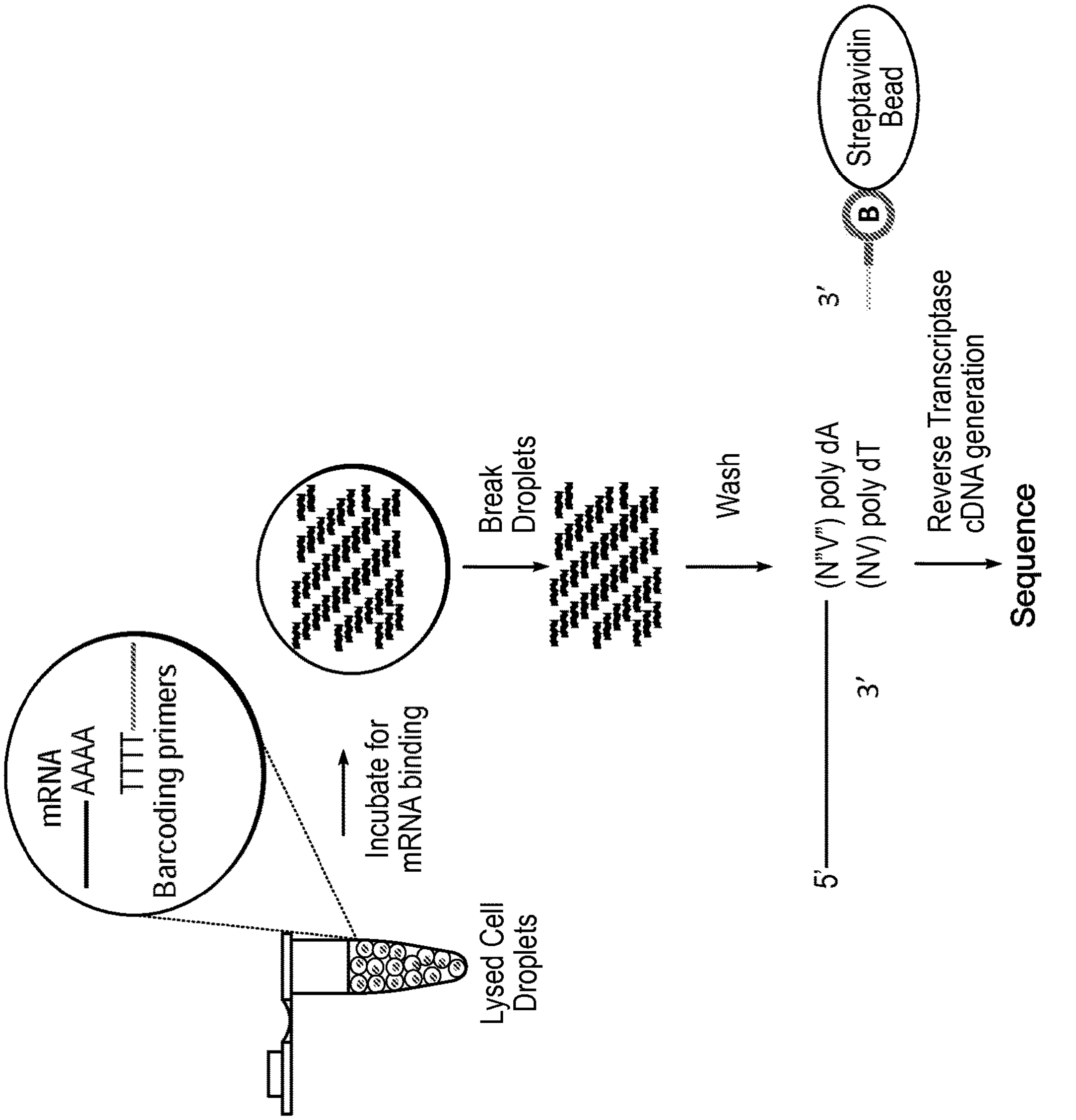

Average Cell Biomarker Barcoding w/o Universal Barcoding for Single Cells

B: Bind Barcoded Binders to Cell Population

C: Wash Labeled Cell Population

D: Release Bound Barcodes

E: Identify and Count (Sequence) Barcodes

Universal Barcode Droplet Library: Single Cell Digital Biomarker Counting#1

FIG. 28C
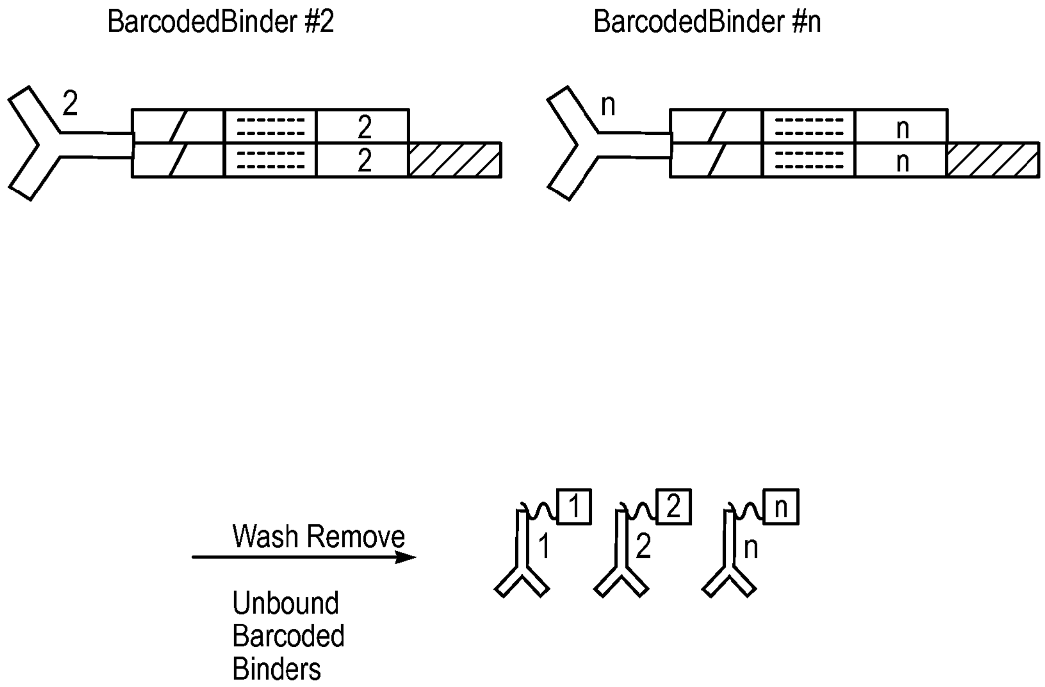
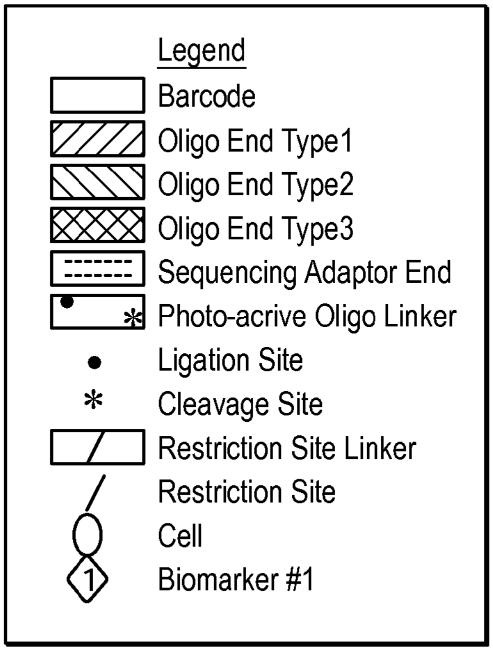

Universal Barcode Droplet Library: Single Cell Digital Biomarker Counting#2

E: Single Cell Droplets are Combined with Universal Barcode Droplet Library

Universal Barcode Droplet Library: Single Cell Digital Biomarker Counting#3

F: Release from Droplets

G: Wash/Remove Unbound Barcodes
H: Ligate Added Barcode

Universal Barcode Droplet Library: Single Cell Digital Biomarker Counting#4

Barcoding Binders

Universal Barcode Droplet Library: High-Plex Barcoding Antibodies

Single Target

Complex

Complex

Modified Analytes (e.g. Post Translational-PTM)

Protein:Nucleic Acid Complex

RNA
Full length

RNA
Splice variant

DNA

DNA
Gene fusion

Methyl or 3-OH Methyl:DNA

*Phenotypic sorting and barcoded genomic analysis of single cells*

Sequencing Error Revealed by BC1

| Barcode | Site X - C | Site X - T | Site Y - A | Site Y - G |
|---|---|---|---|---|
| BC1 | 3 | 1 | 4 | |
| BC2 | 4 | | | 4 |

FIG. 44

Results from the 5x multiplexed droplet library B were compared to the singleplex droplet library A

| Sample | Total reads | Mapped reads | Specificity | Mean base coverage | C1 | C20 | C100 | Base coverage (0.2x of mean) |
|---|---|---|---|---|---|---|---|---|
| Library A with Sample 1 | 27431697 | 99.4% | 0.813 | 1394 | 99.5% | 99.0% | 98.2% | 92.8% |
| Library A with Sample 2 | 15147288 | 99.4% | 0.862 | 819 | 99.1% | 98.2% | 87.6% | 78.0% |
| Library B with Sample 1 | 27861378 | 99.5% | 0.847 | 1472 | 99.7% | 99.3% | 97.6% | 89.9% |
| Library B with Sample 2 | 25758406 | 99.1% | 0.837 | 1321 | 99.8% | 99.4% | 97.6% | 91.3% |

FIG. 45

Gene copy number measurements from the 3x3x3 assay.

| Gene or genotype | Measured copy number | Expected copy number |
|---|---|---|
| SMN1 | 1.98 ± 0.09 | 2 |
| SMN2 | 0.99 ± 0.04 | 1 |
| c.5C in SMN1 | 3.01 ± 0.06 | 3 |
| c.88G in SMN1 | 2.15 ± 0.08 | 2 |
| BCKDHA | 2.00 ± 0.05 | 2 |
| RNaseP | 2.11 ± 0.16 | 2 |

FIG. 46

- Mixture of multiple primers and probes
- 5 Taqman Assays in each droplet
  - Expression Analysis
  - Precise Quantification of copy number
  - Requires 1/5 the DNA of 5 opti-plex reactions
- Each reaction has a unique location in 2D scatter plot

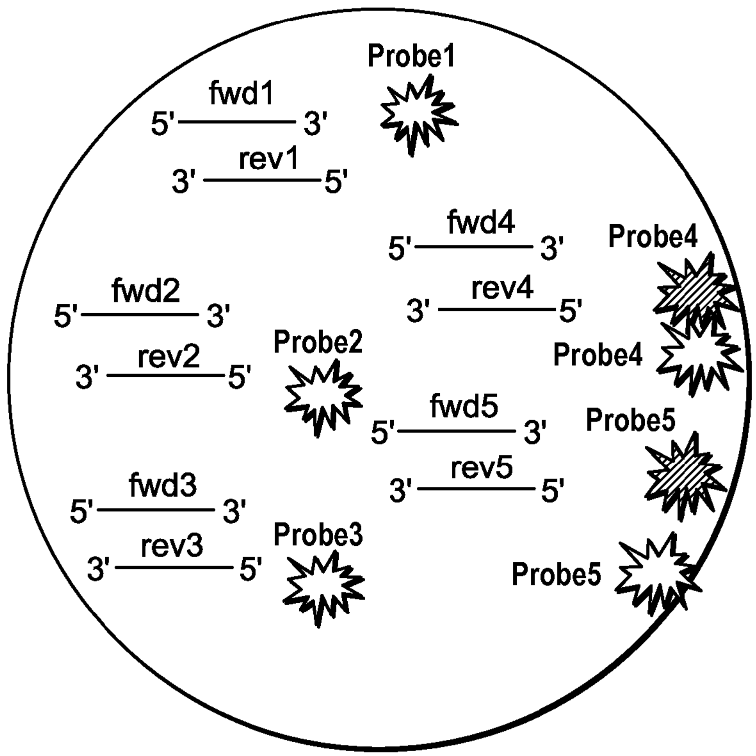
- Off-axis populations are generated by making blends of probes
- Expands optical space available for multiplexing assays
FIG. 51
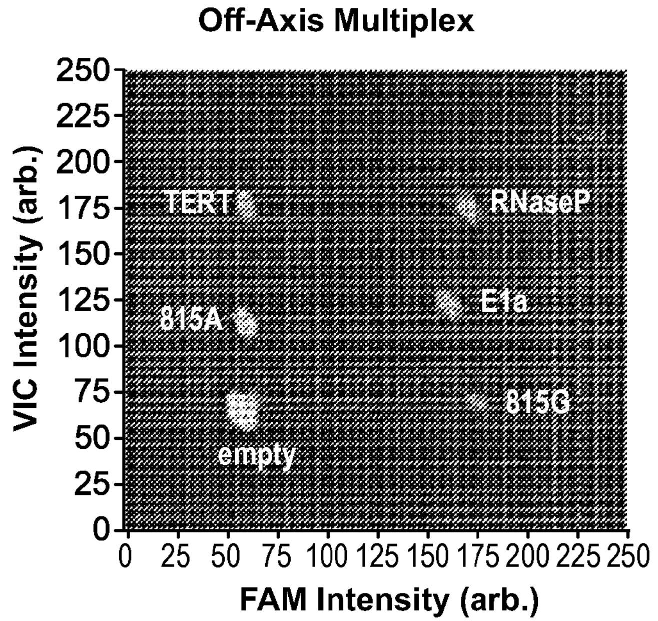
FIG. 52A
| NA03814+815G 215,897 drops | Copy Number | Measured Ratio/TERT |
|---|---|---|
| RNaseP | 2 | 1.01 |
| E1a | 2 | 0.997 |
| 815A | 6 | 3.02 |
| 815G | 1 | 0.497 |
| TERT | 2 | 1 |
FIG. 52B Two Colors THREE Targets Histogram showing four populations of droplets; with target1, with target2, with target3 and without any of the three targets.

FIG. 58A

Tuning the Intensity of Target 2

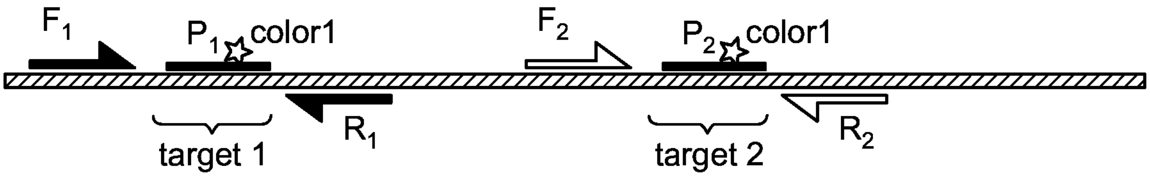

Probe 2 has a single base missmatch to target two and will produce a digital read-out of lower signal intensity

FIG. 58B

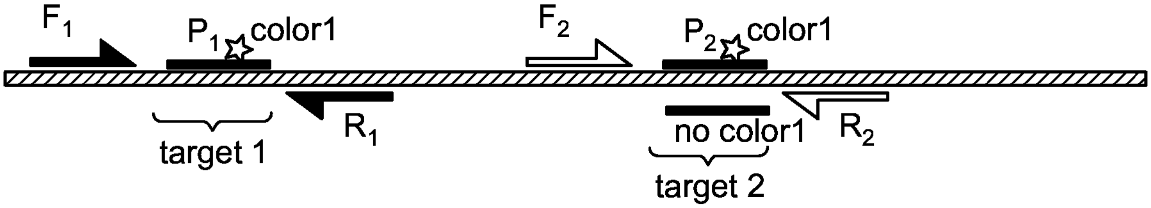

Probe 2 is a blend of identical probes both with and without a fluorophore to reduce the overall intensity of the fluorescent signal

FIG. 58C

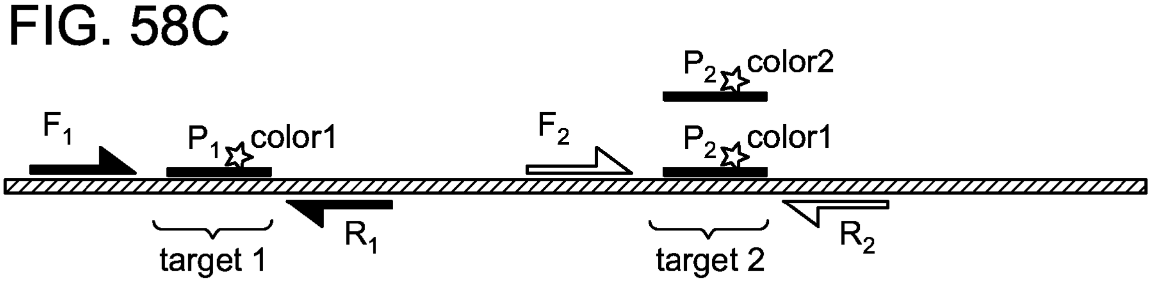

Probe 2 is a blend of identical probes each with a different color fluorophore to produce a multi-color fluorescent burst.

Relative intensity of signals from multiple targets of the same color can be generated in a variety of ways. Examples include: A) using a single base missmatch of the probe and target to distinguish different targets. B) blend identical probes with and without fluorophores. C) blend identical probes with two or more different color fluorophores.

Cell and Virus Binding

Bead and ELISA Sandwich Binding

SEQUENCE LISTING

```
Sequence total quantity: 11
SEQ ID NO: 1            moltype = DNA  length = 10
FEATURE                 Location/Qualifiers
misc_feature            1..10
                        note = Synthetic Sequence
source                  1..10
                        mol_type = other DNA
                        organism = synthetic construct
SEQUENCE: 1
aattccaagg                                                         10

SEQ ID NO: 2            moltype = DNA  length = 18
FEATURE                 Location/Qualifiers
misc_feature            1..18
                        note = Synthetic Sequence
source                  1..18
                        mol_type = other DNA
                        organism = synthetic construct
SEQUENCE: 2
tctggatcca cgggacgt                                                18

SEQ ID NO: 3            moltype = DNA  length = 10
FEATURE                 Location/Qualifiers
misc_feature            1..10
                        note = Synthetic Sequence
source                  1..10
                        mol_type = other DNA
                        organism = synthetic construct
SEQUENCE: 3
tgactgcatt                                                         10

SEQ ID NO: 4            moltype = DNA  length = 28
FEATURE                 Location/Qualifiers
misc_feature            1..28
                        note = Synthetic Sequence
source                  1..28
                        mol_type = other DNA
                        organism = synthetic construct
SEQUENCE: 4
agacctaggt gccctgcaac tgacgtaa                                     28

SEQ ID NO: 5            moltype = DNA  length = 28
FEATURE                 Location/Qualifiers
misc_feature            1..28
                        note = Synthetic Sequence
source                  1..28
                        mol_type = other DNA
                        organism = synthetic construct
SEQUENCE: 5
tctggatcca cgggacgttg actgcatt                                     28

SEQ ID NO: 6            moltype = DNA  length = 27
FEATURE                 Location/Qualifiers
```

-continued

```
misc_feature          1..27
                      note = Synthetic Sequence
source                1..27
                      mol_type = other DNA
                      organism = synthetic construct
SEQUENCE: 6
tctggatccg ccactgacga ctgcatt                                  27

SEQ ID NO: 7          moltype = DNA  length = 21
FEATURE               Location/Qualifiers
misc_feature          1..21
                      note = Synthetic Sequence
source                1..21
                      mol_type = other DNA
                      organism = synthetic construct
SEQUENCE: 7
agacctaggc ggtgactgct g                                        21

SEQ ID NO: 8          moltype = DNA  length = 22
FEATURE               Location/Qualifiers
misc_feature          1..22
                      note = Synthetic Sequence
source                1..22
                      mol_type = other DNA
                      organism = synthetic construct
SEQUENCE: 8
tctggatcca cgggacggcc ac                                       22

SEQ ID NO: 9          moltype = DNA  length = 13
FEATURE               Location/Qualifiers
misc_feature          1..13
                      note = Synthetic Sequence
source                1..13
                      mol_type = other DNA
                      organism = synthetic construct
SEQUENCE: 9
tgacgactgc att                                                 13

SEQ ID NO: 10         moltype = DNA  length = 21
FEATURE               Location/Qualifiers
misc_feature          1..21
                      note = Synthetic Sequence
source                1..21
                      mol_type = other DNA
                      organism = synthetic construct
SEQUENCE: 10
agacctaggc ggtgactgct g                                        21

SEQ ID NO: 11         moltype = DNA  length = 13
FEATURE               Location/Qualifiers
misc_feature          1..13
                      note = Synthetic Sequence
source                1..13
                      mol_type = other DNA
                      organism = synthetic construct
SEQUENCE: 11
gatccacggg acg                                                 13
```

COMPOSITIONS AND METHODS FOR MOLECULAR LABELING

REFERENCE TO A "SEQUENCE LISTING"

A "Sequence Listing XML" is submitted herewith in XML file format and (i) the name of the file is RDT-555-US14.xml; (ii) the date of creation is Mar. 2, 2023; and (iii) the size of the file is 14,705 bytes and the material in the XML file is incorporated by reference.

FIELD OF THE INVENTION

The present invention generally relates to methods and materials for building barcode libraries and labeling target materials, such as individual cells or molecules, with labels such as barcode-type and probe-type labels.

BACKGROUND OF THE INVENTION

The analysis of nucleic acids and proteins is an essential element of molecular biology. The ability to detect, discriminate, and utilize genetic and proteomic information allows sensitive and specific diagnostics, as well as the development of treatments. Most genetic and proteomic analysis requires labeling for detection of the analytes of interest. For example, in sequencing applications, nucleotides added to a template strand during sequencing-by-synthesis typically are labeled, or are intended to generate a label, upon incorporation into the growing strand. The presence of the label allows detection of the incorporated nucleotide. Effective labeling techniques are desirable in order to improve diagnostic and therapeutic results.

SUMMARY OF THE INVENTION

The present invention generally provides products and methods for labeling target material in a fluid compartment. In particular, the invention provides fluid compartments such as droplets for the sequestration, isolation, labeling, detection, identification, and analysis of target material. The invention further provides labels. Labels according to the invention include barcode-type labels and probe-type labels.

Principles of the invention can be applied to analyze all or a portion of an entire genome, transcriptome, or proteome. Techniques disclosed herein provide labeled materials isolated in fluid compartments for use with analytical techniques such as sequencing, haplotyping, and multiplex digital-PCR.

As disclosed herein, target material can be sequestered in a fluid compartment or partition such as a single droplet. Other reagents including labels (e.g., barcoded or optically-labeled N-mers) can be provided, optionally also sequestered in droplets. The other reagents can be introduced into the fluid partitions containing the target material, for example, by merging droplets, resulting in the labeling of the target molecules (e.g., by hybridization of N-mers to target nucleic acids). Target material can undergo optional processing such as selective enrichment, amplification, or capture on a substrate (e.g., beads). Where the labels are of the barcode type, the invention provides analytical methods including selective capture or enrichment, sequencing, haplotype phasing, genotyping, and improved sequence read assembly, as well as methods of producing barcode droplet libraries. Where the labels are of the probe-type, the invention provides novel digital PCR assays including multiplex assays.

Target material can be obtained from a sample, and can include nucleic acid, proteins, carbohydrates, or other materials. The sample may be a human tissue or body fluid. Exemplary body fluids include pus, sputum, semen, urine, blood, saliva, and cerebrospinal fluid.

In certain aspects, the invention provides fluidic compartments to contain all or a portion of a target material. In some embodiments, a compartment is droplet. While reference is made to "droplets" throughout the specification, that term is used interchangeably with fluid compartment and fluid partition unless otherwise indicated. A fluid compartment can be a slug, an area on an array surface, a globule, or a reaction chamber in a microfluidic device, such as for example, a microfluidic device fabricated using multilayer soft lithography (e.g., integrated fluidic circuits). Except where indicated otherwise, "droplet" is used for convenience and any fluid partition or compartment may be used.

A droplet according to the invention generally includes an amount of a first sample fluid in a second carrier fluid. Any technique known in the art for forming droplets may be used with methods of the invention. An exemplary method involves flowing a stream of the sample fluid containing the target material (e.g., nucleic acid template) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant, such as a fluorosurfactant.

The same method may be applied to create individual droplets that contain other reagents such as labels or reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases such as Taq polymerase, forward and reverse primers, deoxynucleotide triphosphates (dNTPs), and one or more buffers. Suitable reagents for conducing non-PCR amplification reactions include, for example, a high fidelity enzyme such as $\phi$29. Alternatively, a transposase can be used.

Either the droplets containing the first fluid, the droplets containing the second fluid, or both, may be formed and then stored in a library for later merging, aspects of certain implementations of which are described in U.S. Pub. 2010/0022414, hereby incorporated herein in its entirety for all purposes.

Once formed, droplets containing the target material can be merged with droplets containing other reagents. Merging can produce a set of droplets, each containing target and other reagents such as, in each droplet, a single nucleic acid template and heterogeneous mixture of primer pairs and probes. Merging can be accomplished, for example, in the presence of an electric field. Moreover, it is not required that both fluids be in the form of droplets when merging takes places. One exemplary method for merging of fluid portions with droplets is taught, for example, in U.S. Patent Application No. 61/441,985 and Ser. No. 13/371,222, the contents of each of which are incorporated by reference herein.

In certain embodiments, fluidic compartments are formed by providing one or more of a first fluid partition (e.g., a droplet) comprising a target material and a second fluid (e.g., as a fluid stream or within droplets) comprising a plurality of nucleic acid constructs, each containing a functional N-mer capable of hybridizing to a unique region of the target material, and a unique N-mer to label the target. The first and second fluids are merged to form a droplet. Merging can be accomplished by application of an electric field to the two fluids. In certain embodiments, the second fluid additionally contains reagents for conducting an amplification reaction, such as a polymerase chain reaction or a multiple displacement amplification reaction. Optionally, the genetic material can be fragmented or sheared using methods well known to those of skill in the art, for example, prior to sequestering into droplets or hybridizing to N-mers.

In certain aspects, the invention provides a method of making a barcode library including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional construct to each compartment in a set, and repeating that for each set to produce NXM compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

In certain aspects, the invention provides a method for labeling target material comprising segregating each of a plurality of targets into a fluid compartment and providing one or more copies of a construct that is unique for each fluid compartment, in which each construct includes a unique N-mer and a functional N-mer. The method can include associating each target with a copies of a construct, for example, by hybridization. Optional steps of methods of the invention can include performing an amplification reaction to produce amplicons that each contain a copy of the construct; releasing the contents of fluid compartments into a bulk phase; performing a second amplification reaction on amplicons; sequencing products of the invention; and detecting products of the invention by digital PCR. Higher levels of complexity (e.g., for arbitrary high levels of multiplex parallel analysis) can obtained by introducing into each fluid partition one or more copies of an additional construct (for example, that are unique to a specific portion of a target) and linking each additional construct to a copy of the construct unique to each fluid partition. Target material can be unlabeled when segregated into the fluid compartments.

In certain aspects, the invention provides a compartment containing all or a portion of a target material, and a plurality of constructs including unique N-mers and functional N-mers (e.g., capable of hybridizing to a unique region of the target material). Examples of target material include but are not limited DNA, genomic DNA, chromosome(s), RNA, expressed RNA and/or protein molecules. In some embodiments, the target material includes a single cell segregated into a fluid compartment. The cell can be lysed within the compartment, and the lysate can be targeted for labeling. Lysate can include the genetic or proteomic material derived from the single cell (prokaryotic or eukaryotic) or a subset thereof (e.g., an entire genome, transcriptome, proteome, or a portion thereof). Droplets containing cells may be sorted according to a sorting operation prior to merging with the other reagents (e.g., as a second set of droplets). The other reagents may contain reagents or enzymes such as a detergent or a protease (e.g., a heat activatable protease) that facilitates the breaking open of the cell and release of the nucleic acids therein. Once the reagents are added to the droplets containing the cells (for example, through droplet merging) and the cells are lysed, primers can be hybridized to the target and then target (e.g., nucleic acid) can be amplified, for example, by PCR.

In certain embodiments, the invention provides a plurality of nucleic constructs including a functional N-mer that comprises a random sequence, for example, a 6-mer for use in a multiple displacement reaction (MDA). Alternatively, the N-mers can comprise a target specific sequence, such as a sequence specific for a gene, a gene mutation, a gene motif, a splice site, a regulatory region of a gene, or a single nucleotide polymorphism. In some embodiments, the N-mers can correspond to one or more consensus sequences, such as, for example, CPG motifs, or other sequence motifs that are related to known or suspected sequences indicative of splice sites, promoter regions, regulatory regions, or other functional genomic units, etc. The N-mers can each further comprise a common sequence, such as a universal primer sequence. In certain embodiments, the N-mers comprise oligo-dT labeled primers.

The invention generally provides methods and materials for labeling a target material (e.g., protein or nucleic acid). Labeling can involve barcode-type labeling using nucleic acid constructs or a probe-type label (e.g., for digital PCR). Nucleic acid constructs can involve informational (i.e, unique or of known sequence) or functional N-mers. In certain embodiments, one or more constructs contain different unique N-mers (i.e., unique labels). The label is preferably associated with a 5' end of the N-mers. However, the label can be associated with a 3' end of the N-mers.

The label associated with each of the N-mers can be a nucleic acid tag, or "barcode" sequence. Where a barcode is included, the N-mer generally hybridizes to the target material and is copied throughout subsequent steps such that the barcode is included in amplicons or sequence reads that may result. Where a probe-type label is included, the N-mer generally hybridizes to a specific material, for example, PCR product containing the target region, and can be detected in assays such as digital PCR. A probe-type label can include an optical label such as a fluorescent label. In some embodiments, an optical label is attached to an antibody specific for a target region of interest in a target material. Applications involving probe-type or barcode-type labels will be discussed in greater detail below.

Whatever construct is used, a target material can be labeled by merging droplets containing the target material with a fluid stream or droplet stream containing the desired construct or merging a fluid stream of the target material with the construct into droplets.

The methods of the invention can further include the step of amplifying or copying the target material so as to preserve, for each amplified product, an association between the amplified product and the label. In certain aspects of the invention, the amplified product is indicative of a haplotype. The nucleic acid template in each of the merged/formed droplets is amplified, e.g., by thermocycling the droplets under temperatures/conditions sufficient to conduct a PCR reaction. The resulting amplicons in the droplets can then be analyzed. For example, using probe-type labels, the presence or absence of the plurality of targets in the one or more droplets is detected optically, e.g., by the detectable label on the plurality of probes. Alternatively, amplicons can be sequenced and reads assembled based on the presence of barcode-type labels.

In some embodiments, capture sequences are introduced into droplets containing target material, for example, by merging the droplets with a second set of droplets containing the capture sequences. Capture sequences can include a barcode label and a portion that is capable of being captured on a solid surface (e.g., biotin/streptavidin on a surface; antibody/antigen; aptamers; anchored oligonucleotides; etc.). A droplet containing a nucleic acid can be merged with a second droplet containing the capture sequence, preferably with a tag (i.e., a barcode-type label). The capture sequence is allowed to hybridize to the target nucleic acid. The emulsion is then broken to release the hybridized capture sequence and target nucleic acid. The released nucleic acid is then captured on a solid support allowing the removal of elements such as cell debris, proteases and detergents that may inhibit subsequent steps. The tag is then incorporated by replication of the captured nucleic acid using the capture sequence with the tag as a primer. Replication can generate DNA from either DNA or RNA (cDNA synthesis). This material can either be processed directly or amplified further using methods known in the field such as PCR or multi-strand displacement amplification.

The capture sequences can be synthesized directly onto the beads or be attached by such means as biotinylated sequences and streptavidin beads. The use of streptavidin beads and biotinylated sequences has the advantage of allowing a generic bead to be used with new libraries of biotinylated capture sequences that can be assembled on demand. However, any method known in the art for attaching nucleic acid sequences to beads can be utilized.

In certain embodiments, droplets containing target material may be merged with droplets containing beads that are designed to capture the target. After capture, the emulsion (i.e., set of droplets) is broken and the beads are used to purify the target away from other components of the reaction that may inhibit subsequent steps such as cell debris, proteases and detergents. Target (e.g., nucleic acid) can be captured on beads by using random N-mers designed to capture all sequences. In some embodiments, N-mers that are designed to capture only portions of the target are attached to the beads. Where the N-mers include a barcode-type tag, the tag can be incorporated by replication of the captured nucleic acid using the capture sequence with the tag as a primer. The replication can generate DNA from DNA or RNA (cDNA synthesis). This material can either be processed directly or amplified further using methods known in the art such as PCR or multi-strand displacement amplification.

In certain embodiments, methods of the invention include enriching all or selected portions of a target material. N-mers can be provided that further contain a common nucleotide sequence, such as a universal PCR sequence. In an exemplary embodiment, the enrichment step is accomplished by incorporating an adapter onto 5' end of the amplified genetic material, such as a universal PCR primer sequence, and further amplifying the genetic material. Only those strands having a label will be amplified, thereby enriching for the labeled genetic material. Alternatively, enrichment of sequence specific labeled strands can be achieved through amplification using a primer specific for the universal priming sequence incorporated into the labeled strand, and a primer specific for a desired target sequence. An enrichment step can be specific for target regions of interest in the genetic material, such as consensus sequences like CPG motifs, or other sequence motifs that are related to known or suspected sequences indicative of splice sites, promoter regions, regulatory regions, poly-A tail etc. In some embodiments, a first portion of amplified product associated with the label is enriched relative to a second portion of amplified product not associated with the label (e.g., through the inclusion of universal priming sites with the label).

In certain embodiments, the invention provides long sequences from short-read sequencing technologies. A set of primers is used that is tiled across the sequence of interest. Target nucleic acid is isolated in fluid partitions (e.g., droplets). Optionally, a plurality of targets are isolated in droplets and analyzed in parallel. For each droplet, a set of primers is provided in which each primer includes a label sequence that is unique for the droplet. the target nucleic acid is amplified in each droplet, with the result that every amplicon strand includes the label sequence at each end. In some embodiments, the droplets are ruptured and the amplicons are sequenced in such a way that each sequence read contains the target label sequence. Since the primer pairs were tiled to cover a long sequence, the reads can be assembled into "long reads" covering the sequence. Because each read is associated with a unique starting molecule through the presence of the label sequence, each "long read" that is produced from short read assembly will correspond to a single molecule of template. Thus, the sequence reads can be mapped back to the targeted genome, transcriptome, proteome, or a portion thereof.

Suitable sequencing methods include, but are not limited to, sequencing by hybridization, sequencing by synthesis technology (e.g., HiSeq™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLID™, Applied Biosciences; Solexa and HiSeq™, Illumina), massively parallel semiconductor sequencing (e.g., Ion Torrent), and pyrosequencing technology (e.g., GS FLX and GS Junior Systems, Roche/454).

In certain aspects, the invention provides a barcode library, which can be, for example, a stable barcode library which can be stored (e.g., for a year or longer). A barcode library can comprise a plurality of fluid compartments, each containing one or more copies of a unique construct, in which each construct includes a unique N-mer and a functional N-mer. For a universal barcode library of general applicability, each functional N-mer may be a sticky end, capable of being associated with another sticky end. Other functional N-mers can include sequence-specific primers; random N-mers; antibodies; probe targets; and universal primer sites. The fluid compartments can be water-in-oil droplets. The unique N-mer offers a barcode of information and can generally be between about 2 and 21 nucleotides in length, and optional longer, e.g., up to 50, 100, or any length.

In certain aspects, the invention relates to methods for detecting or identifying one or a plurality of targets in a biological sample using digital PCR in fluid partitions. Methods of the invention include labeling target material with a probe-type label. A probe type label can include an optical label, and labeled target material can be identified or analyzed using digital PCR.

Target material can be labeled with any suitable probe-type label known in the art. Probes may generally include sequences designed to hybridize to a target of interest. Detection of hybridization can indicate that the target of interest is present. Hybridization can be detected, for example, by including a fluorescent label on a probe structured so that the label is quenched unless hybridized to the intended target of the probe. Quenched and unquenched probes can be detected optically.

One or a plurality of such probes can be provided in a fluid partition. Members of the plurality of probes can each include the same detectable label, or a different detectable label. The plurality of probes can include one or more groups of probes at varying concentrations. The one or more groups of probes can include the same detectable label which varies in intensity upon detection, due to the varying probe concentrations. The droplets of the invention can further contain one or more reagents for conducting a polymerase chain reaction (e.g., polymerase, dNTPs, primers, etc.), for example, to enable probes to hybridize to amplified product (i.e., amplicons).

In some embodiments, the invention provides microfluidic droplets for multiplex analysis. Each droplet can contain a plurality of probes that hybridize to amplicons produced in the droplets. Preferably, the droplet contains two or more probes, e.g., 2, 3, 4, 5, 6, 7, 8, 9, 10, 12, 14, 16, 18, 20, 25, 30, 35, 40, 45, 50, 55, 60, 65, 60, 75, 80, 85, 90, 95, 100, 110, 120, 130, 140, 150, 160, 170, 180, 190, 200, 500, or more probes.

The ability to amplify and detect single nucleic acids in droplets enables digital PCR, detection, counting, and differentiation among nucleic acids, especially those present in heterogeneous samples. Thus, the invention applies to digital amplification techniques and, in specific embodiments enables multiplex PCR in droplets. For example, multiplexing primers in droplets enables the simultaneous increase in the number of PCR droplets while keeping the amount of input DNA the same or lower and generate the same or greater amplicon yield. This results in an overall increase in the amount of PCR positive droplets and amplicon yield without the consumption of more DNA. In some embodiments, even though the number of PCR primer pairs per droplet is greater than one, there is only one template molecule per droplet, and thus, in some implementations, there is only one primer pair per droplet that is being utilized at one time. As such, the advantages of droplet PCR for eliminating bias from either allele specific PCR or competition between different amplicons is maintained. However, as described below in relation to detection of haplotypes, other implementations advantageously allow detection of multiple loci on a single template using multiple primer pairs, preferably designed to minimize bias.

In certain aspects, the invention provides methods of forming fluid partitions including target and reagents for digital PCR in which the methods enable multiplex digital PCR at high "plexity" in fluid partitions. In some embodiments, one or more droplets are formed, each containing a single nucleic acid template and a heterogeneous mixture of primer pairs and probes, each specific for multiple target sites on the template. For example, a first fluid (either continuous, or discontinuous as in droplets) containing a single nucleic acid template (DNA or RNA) is merged with a second fluid (also either continuous, or discontinuous as in droplets) containing a plurality of primer pairs and a plurality of probes, each specific for multiple target sites on the nucleic acid template, to form a droplet containing the single nucleic acid template and a heterogeneous mixture of primer pairs and probes. The second fluid can also contain reagents for conducting a PCR reaction, such as a polymerase and dNTPs. The droplet contents can be amplified (e.g., by thermocycling). The probes are hybridized to the amplicons and hybridization is optically detected.

BRIEF DESCRIPTION OF DRAWINGS

In the drawings, like reference characters generally refer to the same or similar parts throughout the different views. Also, the drawings are not necessarily to scale, emphasis instead generally being placed upon illustrating the principles of the invention.

FIGS. 15A-B show processing for amplification-free haplotyping.

FIGS. 26A-B show a bead-in-droplet workflow for barcoding transcriptomes.

FIGS. 28A-C show barcoding biomarkers on a per-cell basis.

FIGS. 32A-C also shows SEQ IDs: 2-11.

FIG. 44 shows sequencing results.

FIG. 45 shows results from the 5× multiplexed droplet library

FIG. 46 shows results from a multiplexed copy number analysis.

FIG. 51 is a schematic representation of a droplet having 5 sets of primers.

FIG. 52A is a scatter plot showing clusters representing amplified sequences.

FIG. 52B is a table showing the copy number of specific sequences.

FIGS. 58A-C illustrate a schematic for tuning the intensity of a detectable label to a particular target with a microfluidic device.

DETAILED DESCRIPTION OF THE INVENTION

The invention generally provides materials and methods for labeling target nucleic acid, protein, or other material using microfluidic droplet-based technology, and droplets produced using the same. The invention also provides the ability to associate sequencing reads with single cells in a heterogeneous mixture of cells. For example, one or more mutations are identified in subpopulations of cancer cells in a sample using the labeling methods of the invention. The ability to identify multiple mutations existing in one cell better informs research and physicians on the possibility of drug resistance or reoccurrence of disease, and also inform treatment. The invention further provides for the ability to identify metagenomic loss of identity in individual bacteria (e.g., bacteria having multiple mutations in the same organism versus multiple bacteria, each having different mutations, in the same population). In another aspect, the invention provides for the ability to pool multiple patient samples in a multiplex sequencing reaction and to accurately identify the source of the multiple samples after sequencing. Similarly, in proteomic assays (e.g., assays in which a labeled antibody or nucleic acid identifier (such as an aptamer) are used), methods of the invention provide accurate labeling and detection.

As discussed herein, the invention provides (I.) droplets for the analysis and labeling of target material. The invention further provides (II.) barcode-type labels and (III.) probe-type labels.

I. Droplets

Figure 1:
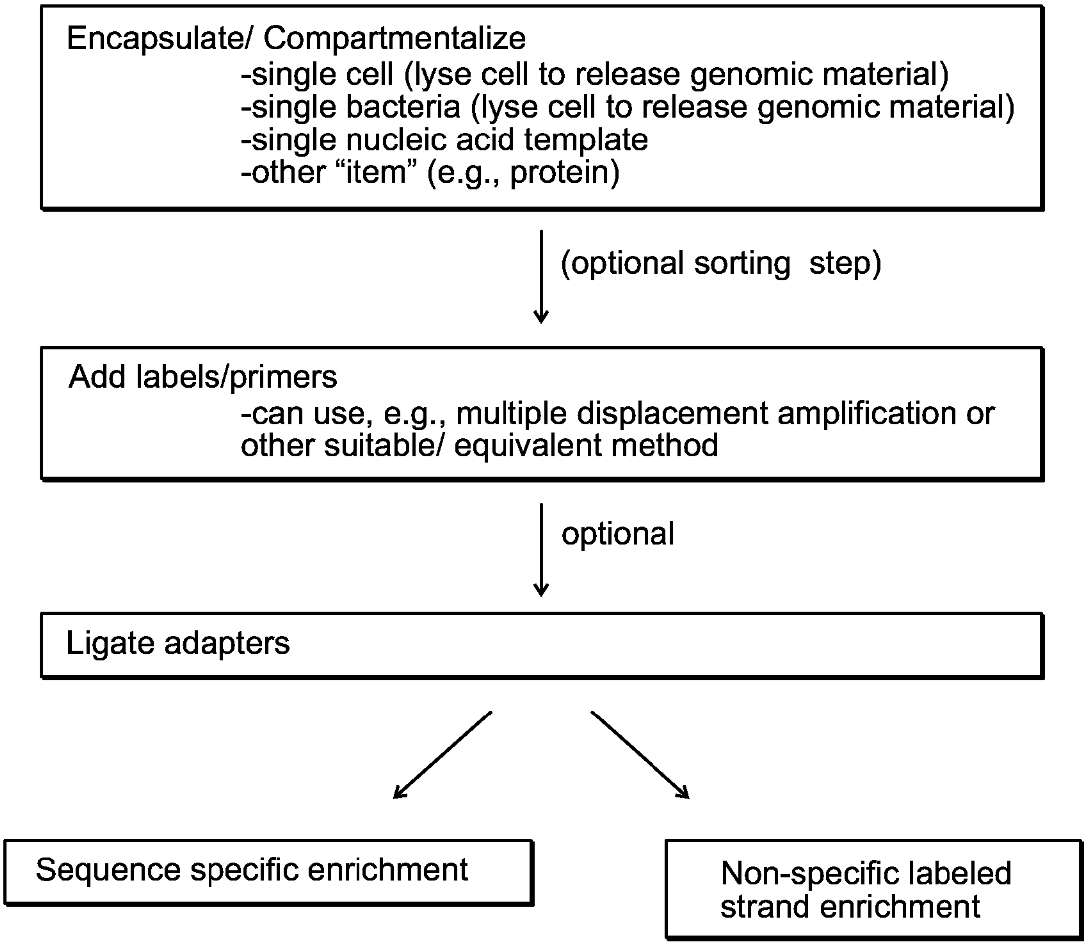
FIG. 1 is a flow chart of the depicting an example of a labeling method according to the invention.
Figure 2A:
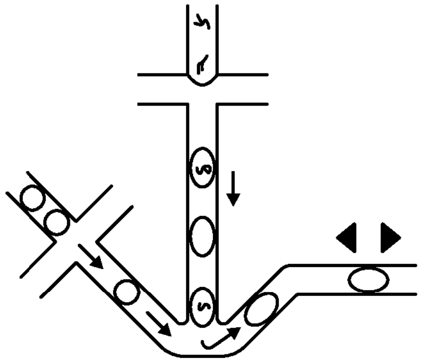
FIG. 2A shows a method of merging droplets.
Figure 2B:
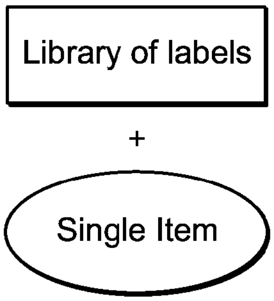
FIG. 2B is a block diagram of droplets for merging.
Figure 2C:
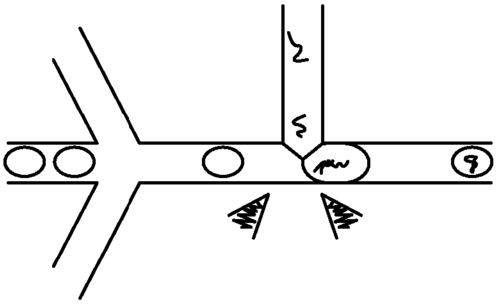
FIG. 2C shows a method of sequestering material in droplets
Figure 2D:
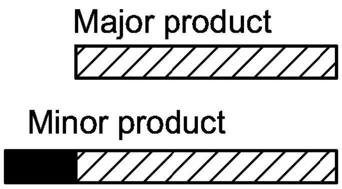
FIG. 2D shows products of a labeling step
Figure 2E:
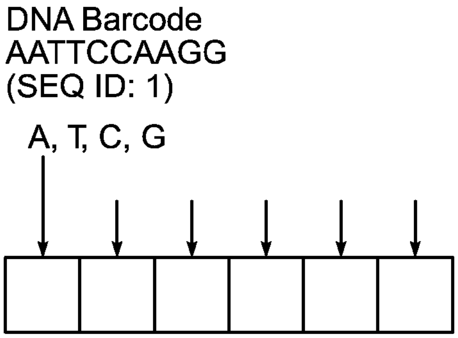
FIG. 2E shows a 10-mer (SEQ ID: 1) and a schematic for a 6-mer.

The invention provides microfluidic devices and systems for the formation of droplets and their manipulation (e.g., merging, sorting, rupturing, storing) for the analysis (e.g., amplification, labeling, detecting) of a variety of target materials FIG. 1 depicts a flow chart of the general methods of the invention. As shown in FIG. 1, the target material is encapsulated in a droplet, for example, using a microfluidic system. FIG. 2A-2C show droplet manipulation. FIG. 2D shows products of a labeling step. FIG. 2E shows a 10-mer and a schematic for a 6-mer. FIG. 2C shows one exemplary method of sequestering material in droplets. Preferably, the genetic material is diluted such that each droplet contains a single element (e.g., nucleic acid molecule, chromosome, genome, cell, protein, biological macromolecule, etc.). The elements can be from a single cell (prokaryotic or eukaryotic), or a portion or subset thereof (e.g., a single nucleic acid template). The droplets can optionally be sorted (e.g., to identify subspecies that will be subsequently labeled). Where the genetic material is a single cell, the cells are lysed to release the genetic element in the single cell. Lysis can be performed prior to encapsulation or after encapsulation (e.g., using proteases, alkaline reagents, and/or detergents). Labels (e.g., barcodes, fluorescent labels) can be introduced into the droplet and incorporated into or on the target. Optionally, an enrichment step can be performed to enrich for the labeled genetic element, or sequence specific enrichment.

Microfluidic Systems

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

Specifically, the devices and methods described herein are based on the creation and manipulation of aqueous phase droplets (e.g., droplet libraries) surrounded by an immiscible carrier fluid. This combination enables precise droplet generation, highly efficient, electrically addressable droplet coalescence, and controllable, electrically addressable single droplet sorting.

Generally, microfluidic devices include one or more channels in one or more analysis units. An "analysis unit" is a microsubstrate, e.g., a microchip. The terms microsubstrate, substrate, microchip, and chip are used interchangeably herein. An analysis unit typically includes at least an inlet channel and a main channel. The analysis unit can further include coalescence, detection, or sorting modules. The sorting module can be in fluid communication with branch channels which are in fluid communication with one or more outlet modules (e.g., collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The dimensions of the substrate are those of typical microchips, ranging between about 0.5 cm to about 15 cm per side and about 1 micron to about 1 cm in thickness. The analysis unit and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227.

A variety of materials and methods can be used to form devices of the invention. For example, components can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Angell, et al., Scientific American, 248:44-55, 1983. At least a portion of the fluidic system can be formed of silicone by molding a silicon chip. Devices of the invention can also be formed of a polymer, for example, an elastomeric polymer such as poly-dimethylsiloxane (PDMS), polytetrafluoroethylene (PTFE), Teflon®, or the like. PDMS polymers include those sold under the trademark Sylgard by Dow Chemical Co., Midland, Mich., and particularly Sylgard 182, Sylgard 184, and Sylgard 186. Silicone polymers such as PDMS are generally inexpensive, readily available, and can be solidified from a prepolymeric liquid via curing with heat. For example, PDMS is typically curable by exposure of the prepolymeric liquid to temperatures of about, for example, about 65° C. to about 75° C. for exposure times of, for example, about an hour. Also, silicone polymers can be elastomeric and thus may be useful for forming very small features with relatively high aspect ratios, necessary in certain embodiments of the invention.

Because PDMS can be oxidized, for example by exposure to an oxygen-containing plasma such as an air plasma, devices of the invention may contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces or to the surfaces without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Further, PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Molding, oxidation and sealing methods are described in the art, for example, in Duffy et al., "Rapid Prototyping of Microfluidic Systems and Polydimethylsiloxane," Anal. Chem., 70:474-480, 1998.

Another advantage of oxidized silicone polymers is that these surfaces can be much more hydrophilic than the surfaces of typical elastomeric polymers (where a hydrophilic interior surface is desired).

Thus, a channel can have a hydrophilic surface, which can be more easily wetted compared to other surfaces, which makes the channel easier to fill with aqueous solutions Generally, "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet. A channel can be formed, for example by etching a silicon chip using conventional photolithography techniques, or using a micromachining technology called "soft lithography" as described by Whitesides and Xia, Angewandte Chemie International Edition 37, 550 (1998).

A fluid within a channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases.

Channels can be configured to coalesce droplets or to flow material by a detection module or a sorting module. A main channel is typically in fluid communication with any coalescence, detection and/or sorting modules, as well as inlet, branch, or outlet channels and any collection or waste modules. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. A microfluidic device can also include fluid channels to inject or remove fluid in between droplets in a droplet stream for the purpose of changing the spacing between droplets.

A microfluidic substrate can also include a specific geometry designed to prevent the aggregation of material prior to encapsulation in droplets. The geometry of channel dimension can be changed to disturb the aggregates and break them apart by various methods, that can include, but is not limited to, geometric pinching (to force cells or particles through a narrow region, whose dimension is smaller or comparable to the dimension of a single cell) or a barricade (place a series of barricades on the way of the moving cells to disturb the movement and break up the aggregates of cells).

To prevent target material (e.g., cells, molecules, or other material as discussed below) from adhering to the sides of the channels, the channels (and coverslip, if used) may have a coating to minimize adhesion. The surface of the channels can be coated with any anti-wetting or blocking agent for the dispersed phase. The channel can be coated with any protein to prevent adhesion of the biological/chemical sample. Channels can be coated by any means known in the art. For example, the channels can be coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of perfluoro-alkylalkylsilane, described in U.S. Pat. No. 5,523,162. The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination. By fluorinating the surfaces of the channels, the continuous phase preferentially wets the channels and allows for the stable generation and movement of droplets through the device. The low surface tension of the channel walls thereby minimizes the accumulation of channel clogging particulates, enhancing the processing of target material.

Target Material

Target materials for labeling, analysis, or detection according to the methods of the invention include, but are not limited to, cells, nucleic acids, proteins, multi-component complexes such as nucleic acid with associated proteins (e.g., histones), chromosomes, carbohydrates, or similar materials. Methods of the invention are applicable to whole cells or to portions of genetic or proteomic material obtained from cells. Target material generally includes anything that can be sequestered into a fluid partition (e.g., droplet) and labeled.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule. Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Proteins or portions of proteins (amino acid polymers) that can bind to high affinity binding moieties, such as antibodies or aptamers, are target molecules for oligonucleotide labeling, for example, in droplets, in some embodiments of this invention.

Droplet Formation

Methods of the invention involve forming droplets, which may contain no target material, target material from a single cell (e.g., a nucleic acid such as genomic DNA or expressed RNA), all or a portion of a target from a single cell, or all or a portion of target from multiple cells (corresponding to limiting or terminal dilution, respectively, as defined above).

In certain embodiments, the distribution of material within droplets obeys the Poisson distribution. However, methods for non-Poisson loading of droplets are known to those familiar with the art, and include but are not limited to active sorting of droplets, such as by laser-induced fluorescence, or by passive one-to-one loading.

The droplets are aqueous droplets that are surrounded by an immiscible carrier fluid. Methods of forming such droplets are discussed in U.S. Pub. 2008/0014589; U.S. Pub. 2008/0003142; U.S. Pub. 2010/0137163; U.S. Pat. No. 7,708,949; U.S. Pub. 2010/0172803; and U.S. Pat. No. 7,041,481, the content of each of which is incorporated by reference herein in its entirety.

Figure 4A:
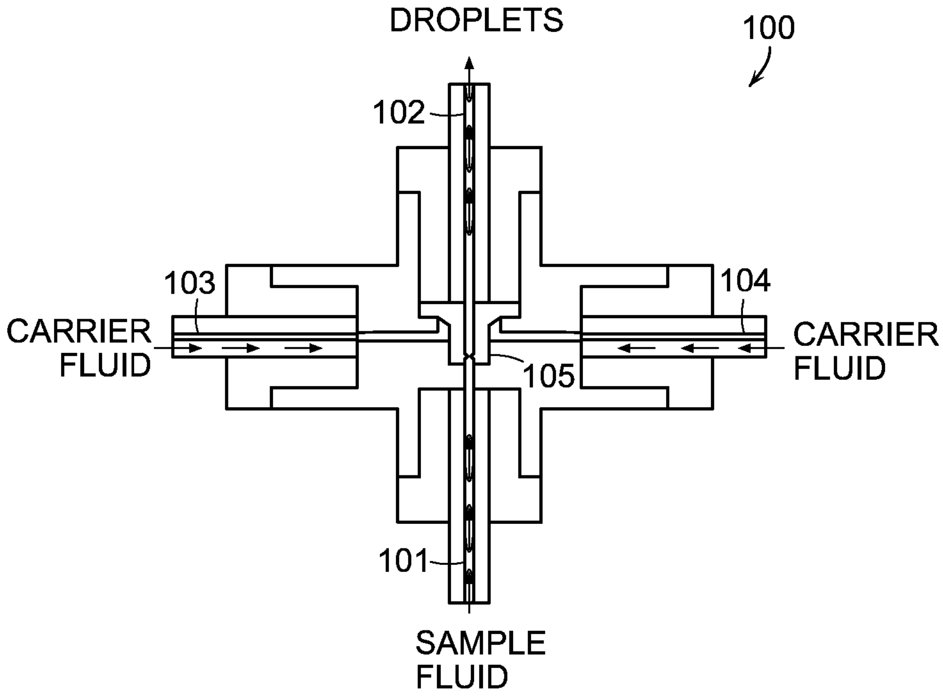
FIG. 4A depicts a droplet formation device.
Figure 4B:
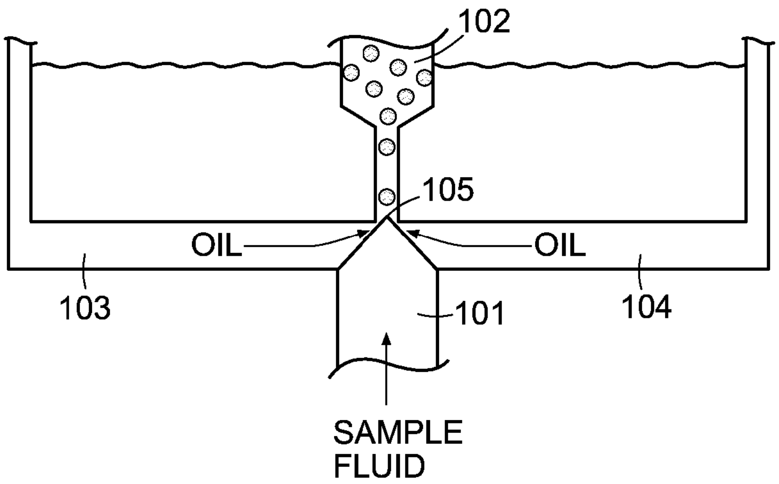
FIG. 4B depicts a portion of the droplet formation device of FIG. 4A.

FIG. 4A shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 4B). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with target material can be used. The carrier fluid is immiscible with the sample fluid. The carrier fluid can be a non-polar solvent, decane (e.g., tetradecane or hexadecane), fluorocarbon oil, silicone oil or another oil (e.g., mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. Suitable surfactants are known in the art. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with ammonium hydroxide in a fluorinated solvent. The solvent, water, and ammonia can be removed with a rotary evaporator. The surfactant can then be dissolved (e.g., 2.5 wt %) in a fluorinated oil (e.g., Flourinert (3M)), which then serves as the carrier fluid.

Another approach to merging sample fluids involves forming a droplet, and contacting the droplet with a fluid stream, in which a portion of the fluid stream integrates with the droplet to form a mixed droplet.

A droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet, which, as discussed below, form a basis for droplet libraries according to certain embodiments of the invention.

The monodisperse droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first or second sample fluids. Applying electric charge is described in U.S. Pub. 2007/0003442, the content of which is incorporated by reference herein in its entirety. Electric charge may be created in a sample fluid within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of a bolus of the second sample fluid and the first sample fluid droplet. The forming mixed droplet continues to increase in size until breaks free from the second sample fluid stream, for instance prior to the arrival of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel (e.g., for possible use in a droplet library).

Where material in droplets will be subject to PCR, those droplets can be merged with a second fluid containing reagents for a PCR reaction (e.g., Taq polymerase, dNTPs, magnesium chloride, and forward and reverse primers, all suspended within an aqueous buffer). The second fluid may also include detectably labeled probes and/or universal barcodes for detection of the amplified target material, the details of which are discussed below. A droplet containing the target or portion thereof is then caused to merge with the PCR reagents in the second fluid as described above, producing a droplet that includes target and PCR reagents as well as, optionally, detectably labeled probes.

Droplet Libraries

Droplet libraries are useful to perform large numbers of assays while consuming only limited amounts of reagents. A "droplet," as used herein, is an isolated portion of a first fluid that is surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. In some embodiments, a droplet is a first fluid completely surrounded by a second fluid. As used herein, a first entity is "surrounded" by a second entity if a closed loop can be drawn or idealized around the first entity through only the second entity (with the sometimes exception for portions of the first fluid that may be in contact with a wall or other boundary, where applicable).

In general, a droplet library is made up of a number of library elements that are pooled together in a single collection. Libraries may vary in complexity from a single library element to 1015 library elements or more. Each library element is one or more given components at a fixed concentration. The element may be, but is not limited to, cells, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element can include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8):1262-1264, 2008. The discreet nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids.

Often it is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. The droplets range in size from roughly 0.5 micron to 500 micron in diameter, which corresponds to about 1 pico liter to 1 nano liter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

In certain embodiments, the droplet libraries are using an immiscible fluorocarbon oil. The oil can comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that can be utilized in the droplet libraries of the present invention are described in greater detail herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability can be measured at any temperature. For example, the droplets are very stable and are capable of long-term storage at any temperature; for example, e.g., −70° C., 0° C., 4° C., 37° C., room temperature, 75° C. and 95° C. Specifically, the droplet libraries of the present invention are stable for at least 30 days. More preferably, the droplets are stable for at least 60 days. Most preferably, the droplets are stable for at least 90 days.

The invention provides a droplet library comprising a plurality of aqueous droplets within an immiscible fluid (optionally comprising a fluorosurfactant), wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid (optionally comprising a fluorosurfactant).

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are cancer cells of a tissue biopsy, and each cell type is encapsulated to be screened for genomic data or against different drug therapies. Another example is that 10^11 or 10^15 different type of bacteria; each having a different plasmid spliced therein, are encapsulated. One example is a bacterial library where each library element grows into a clonal population that secretes a variant on an enzyme.

In certain embodiments, a droplet library comprises a plurality of aqueous droplets within an immiscible fluid, such that there is a single molecule contained within a droplet for every 20-60 droplets produced (e.g., 20, 25, 30, 35, 40, 45, 50, 55, 60 droplets, or any integer in between). Single molecules are encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries relies on limiting dilutions.

The present invention also provides a droplet library comprising at least a first aqueous droplet and at least a second aqueous droplet within a fluorocarbon oil comprising at least one fluorosurfactant, wherein the at least first and the at least second droplets are uniform in size and comprise a different aqueous fluid and a different library element. The present invention also provides a method for forming the emulsion library comprising providing at least a first aqueous fluid comprising at least a first library of elements, providing at least a second aqueous fluid comprising at least a second library of elements, encapsulating each element of said at least first library into at least a first aqueous droplet within an immiscible fluorocarbon oil comprising at least one fluorosurfactant, encapsulating each element of said at least second library into at least a second aqueous droplet within an immiscible fluorocarbon oil comprising at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil comprising at least one fluorosurfactant thereby forming an emulsion library.

For example, in one type of emulsion library, there are library elements that have different particles, i.e., cells or beads in a different medium and are encapsulated prior to pooling. In one example, a specified number of library elements, i.e., n number of different cells or beads, are contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

FIG. 71A-D shows droplet generation, merging, and combining. As shown in panel A, monodisperse aqueous droplets are formed in a fluorocarbon oil using pressure-driven flow into a microfluidic nozzle. Panel B presents a schematic showing surfactant "wall" which provides stability for droplet manipulations. Panel C includes an image from a sequence enrichment application, combining DNA samples with PCR reagents (merging with Primer Droplet Library). The mixed droplets can be taken off-chip for PCR. In panel D, the top image shows ~2×108 droplets before PCR, and bottom shows a microscope image of intact droplets after thermocycling.

FIG. 72A-D shows droplet library generation and use in binding assays (discussed in greater detail herein). As shown in Panel A, stable droplet library reagents can be formulated (5-member library shown) and aliquoted for later use. Panel B shows reinjection of a droplet library and re-spacing into single file droplets. Panel C presents two binding assays: microscope image on the top shows virus particles binding to embryonic fibroblasts; the image on the bottom shows individual beads binding to ELISA sandwich reagents in droplets.

Droplet Sorting

Methods of the invention may further include sorting the droplets based upon whether the droplets contain a homogeneous population of molecules or a heterogeneous population of molecules. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown in U.S. Pub. 2008/0014589; U.S. Pub. 2008/0003142, and U.S. Pub. 2010/0137163.

Based upon the detected signal at the detection module, droplets containing a heterogeneous population of molecules are sorted away from droplets that contain a homogeneous population of molecules. Droplets may be further sorted to separate droplets that contain a homogeneous population of amplicons of the target from droplets that contain a homogeneous population of amplicons of the variant of the target.

Target Amplification

Methods of the invention may further involve amplifying the target genetic material in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos.

4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other and by cycling parameters, and therefore, this length is a controllable parameter.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets.

In embodiments involving merging of droplets, two droplet formation modules are used. In one embodiment, a first droplet formation module produces the sample droplets consistent with limiting or terminal dilution of target nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acid, the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule ($Td=2(A+T)+4(G+C)$). Another method for determining the melting temperature of primers is the nearest neighbor method (SantaLucia, "A unified view of polymer, dumbbell, and oligonucleotide DNA nearest-neighbor thermodynamics", 1998, P.N.A.S., 95 (4): 1460-5). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

In one embodiment, the droplet formation modules are arranged and controlled to produce an interdigitation of sample droplets and PCR reagent droplets flowing through a channel. Such an arrangement is described U.S. Pub. 2008/0014589; U.S. Pub. 2008/0003142, and U.S. Pub. 2010/0137163.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Further discussion can be found in U.S. Pub. 2007/0003442.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, New York, 2001).

In certain embodiments, the three temperature zones are controlled to have temperatures as follows: 950 C (TH), 550 C (TL), 720 C (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 950 C, where the sample is first separated into single stranded DNA in a process called denaturation. The sample then flows to the low temperature, of approximately 550 C, where the hybridization process takes place, during which the primers anneal to the complementary sequences of the sample. Finally, as the sample flows through the third medium temperature, of approximately 720 C, the polymerase process occurs when the primers are extended along the single strand of DNA with a thermostable enzyme. Methods for controlling the temperature in each zone may include but are not limited to electrical resistance, peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 950 C (TH) and 600 C (TL). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 950 C, where the sample is first separated into single stranded DNA in a process called denaturation. The sample then flows through the device to the low temperature zone, of approximately 600 C, where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

Release from Droplet

Methods of the invention may further involve releasing amplified target molecules from the droplets for further analysis. Methods of releasing amplified target molecules from the droplets are shown in publications and patents referenced above.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto 5' end of the sequence specific portion of the primer. The sequences for the tailed regions are the same for each primer pair and are incorporated onto 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer.

During the secondary PCR cycling these additional regions also become incorporated into the amplicons. These additional sequences can include, but are not limited to: adaptor regions utilized by sequencing platforms for library preparation; barcode sequences for the identification of samples multiplexed into the same reaction; molecules for the separation of amplicons from the rest of the reaction materials (e.g., biotin, digoxin, peptides, or antibodies); or molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown in U.S. Pat. Nos. 7,169,560; 6,818,395; 7,282,337; U.S. Pub. 2002/0164629; and Braslavsky, et al., PNAS (USA), 100:3960-3964 (2003), the contents of each of these references are incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in U.S. Pat. No. 7,666,593. The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

II. Barcode-Type Labels

Barcode Sequences

The invention provides labels for target materials comprising a detectable barcode-type label. A detectable barcode-type label can be any barcode-type label known in the art including, for example, radio-frequency tags, semiconductor chips, barcoded magnetic beads (e.g., from Applied Biocode, Inc., Santa Fe Springs, CA), and nucleic acid sequences. In certain embodiments, a barcode-type label is a nucleic acid construct such as a nucleic acid construct including a barcode-type sequence (e.g., a unique N-mer). A construct of the invention generally includes a functional portion. Thus, a barcode sequence generally refers to a nucleic acid construct that includes at least a unique N-mer portion and a functional N-mer portion. For example, the unique N-mer portion can be used to tag—by means of its unique sequence information—any target material labeled with that construct. The functional N-mer portion may be used to attach the construct to a target (e.g., cells, proteins, nucleic acids, other molecules, solid substrates, and other barcode constructs). Where, for example, the target material includes nucleic acid, the functional N-mer can include a complementary nucleic acid (primer, hexamer, randomer, universal primer, etc.) to hybridize to the target. In some embodiments, the unique N-mer ("barcode sequence") is attached to the functional N-mer (e.g., "primer") such that the barcode sequence is incorporated into a 5' end of the primer. Alternatively, the barcode sequence may be incorporated into the 3' end of the primer.

In some embodiments, more than one type of barcode-type label are included, for example, to be cross-combined. In one illustrative embodiment, nucleic acid constructs of the invention are combined (e.g., a set of constructs is cross combined one of each at a time with a set of other labels) with a labels of another type, such as magnetic barcoded beads from Applied BioCode.

The functional N-mer can operate as a primer sequence or sticky end to hybridize to nucleic acid. Functional N-mers can be designed to favor hybridization under certain conditions. For example, length or GC content can be varied to favor high-temperature (or stringent) conditions. Where a nucleic acid construct (barcode) will be made with sticky ends to append to other constructs, the melting temperature of the sticky ends can be tuned, for example, by tuning the length of those ends. No particular length is required in general, so any given length can be chosen based on intended melting temperature or other design considerations.

Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6,172,218; and 5,863,722, the content of each of which is incorporated by reference herein in its entirety.

Barcode sequences typically include a set of oligonucleotides ranging from about 4 to about 20 oligonucleotide bases (e.g., 8-10 oligonucleotide bases), which uniquely encode a discrete library member preferably without containing significant homology to any sequence in the targeted genome. The barcode sequence generally includes features useful in sequencing reactions. For example the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence.

Synthesis of oligonucleotides for use as constructs (e.g., barcodes or functional portions) can be by any means known in the art. Oligonucleotides can be synthesized on arrays, or in bulk, for example.

In certain embodiments, the barcode sequences are designed to be correlated to a particular patient, allowing patient samples to be distinguished. The barcode sequences incorporated into a plurality of primers (and subsequently into DNA or RNA targets) within a single droplet may be the same, and vary from droplet to droplet. Alternatively, the barcode sequences incorporated into the plurality of primers (and subsequently into DNA or RNA target) within a single droplet may be different. Designing barcodes is shown U.S. Pat. No. 6,235,475, the contents of which are incorporated by reference herein in their entirety. In certain embodiments, the barcode sequences range from about 2 nucleotides to about 25 nucleotides, e.g., about 5 nucleotides to about 10 nucleotides. Since the barcode sequence is sequenced along with the template nucleic acid to which it is attached, the oligonucleotide length should be of minimal length so as to permit the longest read from the template nucleic acid attached. Generally, the barcode sequences are spaced from the template nucleic acid molecule by at least one base (minimizes homopolymeric combinations).

Methods of the invention include attaching the barcode sequences to a functional N-mer such as a primer, then incorporating the barcode into a target, or portion thereof using, for example, multiple displacement amplification. The labeled strands produced by MDA are able to be fragmented or sheared to desired length, e.g. generally from 100 to 500 bases or longer, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA before or after fragmentation.

Barcode Droplet Libraries

In certain embodiments, the invention provides libraries of barcodes in droplets, as well as methods of making and using them. Making a barcode library is shown in FIGS. 5A-FIG. 9B. A barcode droplet library generally is a set of droplets containing barcodes (e.g., unique N-mers) for incorporation into a target molecule. Barcodes can be provided in an oligonucleotide containing sequence to function as an amplification primer with the result that a nucleic acid subsequently introduced into the droplet will be amplified, and the copies that result will include the barcode of that droplet. However, barcodes can also be provided that are used to label proteins or other molecules of interest.

In various embodiments, there is a distinction between a droplet library that is used directly with samples (function N-mer is PCR primer, random hexamer, etc), and a library that can be used either for continued building of higher complexity composite barcodes, or directly with samples that have been prepared to contain appropriate sticky-ends (functional N-mer is a sticky end; the haplotyping with annealed samples is one example of this case).

Regardless of the library type, the functional N-mer can be chosen based on a type of target material. For example, for barcoding antibodies, one set of antibodies could all have a sticky-end that binds one class of barcodes, and another antibody set would have a different sticky end, for example, to bind a capture tag. In another example, a set of barcoded PCR primers could include one forward/reverse pair that could bind to one class of barcodes and a different 'universal' forward/reverse pair that binds to a different class of barcodes (with the compliment to the second for/rev pair).

Figure 7A:
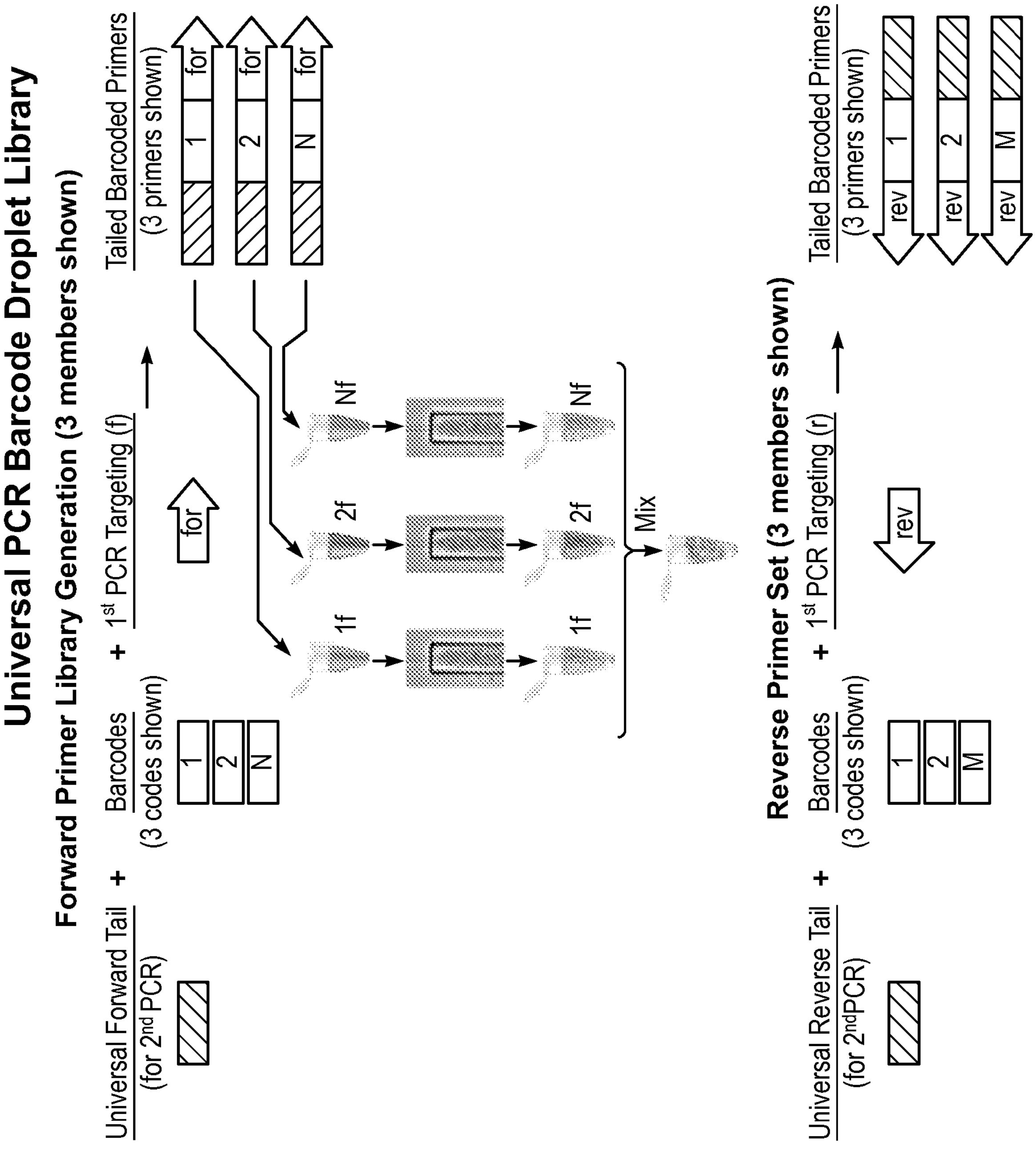
FIGS. 7A-B show a universal barcode droplet library with targeting primers.
Figure 7B:
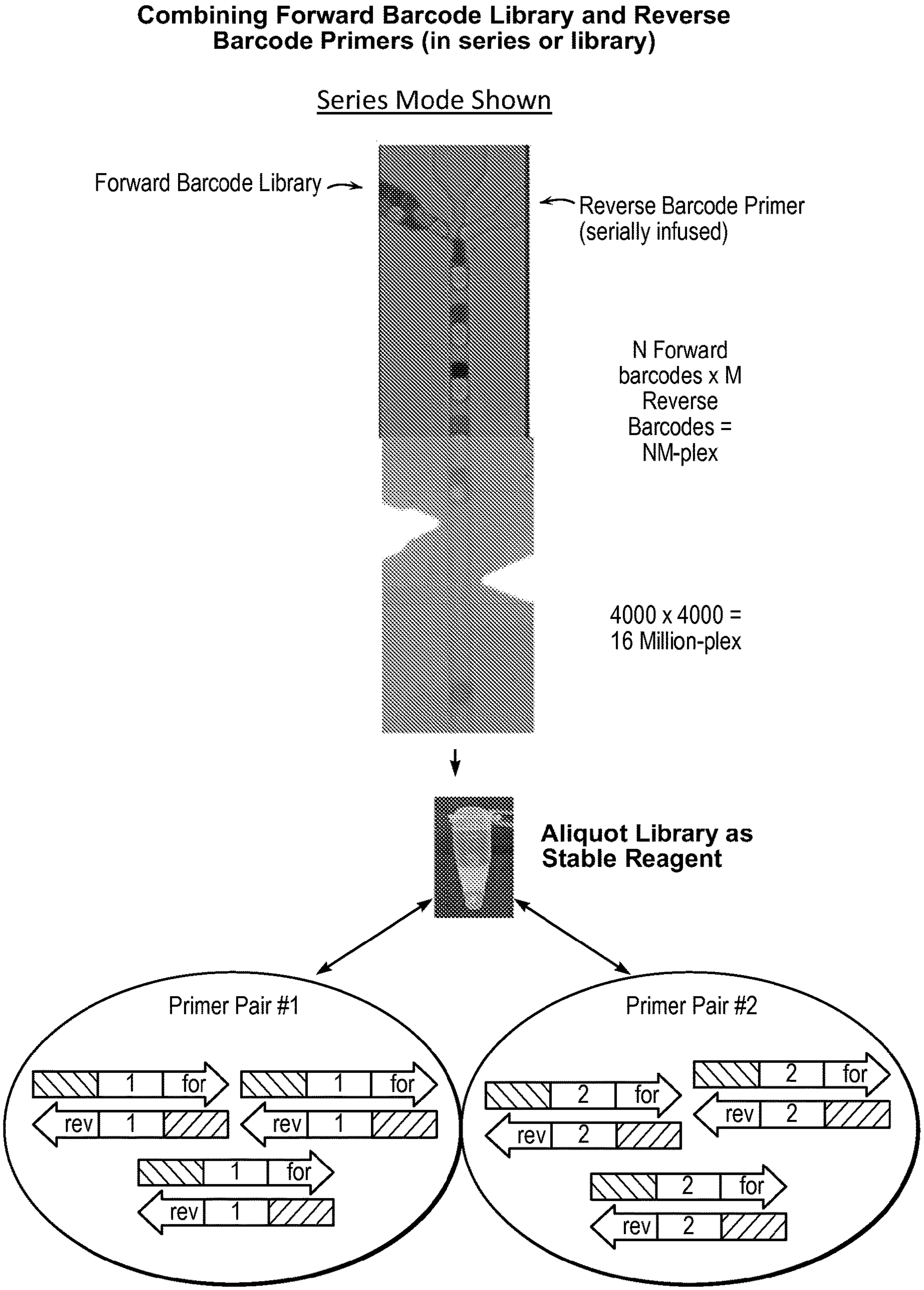

Barcodes can be provided as oligonucleotides as discussed above. In certain embodiments, a barcode is provided as part of a tripartite construct (e.g., as shown in FIG. 7A-B) including a universal priming site, a barcode, and a sequence specific region. The sequence specific region can provide a PCR primer of known sequence, a random hexamer for MDA, or any other suitable nucleotide sequence that will bind to target. In other embodiments, the invention provides universal barcode libraries (e.g., droplets that each contain a plurality of universal primers or priming sites all having a single unique barcode, but without a sequence-specific region). A universal barcode generally includes a unique N-mer and a sticky end.

For creation of a library, a number of different barcodes will be obtained. For any given length, L, in nucleotides, the number N of unique barcodes that can be made using standard nucleotides (A, T, C, G) is given by N=4L. It can be seen by simple calculation, for example, that if barcodes are to be five nucleotides long, then 1,024 unique barcodes are possible. Six, seven, and eight nucleotides in a barcode allow for 4096, 16384, and 65536 unique barcodes, respectively. If each barcode includes 10 nucleotides, then more than one million unique libraries can be made. At 15 nucleotides, then N is greater than one billion. Combining such barcodes using sticky ends (shown in FIGS. 5A-B) gives N'=N×N. In creating a barcode droplet library, a number of droplets are formed, each preferably containing copies of a uniquely-barcoded construct.

For embodiments in which primer pairs are used, for example, where target nucleic acid is to be amplified using PCR, one step of creating a barcode droplet library involves creating a forward library. In a tripartite construct-based embodiment, each droplet in the forward library will contain a plurality of copies of uniquely-barcoded tripartite "forward" primers. That is, each tripartite construct in the forward library will comprise 5'-universal forward tail-barcode-forward primer-3'. While any number of droplets can be made in the forward library, in a preferred embodiment, the forward library contains sets that include a number of droplets equal to or less than the number of possible unique barcode given the number of nucleotides in each barcode. Thus, if a six nucleotide barcode is to be used, sets of approximately 4,000 droplets (or any arbitrarily-lower number) can be made.

A corresponding number of reverse tripartite constructs can be made (e.g., universal reverse tail-barcode-reverse primer). Then, microfluidic methods and devices as discussed herein can be used to add reverse constructs to each droplet containing forward constructs. Forward and reverse constructs can be put into droplets together in a variety of ways. For example, the forward and reverse constructs can be put into droplets a single well at a time. In some embodiments, flowing microfluidic systems are used. For example, a stream containing reverse constructs can be merged with a stream containing the forward droplets. As each droplet passes the merge point, the reverse construct is added.

Forward and reverse constructs can be put together randomly, or they can be put together in a serial fashion. In a serial approach, the first reverse construct can be added to all droplets (e.g., about 4,000) of a set of forward droplets by flowing those droplets through the merge point. Then, the second reverse construct can be used, and the steps repeated. A second complete set of forward droplets can be streamed into the second reverse construct, thereby creating 4,000 droplets, each of which contains a unique forward primer and the second reverse primer construct. After this process is repeated 4,000 times, 4,000×4,000 droplets will have been made, each containing uniquely-barcoded primer pairs (e.g., as tripartite constructs). Production of a large barcode library by these means need not include tripartite constructs and can use any constructs that include barcodes (e.g., primer pairs+barcodes; random hexamers+barcodes; universal primers+barcodes; etc.).

Where primer pairs are used, any number of primers or primer pairs can be used. Where a large number of cells will be assayed for information about a single locus of interest, a single PCR primer pair may be used in a large barcode droplet library. Where a barcode droplet library will be used to assay a number X of loci on a plurality of genomes, X primer pairs will be used. Where MDA will be used to amplify one or more target regions, a number of random hexamers will be used according to calculations discussed elsewhere.

In certain embodiments, only one type of construct is provided per droplet (i.e., forward only or reverse only, without a corresponding reverse). Thus, methods of the invention include preparation of barcode droplet libraries in which each droplet contains a single barcoded construct without a corresponding partner-pair barcode.

In certain embodiments, primers for an initial round of amplification are universal primers, for example, where the target to be amplified includes universal priming sites.

As discussed elsewhere herein, droplets of the invention are stable when stored. Thus a barcode droplet library can be prepared having any arbitrarily large size and stored to be later used in any of the suited assays described herein or known in the art.

In some embodiments, the invention provides methods involving a two-step "drop" PCR wherein multiple sets of primers are provided in a droplet. Either, both, or neither set of primers can include barcodes. Target material is added to the droplet. A first round of amplification is performed, and then a condition is changed, and amplification is performed again. For example, low-stringency conditions are created for the first amplification, through manipulation of temperature or chemical environment. Thus, even though other primers are present, an intended first set of primers outcompetes or predominates in amplification. By these means, target nucleic acid can be amplified and barcoded in multiple steps.

As discussed above, a barcode library generally includes constructs having a functional N-mer and a unique N-mer. In some embodiments, a functional N-mer is a sticky end.

The invention provides methods and materials to generate large, complex, or extensible barcode libraries, and applications for barcode libraries.

In order to facilitate generation of a sufficiently high number of barcoding oligonucleotide species for labeling a wide range of molecules, particles, or cells, one can generate a “Universal Barcoding Droplet Library” for combining with samples. This reagent can be used to barcode DNA, RNA, proteins, chemicals, beads or other species present in the sample if they contain complimentary binding moieties.

The concepts for generation and use of a droplet library for massively parallel molecular barcoding apply to all forms of binding agents that can have a readable identifying barcode appended. Expanded ‘plex’ for barcode identifiers is provided via the use of barcodes in droplets, such that one barcode can be linked to other barcodes via one or more library combinations, resulting in multiplicatively larger sets of unique barcodes.

In certain embodiments, antibodies or oligonucleotides are used as functional N-mers for binding to sample molecules with (optionally releasable) unique N-mers as barcodes. Both the types and numbers of each type of barcodes are determined by a digitally quantified readout, and thus correlated with the presence and concentration of various biomarker species in a sample.

Two basic types of universal barcoding droplet libraries are described as examples of the general concept for providing a means to append unique barcodes to target material for identification or quantification, but the concept is not limited to these examples and at least one example will be given where the two described library types are used together.

In the first set of examples, a universal binding barcode droplet library is described for use in a ‘bind and ligate’ approach (see FIG. 6). This library type consists of droplets containing oligonucleotide strands that encode barcodes and contain ligation competent ends, enabling the modular linking of barcodes by specific hybridization (also referred to as ‘annealing’ or ‘binding’) in droplets followed by ligation into a covalently bonded strand (or duplex) of bases. The Universal Binding Barcode Droplet Library can be used directly with samples that contain pre-bound barcoded binding moieties, as a ‘primary’ library that is combined with binding moieties targeting specific sample molecules, or can be used in the construction of ‘secondary’ or higher order binding barcode libraries through the successive combination of droplet libraries. The end use of such libraries can include assembly of the barcoded specific binding agents into a release-able and readable single molecule for use in digital quantification of bound targets for a variety of applications.

In the second set of examples, a universal priming barcode droplet library is described for use in a ‘bind and prime’ approach. FIGS. 7A-B show one example of a universal barcode droplet library with targeting primers (e.g., to “bind and prime”). This library type consists of droplets containing barcoded primers for PCR (or other polymerase) priming, such that after combination with a sample droplet containing at least one target sequence from the same single DNA or RNA molecule, or multiple molecules co-localized in a single droplet, a digitally readable oligonucleotide barcode is attached to the target molecule’s sequence. Since all polymerase generated molecules in the same droplet will have the same barcode, the co-localization information is retained after release from the droplet, and any sequencer can be used to both determine the sequence and count the number of templates traceable to each original droplet.

Figure 9A:
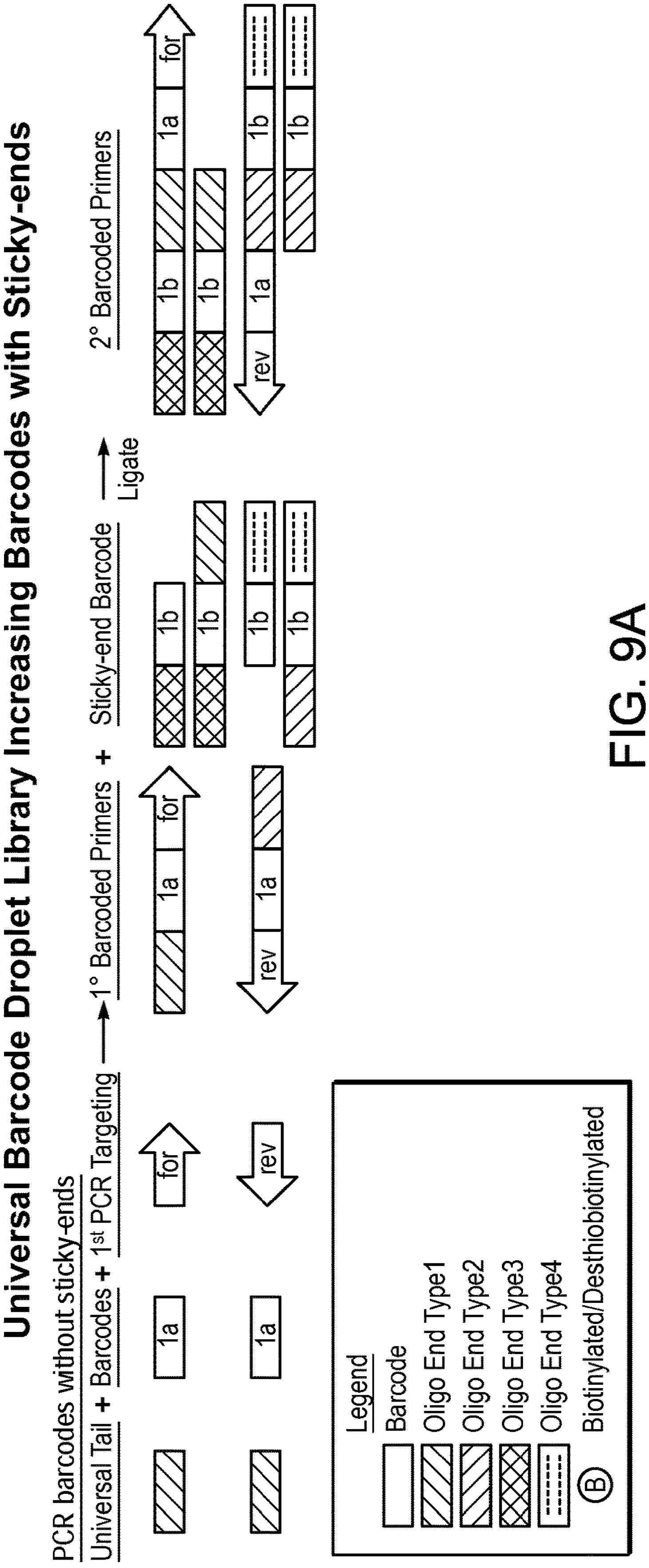
FIGS. 9A-B show ligating sticky-ended universal barcodes to barcoded PCR primers.
Figure 9B:
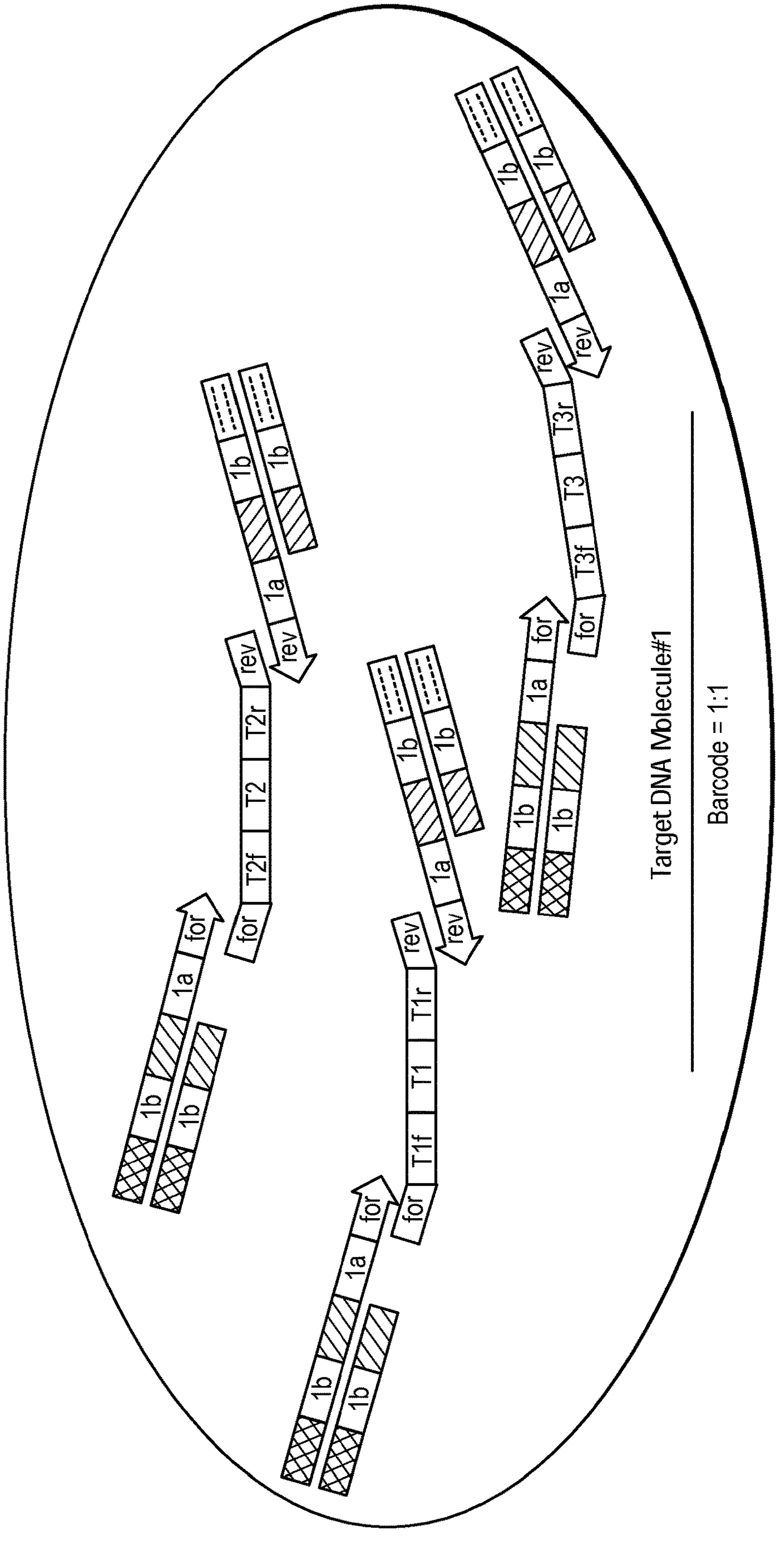

Both library types enable molecular barcoding in droplets, providing a large excess of unique identifying barcodes compared to the number of sample droplets, or compared to the number of sample objects or molecules contained in the droplets, thus allowing digital quantification of many targets of interest on various reading platforms. Significantly, the two types are not exclusive of each other. For example, FIG. 9A-B shows ligating sticky-ended universal barcodes to barcoded PCR primers.

Sticky End Libraries

Figure 5A:
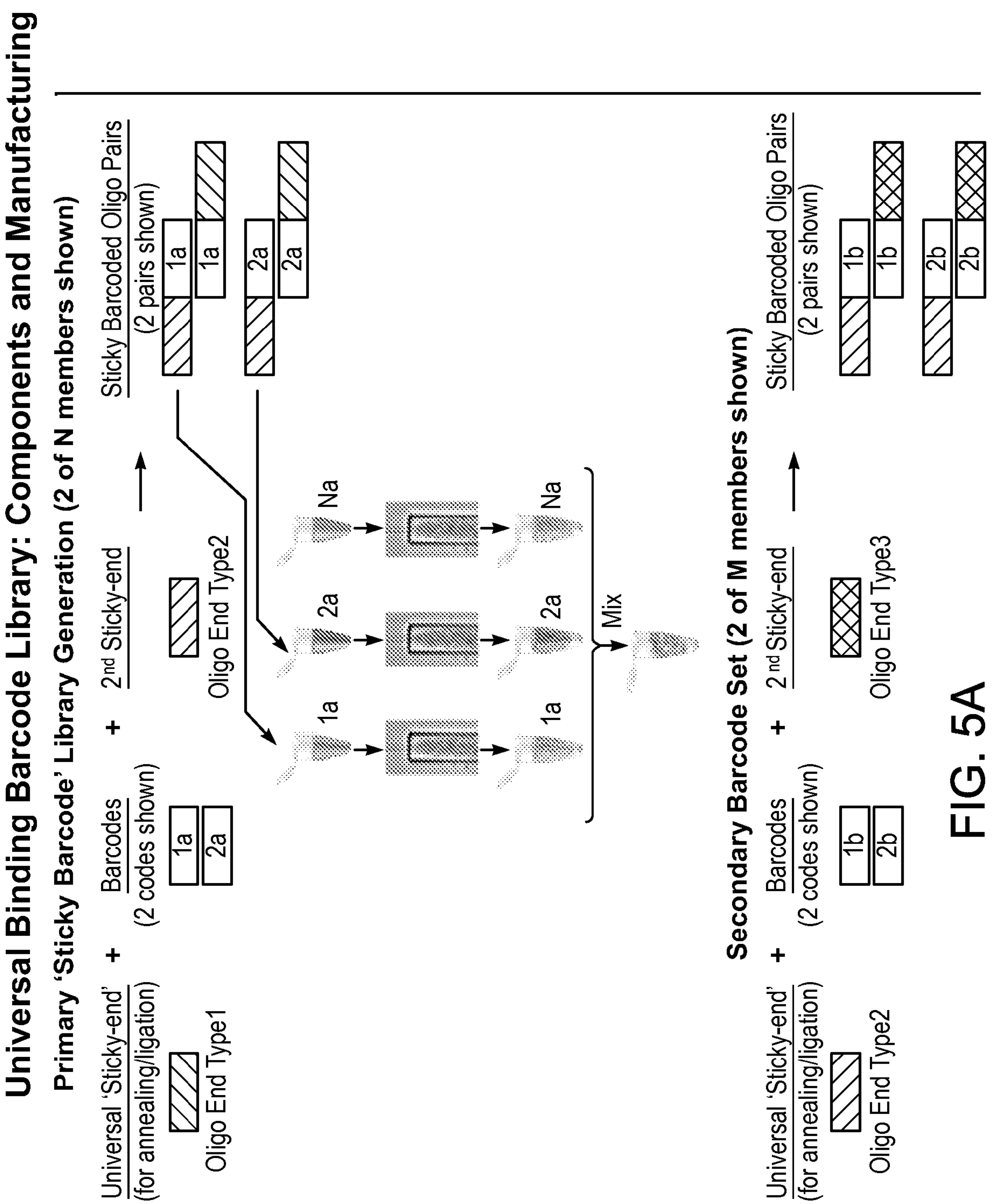
FIGS. 5A-B show a method of making a universal barcode library.
Figure 5B:
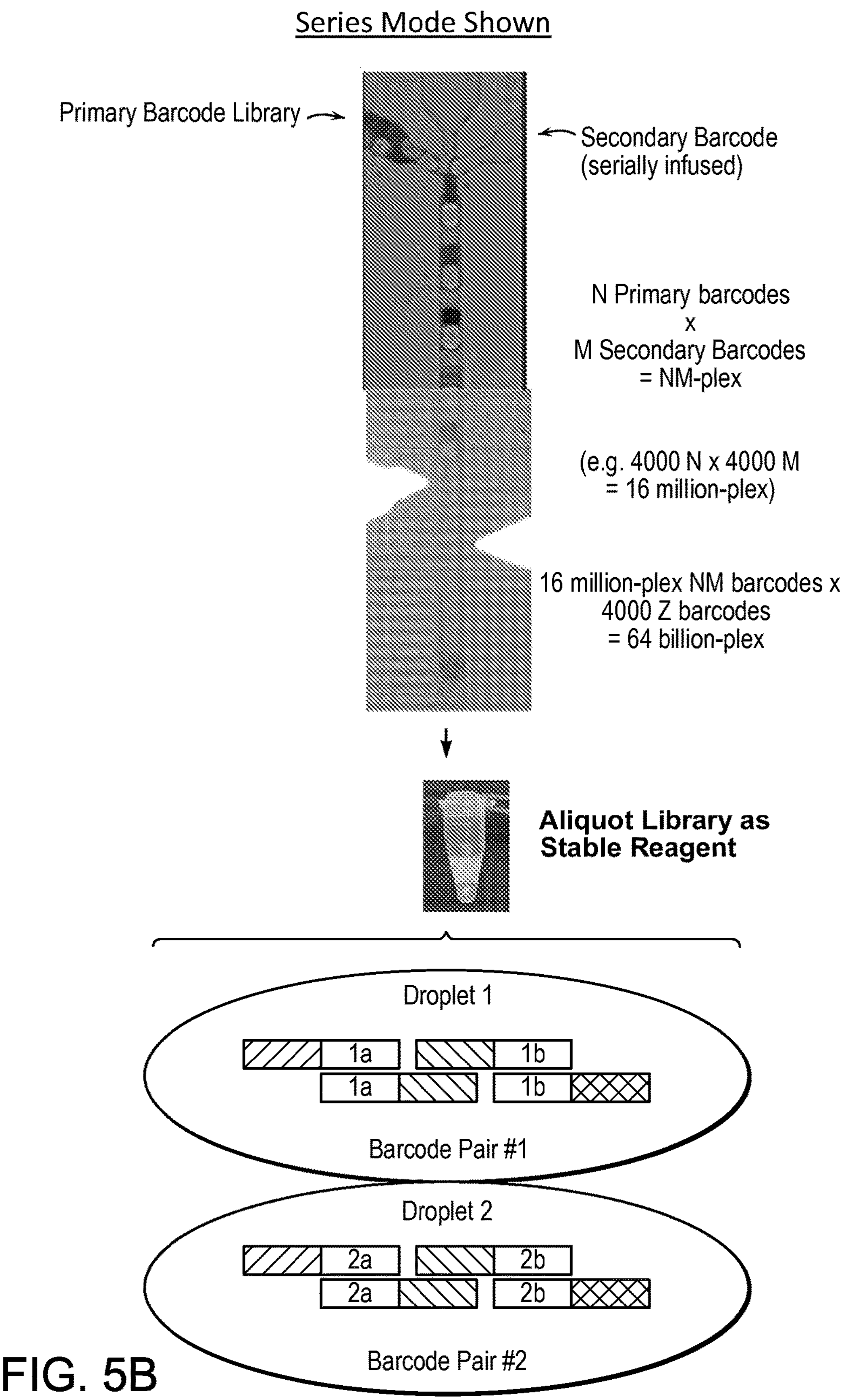

FIGS. 5A-B show the overall scheme for construction of a universal binding barcode droplet library. Pairs of overhanging complimentary oligonucleotide barcodes are chemically synthesized (using standard commercial manufacturing methods) such that the complementary barcoding sequences are flanked by ‘sticky-ends’ for subsequent annealing and ligation to the target species or other barcodes, or for polymerase or other enzymatic priming. The oligonucleotides may include 5-prime or 3-prime phosphorylation, or combinations of these or other modifications. Methods to make oligonucleotides resistant to nuclease activity may be used, including the use of 2'O-Methyl RNA bases and/or phosphorothioated bonds to form the entire backbone of the oligo or to cap the ends of the sequence. PNA, LNA, or other modified nucleotide structures can also be used. A sticky-end may be any length and sequence, with preferred embodiments containing base pairs including restriction endonuclease cleavage sites, or priming sites for sequencing or digital PCR, or array hybridization, and any number of sticky-ends with different sequences can be utilized. Sticky-end sequences may be used as barcode identifiers as part of composite barcodes.

Two example barcoded oligonucleotide pairs are shown in FIGS. 5A-B (1*a* and 2*a*, flanked by sticky-end Type1 and sticky-end Type2). To construct a droplet library each discrete complementary oligonucleotide pair can be placed together into a standard microtiter-plate well and formed into droplets, which can be subsequently mixed with other oligonucleotide pair-containing droplets to make a ‘primary barcode droplet library’. Forming droplets for a library is discussed in U.S. Pub. 2010/0022414. The number of pair types (N members) is not limited.

These storable stable droplets can either be used directly as an N-member barcoding library, or combined with another barcoding oligonucleotide set (M-members) to form a ‘tandem’ barcoded library with N×M=NM-plex. A 4000 N-member library combined with a 4000 M-member library will generate a 16 million-plex barcode library.

Combination of the N-member primary barcode library with the M secondary barcodes can be done in series (with each member of the M-barcode combined as an aqueous liquid one at a time with the N-member primary barcode library, using various methods including lambda or pico-injection modes and co-flow) or by combining the N-member and M-member library droplets in parallel (primary library combined with secondary library).

Heterogeneous mixtures of barcodes (e.g. barcodes synthesized using degenerate bases) can be converted into a unique set of droplet barcodes by addition of a unique sticky-end. Manipulation of droplets is described in U.S. Pat. No. 7,718,578 and U.S. Pub. 2011/0000560.

Figure 6A:
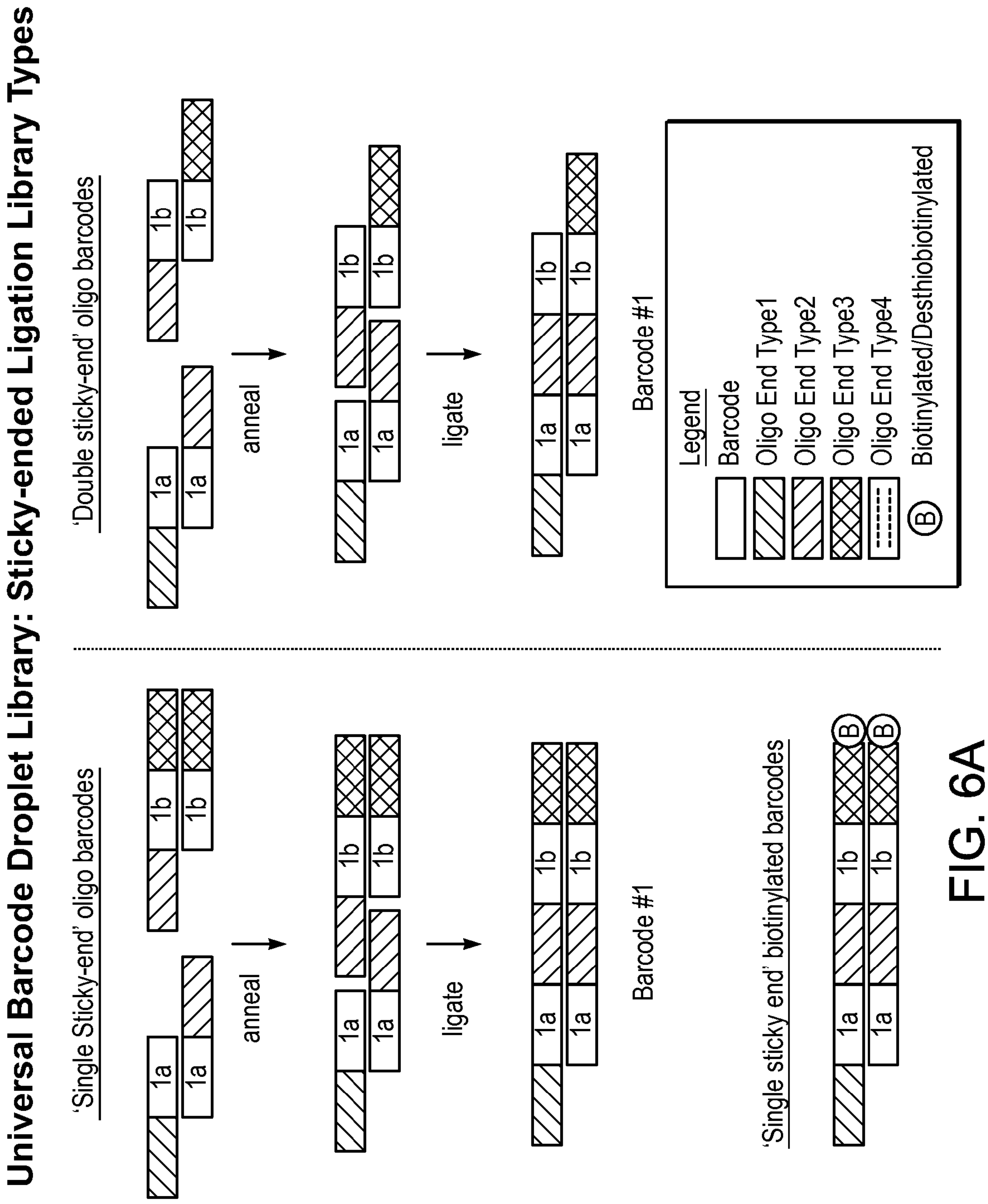
FIGS. 6A-B show six types of barcodes with sticky end components.
Figure 6B:
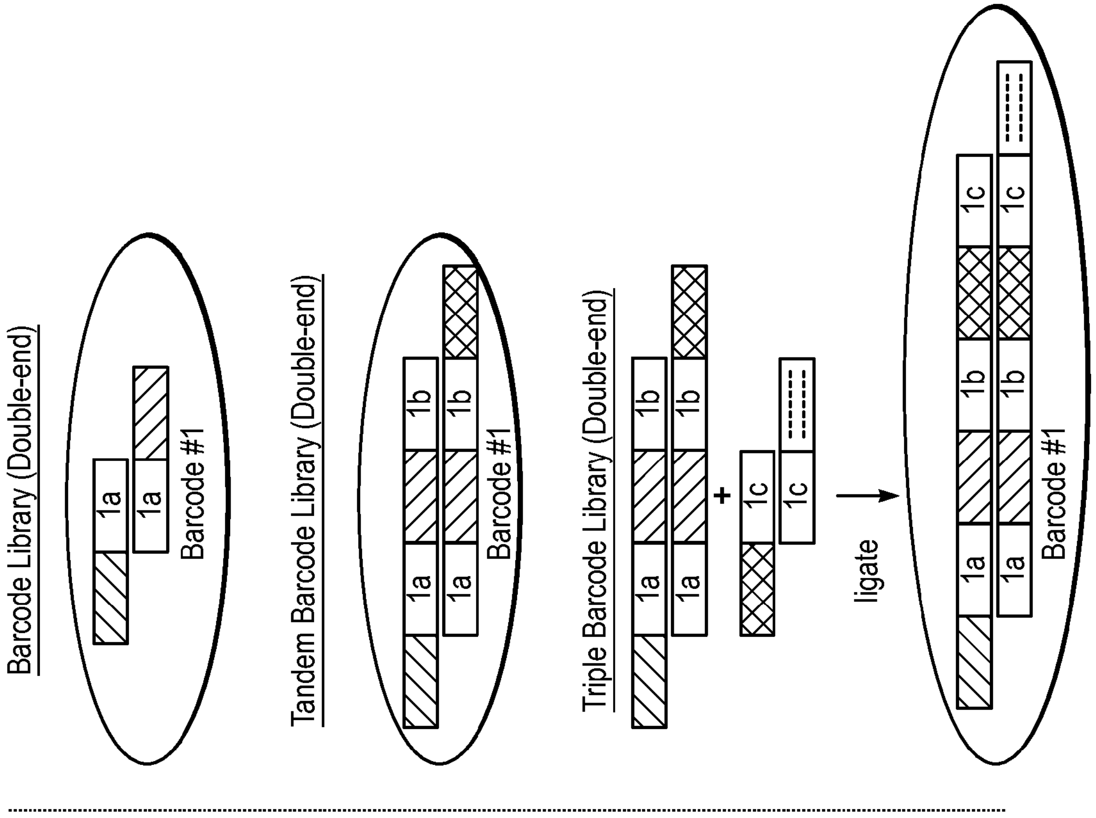

By combining complimentary sticky-ends from two barcode sets, the four oligonucleotide types present in the final combined droplet will specifically hybridize to create a sticky-ended tandem barcode (e.g., droplet 1 or 2 in FIG. 5A-B). This can then be ligated together. A similar specific hybridization will occur for additional numbers of barcodes containing complimentary sticky-ends. This is illustrated in FIG. 6A-B, with 'single sticky-ended' barcoded oligonucleotide pairs shown on the left, where one end is capped such that there is no overhang, and 'double sticky-ended' barcode oligonucleotides shown in the middle panel (either different or similar sticky-ends can be used, with different ends precluding promiscuous concatamer formation). Additional modifications of the sticky-ends can also be included (e.g. biotin or desthiobiotin, shown on the bottom left of the figure).

After annealing the sticky ends together, adjacent strands can be ligated together.

The panel on the right of FIGS. 6A-B shows the initial binding barcode droplet library (only one droplet and one molecule of each type shown, with a barcode identifier 1a) on the top, a tandem barcoded droplet library formed by combination of a primary barcode and a secondary barcode in the middle (e.g. barcode identifier 1a:1b), and a triple barcoded library at the bottom (formed by combining a secondary barcoded library with a third barcode, resulting in barcode identifier 1a:1b:1c).

This modular construction is not limited to the combinations shown, with any composite sticky-ended barcode library able to be combined with additional barcodes in subsequent rounds of droplet combination. Even a low number of combinations can result in a very high level of barcode-plex.

For example, a 16 million-plex tandem barcode library (made from 4000 N×4000 M barcoded oligos) can be combined with another sticky-ended set of 4000 Z barcoded oligos to form a 64 billion-plex barcode library (16 million NM members×4000 Z-members=64 billion). As shown in FIGS. 6A-B, the oligonucleotides can be designed such that the resulting annealed oligo set can have a single or double sticky-ends (with different or similar ends).

A barcode library can also be made to include a sticky-end adapter specific for a sequencing platform. In certain embodiments, a construct is made that includes a sequencing platform N-mer and a sticky-end N-mer. A library of these constructs can be made. Separately, a universal barcode library as discussed above can be made. The, the universal barcode library can be combined with the sequencing platform adapter library by means of the sticky ends in view of a particular application. Thus products of any analysis discussed herein can be adapted to go directly into the workflow of any given sequencing platform (e.g. sticky-ended Illumina adaptors to anneal/ligate onto either the primer library or the output from a targeted sequencing run, so that it could be hybridized directly onto their flow cell. A different sticky-end adaptor set could be used for 454, etc.). This approach can minimize PCR bias.

A universal PCR primer barcode library can also be prepared with an unlimited amount of plex by creating sticky-ended forward and reverse primers that can be further combined with additional numbers of sticky-ended barcodes to generate combinatorial barcodes, as shown at the top of FIGS. 9A-B. The forward and reverse universal primers are constructed in an identical fashion as described above and in FIGS. 7A-B (primary barcoded primers) and then annealed to a sticky-ended barcode oligonucleotide pair (either single or double sticky-ended as shown in FIGS. 5A-B) and subsequently ligated, to make a contiguous forward (and/or reverse) primer annealed to the complimentary oligo that was used to anneal to the primary barcoded primer. The top right side of FIGS. 9A-B shows the ligated product after addition of both forward and reverse single sticky-ends to create a 'secondary' barcoded priming set. The bottom of FIGS. 9A-B shows a single droplet after combination of one prepared template-containing sample droplet with one universal PCR primer barcode library droplet. The annealed PCR primers can be amplified by using polymerase and dNTPs, and all of the amplicons from this droplet will be barcoded 1b:1a:1a:1b (with 1b:1a 5-prime to the target loci sequence, followed by 1a:1b, as read 5-prime to 3-prime).

Haplotype Phasing

The invention provides systems and methods for haplotype phasing and genotyping. A nucleic acid can be isolated from a sample and haplotyped through the examination of a number of loci. For example, the allelic form present for a number of suspect SNPs of interest can be determined along a single chromosome. By including barcodes in multiplexed tiled PCR reactions within droplets, this aspect of the invention enables 'haplotype phase' assignments to be made using existing sequencing platforms.

Several aspects of the invention are combined to enable assignment of sequencing information (e.g., a series of SNPs) to target DNA stretches. In certain embodiments, haplotype phasing involves preparing a barcode droplet library in which each droplet contains the set of primers to amplify the loci of interest. Preferably, each primer is part of a tripartite construct that also includes a universal priming site (for subsequent amplification, capture, or sequencing) and a barcode. In each droplet, every tripartite construct will preferably contain the same barcode. Multiplexed PCR primers that will not cross-hybridize with each other and which will uniquely amplify the target DNA locus can be used.

Figure 10A:
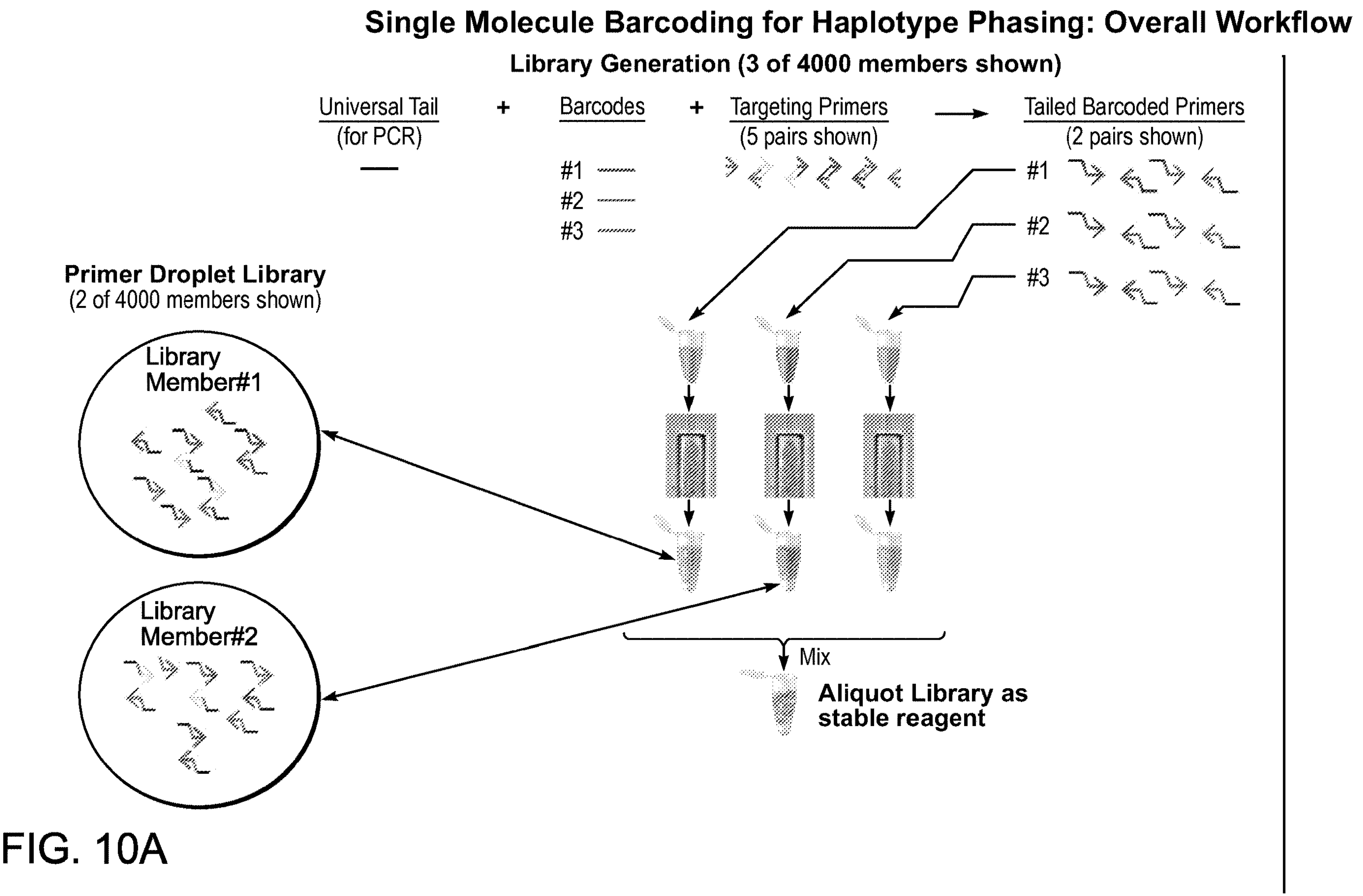
FIGS. 10A-B show an overall workflow for single molecule barcoded haplotype phasing.
Figure 10B:
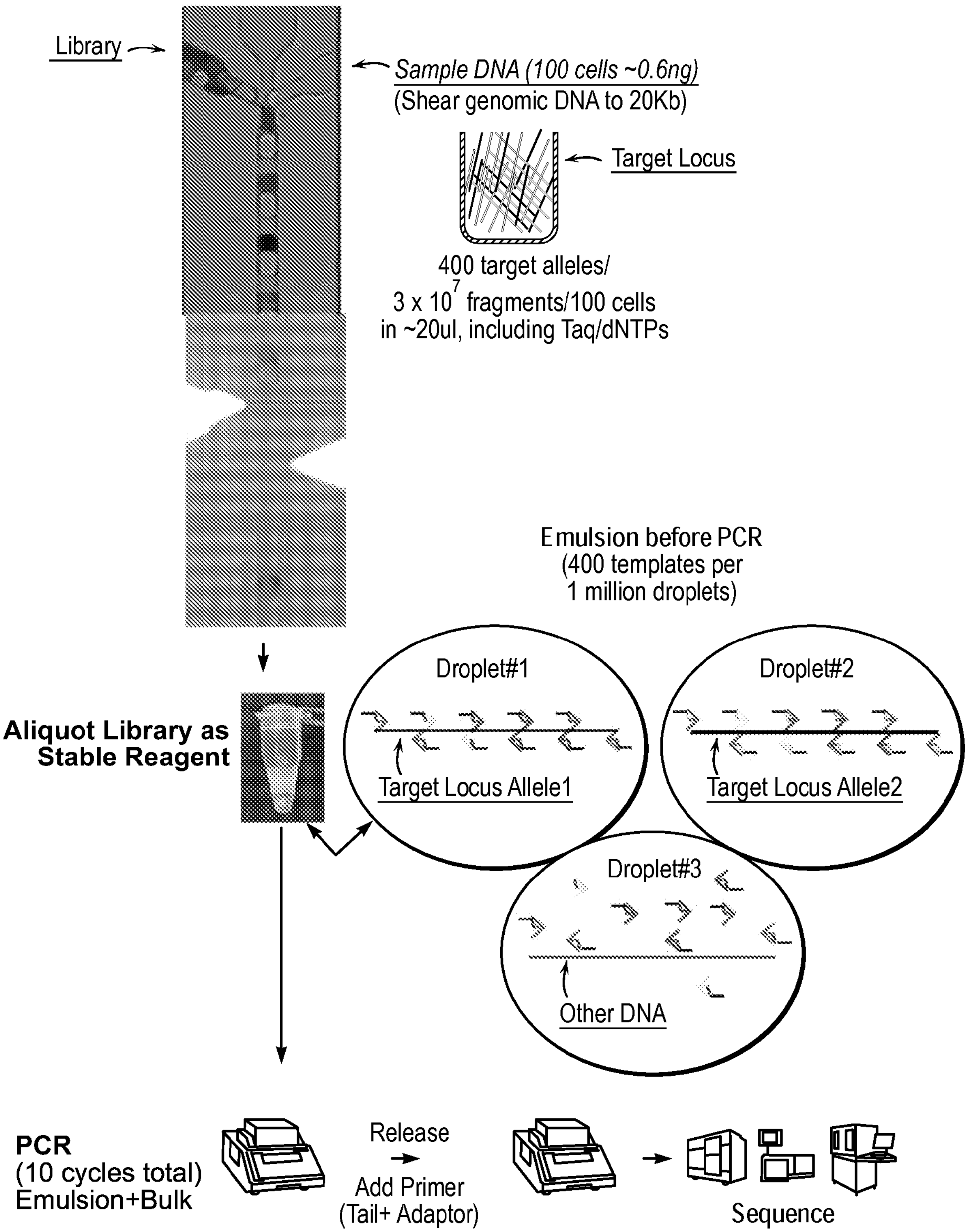

The overall workflow example is shown in FIG. 10A-B. Optionally, the target locus can be pre-amplified using a single pair of PCR primers that flanks the entire locus, before appropriate loading of the sample into droplets for amplification and barcoding (not depicted in the workflow in FIG. 10A-B).

Preferably, each tripartite construct includes a universal tail portion immediately 5' to a barcode sequence followed by the sequence-specific targeting primer bases. A primer droplet library 'member' includes a droplet that contains all of the targeted primers sufficient for covering the target bases, each with the same barcode that will enable post-sequencing correlation to the target strand. The number of library members is determined by the ratio of barcode number to the number of target alleles to be analyzed. By way of example, without limitation, FIG. 10A-B shows 100 cells as input, with 4000 barcodes giving a 1/10 chance of duplicate barcodes for any allele. In this example, the DNA from 100 cells provides 400 target alleles, which are loaded (together with polymerase, buffer, and nucleotides) into one million droplets and combined with the barcoding primer library to generate a PCR-competent droplet emulsion. As an example for a 3 kb target region, 13 tiled primer pairs can be used to cover the target bases. Fewer primer pairs can be used if only subsets of the target bases are to be phased.

Droplets from the droplet library are merged with target nucleic acid. In the example pictured in FIG. 10A-B, genomic DNA has been sheared to a length of about 20 kilobases. Fragments of the target are introduced into droplets such that on average each droplet will generally contain no more than one molecule of target nucleic acid.

After this merging step, each droplet contains at least: a pair of tripartite constructs for each locus of interest; a single nucleic acid molecule; and PCR reagents (e.g., Taq, dNTPs). Each droplet is then thermocycled, producing numerous copies of each locus of interest in which each of those copies has a unique pair of barcodes at each end.

Droplet libraries are generally discussed herein as having pairs of barcodes and in some embodiments those barcodes may be necessarily the same or different, while in other embodiments, it may not matter whether the forward and reverse barcodes are the same or different. For example, if barcodes have six nucleotides, and millions of targets are to be analyzed, then using different forward and reverse barcodes will create ample unique barcode pairs. Here, an embodiment of haplotype phasing is presented in which the forward and reverse barcodes need not be the same. In some embodiments, those bar codes may be the same.

Figure 11A:
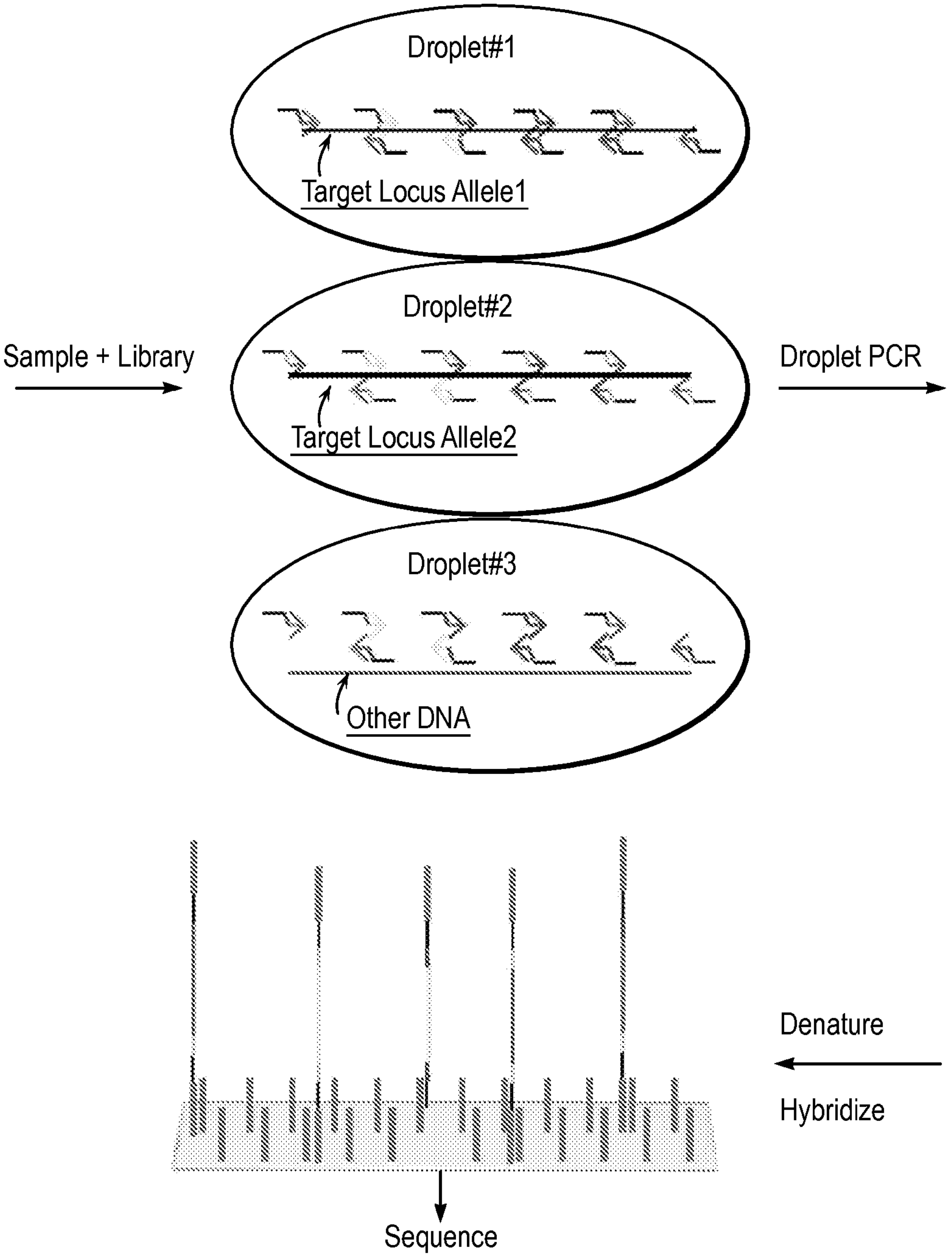
FIGS. 11A-C show is a schematic depicting the PCR details of the schematic depicted in FIG. 35A-B.
Figure 11B:
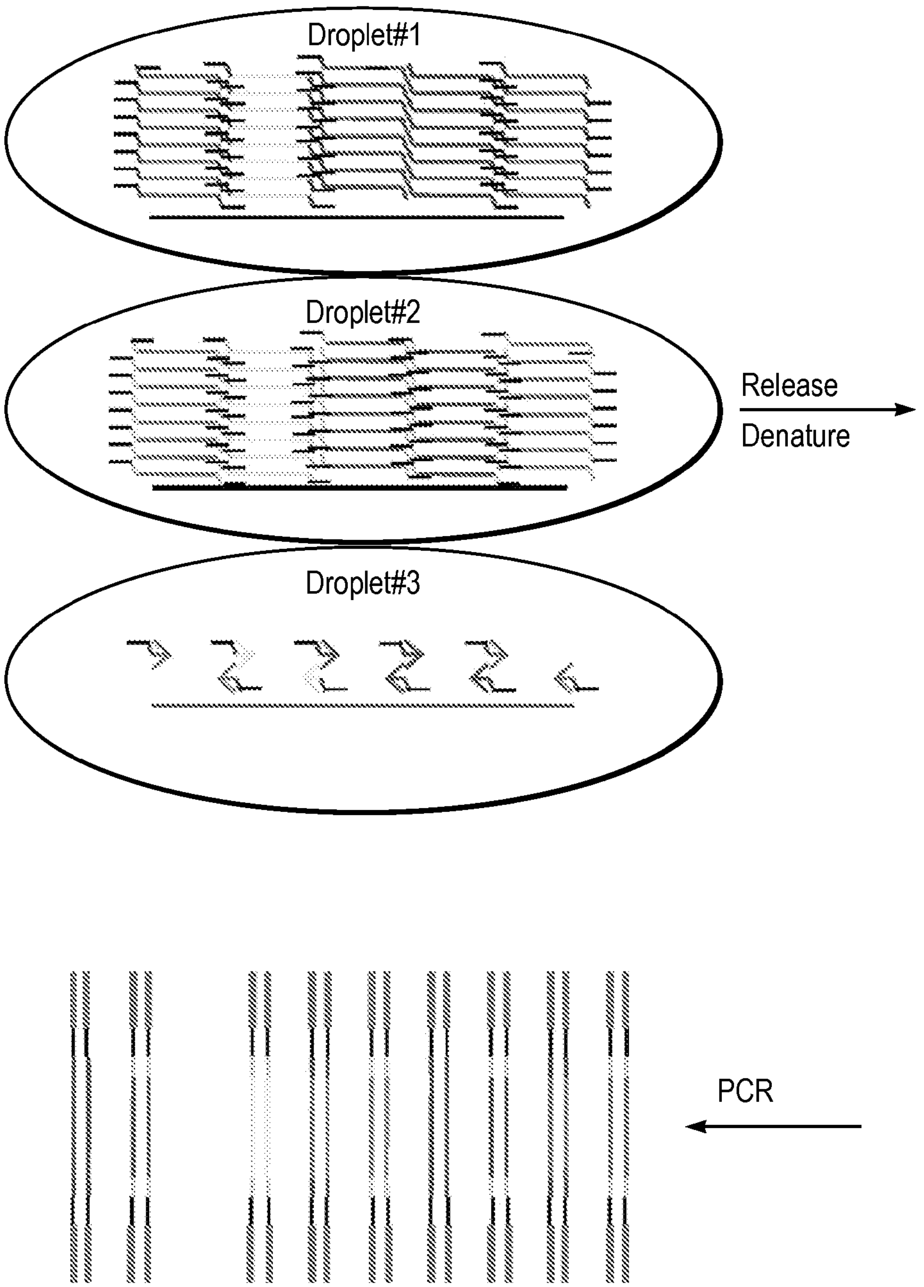
Figure 11C:
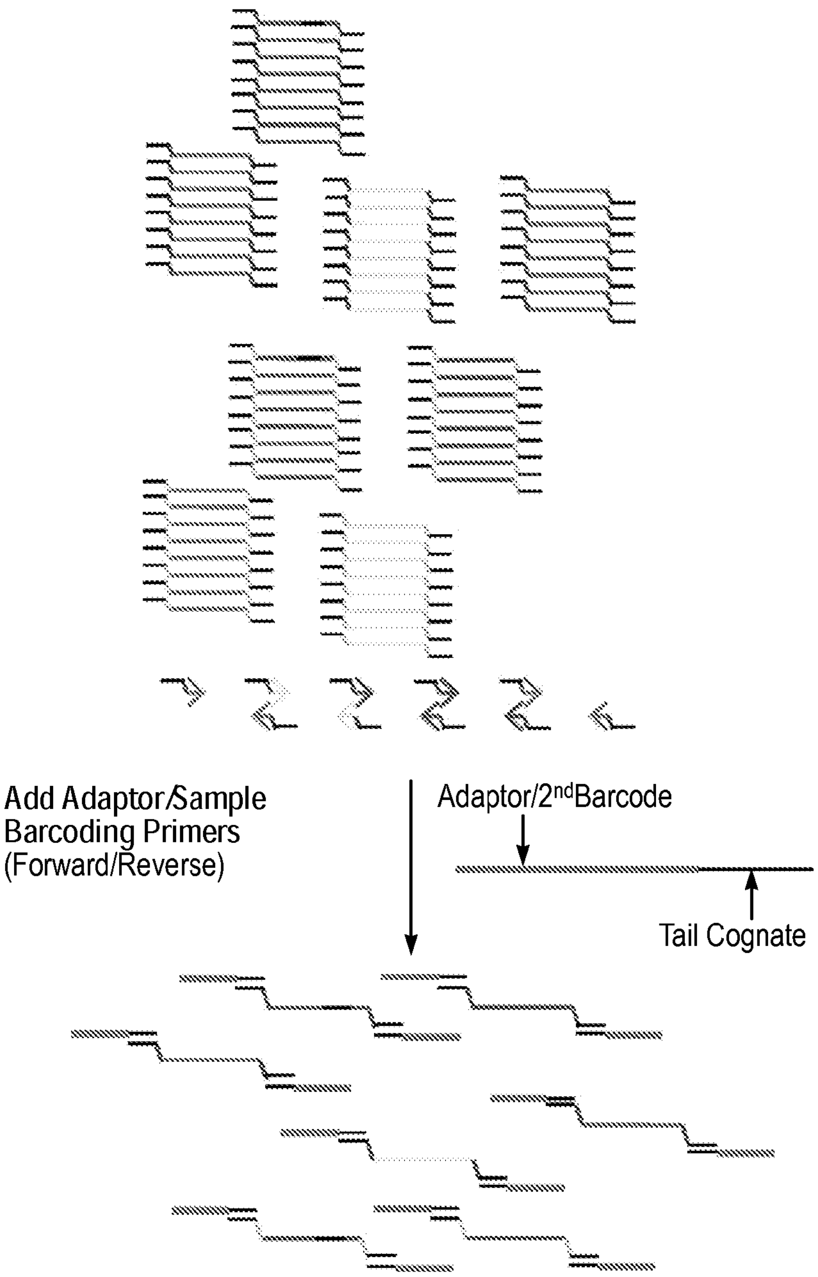

After thermocycling, the amplified products are released into a single bulk aqueous phase (e.g., using a droplet de-stabilizing reagent), and a subsequent amplification, sequencing, or capture is performed using the universal primer tail as well as any sequencing platform-specific adaptor (and additional barcodes) needed before sequencing. Examples of the PCR inputs and outputs are shown in FIG. 11A-C. Using a yield threshold of ~150 sequencing reads as being more than sufficient for high confidence SNP calling, the total number of PCR cycles (droplet PCR plus bulk PCR) can be limited to 10 cycles (sufficient to generate 150 copies).

The amplified products are then sequenced according to any method known in the art including those discussed herein. Even though, in certain embodiments, the amplified products are provided for sequencing in a bulk aqueous phase, sequencing results can be haplotyped based on the presence of the barcode in the sequence reads. Particularly in embodiments in which the barcode is immediately 3' to a sequencing primer binding site, every sequence read will have barcode information.

Figure 8A:
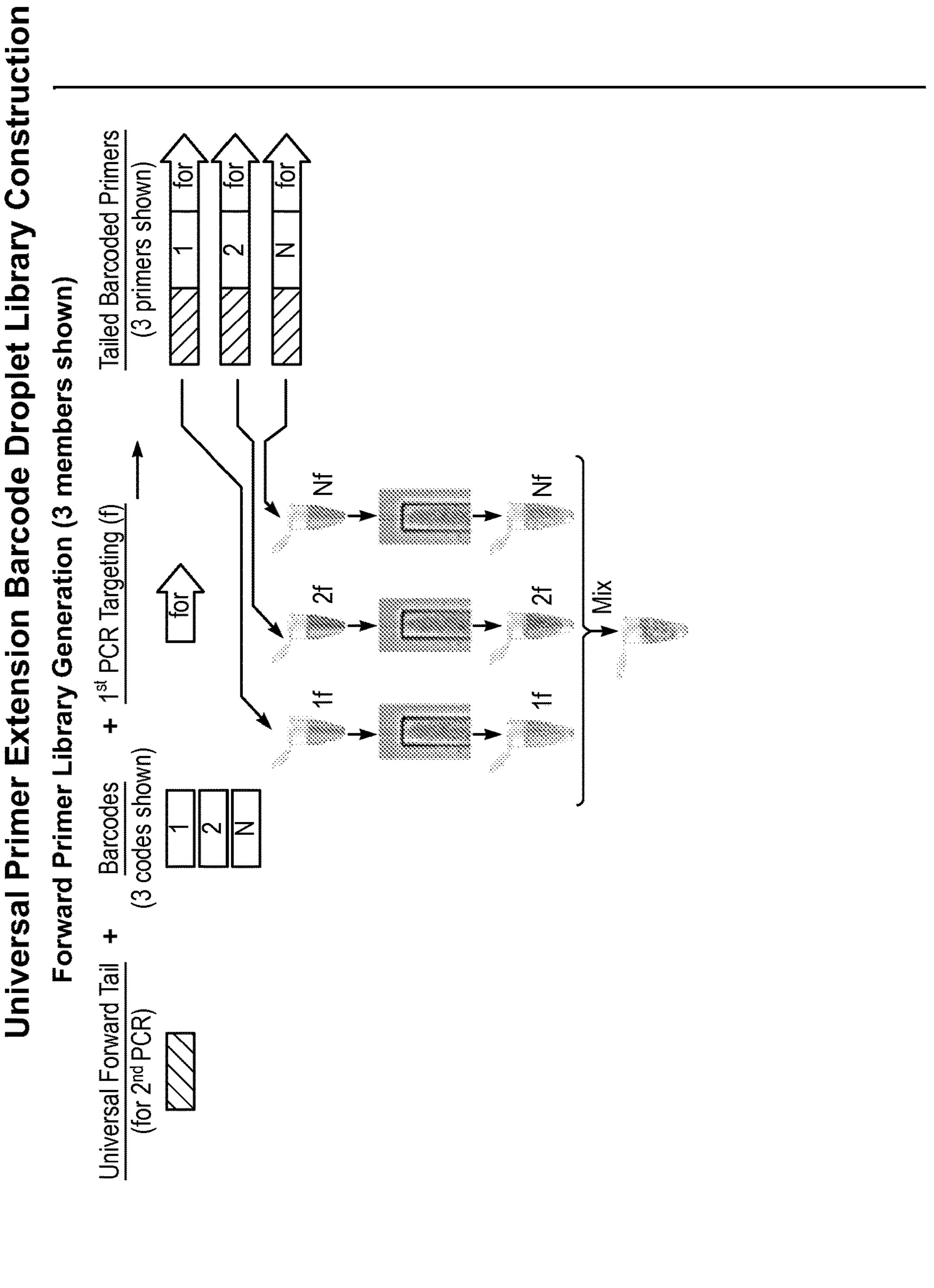
FIGS. 8A-B show a universal barcode droplet library.
Figure 8B:
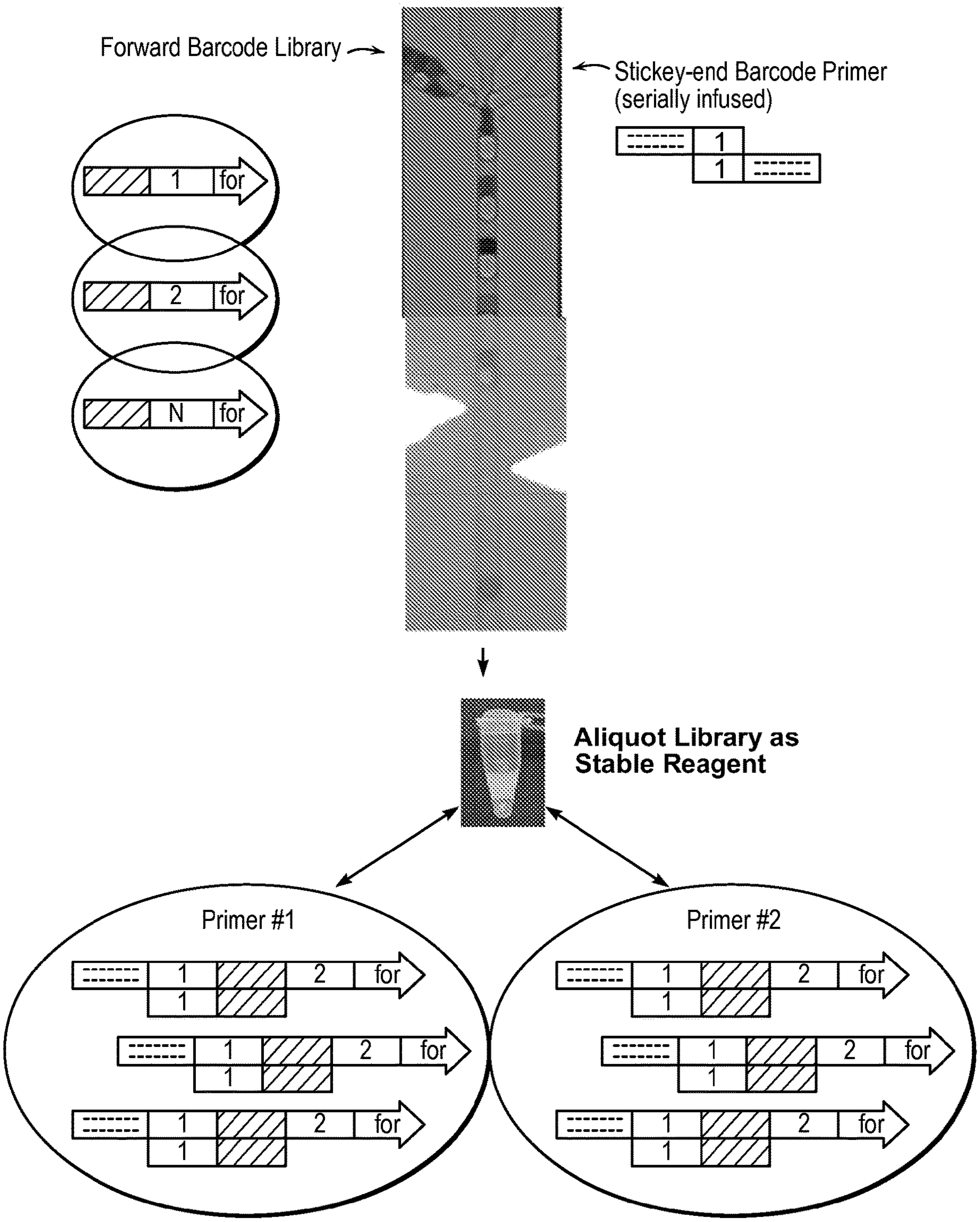

In certain embodiments, genetic material is haplotyped without amplification as shown in FIG. 15A-FIG. 17B. FIG. 8A-B shows the overall scheme for construction of a universal priming barcode droplet library for use in a 'Bind and Primer Extend' application (addition of sticky end component on right of FIG. 8A-B is optional). Primers as shown in FIG. 8A-B can be used as shown in FIGS. 15A-1B to provide haplotype information without amplification. In this example, a the initial 'primary' droplet library contains single universal priming barcodes for primer extension, constructed using similar methods as that described for construction of a universal binding barcode droplet library. Contiguous oligonucleotides are chemically synthesized with each of the sequence components including a universal forward tail (consisting of bases to be annealed to an analogous sticky-end), a sequence of bases used as a barcoding component, and a priming sequence that will anneal to the universal 5-prime end of the target sequence to be counted (the complimentary target is designated as 'for' in, for example, FIG. 15A-FIG. 17B).

Figure 15B:
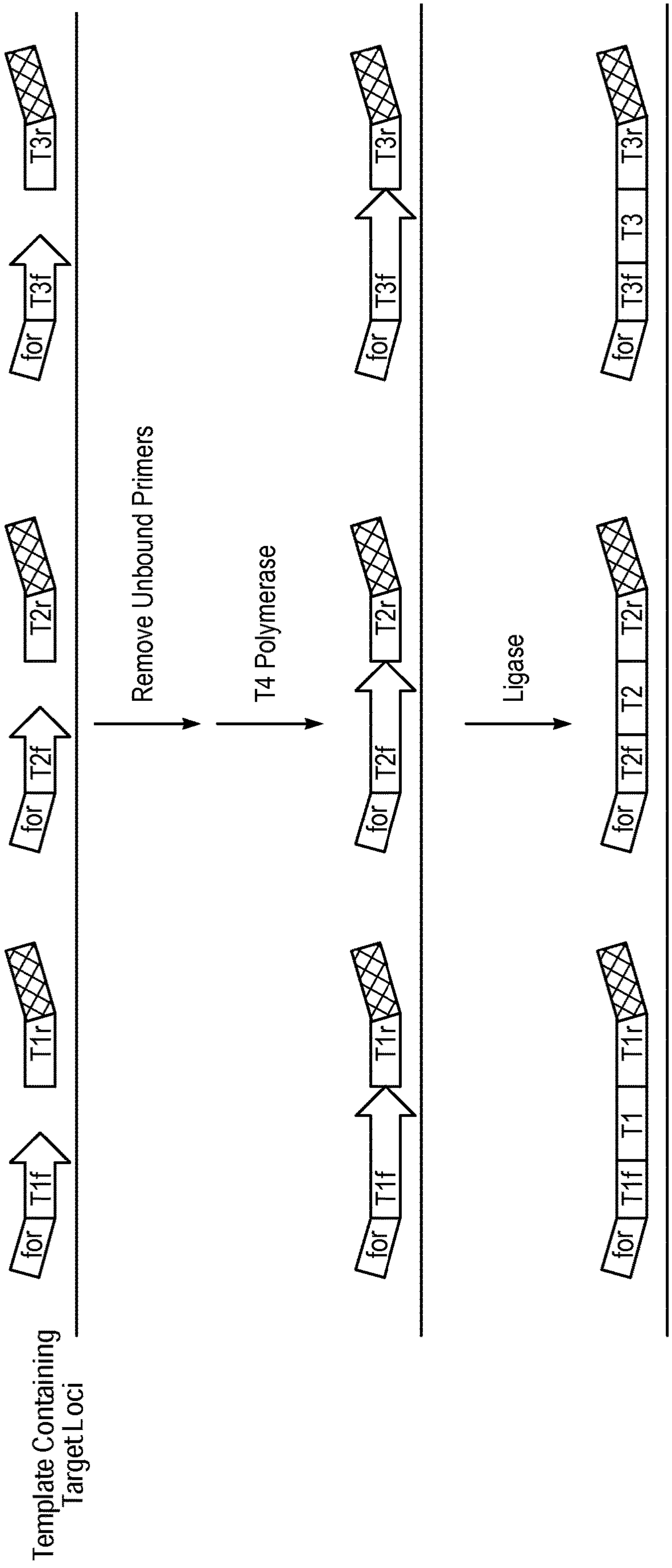

FIG. 15A-B shows up-front processing for haplotyping a single molecule of DNA using a universal priming barcode library. A forward primer is used with a corresponding oligonucleotide (here labeled 3' Tailed primer). Note that the corresponding 3' oligonucleotide need not function as a primer. For convenience, they will be referred to as primers. To prepare for target molecule haplotyping, a set of specific targeting primers are prepared and annealed to the target DNA, with a 5' oligonucleotide comprising oligonucleotides complimentary to 5' end of the target locus (3 loci are shown in FIG. 15A-B) and a universal 'for' sequence that will be used to anneal to the barcode library, and a 3-prime oligo comprising oligos complimentary to the 3-prime end of the target locus followed by a universal 3-tailed end. The target molecule to be haplotyped can be targeted by any number of primer pairs and targeted loci can be any distance from other loci (the shear length of the genome will limit the maximum distance that can be haplotyped).

Each of the uniquely barcoded primers can be reformatted from a well plate into a droplet format, either for direct use with samples or to be used in optional subsequent rounds of droplet combination to add complimentary sticky-ended barcoding sequences (right side of FIG. 8A-B, also shown in right side of FIG. 9A-B). Combination of the primary 'forward barcode library' with sticky-ended barcodes (either serial or library combination) provides another barcode encoding level. Alternatively, the primary droplet library can be generated from pairs of primers initially placed together in wells and reformatted into droplets, with a sticky-ended barcode oligo together with various forward barcoded primers. Additional rounds of droplet combination with either single or multiple sets of sticky-ended barcode members can be used to get to any required level of barcode-plex needed for the assay.

A universal priming barcode library having sufficient plex to uniquely barcode the sample targets is used by combination and annealing to target molecules that have been either prepared in bulk or in droplets (bulk prep is shown in FIG. 15A-B).

Hybridization of all of the targeting primer pairs with the target sample is followed by removal of unbound primers (e.g. purification by size or via use of biotinylated primers or targets), elongation of the forward hybridized primer for each locus using a polymerase (e.g. Klenow) that lacks exonuclease activity such that the elongation stops when the polymerase encounters the 3-prime primer, and subsequent ligation using ligase and ATP or photo-ligation or other ligation means. The resulting bulk sample preparation contains the target single stranded molecules with each targeted loci annealed to a contiguous oligonucleotide strand that contains the newly synthesized compliment to the target loci bracketed by the added primer pairs.

Figure 16A:
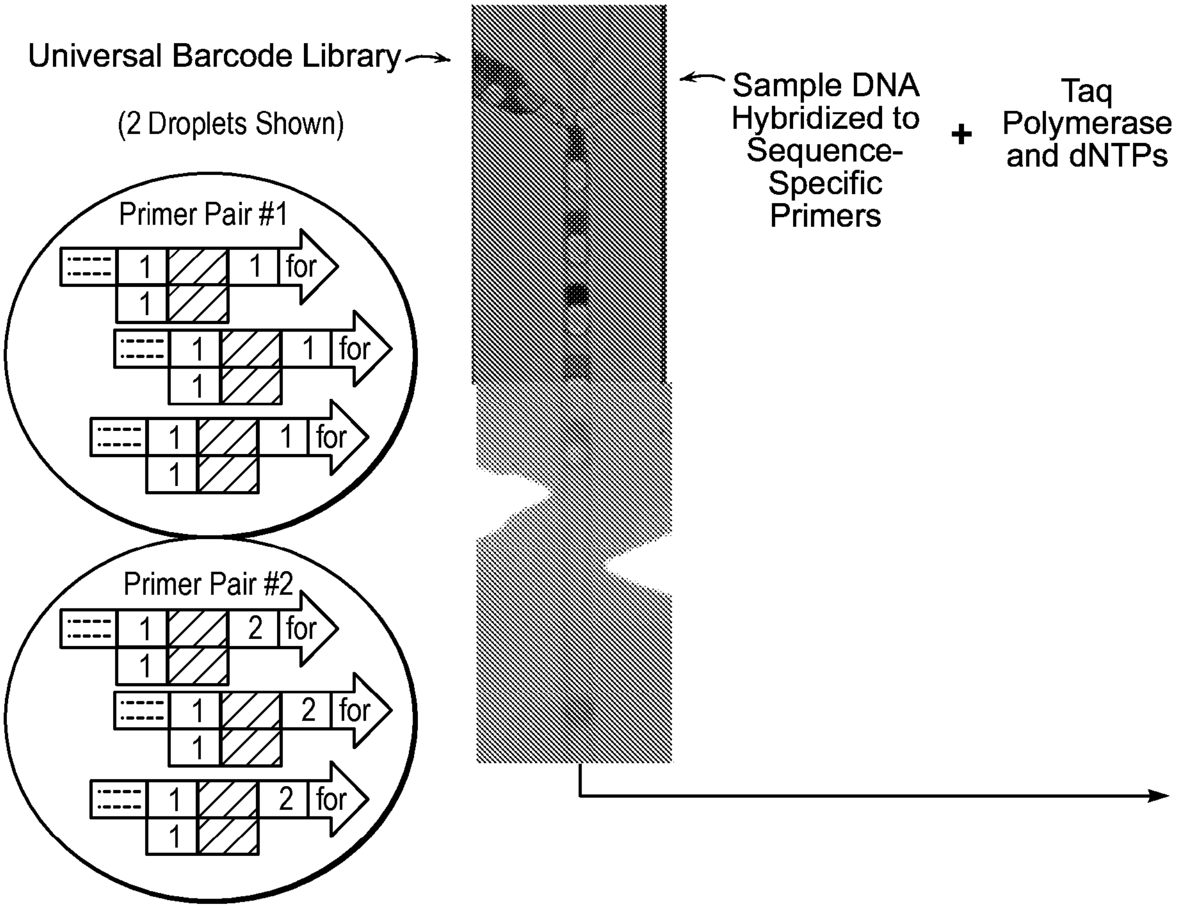
FIGS. 16A-B show barcoding in amplification-free haplotyping.
Figure 16B:
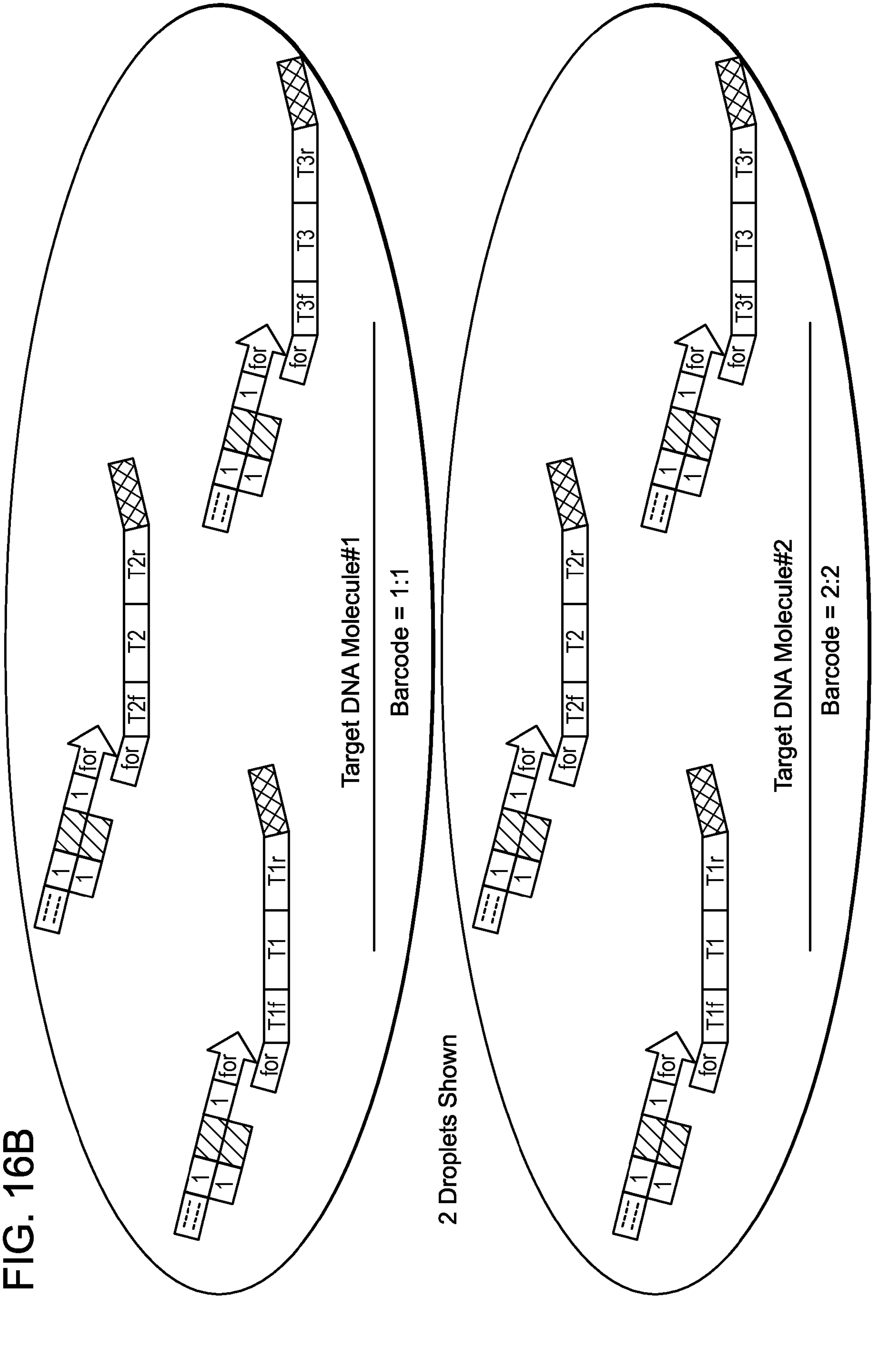

This output of the process shown in FIG. 15A-B is the target which the nucleic acid constructs (primers) shown in FIG. 16A-B bind to.

The bulk annealed sample prep is loaded into droplets, along with polymerase and dNTPs, such that a single contiguous molecule with its set of targets to be haplotyped is contained in a droplet. The Universal Barcode Library is combined with the prepared sample, either in a droplet to droplet combination mode, or in a droplet to aqueous stream combination mode (shown in FIG. 16A-B). FIG. 16A-B shows introducing primer pairs, each bearing a barcode.

Figure 17A:
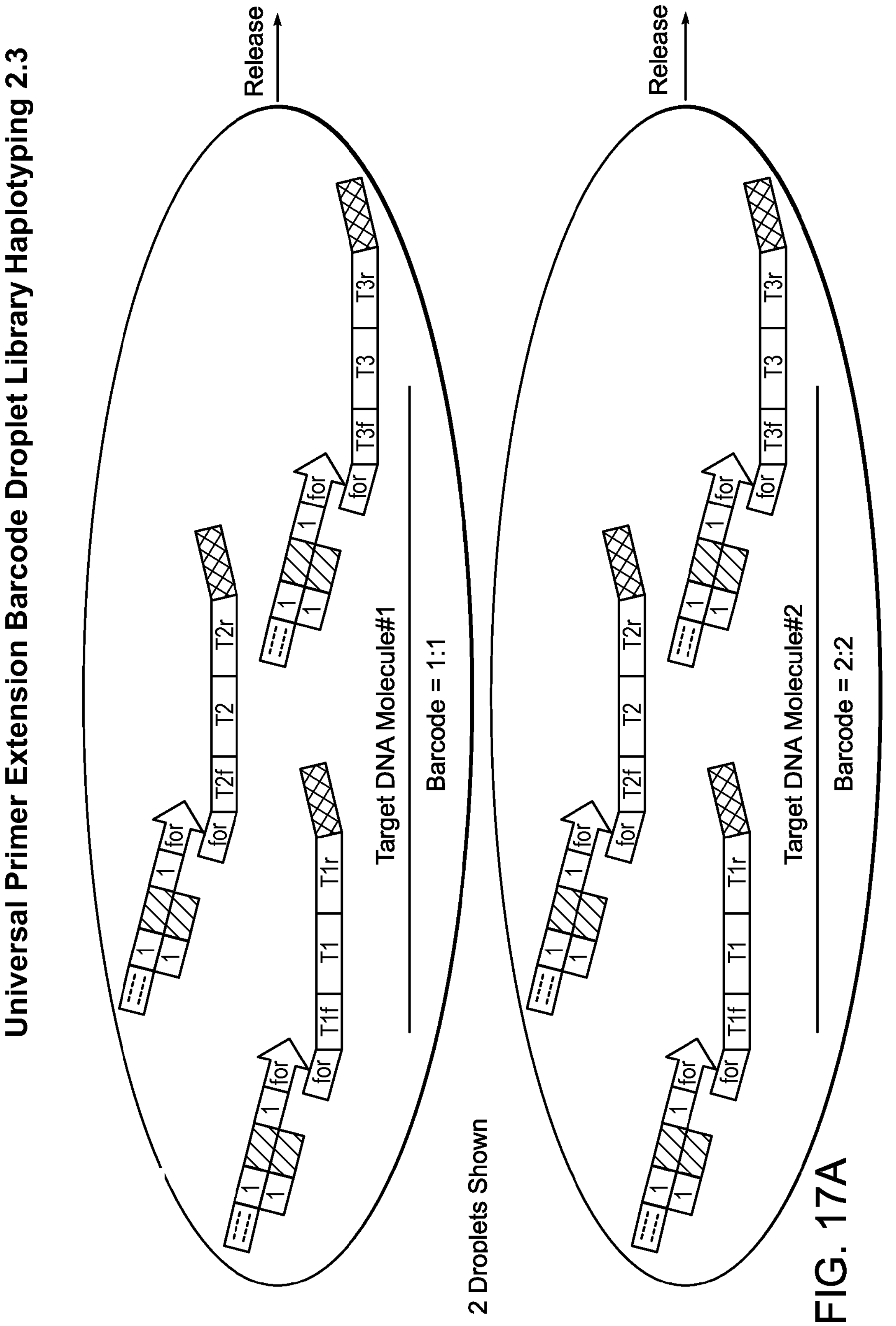
FIGS. 17A-B show amplification free haplotyping.
Figure 17B:
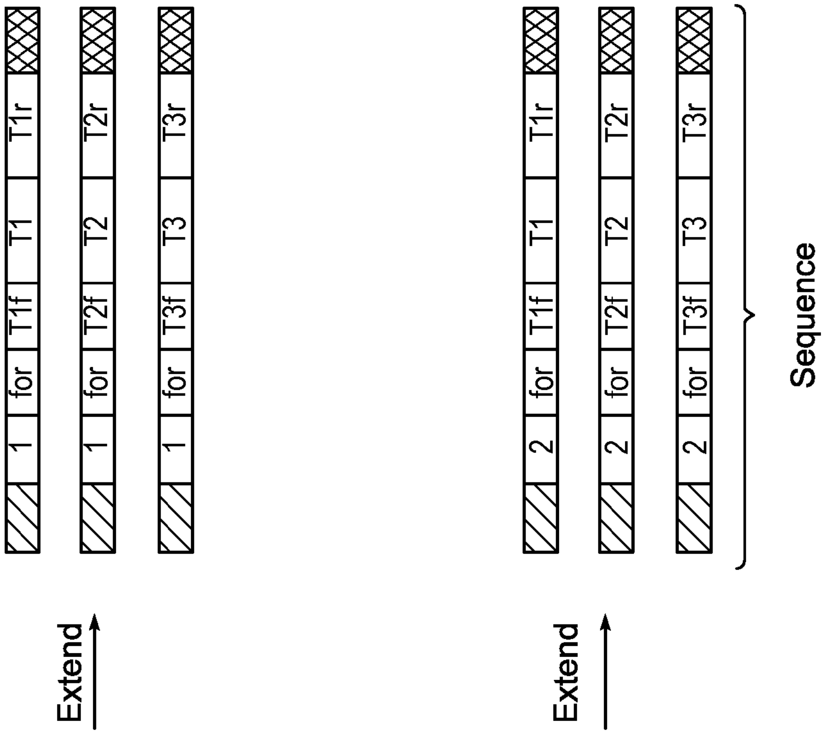

As shown in FIG. 16A-B, a pair of primers for each locus of interest is incubated with a strand of target DNA and allowed to hybridize. Any unbound (un-hybridized) material is removed. The two forward 'for' primers can be elongated either inside droplets that include the polymerase and dNTPs, or following release of the primers annealed to the template (the workflow in FIG. 17A-B shows release before elongation outside of droplets). Polymerase synthesizes a complementary strand from the 5' forward primer to 3' "reverse primer". Ligase then ligates the complementary strand to 3' reverse primer. As a result, a complementary strand has been synthesized representing each locus of interest.

The droplets can be lysed (or "burst", discussed elsewhere herein), and the contiguous strands (e.g., barcoded amplicons) released into bulk phase as shown in FIG. 17A-B.

The resulting contiguous strands containing barcodes are used for sequencing (or sequence determination using microarrays), and the sequences that contain identical barcodes have sequences that derive from the same sample strand (i.e. the same haplotype). This example shows a method for haplotype determination without any amplification (i.e. only elongation and ligation), and has the advantage of elimination of potential amplification bias. In addition, if a locus has copy number variation within the same sample target molecule, this can be seen as variation in the number of sequenced reads that have the same barcode and sequence.

In contrast to the "no-amplification" haplotype methods, the invention also provides methods for single-molecule haplotyping that include amplification. In certain embodiments, amplicons can provide target material according to a "bind and primer PCR" approach.

FIGS. 7A-B show the overall scheme for construction of a Universal Priming Barcode Droplet Library for use in a 'PCR' version of the haplotyping application, which provides haplotype information with amplification. In this example, the initial droplet library contains single 'forward' universal priming barcodes that will be subsequently paired with a 'reverse' barcoded primer to create a Universal PCR Primer Barcoded Droplet Library. Contiguous oligonucleotides are chemically synthesized with each of the sequence components including a universal forward tail (consisting of bases to be used as priming sites or for ligation to adaptors used for sequencing), a sequence of bases used as a barcoding component, and a forward priming sequence that will anneal to the universal 5-prime end of the target sequence to be counted (the complimentary target is designated as 'for' in FIG. 12A-FIG. 14B). Each of the uniquely barcoded primers is reformatted from a well plate into a droplet format. Combination of the forward primer barcoded droplet library with similarly constructed reverse primer barcodes (either serial or library combination, with the serial mode shown in FIG. 7A-B) generates the universal PCR primer barcoded droplet library. Alternatively, the a PCR primer droplet library can be generated from pairs of forward and reverse primers initially placed together in wells and reformatted into droplets, however this type of library will have the same number of unique forward/reverse barcode combinations as the number of paired primers wells.

Figure 12A:
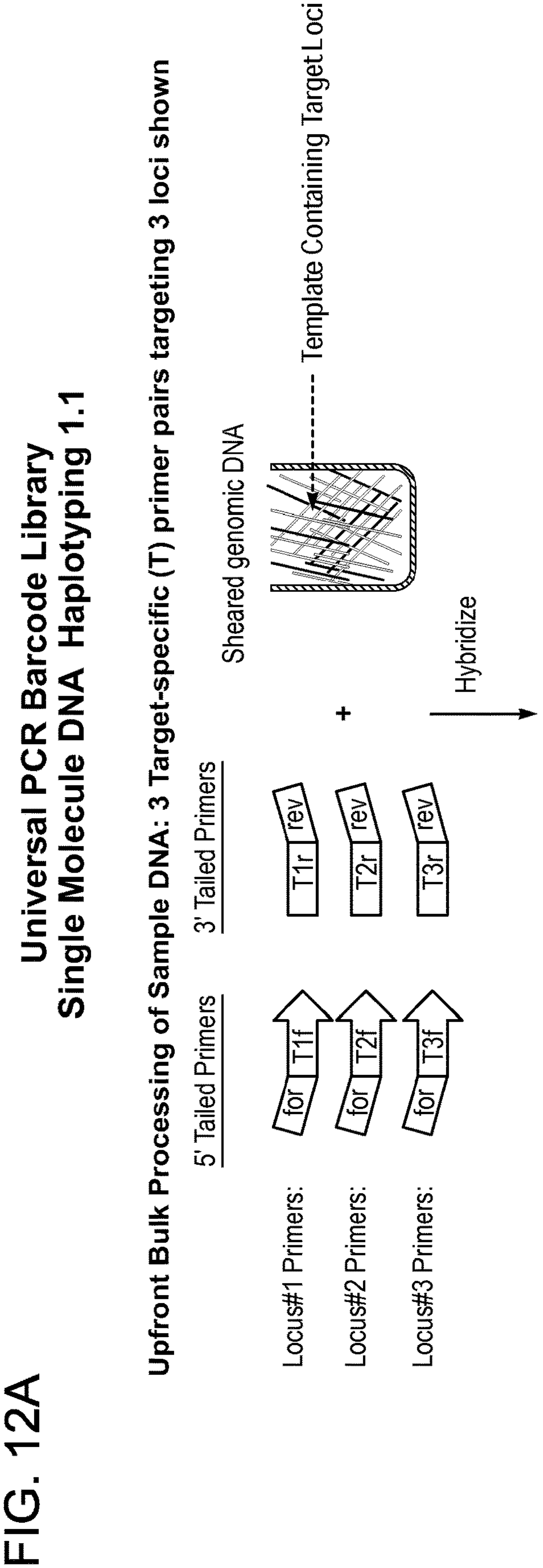
FIGS. 12A-B show up front processing for amplification-based single molecule haplotyping with universal PCR barcodes.
Figure 12B:
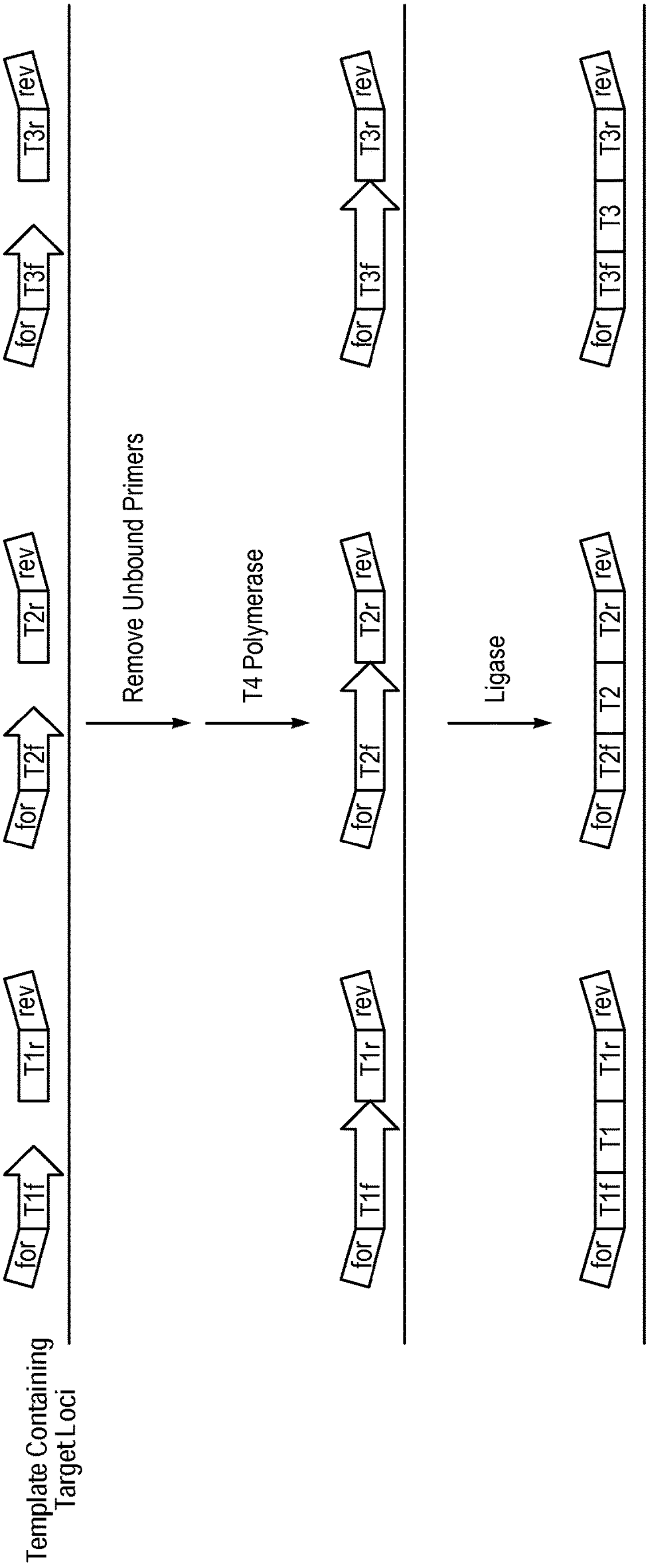

A universal priming barcode library having sufficient plex to uniquely barcode the sample targets is used by combining with samples and annealing to complimentary target molecules present in the sample. An example sample preparation scheme is shown in FIG. 12A-B. To prepare for target molecule haplotyping, a set of specific targeting oligos are prepared and annealed in bulk phase to the target DNA, with a 5-prime oligonucleotide comprising oligonucleotides complimentary to the 5-prime end of the target locus (3 Loci present on the same contiguous target molecule are shown being targeted for haplotyping) and a universal 'for' sequence that will be used to anneal to the Universal Priming Barcode Library, and a 3-prime oligo comprising oligos complimentary to the 3-prime end of the target locus followed by a universal 3-tailed end. The target molecule to be haplotyped can be targeted by any number of primer pairs, and the targeted loci can be any distance from each other (the shear length of the genome will limit the maximum distance that can be haplotyped). Hybridization of all of the targeting primer pairs with the target sample is followed by removal of unbound primers (e.g. purification by size or via use of biotinylated primers or targets), elongation of the forward hybridized primer for each locus using a polymerase (e.g. Klenow) that lacks exonuclease activity such that the elongation stops when the polymerase encounters the 3-prime primer, and subsequent ligation using ligase and ATP or photo-ligation or other ligation means (bottom of FIG. 12A-B). The resulting bulk sample preparation contains the target single stranded molecules with each targeted loci annealed to a contiguous oligonucleotide strand that contains the newly synthesized compliment to the target loci bracketed by the added primer pairs.

Figure 13A:
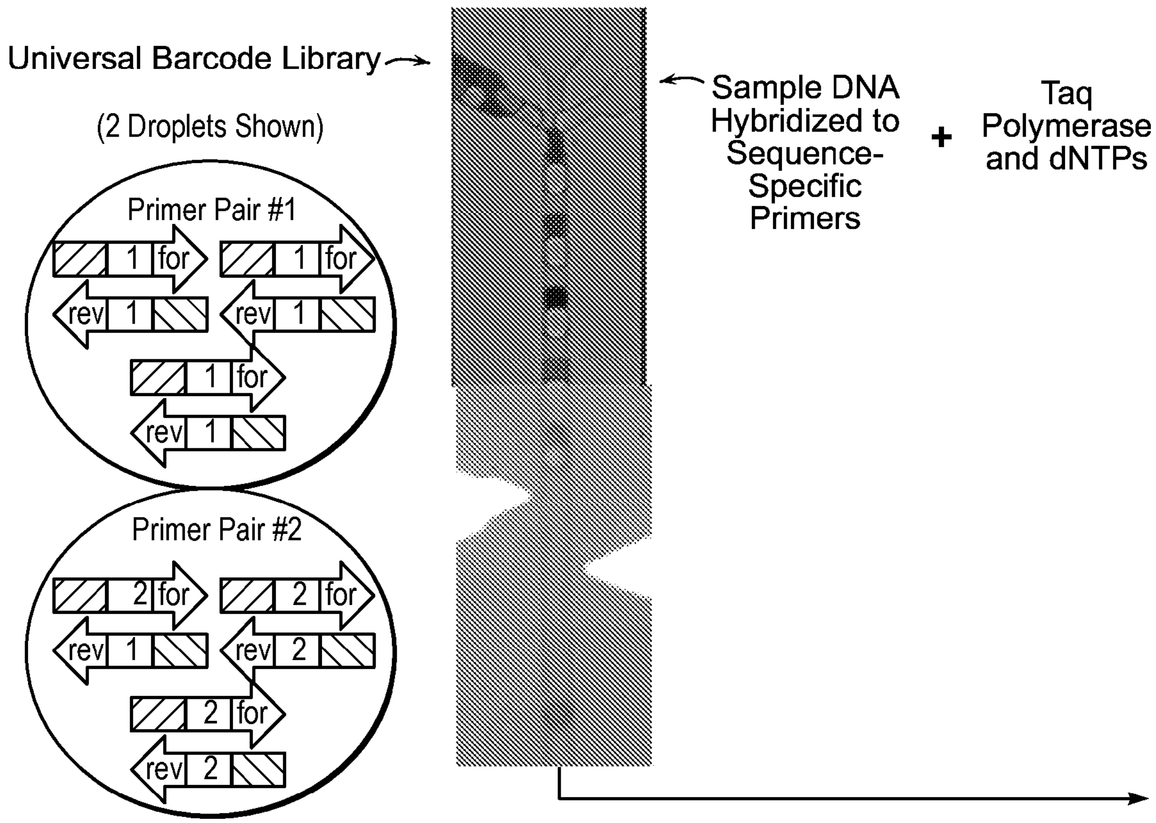
FIGS. 13A-B show barcode addition for amplification-based single molecule haplotyping with universal PCR barcodes.
Figure 13B:
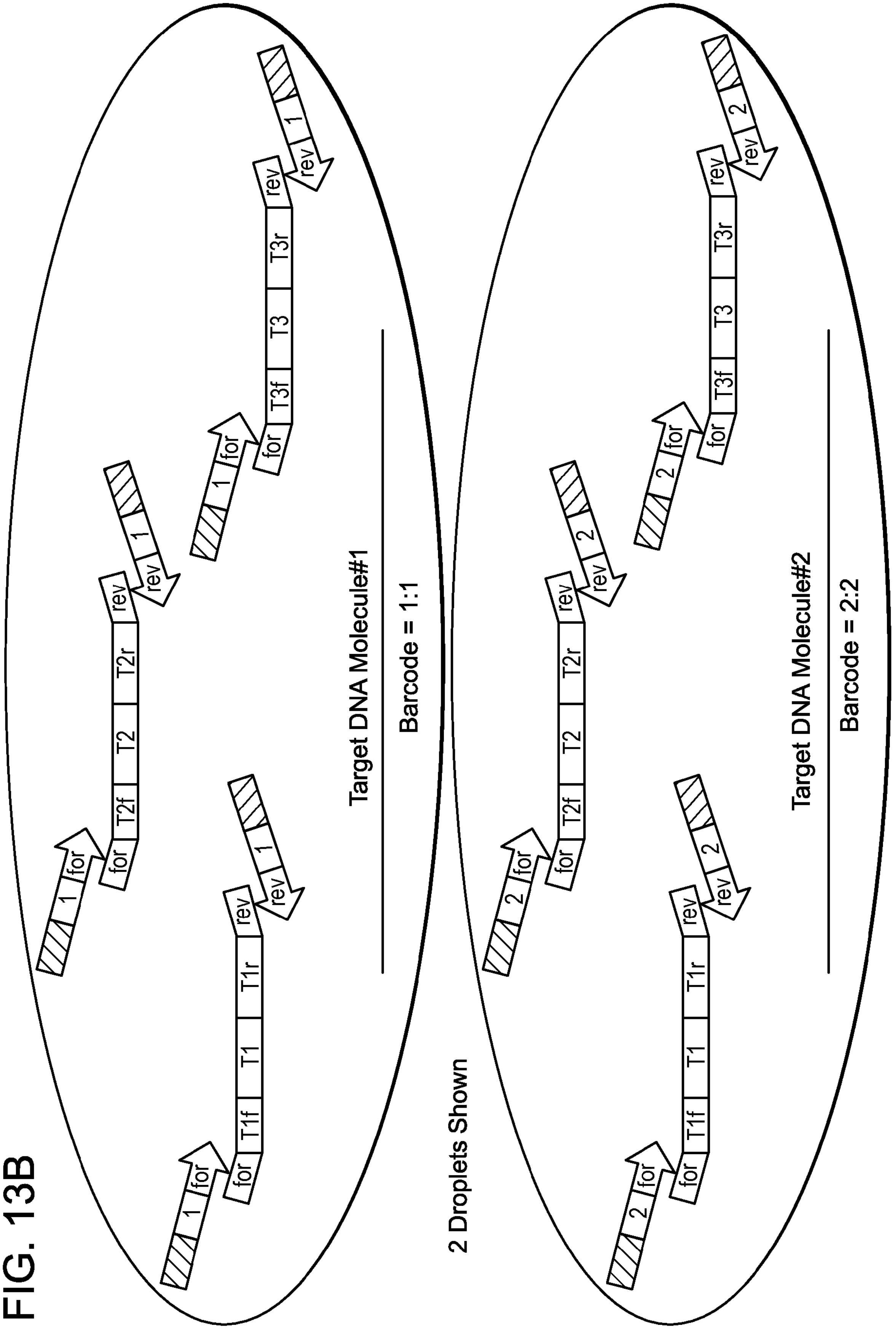

Use of the universal PCR barcode primer library with prepared sample is shown in FIG. 13A-B. The bulk annealed sample prep is loaded into droplets, along with polymerase and dNTPs, such that a single contiguous molecule with its set of targets to be haplotyped is contained in a droplet. The universal barcode library is combined with the prepared sample, either using a droplet to droplet combination mode, or in a droplet to aqueous stream combination mode (shown in FIG. 13A-B).

Figure 14A:
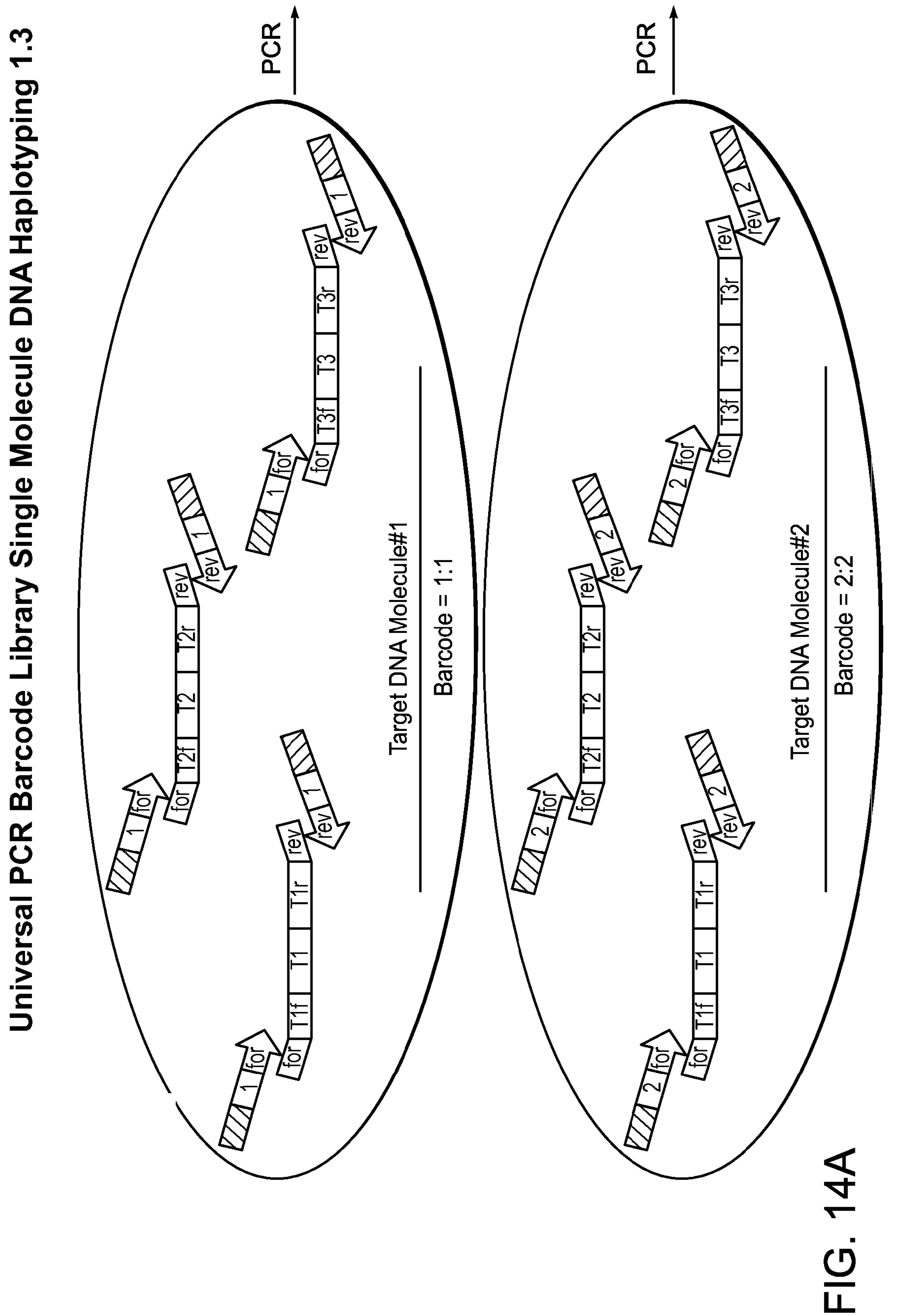
FIGS. 14A-B show labeling and release for amplification-based single molecule haplotyping with universal PCR barcodes.
Figure 14B:
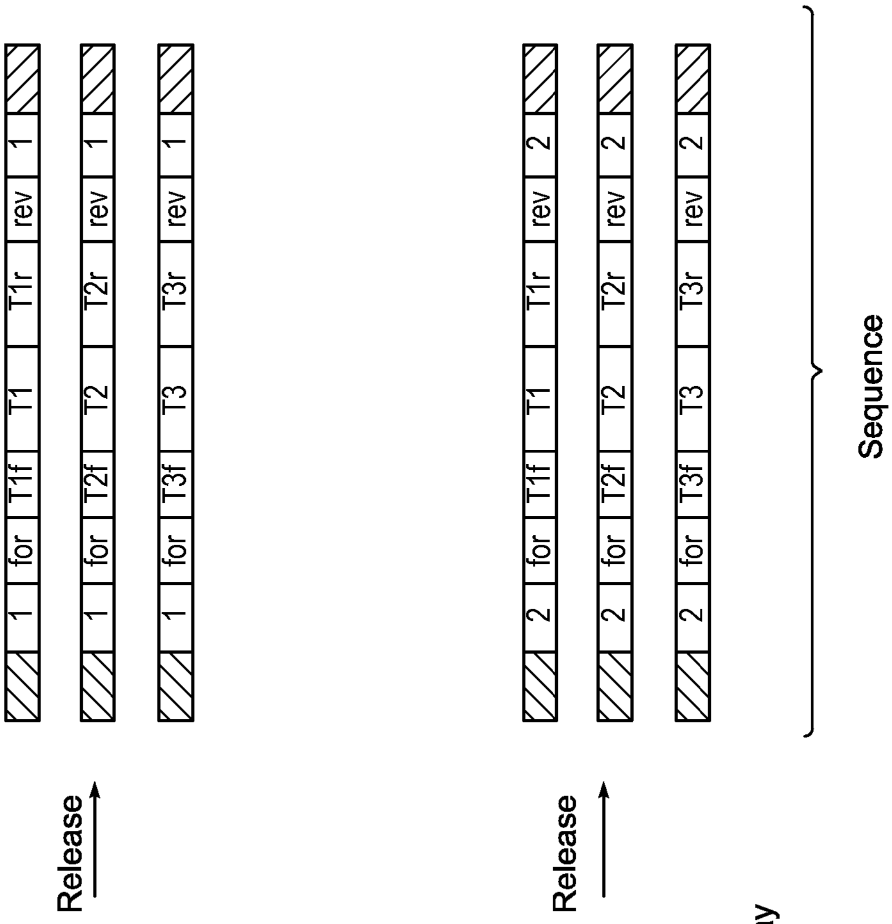

The two forward 'for' complimentary base pairs are allowed to hybridize (two droplets from a combined library and sample are shown in FIG. 13A-B, and elongated either inside droplets that include polymerase and dNTPs, or following release of the primers annealed to the template (the workflow in FIG. 14A-B shows release before elongation outside of droplets), followed by ligation of the 3-prime primer to the elongated strand. The resulting contiguous strands shown on the right side of FIG. 14A-B containing barcodes are used for sequencing (or sequence determination using microarrays), and the sequences that contain identical barcodes have target loci sequences that derive from the same sample strand (i.e. the same haplotype phase).

Single Cell Genomics

Figure 18A:
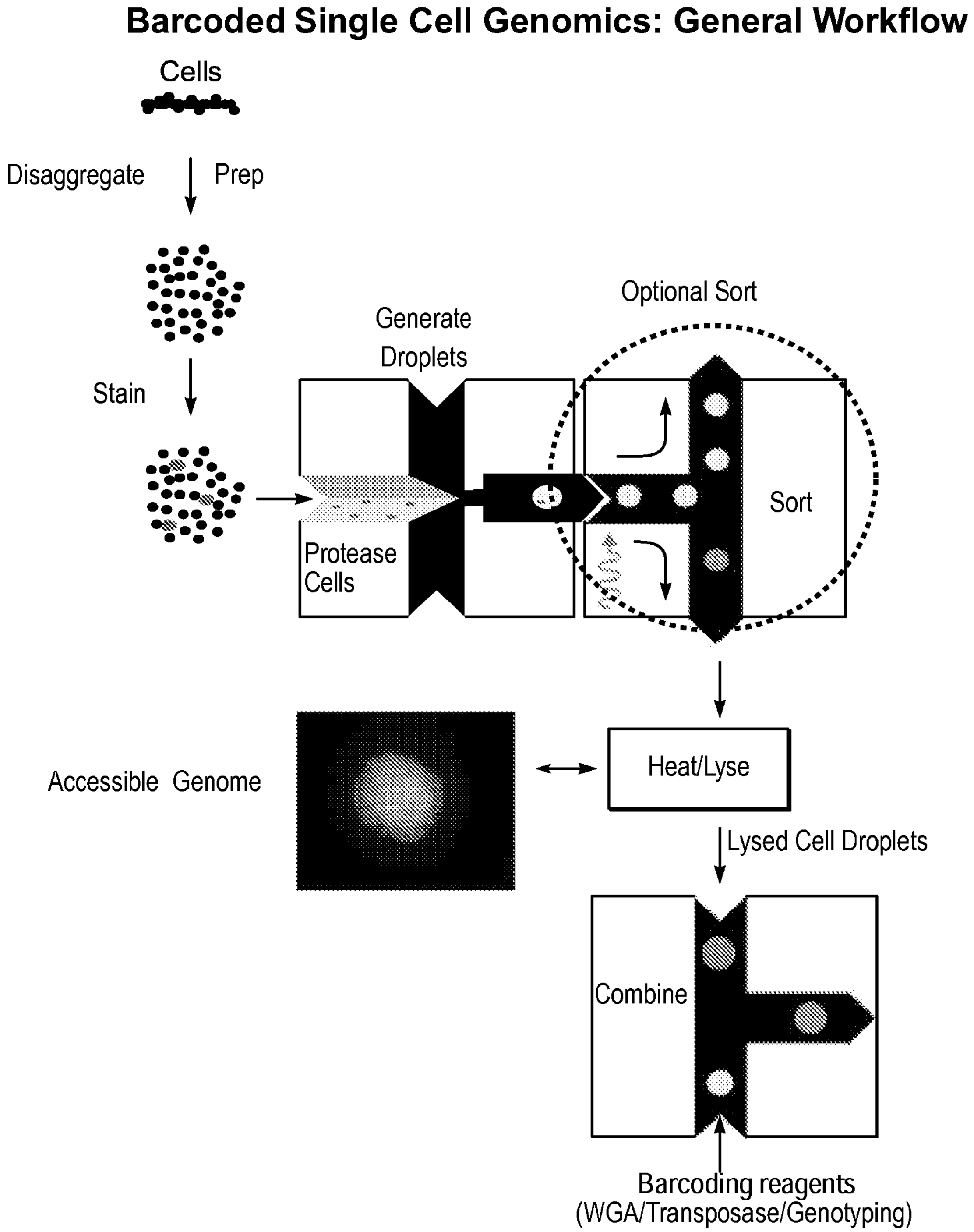
FIGS. 18A-B show a general workflow for single cell genomics.
Figure 18B:
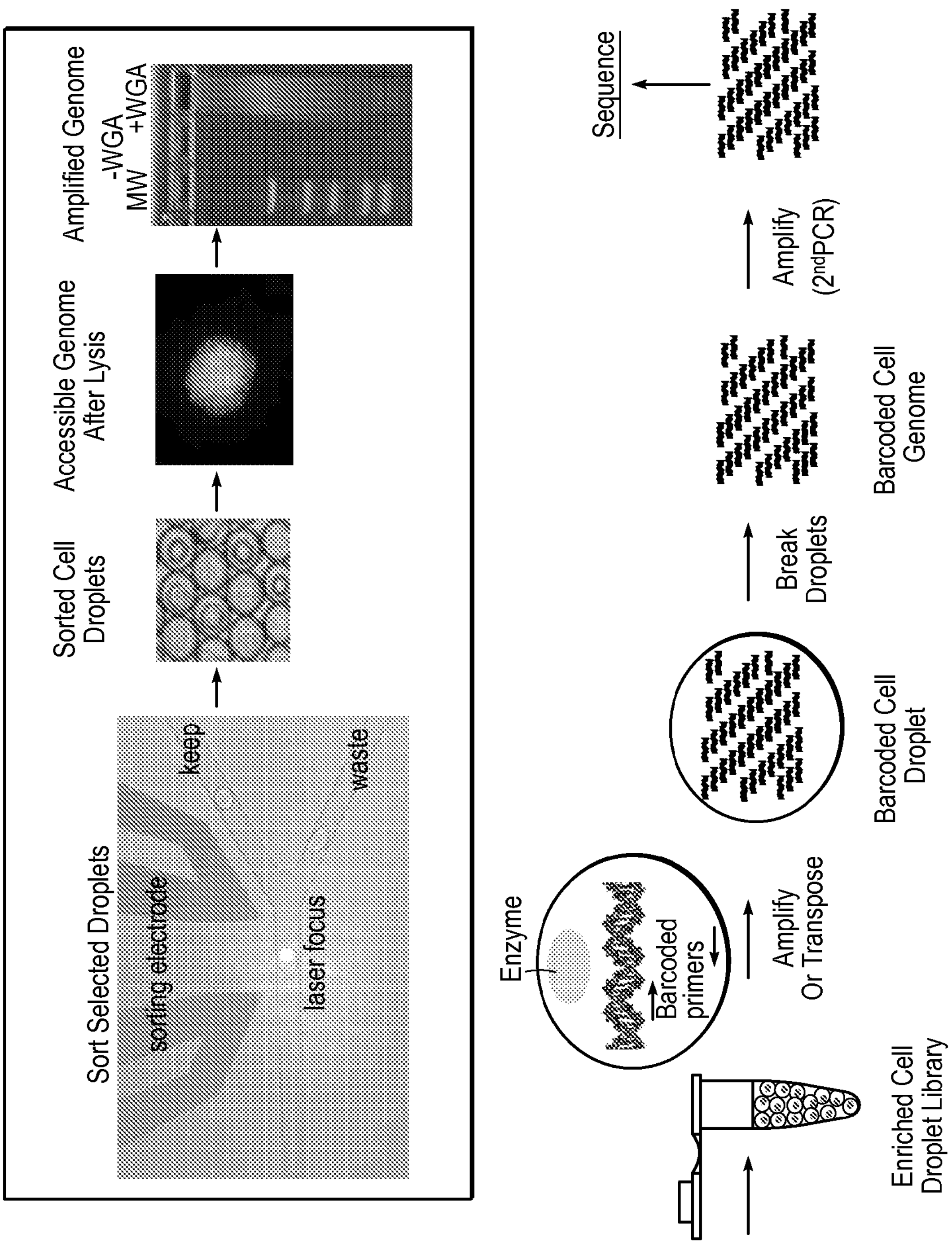

Genotyping of single cells can be performed in a fashion similar to haplotyping discussed above. FIG. 18A-B depicts the steps associated with isolation, encapsulation, molecular labeling, sorting and analysis of single cell genomes using fluidic droplets (including optional upfront sorting, and cell lysis within droplets using a detergent and heat).

Preferably a first library of droplets is formed, each droplet containing genetic or proteomic material (e.g., from a single cell, or a portion thereof). In certain embodiments, single cell droplets are created and then the cells are lysed within the droplets.

The droplets can be merged with droplets from a barcode droplet library (e.g., containing nucleic acid constructs in which the functional N-mers are primer oligonucleotides to hybridize to the genome of the single cell). As a result, each droplet will contain at least: the entire genome from a single cell; nucleic acid constructs for hybridizing to the genome of interest with a barcode; and analysis reagents (e.g., polymerase and nucleotides).

A second library of droplets is formed, each containing a plurality of N-mers, each N-mer containing an associated label. In a preferred embodiment, each droplet in the second library of droplets contains the same label within the given droplet, and the labels preferably vary from droplet to droplet. Each droplet in the second library further contains reagents for the replication of the genetic material in the first droplet and subsequent incorporation of the tag. The replication can be DNA from DNA or DNA from RNA (cDNA). There can be a single replication of the genetic material, there can be a linear amplification of the genetic material or an exponential amplification of the genetic material such as PCR or multi-strand displacement amplification. The reagents for conducting the replication can include such things as polymerase, reverse transcriptase, nucleotides, buffers, etc.).

Alternatively, the second droplet could contain beads which are designed to capture the target nucleic acid. Capture sequences with a tag can be attached to bead and used to capture the genetic material from the first droplet introduced after merging with the second droplet. The capture sequence with the tag can be synthesized directly onto the beads or be attached by such means as biotinylated sequences and streptavidin beads. The use of streptavidin beads and biotinylated sequences has the advantage of allowing a generic bead to be used with new libraries of biotinylated capture sequences that can be assembled on demand. However, any method known in the art for attaching nucleic acid sequences to beads can be utilized.

Alternatively, the second droplet could contain capture sequences that have an attached molecule that is capable of being captured on a solid surface. Biotin would be such a molecule that could be captured by streptavidin attached to a solid surface. Other methods known in the art such as antibody/antigen or aptamers could also be utilized.

Figure 19A:
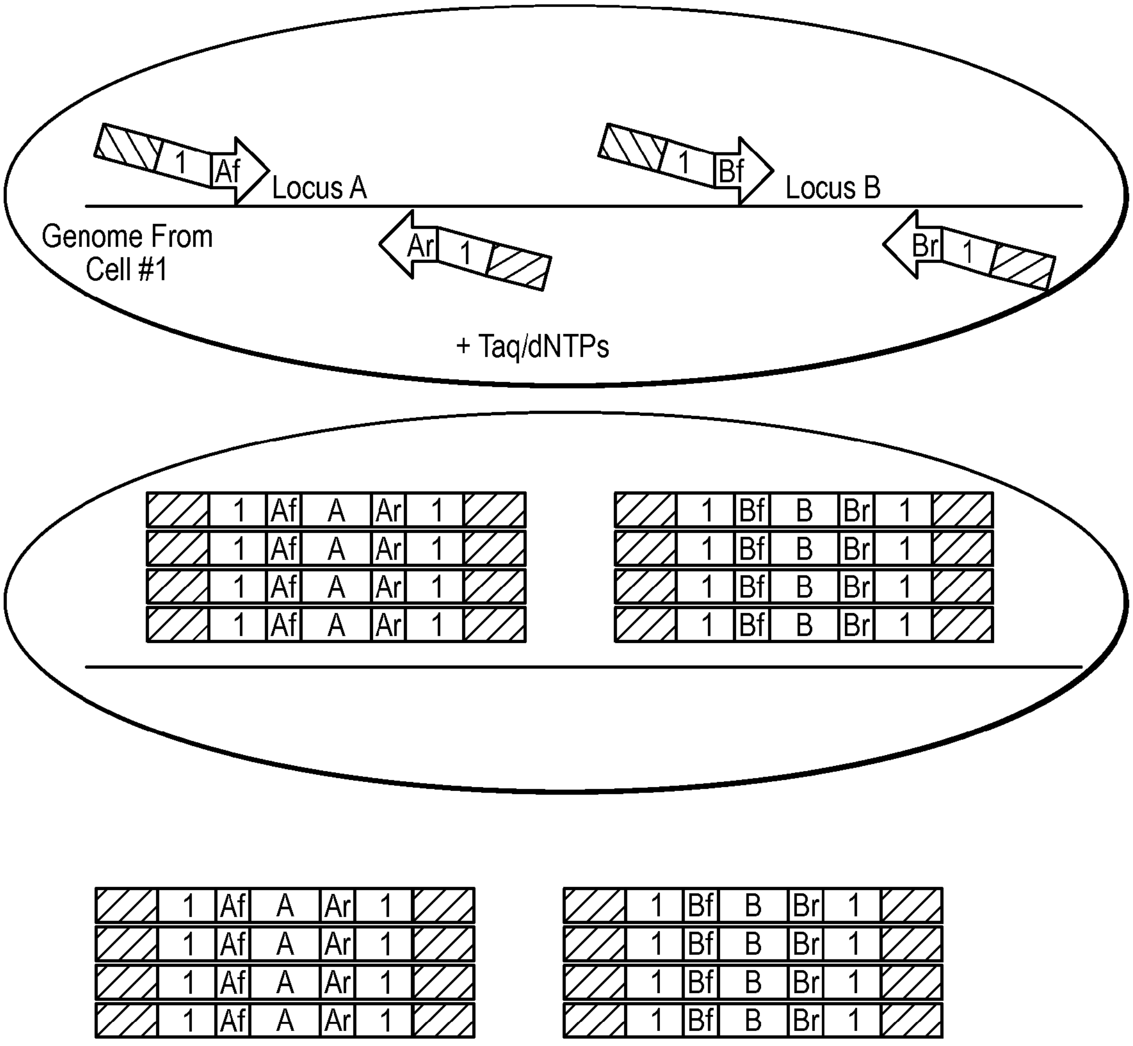
FIGS. 19A-B show single cell genomics using barcoded primers.
Figure 19B:
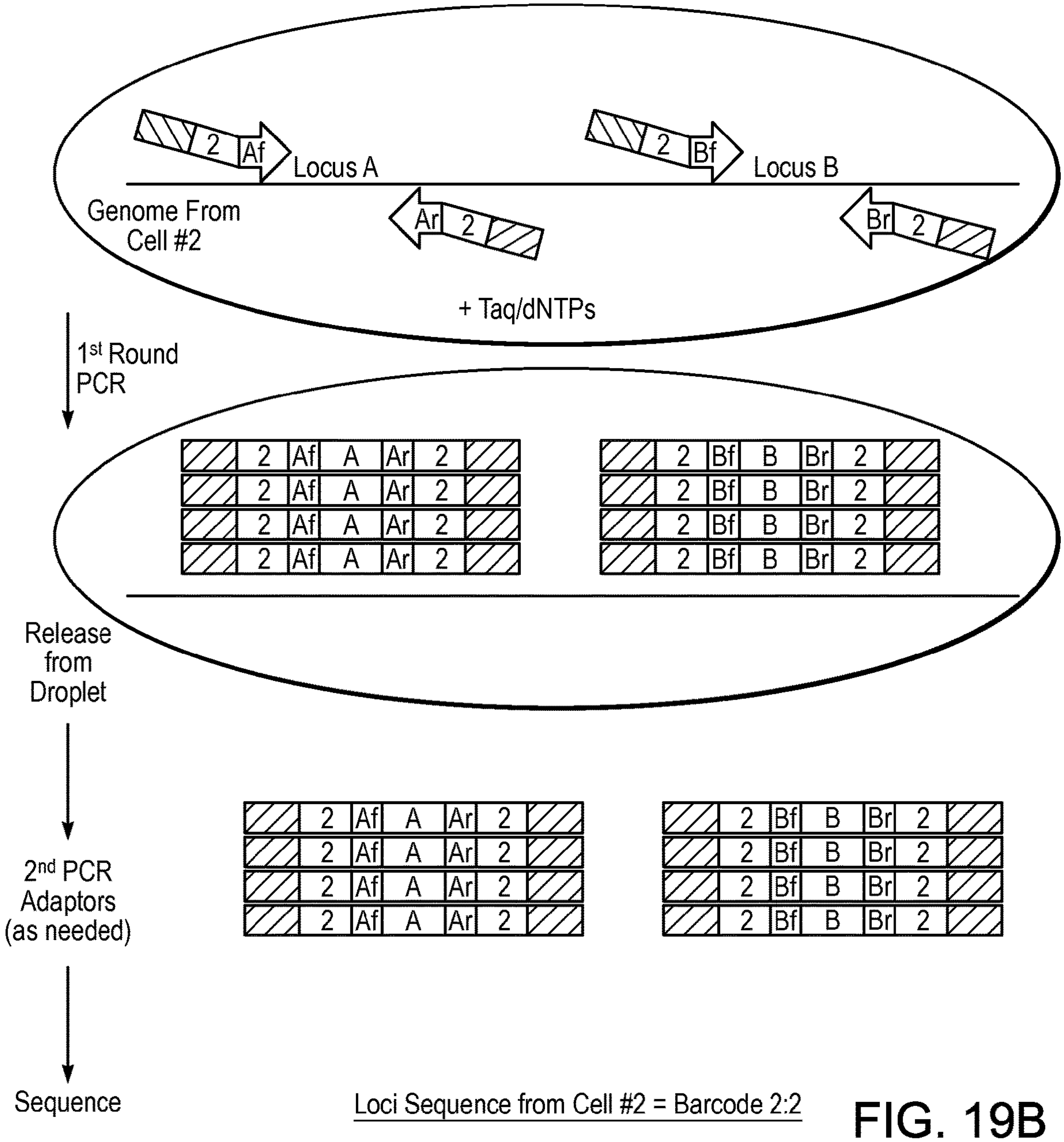
Figure 20A:
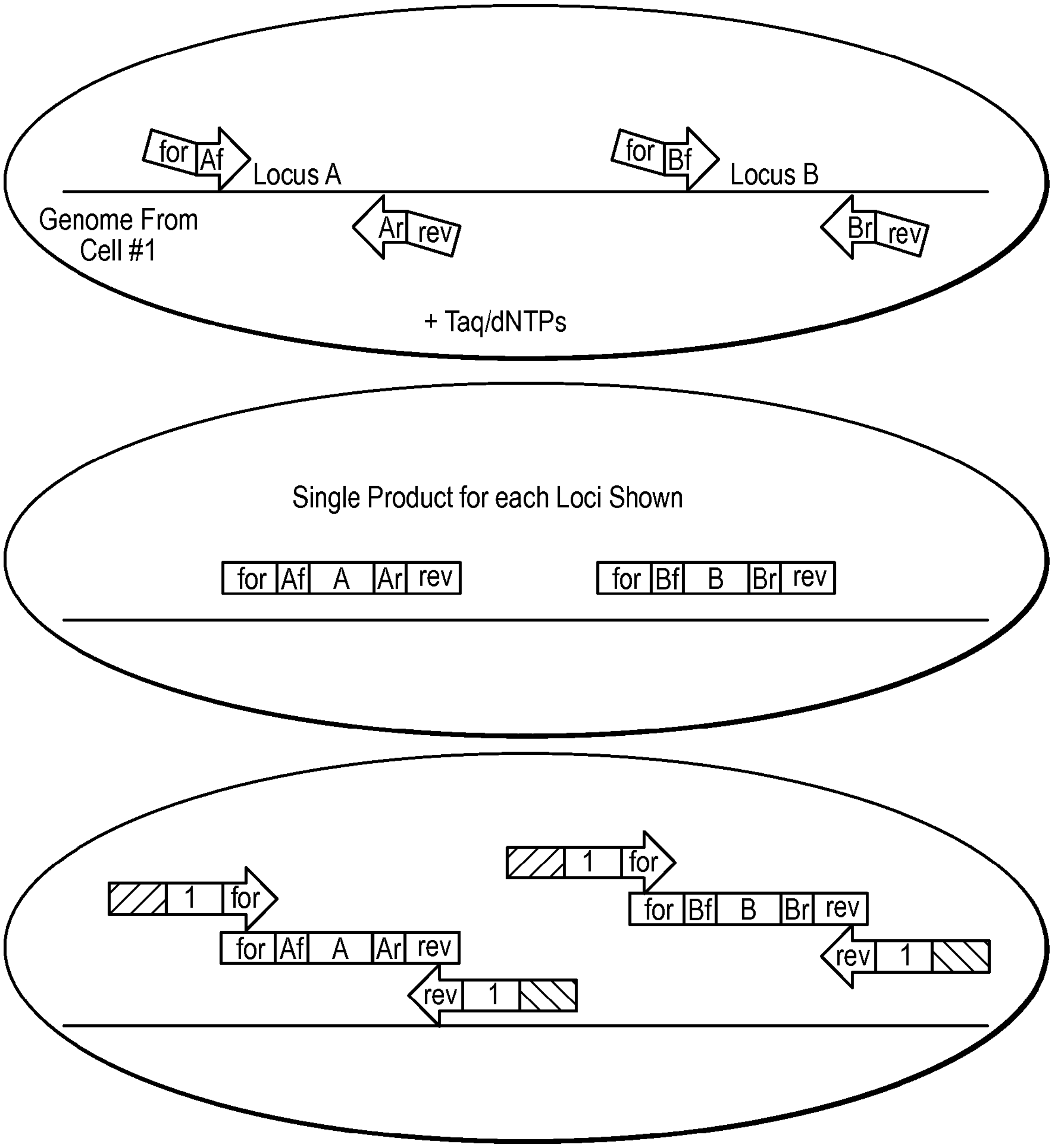
FIGS. 20A-B show single cell genomics using a universal barcode library.
Figure 20B:
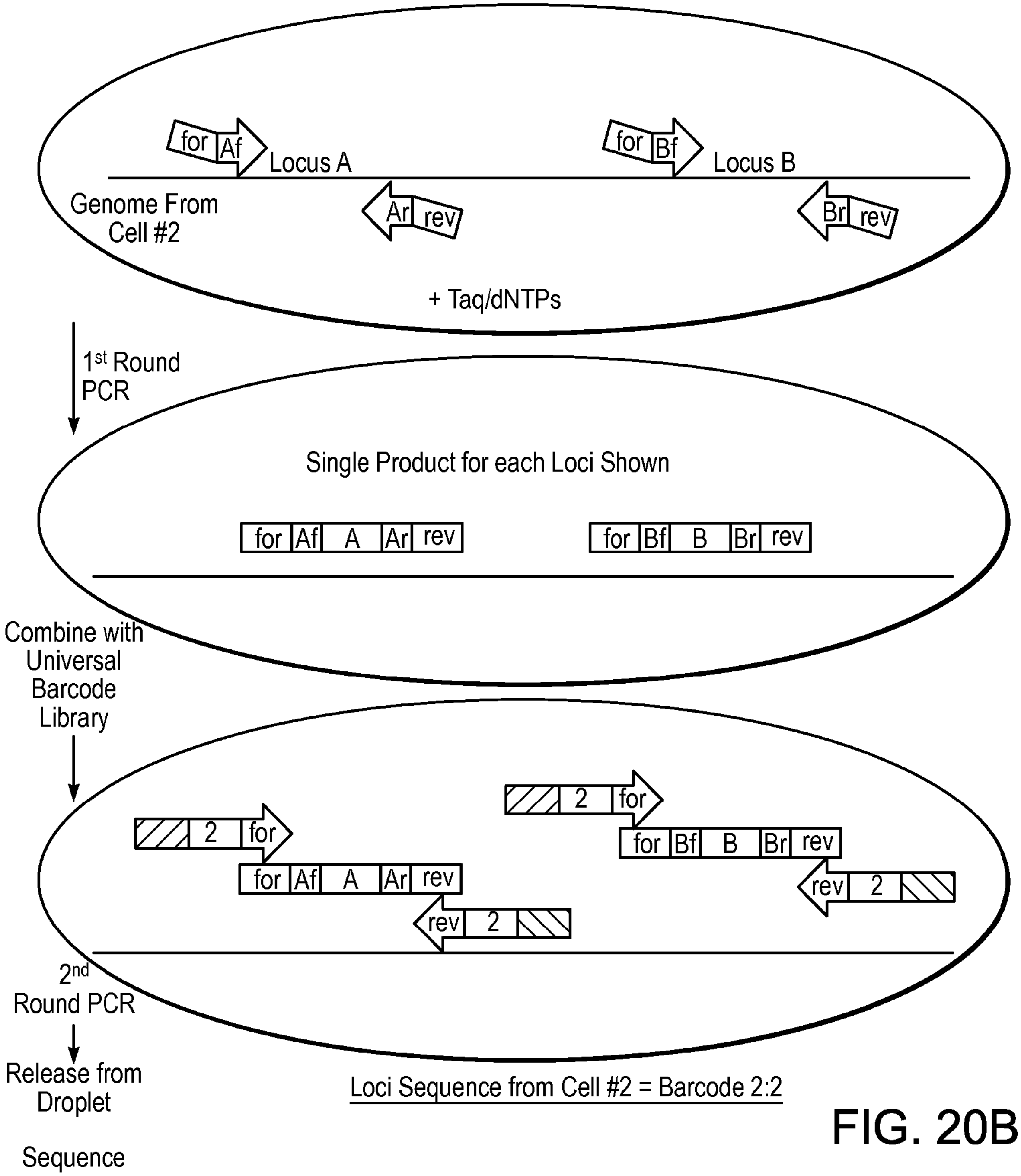

The target regions of the genome can be amplified according to the workflow shown in FIG. 18A-B. Amplification of the target region of the genome can be accomplished by any method known in the art. For example, amplification and barcoding can involve barcoded primers, as shown in FIG. 19A-B. FIG. 20A-B shows single cell genomics using primers for a first round of amplification followed by subsequent merging with a universal barcode library. Primers as shown in FIG. 19A-B or in FIG. 20A-B generally can amplify target material by a PCR reaction.

The new library of droplets then undergoes amplification (see "1st Round PCR" in FIG. 19A-B) to incorporate the labels into the genetic target (i.e., DNA or RNA).

Figure 21:
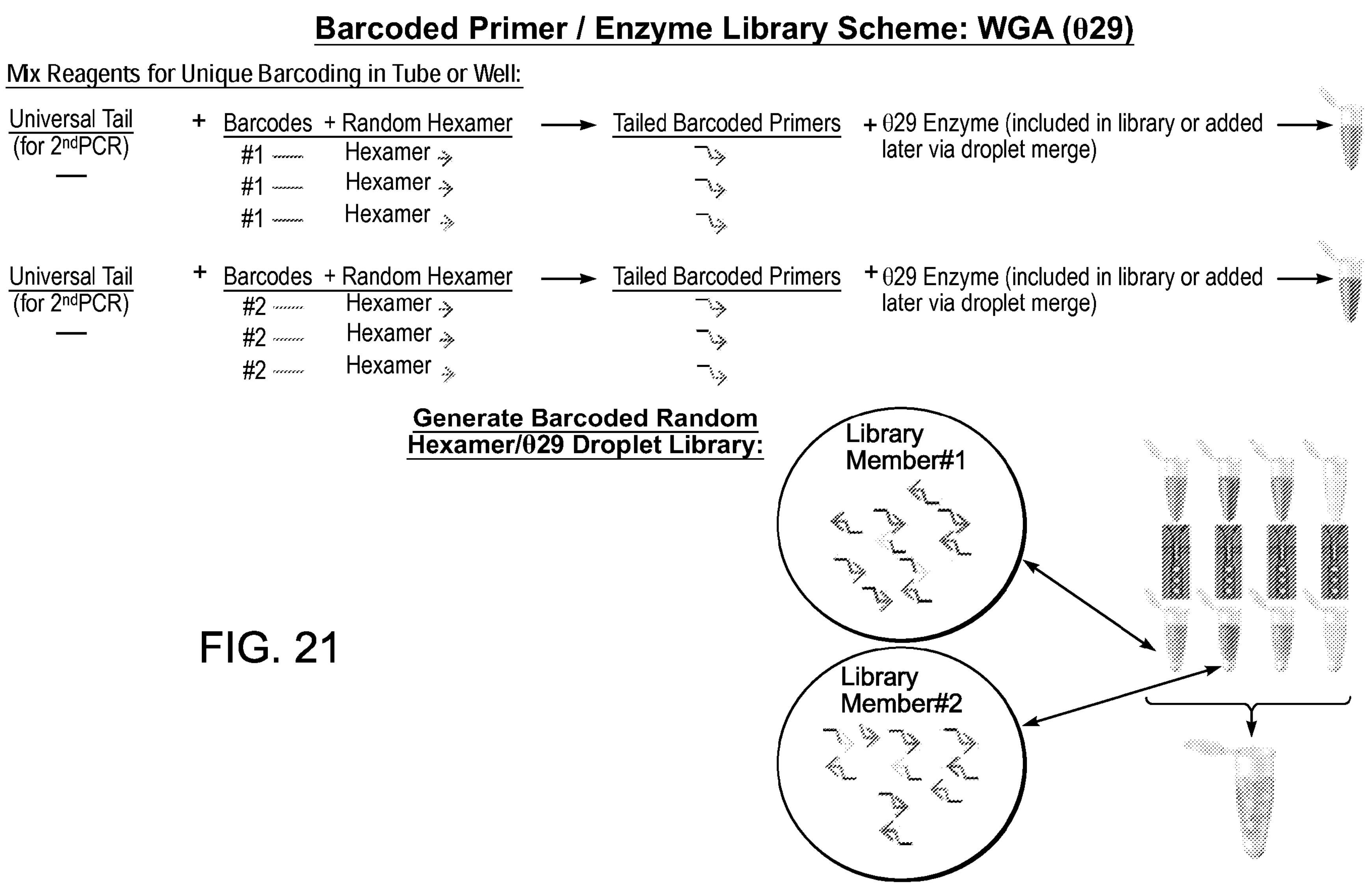
FIG. 21 shows using a random hexamer library with phi29.
Figure 22:
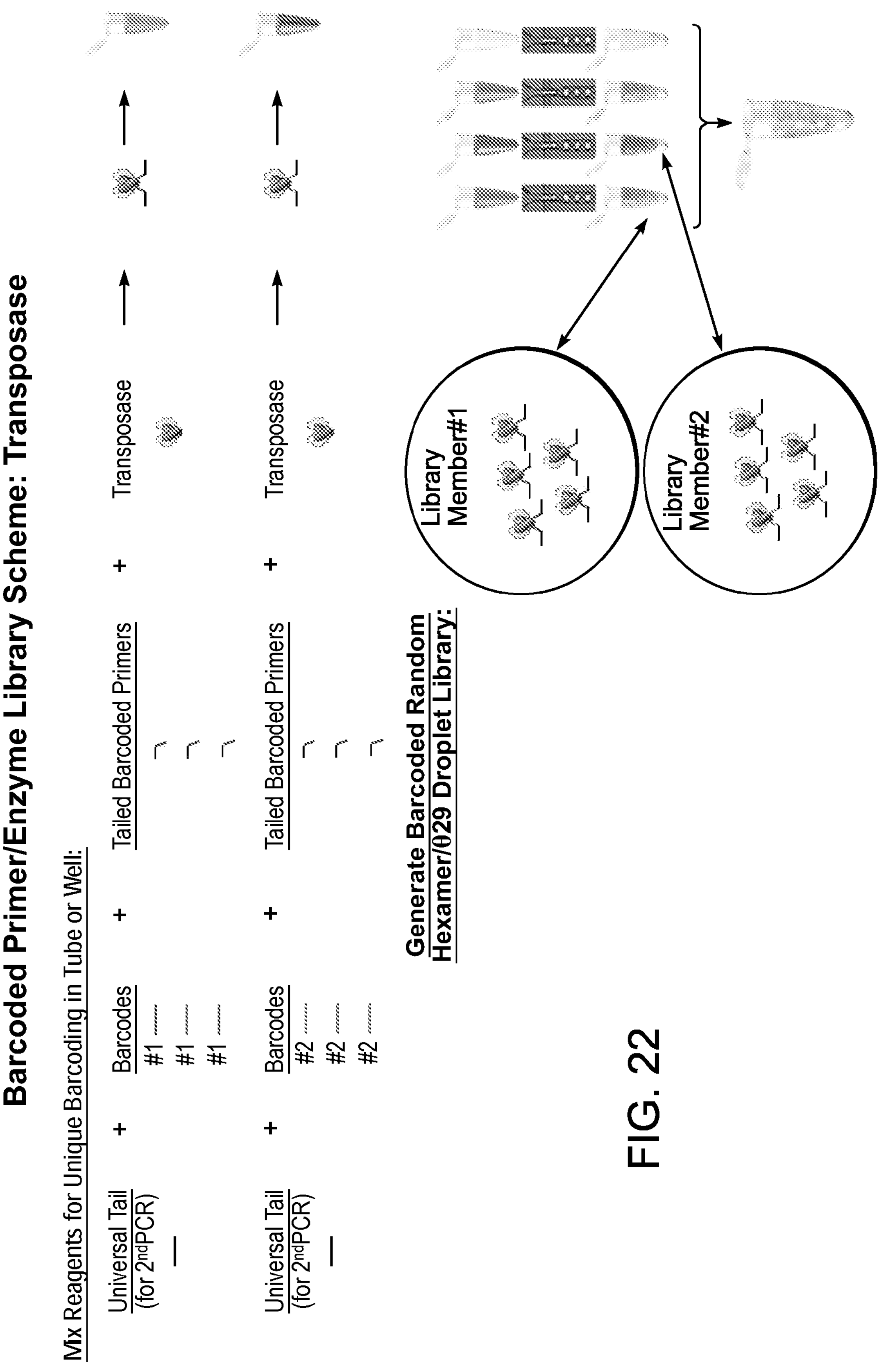
FIG. 22 shows a barcoded random hexamer library.

Target material can also be amplified using multiple displacement amplification (MDA) or any other method known in the art. In certain embodiments (e.g., certain MDA embodiments), a random hexamer (or similar oligo) is used in conjunction with a barcode. For example, FIG. 21 shows generating a barcoded random hexamer library and using the random hexamer library with phi29. FIG. 22 shows a barcode/primer library used with transposase.

In the description that follows, amplification is described in terms of the use of MDA for incorporating the labeled primers into or onto the target material, but it is understood that this choice of description is not limiting for the invention, and that similar methods (e.g., using a transposase) are compatible with all other methods of the reaction. Where the target is genomic DNA, the label can be incorporated into the DNA using, for example, multiple displacement amplification with random hexamer primers having a label incorporated at the 5'end.

Multiple displacement amplification (MDA) is a non-PCR based DNA amplification technique. This method can rapidly amplify minute amount of DNA samples to reasonable quantity for genomic analysis. The reaction starts by annealing random hexamer primers to the template and DNA synthesis is carried out by high fidelity enzyme, preferentially ϕ29 at a constant temperature. Compared with the conventional PCR amplification techniques, MDA generates larger sized products with lower error frequency. MDA reaction starts with the annealing of random hexamer primers to the DNA template and then continues with the chain elongation ϕ29. Increasing number of primer annealing events happens along the amplification reaction. The amplification reaction initiates when multiple primer hexamers anneal to the template. When DNA synthesis proceeds to the next starting site, the polymerase displaces the newly produced DNA strand and continues its strand elongation. The strand displacement generates newly synthesized single stranded DNA template for more primers to anneal. Further primer annealing and strand displacement on the newly synthesized template results in a hyper-branched DNA network. The sequence debranching during amplification results in high yield of the products. To separate the DNA branching network, S1 nucleases is used to cleave the fragments at displacement sites. The nicks on the resulting DNA fragments are repaired by DNA polymerase I. The generated DNA fragments can be directly used for analysis or be ligated to generate genomic libraries for further sequencing analysis. Using MDA, the DNA would simultaneously be amplified and have a barcode incorporated into the sequence.

Alternatively, if the second droplet contains beads to which are attached tagged sequences designed to capture the genetic material, the merged droplets are incubated in a manner that releases the genetic material from a cell if present and allows the hybridization of the genetic material to the capture sequences attached to the bead. Reagents such as proteases, alkaline reagents, detergents or other methods known in the art can be used to release the genetic material from the cells if present. After capture the emulsion is broken and the beads used to purify the genetic material away from other components of the reaction that may inhibit subsequent steps such as cell debris, proteases and detergents. The beads would capture the genetic material using attached sequences that were random N-mers of length N designed to capture all sequences or variations of N-mers designed to capture only portions of the genetic material present. The tag is then incorporated by replication of the captured nucleic acid using the capture sequence with the tag as a primer. The replication can either generate DNA from a DNA strand or DNA from an RNA strand (cDNA synthesis). This material can either be processed directly or amplified further using methods known in the art such as PCR or multi-strand displacement amplification.

The capture sequences can be synthesized directly onto the beads or be attached by such means as utilizing biotinylated sequences and streptavidin beads. The use of streptavidin beads and biotinylated sequences has the advantage of allowing a generic bead to be used with new libraries of biotinylated capture sequences that can be assembled on demand. However, any method known in the art for attaching nucleic acid sequences to beads can be utilized.

Alternatively, if the second droplet contains capture sequences with the tag and an attached binding molecule the merged droplets are incubated in a manner that releases the genetic material from a cell if present and allows the hybridization of the genetic material to the capture sequences with the binding molecule. Reagents such as proteases, alkaline reagents, detergents or other methods known in the art can be used to release the genetic material from the cells if present. The emulsion is then broken to release the hybridized capture sequence and genetic material. The released genetic material hybridized to the capture sequence is then captured on a solid support allowing the removal of elements such as cell debris, proteases and detergents that may inhibit subsequent steps. The tag is then incorporated by replication of the captured nucleic acid using the capture sequence with the tag as a primer. The replication can generate DNA from a DNA strand or DNA from an RNA strand (cDNA synthesis). This material can either be processed directly or amplified further using methods known in the art such as PCR or multi-strand displacement amplification.

Where the target is RNA, the label can be incorporated in the RNA using MDA with random hexamers having barcodes attached at the 5' ends. Alternatively, poly dT primers having barcodes attached at the 5' ends can be used. A promoter region, such as T7 or SP6 RNA polymerase promoter could also be incorporated at the same time, which could be used to amplify the RNA and incorporate a barcode.

After the target is labeled, the amplified genetic material can be analyzed. For example, the amplified material can be released from encapsulation (e.g., "Release from Droplet" in FIG. 19A-B) or from the bead or solid support and prepared for direct sequencing using, for example, sequencing library preparation protocols well known to those skilled in the art. For example, the amplified genetic material can be sheared/fragmented using methods well known to those of ordinary skill in the art, and adaptors can be ligated onto the ends of the fragments to be utilized, for example in direct sequencing, or in an enrichment process.

Figure 3A:
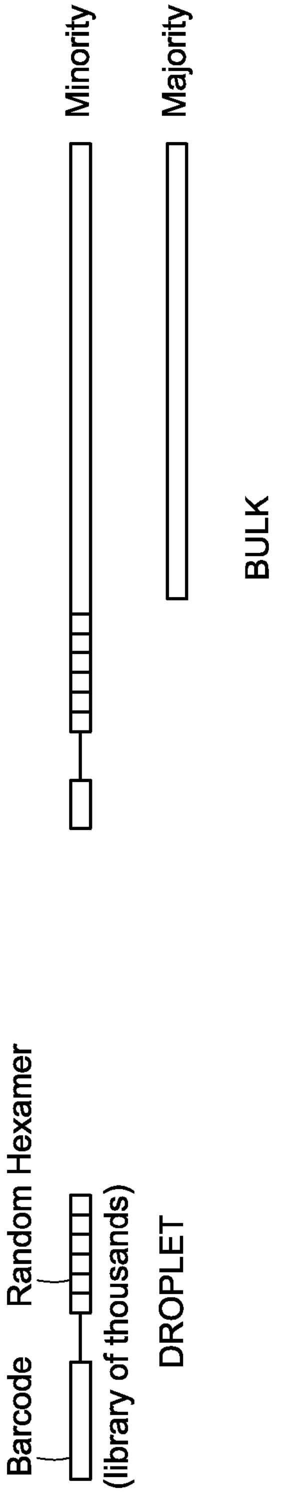
FIG. 3A is a schematic depicting an example of barcode labeled strands in a droplet before sequencing (in droplet) and after sequencing (in bulk).

While the entire encapsulated target can be tiled with a labeled primer using the methods described herein, it should be noted that a majority of the fragments input into the sequencing reaction may not contain a label due to the shearing/fragmentation preparation step required for short read sequencing technology. In other words, each of the MDA amplified labeled strands are sheared/fragmented such that one or more fragments from the same labeled strand become disassociated from the label incorporated into that strand (see FIG. 3A). This issue can be resolved in a number of ways. For example, once encapsulated the target can be fragmented prior to the amplification step to incorporate the labels, thus ensuring that each fragment is labeled when it is input into the sequencing reaction. Alternatively, the MDA amplified labeled strands can be enriched in a subsequent PCR reaction prior to sequencing.

Figure 3B:
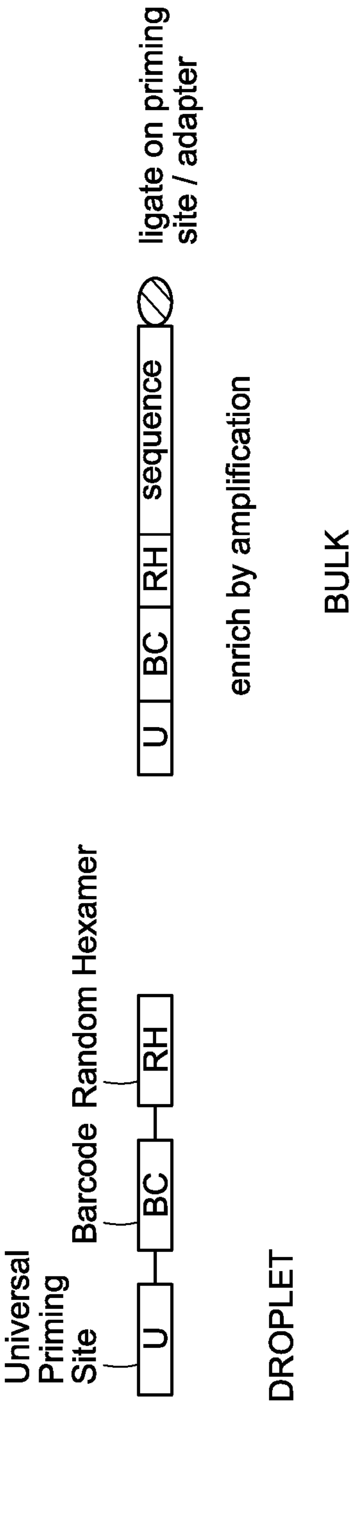
FIG. 3B is a schematic depicting an example of a labeled primer having a universal priming site before incorporation into/onto a target nucleic acid and after incorporation into a target nucleic acid.

In an exemplary embodiment, enrichment of the labeled strands can be accomplished by incorporating a universal sequence into a 5' end of each of the plurality of labeled primers such that each of the primers has a sequence as follows: 3'-(N-mer)-label-(universal priming sequence)-5' (see FIG. 3B). Once the labels are incorporated into the encapsulated genetic material (using, e.g., multiple displacement amplification, as described above), the amplified material can be released from encapsulation using one or more methods described in further detail below. A universal primer can then be ligated onto the 3' ends of the amplified mix and input into a standard PCR reaction (FIG. 3B). Only those strands having the incorporated label with the universal PCR sequence will be amplified, and thereby enriched.

Alternatively, sequence-specific enrichment can be achieved using a similar method to enrich for fragments that have barcodes and for targeted regions of interest. For example, a plurality of labeled primers each having a universal PCR sequence incorporated into a 5' end (i.e., 3'-(N-mer)-label-(universal PCR sequence)-5') is introduced into a droplet containing the target. The labels are incorporated into the encapsulated genetic material using, e.g., amplification. The droplet containing the amplified mixture is then re-merged with another droplet containing a universal primer and a primer specific for a targeted sequence of interest, as well as reagents sufficient for conducting a PCR reaction. This merged droplet is then exposed to conditions sufficient for conducting a PCR reaction, and only those fragments having barcodes and the targeted regions of interest will be amplified.

The labels incorporated within each droplet enables a plurality of sequences from multiple different genomes to be simultaneously amplified, pooled for sequencing, then mapped back to their original genome/transcriptome. Like paired read/paired end sequencing, the methods of the invention provide a researcher/clinician/physician with the ability to link two strands that are physically separated within a single genome/transcriptome to the same genome/transcriptome by tiling the same label along an entire genome/transcriptome. The skilled artisan will readily recognize that reads from high repeat regions and/or regions of high homology can be easily mapped, haplotype information can be obtained, and rearragements or deletions can be identified using the methods described herein. Additionally, mutations in subpopulations of cells in a sample, and metagenomic loss of identity can be traced using the methods of the invention.

Barcoding Transcriptomes

The invention provides methods for analyzing transcriptomes that include labeling transcriptomes with nucleic acid constructs comprising unique N-mers and functional N-mers.

Figure 23A:
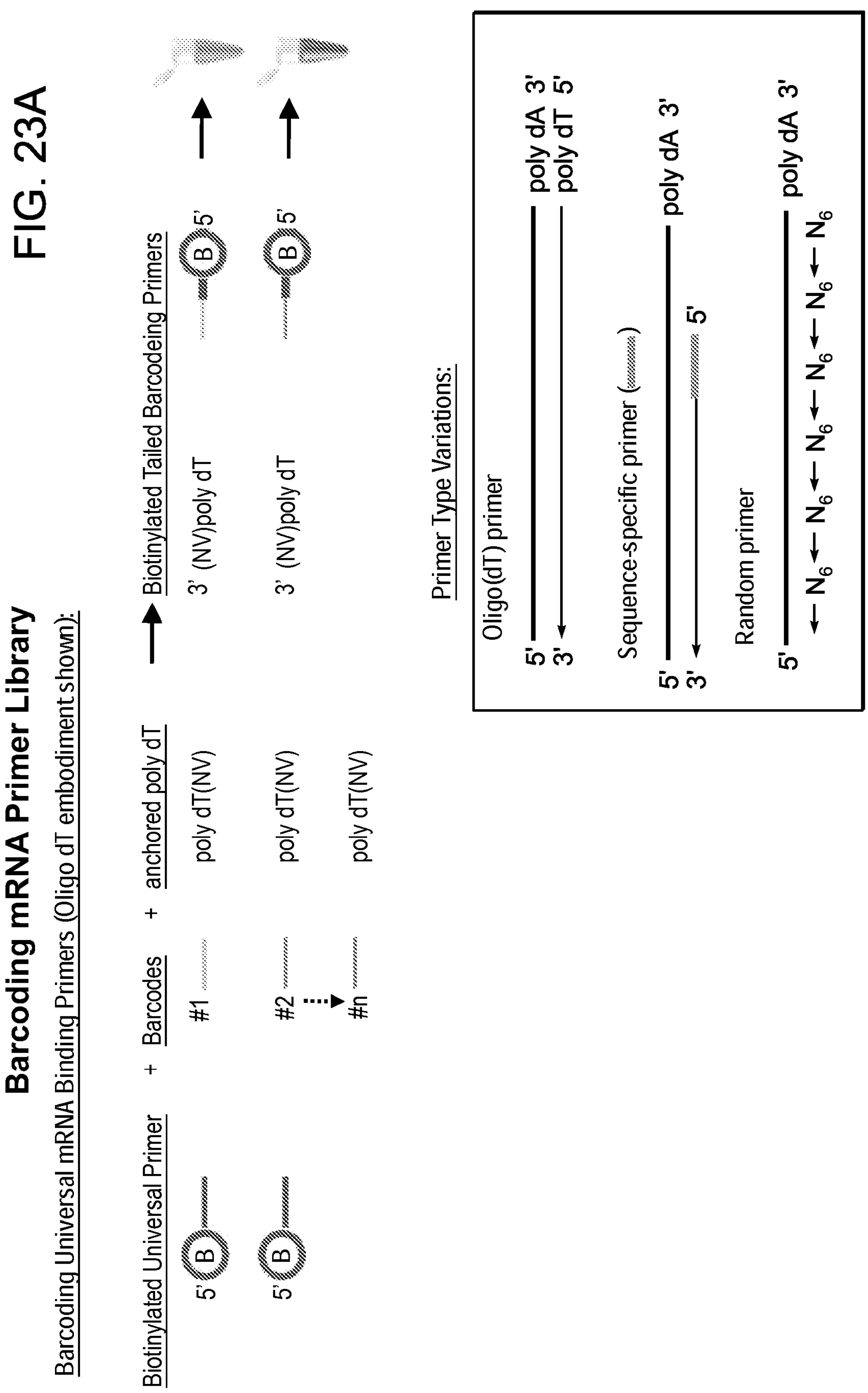
FIGS. 23A-B are a schematic depicting various exemplary barcode schemes for the generation of an barcoded mRNA primer droplet library.
Figure 23B:
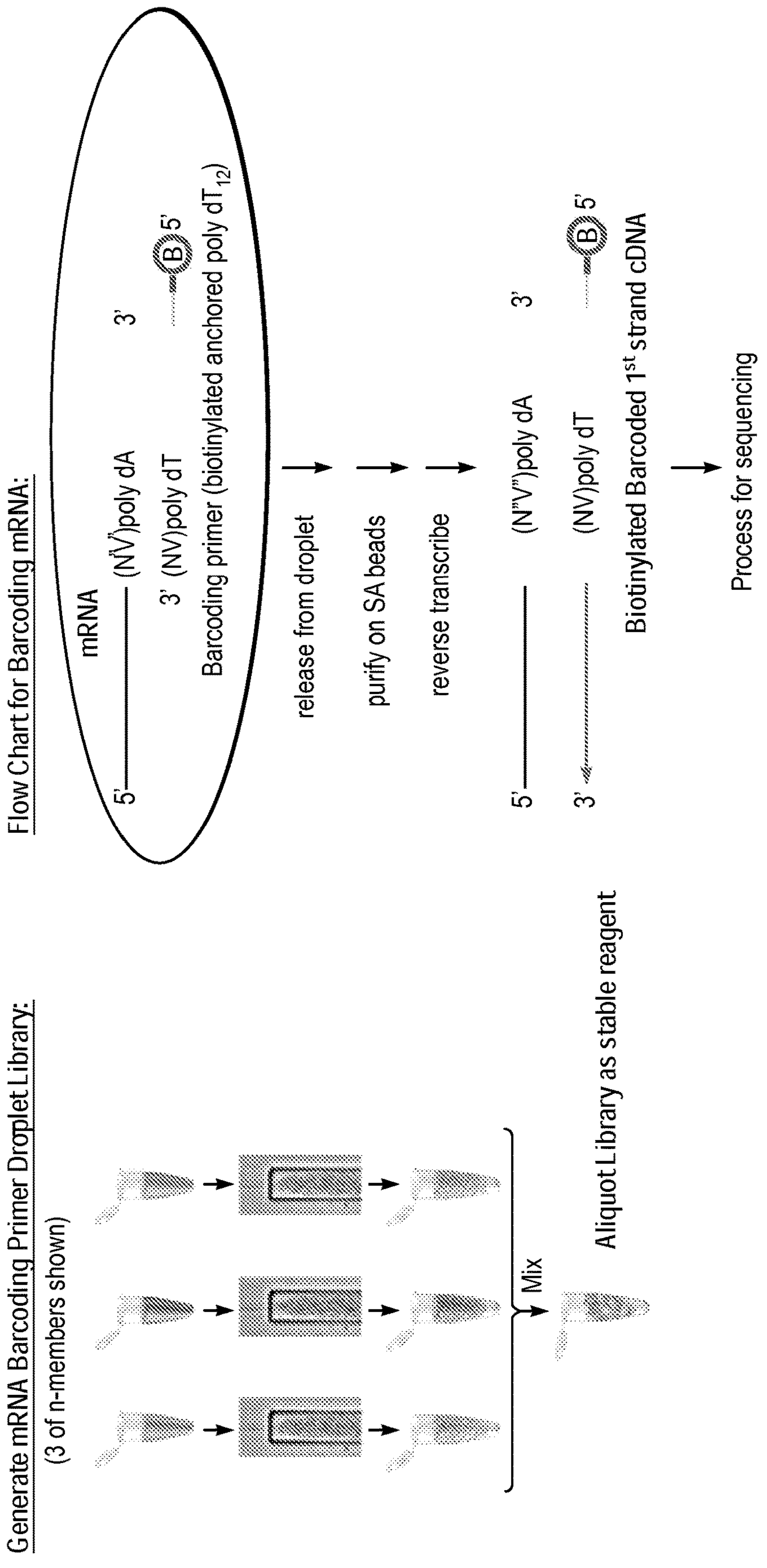

FIG. 23A-B is a schematic depicting various exemplary barcode schemes for the generation of a barcoded mRNA primer droplet library. As shown in FIG. 23A-B, a construct can include a biotinylated universal primer, a barcode, and a poly-T region. These constructs can be used to generate mRNA barcoding primer droplet libraries wherein each droplet contains one or more copies of a unique construct. As shown in FIG. 23A-B, a variety of primer types can be used to copy mRNA. Primer type variations include poly-T oligonucleotides, sequence specific primers, and random hexamers.

FIG. 23A-B shows a flow chart for barcoding mRNA. The mRNA is hybridized to a barcoded primer, released from fluid compartments, purified on streptavidin beads, and copied with reverse transcriptase. The resulting cDNA can be analyzed by sequencing.

Figure 24A:
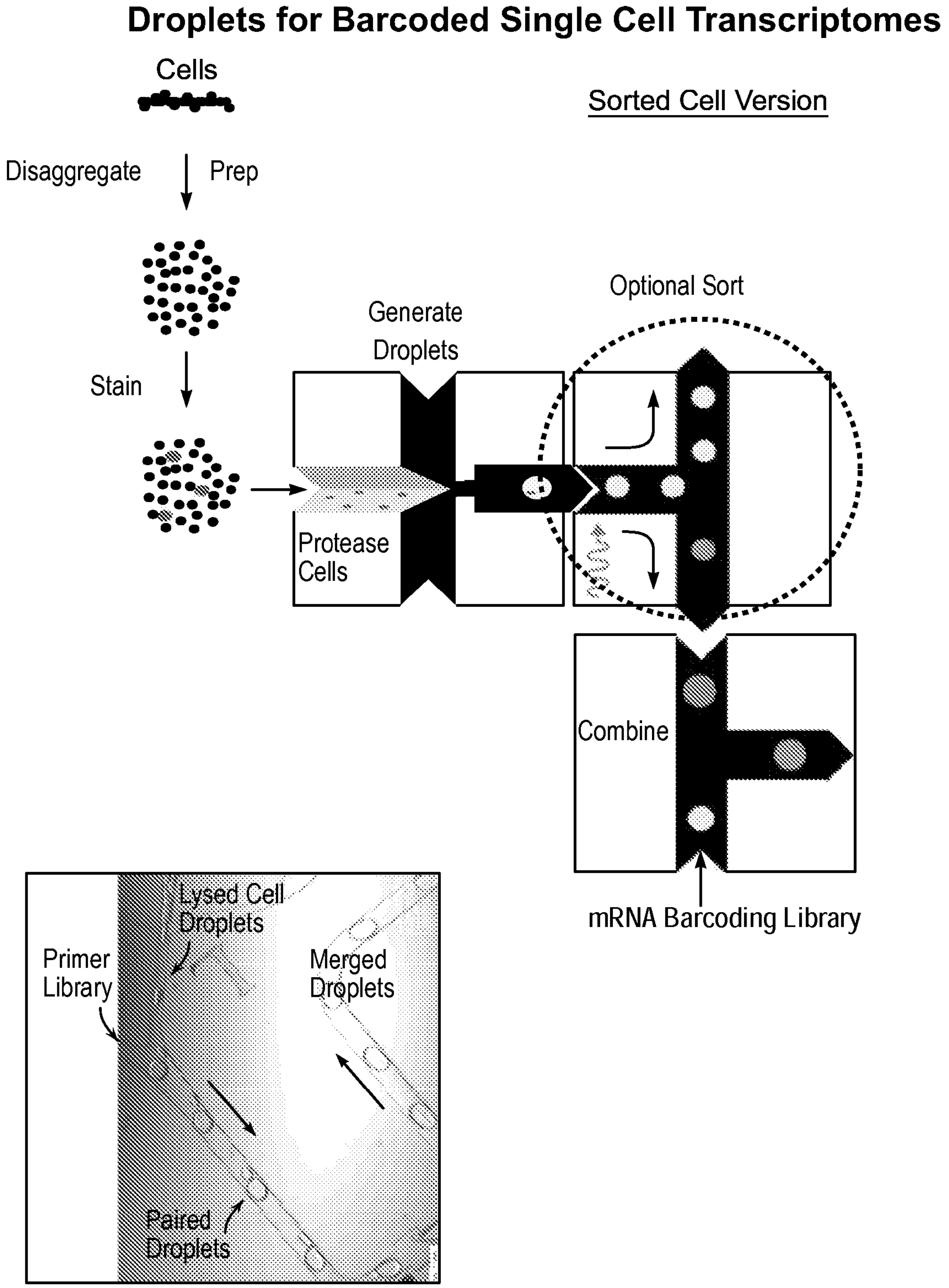
FIGS. 24A-B show a sorted cell workflow for barcoding transcriptomes from single cells.
Figure 24B:
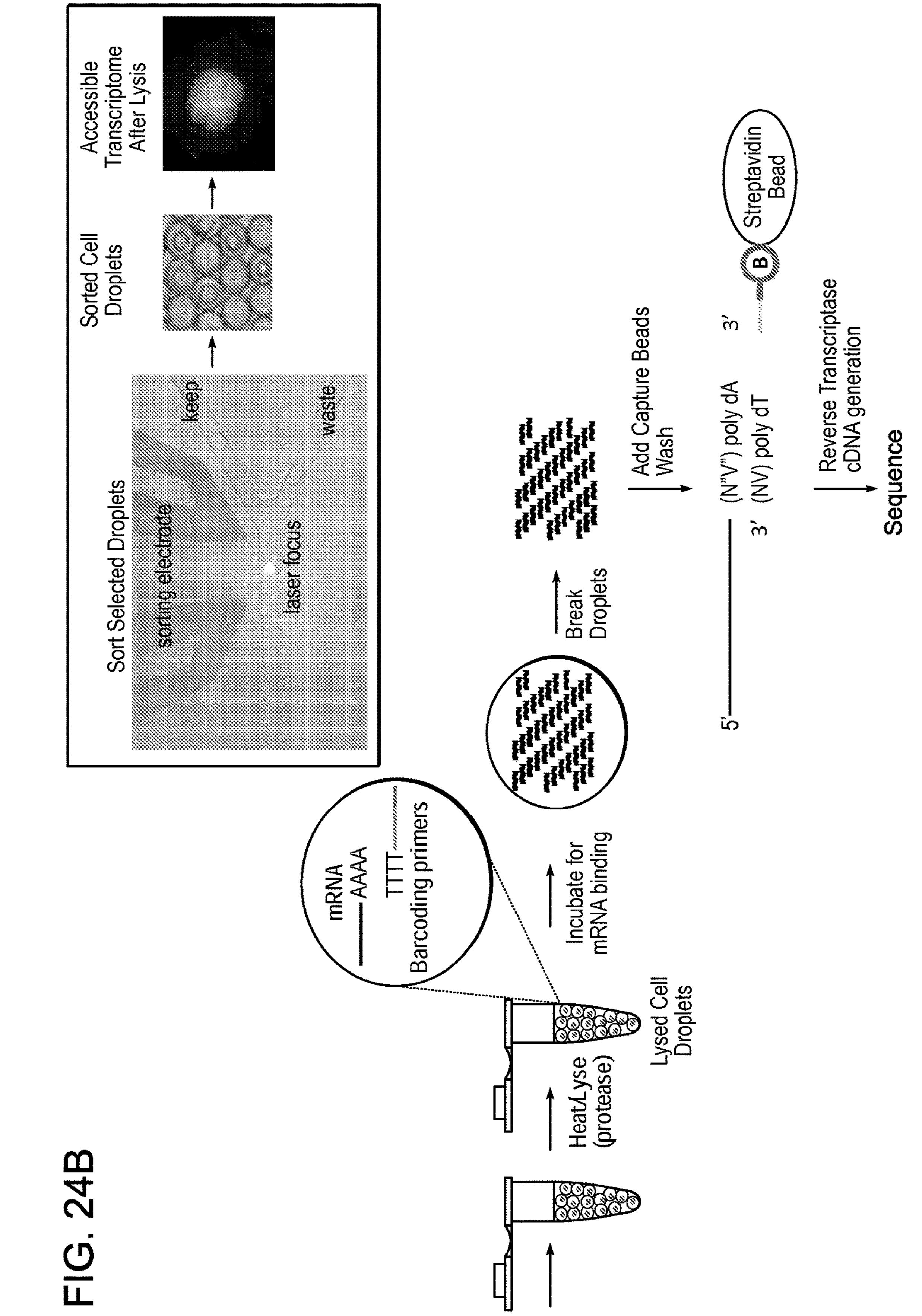

FIG. 24 is a flowchart depicting the steps associated with isolation, encapsulation, molecular labeling, sorting and analysis of single cell transcriptomes using fluidic droplets (including optional upfront sorting, and cell lysis within droplets using a temperature-inducible protease). As shown in FIG. 24, a sorting mechanism can be used to sort the mRNA-containing droplets.

Figure 25A:
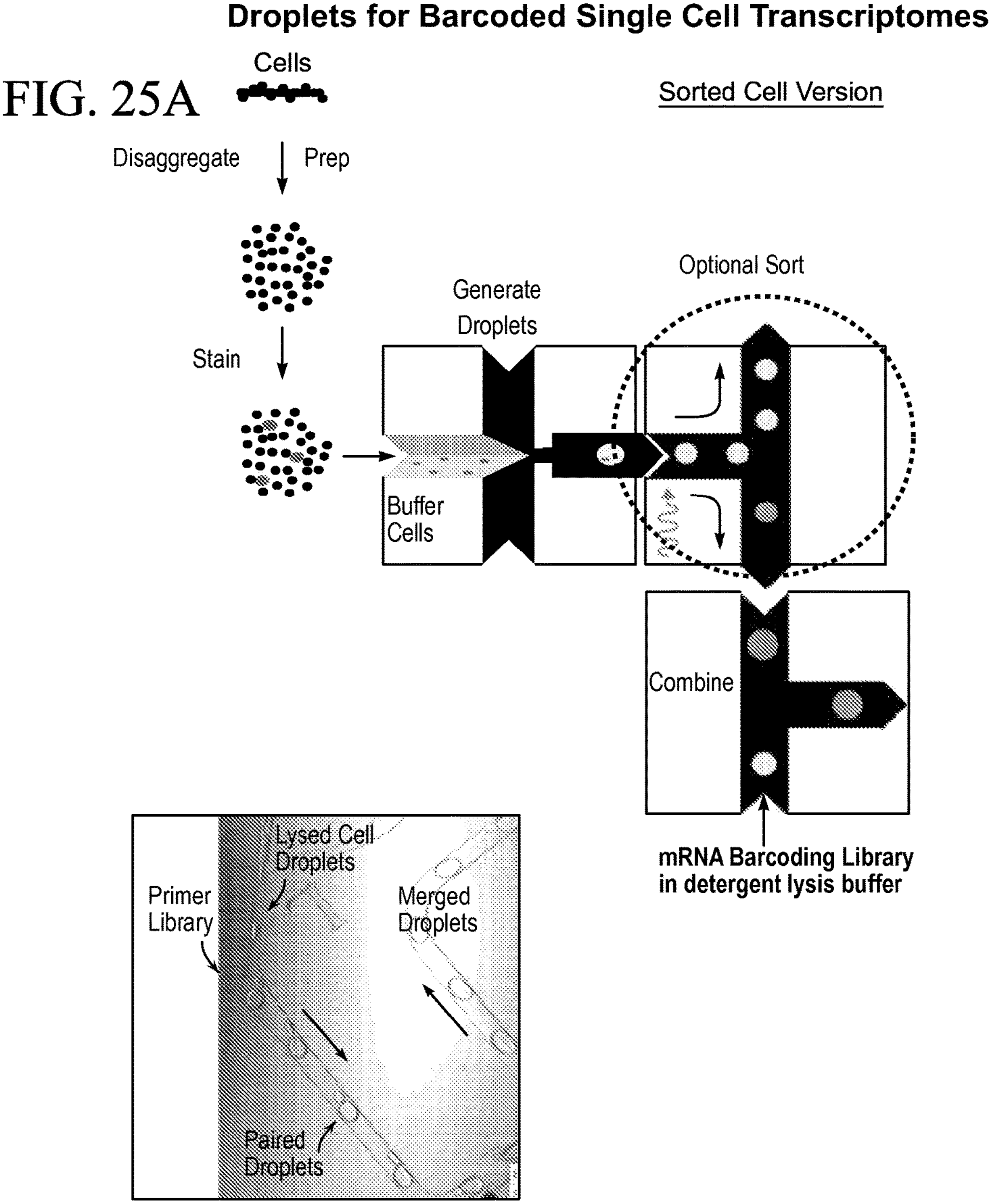
FIGS. 25A-B show a sorted cell workflow for barcoding transcriptomes from single cells using a barcode library in a detergent lysis buffer.
Figure 25B:
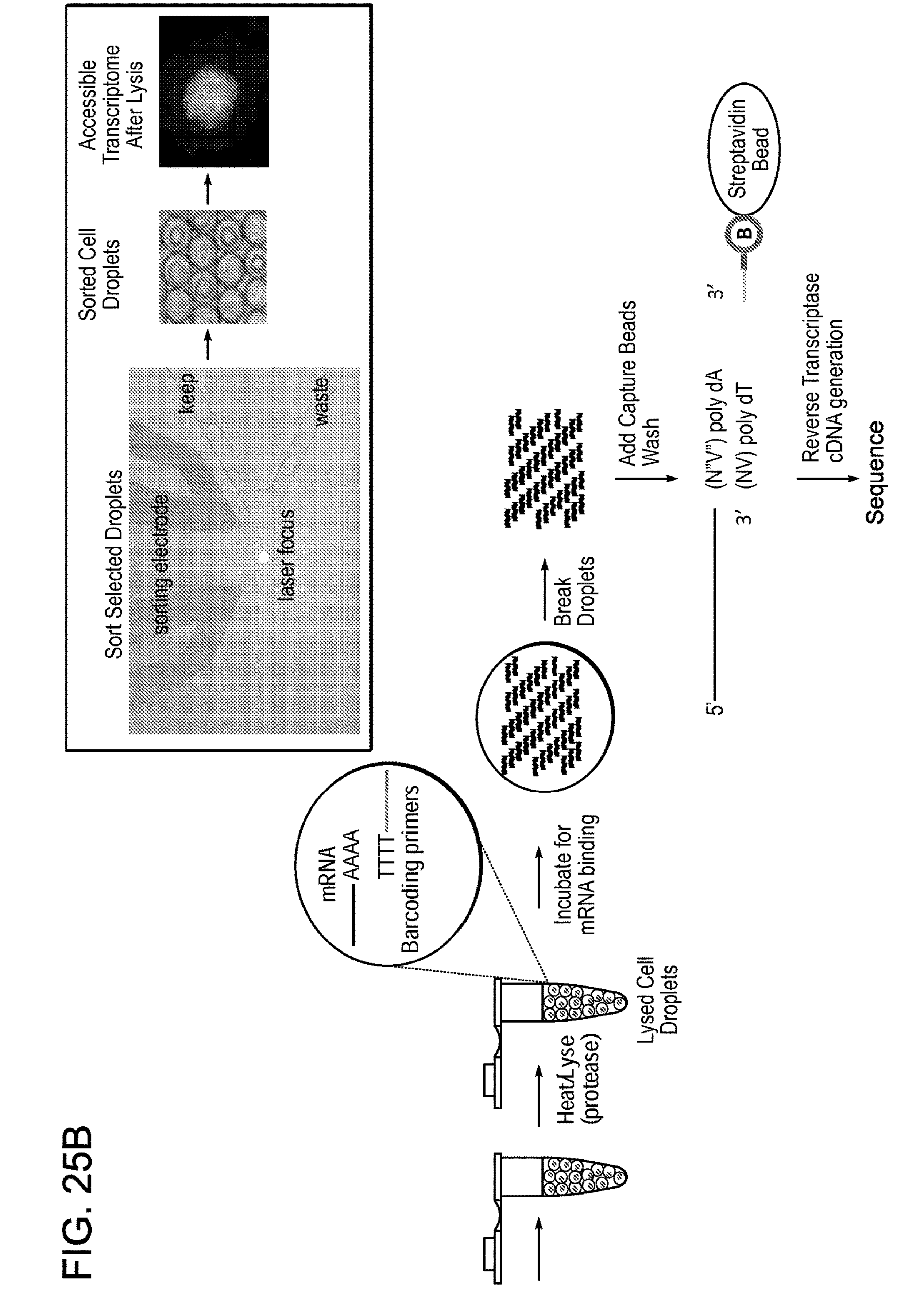
Figure 26A:
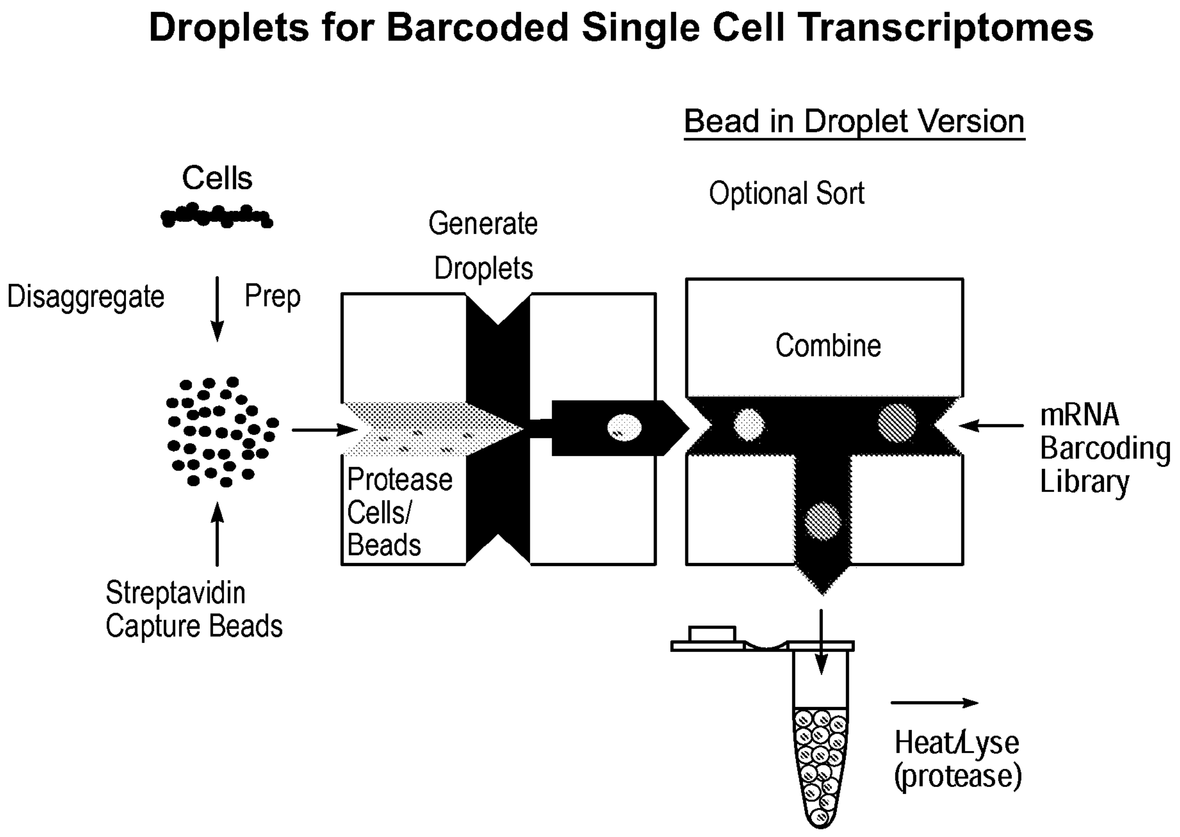

FIG. 25A-B shows a sorted cell workflow for barcoding transcriptomes from single cells using a barcode library in a detergent lysis buffer. FIG. 25A-B shows a workflow for barcoding transcriptomes from single cells. FIG. 26A-B is an alternative flowchart depicting the steps associated with isolation, encapsulation, molecular labeling, sorting and analysis of single cell transcriptomes using fluidic droplets (capture beads are included in the droplet library).

With these described modifications for target material being mRNA, the above described approaches to haplotyping and genotyping can be applied to transcriptomes.

Biomarker Counting

In certain embodiments, a universal barcode droplet library (e.g., of a bind-and-ligate type) is used to count biomarkers associated with a single cell.

Figure 27A:
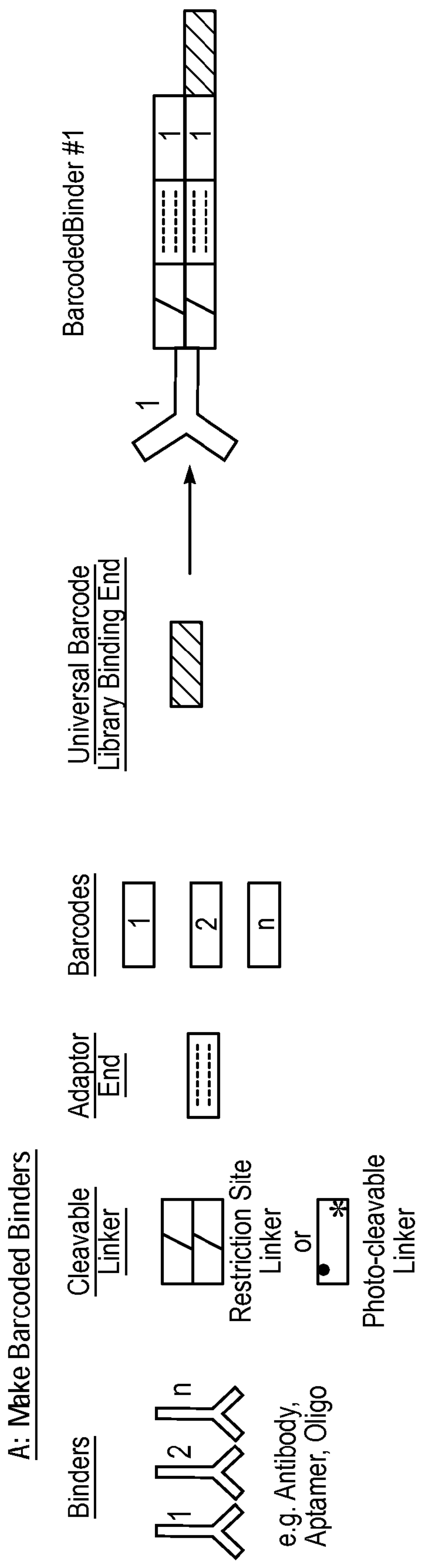
FIGS. 27A-C show barcoding biomarkers.
Figure 27B:
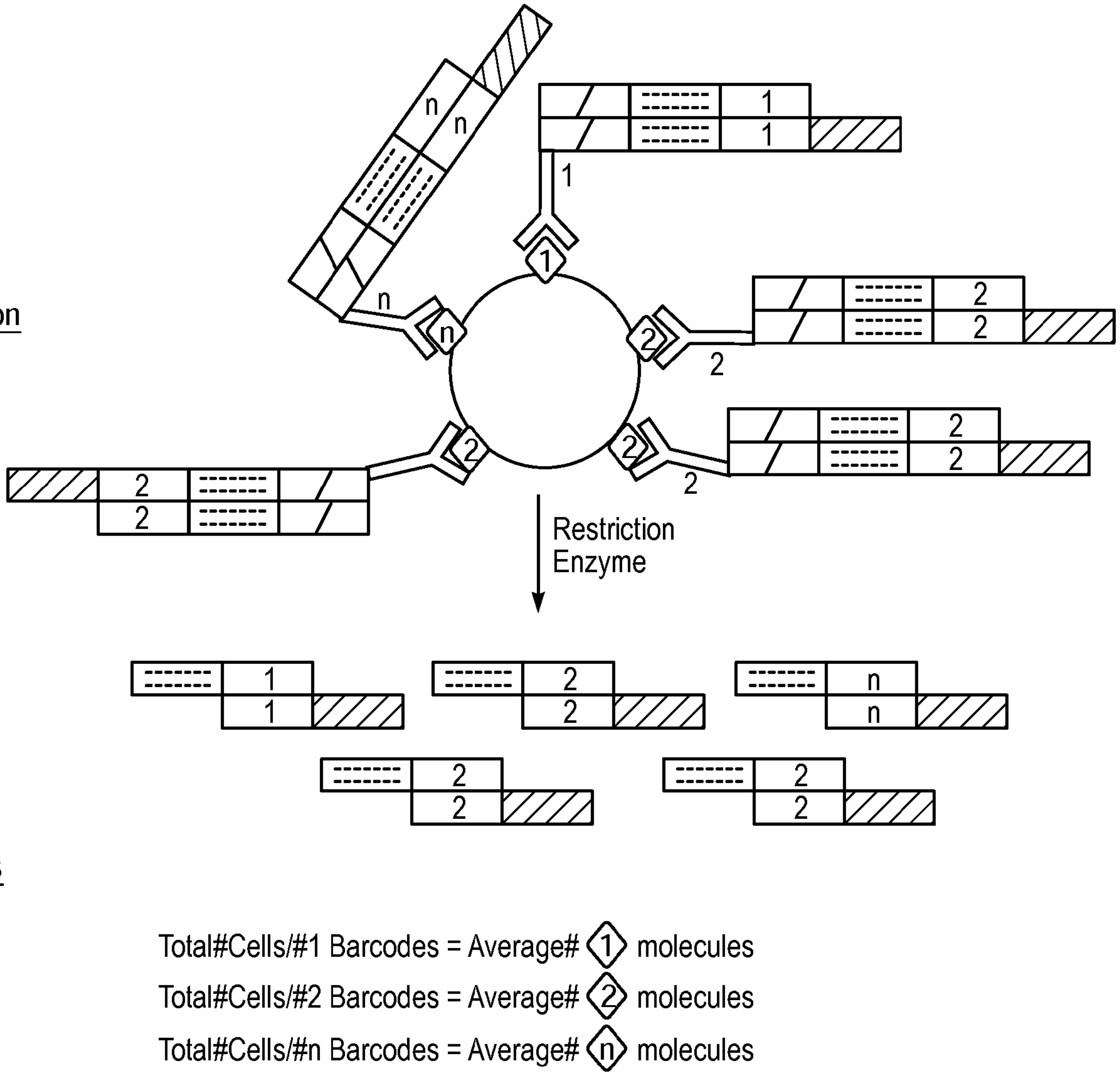
Figure 27C:
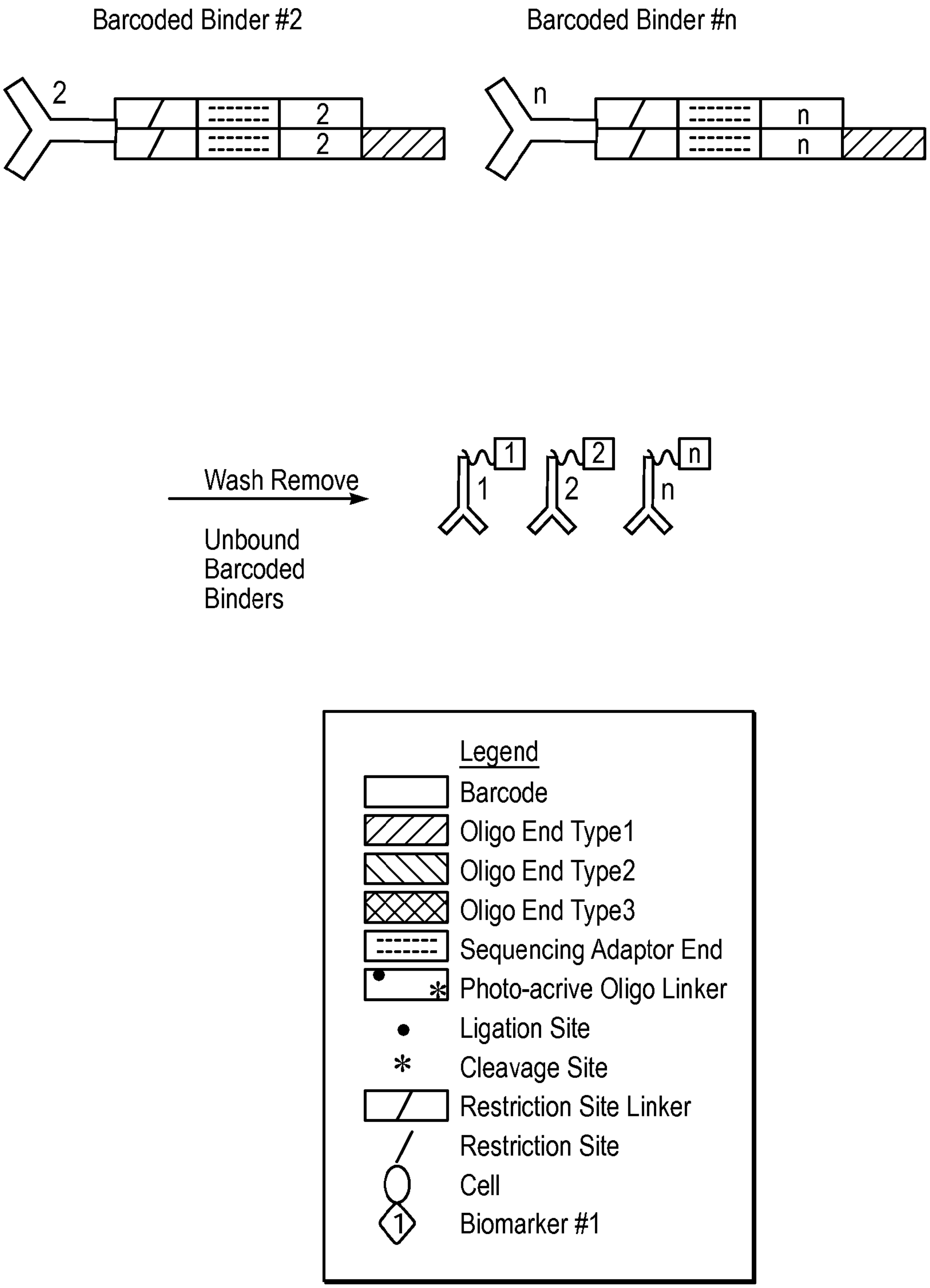

A barcode library can be used in combination with binding molecules that are also barcoded to provide target identification, linking information about the type and number of target molecules present in a sample with their co-incident presence in the same droplet. FIG. 27A-C first illustrates the construction of sticky-ended barcoded binders, and then shows how they can be used for generating cell population averages of the identified biomarkers, before FIGS. 28-31 illustrates how the same sticky-ended barcoded binder constructions work using dropletized versions of both the samples and the barcoded reagents.

Figure 32A:
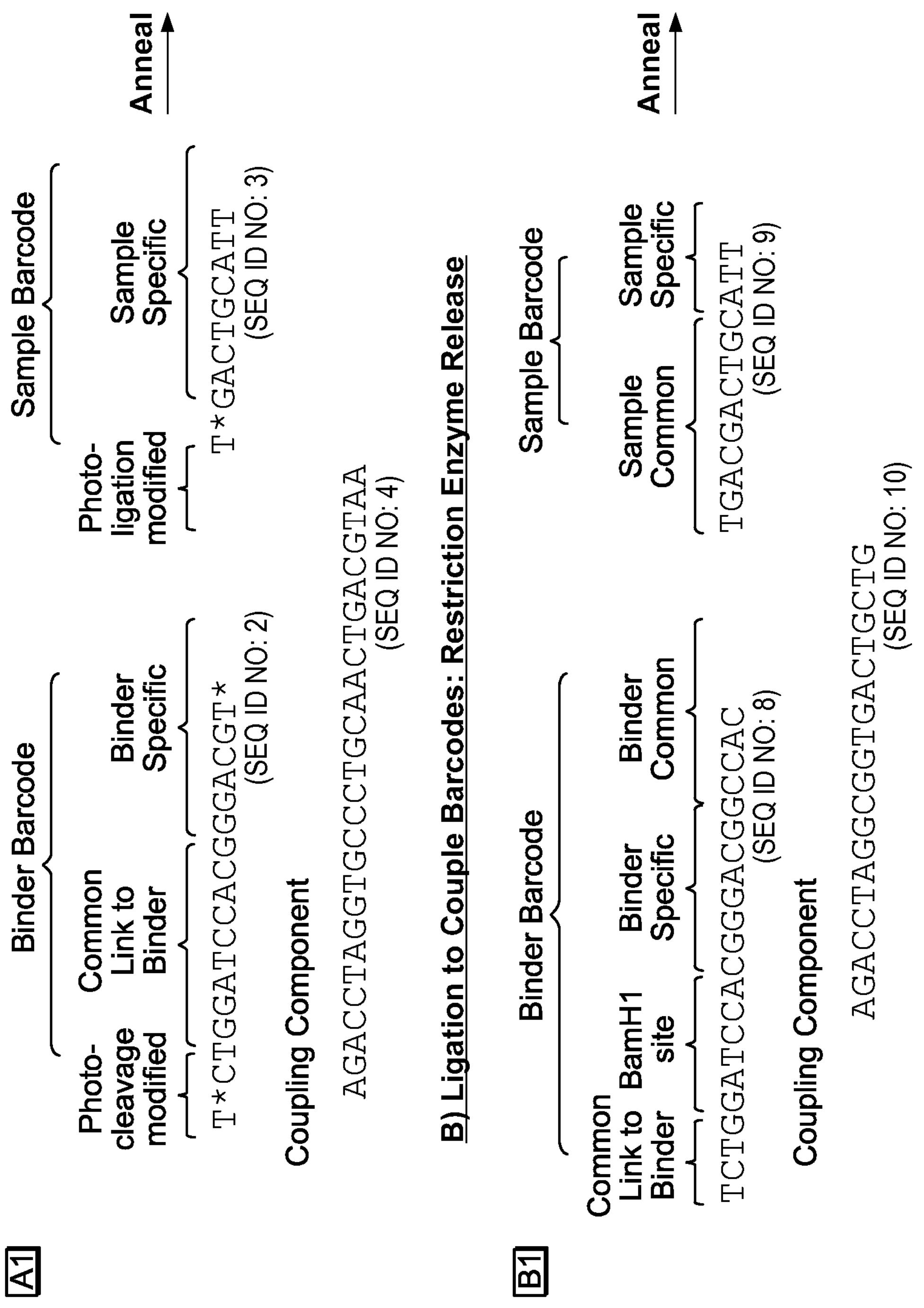
FIGS. 32A-C show motifs for linking and releasing barcodes.
Figure 32B:
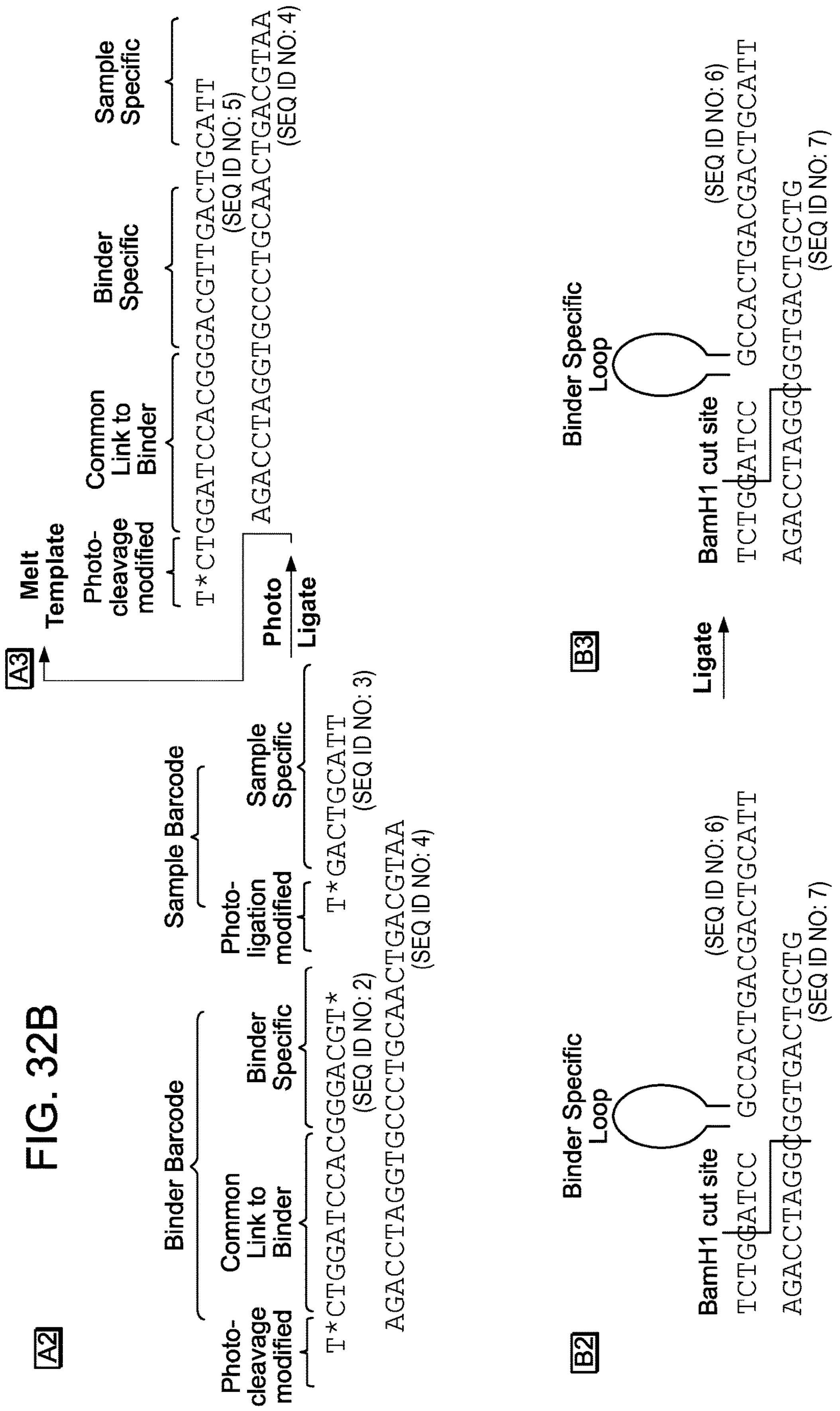
Figure 32C:
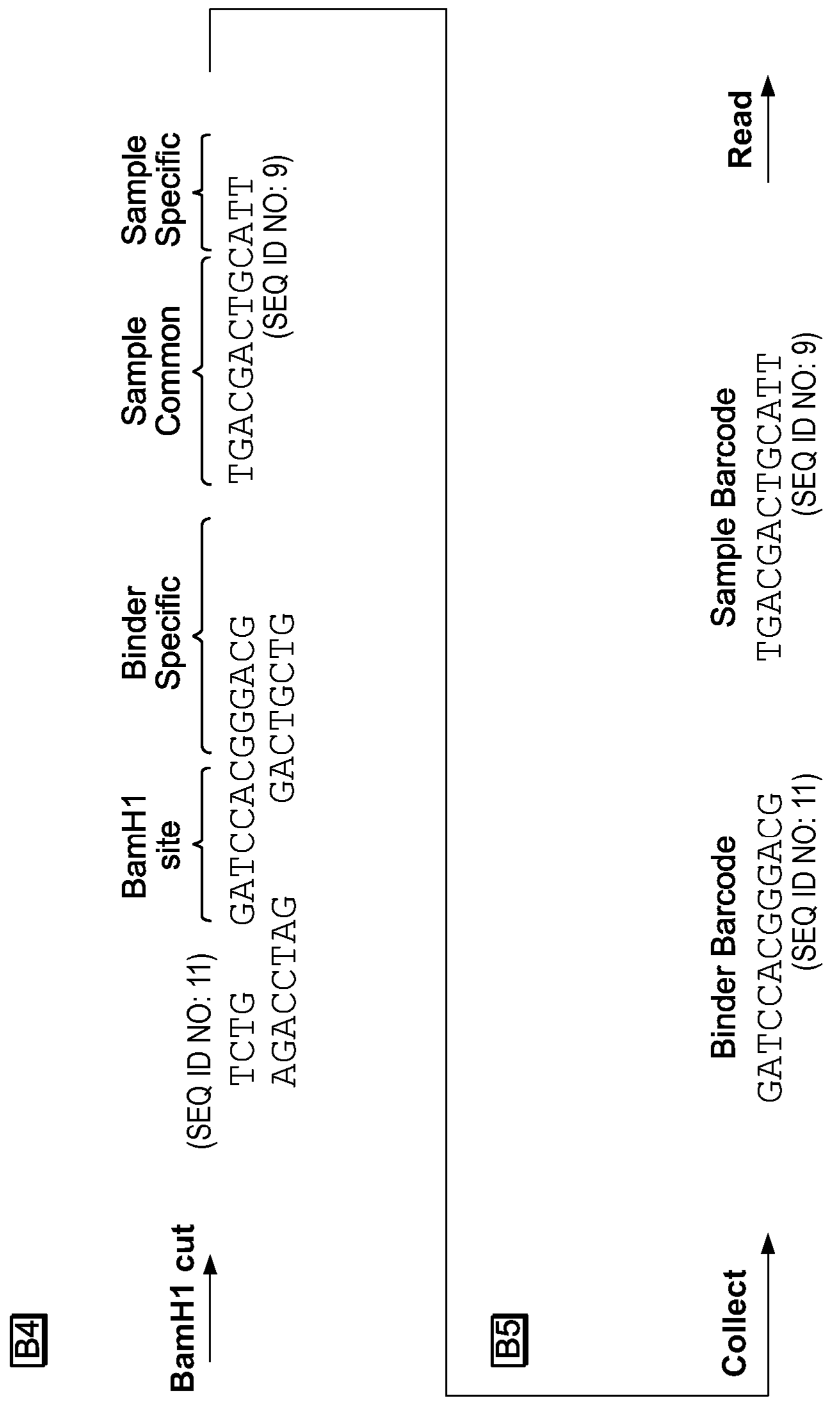

The barcoded binding reagents are constructed by linking in a reversible manner a sticky-end oligonucleotide onto the binding reagent (e.g. antibody binding reagents are shown in FIGS. 27A-31D). Two examples of linking motifs tying the barcode to the binder are shown in FIG. 32A-C, one using a photo-activatable linking base 5-prime to a photo-cleavable base and the other using a restriction enzyme cleavage site 5-prime to the barcode that identifies the binding species. By linking an oligonucleotide that contains a cleavable linker, an optional adaptor sequence (to enable interfacing with the downstream sequencing method), a barcode identifying the binding species, and a sticky-end for combining with the complimentary sticky-ended barcode library to a particular binding species, a 'sticky-ended barcoded binder' is created (e.g. barcoded binder #1 in FIG. 27A-C). A variety of commercial kits and reagents are available for linking the oligonucleotide to the binder (e.g. chemical cross-linking agents for linking to a protein binder, hybridization and ligation or synthesis of the entire sequence for linking with an oligonucleotide binder). A second similar set of motifs linking a second binding species to a second identifying barcode with the same universal sticky-end is constructed as 'barcoded binder #2'. Additional barcoded binders are constructed such that a set of n barcoded binders is available for use either to determine bulk average quantification of biomarkers (FIG. 27A-C), or for droplet-based quantification of single species (e.g. single cells, single capture reagents, etc.).

FIG. 27A-C shows the workflow for determination of biomarker averages for a cell population. The set of barcoded binders is incubated with the cell population, resulting in localization of the barcoded binders on the cell biomarkers (e.g. biomarker #1 on the cell surface is bound by antibody #1, which has a linked oligonucleotide sequence that encodes the identity of antibody #1). After washing unbound binders, the linkage to the binder is cleaved (e.g. with a restriction enzyme), and the released barcode is quantified (e.g. by sequencing). The total number of cells used divided by the total number of antibody #1 barcodes will give the average number of biomarker #1 molecules on a cell in the population. The total number of cells used divided by the total number of antibody #2 barcodes will give the average number of biomarker #2 molecules on a cell in the population, and so on. As there is no limit to the number of different types of barcoded binders that can be used to bind to the cell population (other than the number of separate constructions needed of barcoded binders), this method has unlimited multiplexing capability.

Compared to FIG. 27A-C, which shows steps for average (i.e., "bulk") biomarker analysis, FIGS. 28-31 show a scheme for single-cell biomarker counting. Single-cell biomarker counting can include the same barcode binder construction, binding, and washing steps as shown in FIG. 27A-C. For single-cell biomarker counting, however, the labeled cells are individually loaded into droplets, and each droplet is combined with a droplet from a universal barcode droplet library (FIG. 28A-C and FIG. 29A-B show cell marker barcodes and universal barcodes of a sticky-end type, but any suitable type can be used). The cells can be loaded at a dilution such that most droplets are empty and the cell-containing droplets have a single cell. Each droplet that contains a single cell combines with a droplet that contains a unique barcode, such that all of the biomarkers on one cell will have an identical droplet-identifying barcode appended, thus enabling later determination of the set of biomarkers that were present on the same single cell.

Figure 28A:
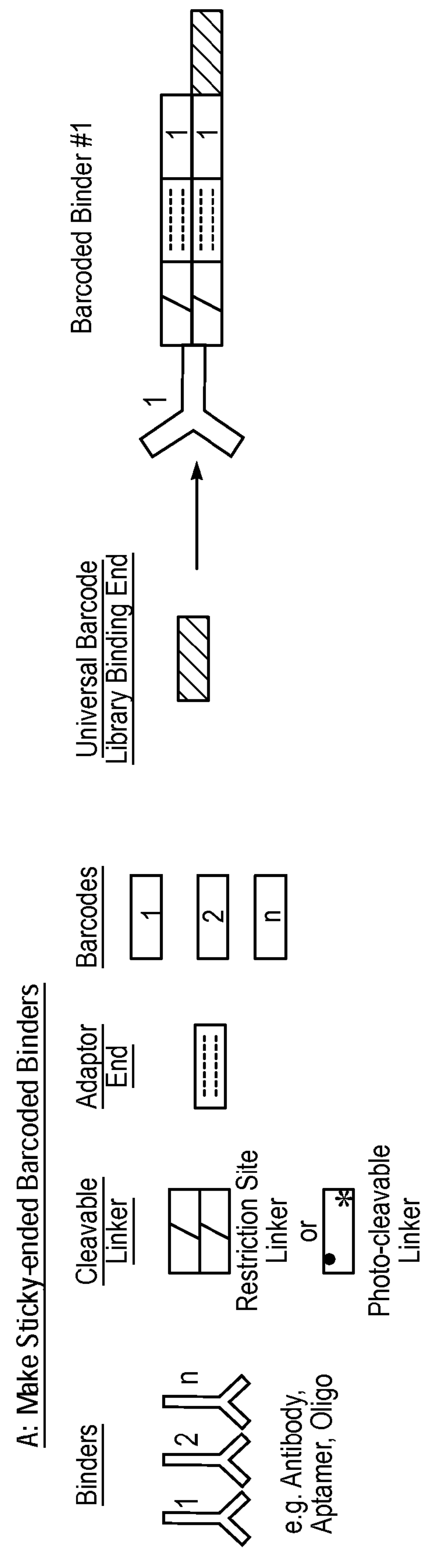
Figure 28B:
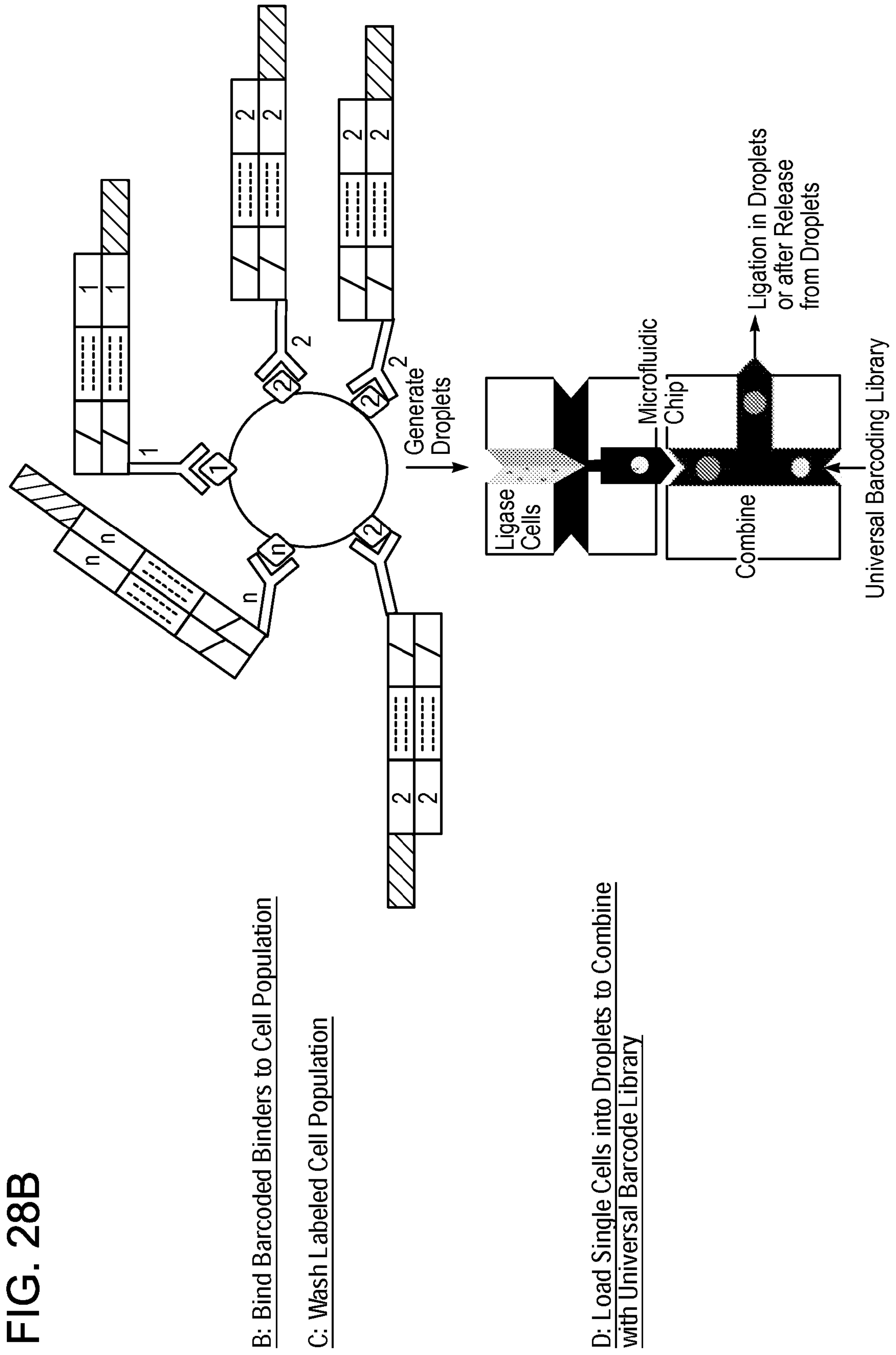
Figure 29A:
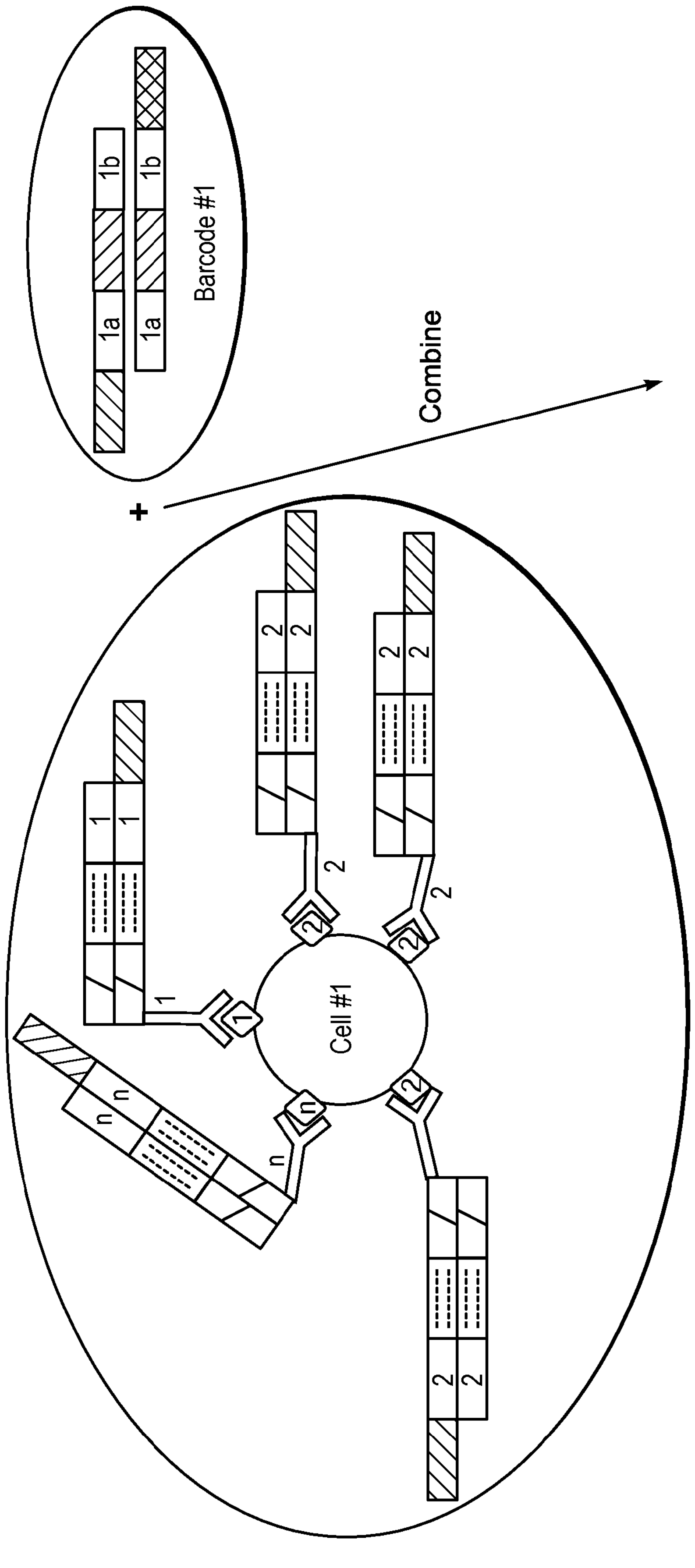
FIGS. 29A-B show a step for single cell digital biomarker counting.
Figure 29B:
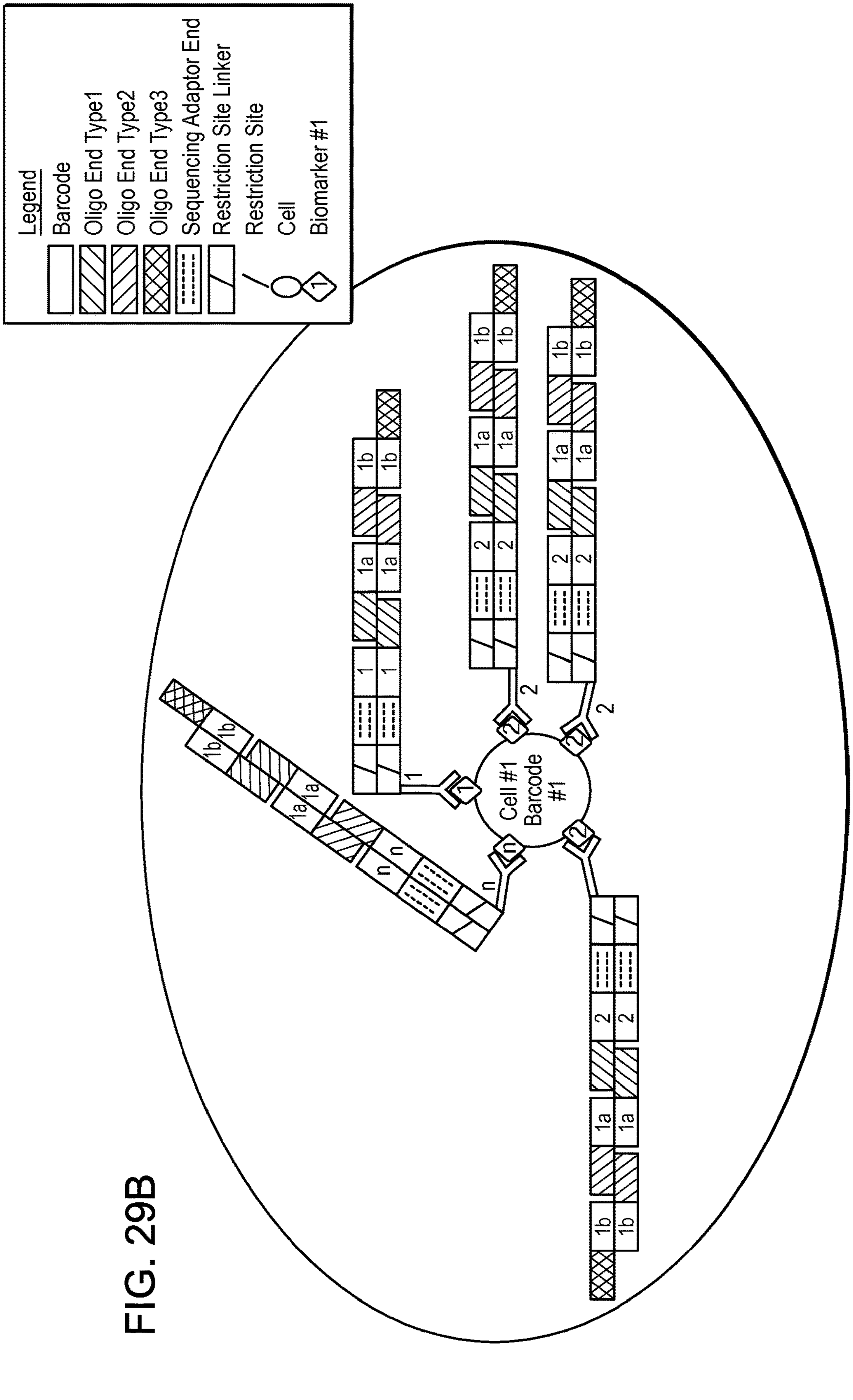
Figure 30A:
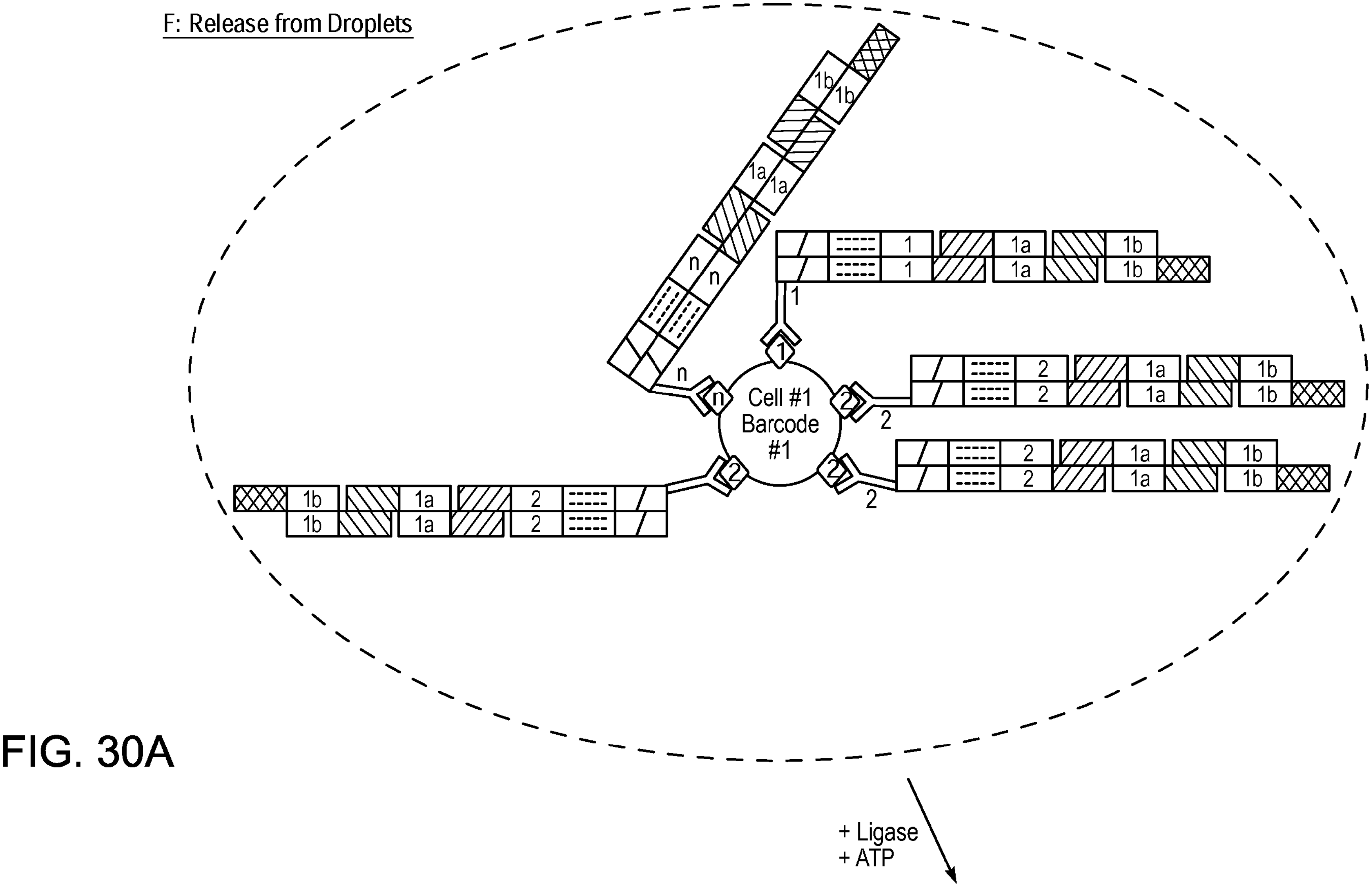
FIGS. 30A-B show a step for single cell digital biomarker counting.
Figure 30B:
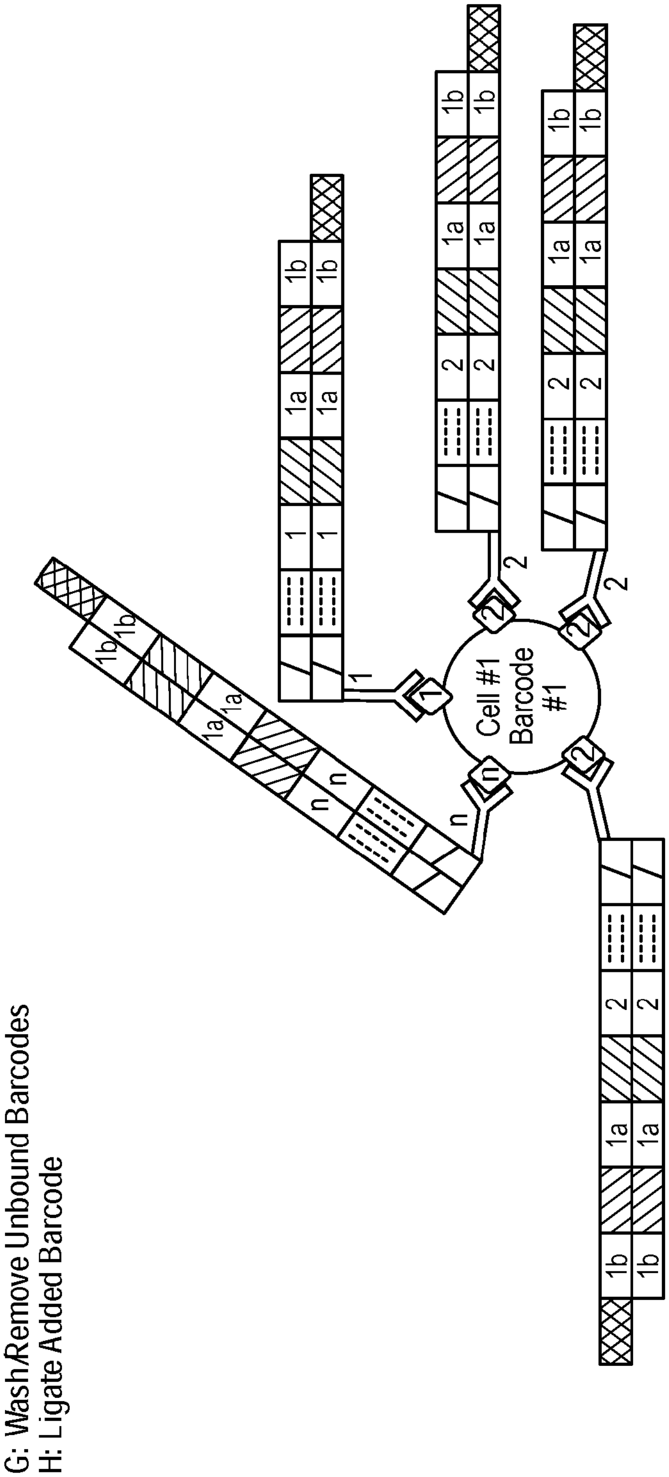
Figure 31A:
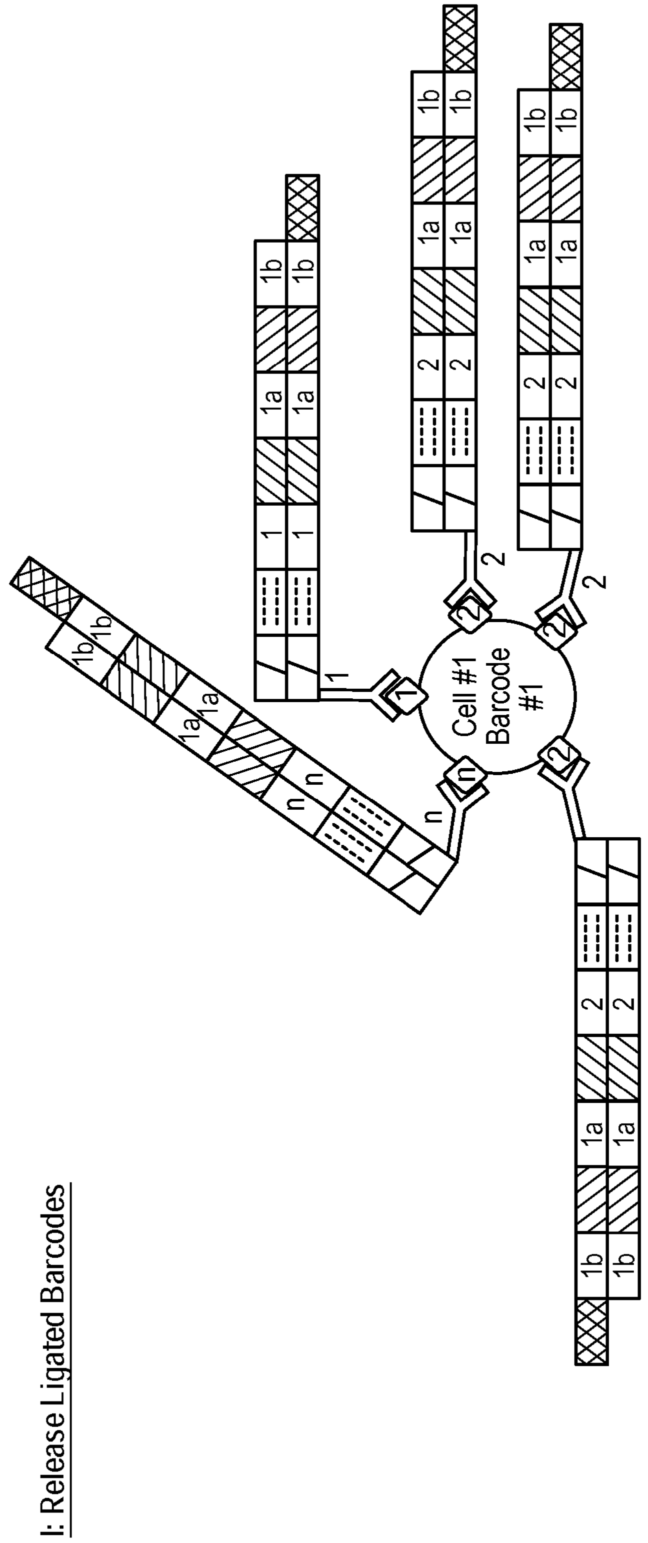
FIGS. 31A-D show a step for single cell digital biomarker counting.
Figure 31B:
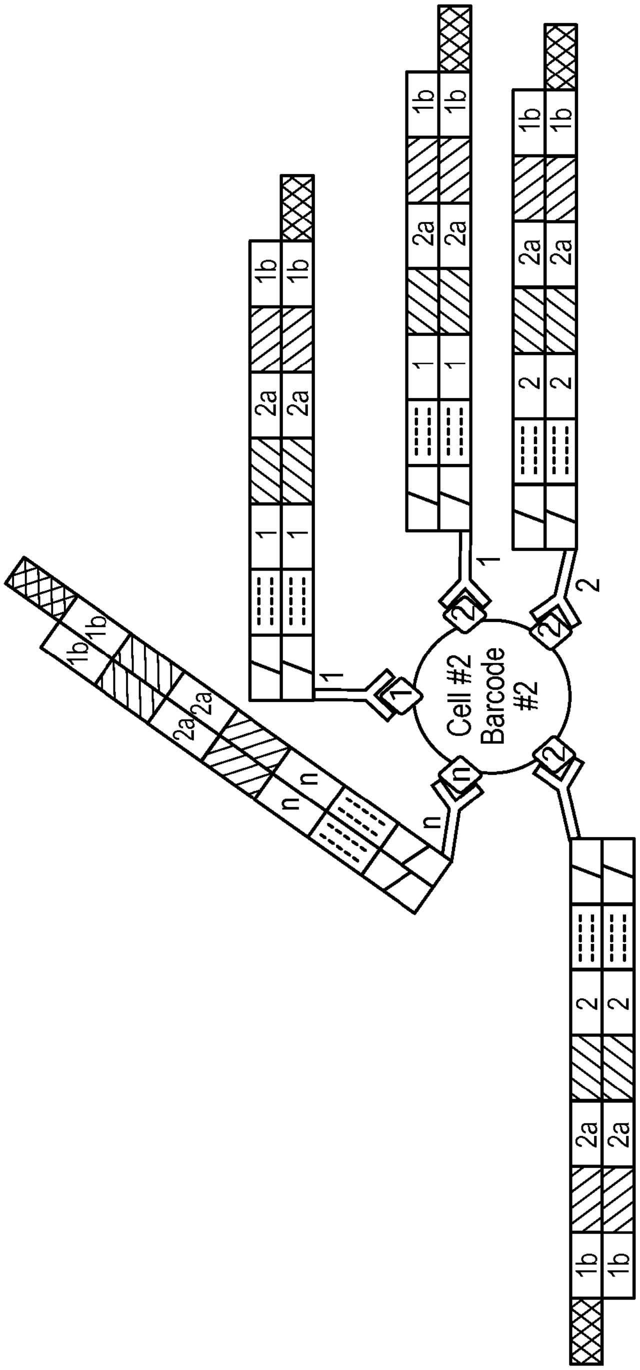
Figure 31C:
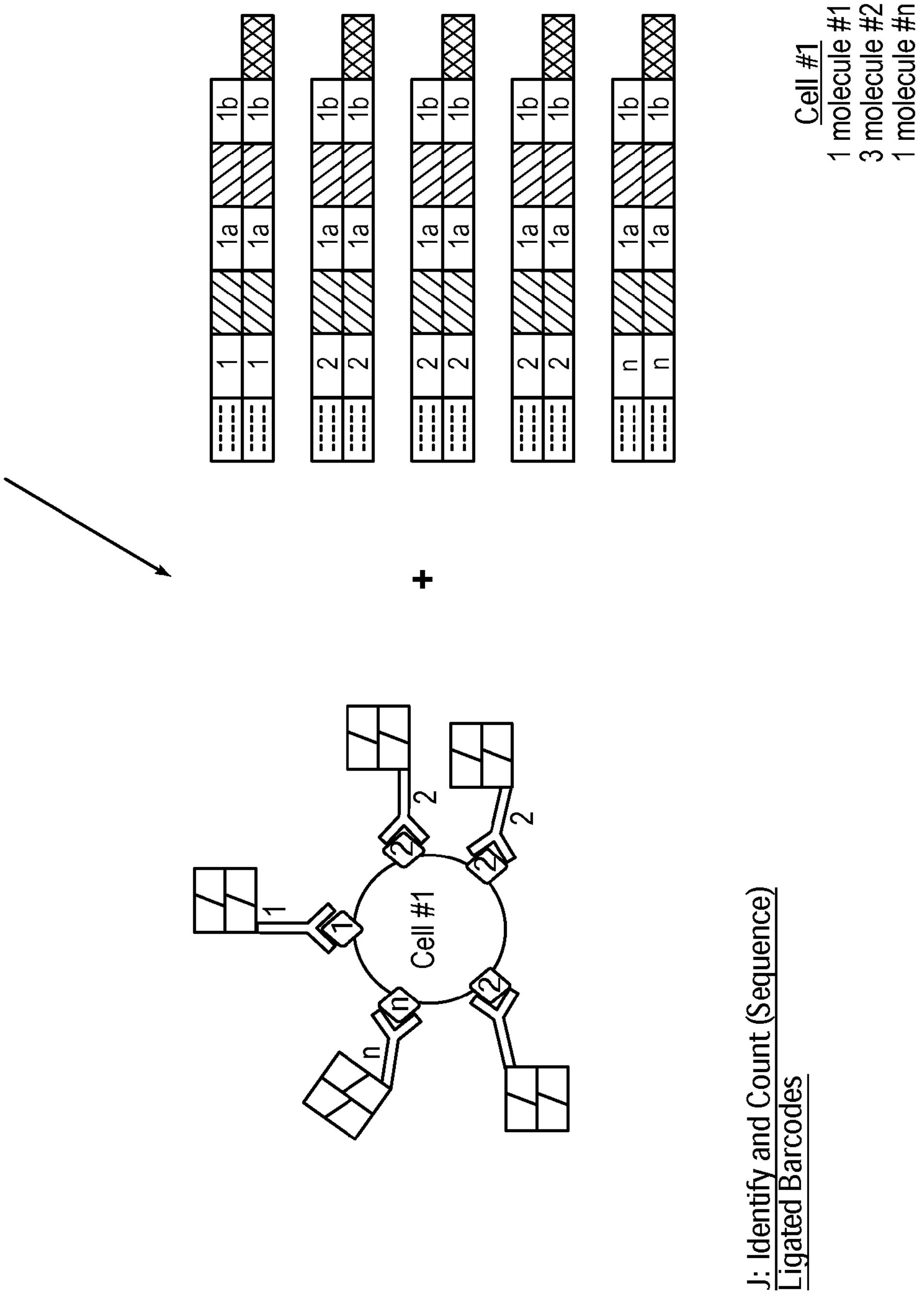
Figure 31D:
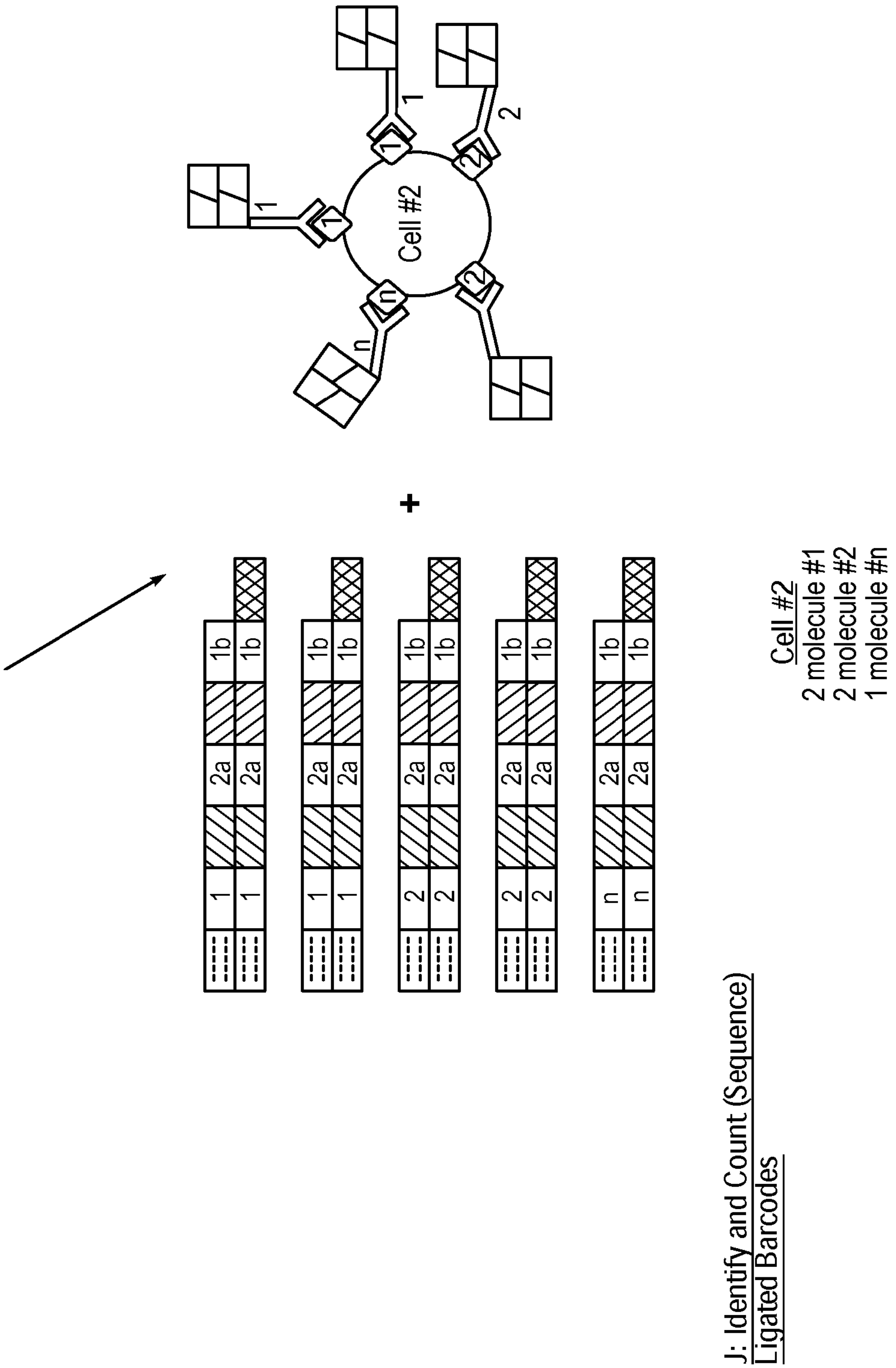

Use of a sticky-ended barcoding droplet library in combination with sample droplets enables collections of individual cells to have their biomarkers digitally counted, with different target components in a droplet being labeled with a unique, droplet-identifying barcode, allowing identification and digital quantification of targets present in the same droplet shown in FIG. 28A-C. The same unlimited multiplexing level for cell biomarker analysis is provided for individual cells as with the bulk averaged cell experiment, and the universal barcoding library can be scaled to have enough binding barcodes to uniquely label a very large number of single cells for digital biomarker analysis. Ligation of the target-identifying and droplet-identifying barcodes into a composite barcode, as shown in FIG. 29A-B, is followed by processing to read both sequence identity and counts of each composite barcode type (e.g. by sequencing, digital PCR, or microarray detection).

The individual steps for this workflow are shown in FIGS. 28A-31D. FIG. 28, panel A shows the preparation of sticky-ended barcoded binders. Panel B shows binding barcoded binders to cell population. Cells can be washed to remove unbound barcoded binders (Panel C) and then loaded into a microfluidic device to generate single cell droplets (Panel D) (e.g., loaded at such a dilution that cell-containing droplets primarily contain single cells according to Poisson statistics). In FIG. 29, Panel E shows sample droplets being combined with the universal barcoding droplet library (combination is achieved by droplet interdigitation followed by dielectrophoretic pair-wise coalescence). Panel F in FIG. 30 releasing the barcoded cells into a single aqueous phase (e.g., lysis by a chemical droplet destabilizer). Cells are washed to remove unbound material (Panel G). Ligase and ATP are added to ligate the annealed composite barcodes (alternatively, the ligase and ATP can be included in the droplet for in-droplet ligation), as shown in Panel H. In FIG. 31, Panel I shows releasing the barcodes by cleavage (e.g. restriction enzyme). According to Panel J, information from the ligated composite barcode can be read (e.g. NextGen sequencer). Note that the barcode members shown in Figure J can be optionally ligated back together into constructs of any length before sequencing according to any known method. Sequencing reveals the type and number of each barcode present. The type and number of each barcode corresponds to the type and number of biomarkers present on each individual cell. Cell #1-associated biomarkers are identified by the 5-prime binder barcode (e.g. biomarker #1 is bound by binder #1 that contains barcode #1 ligated to cell identifier barcode #1a:1b) and the number of each type of biomarker on that cell matches the number of barcodes with all three sequences (i.e. 1:1a:1b). In this example, Cell #1 has 1 molecule of biomarker #1, 3 molecules of biomarker #2, and 1 molecule of biomarker #n; Cell #2 has 2 molecules of biomarker #1, 2 molecules of biomarker #2, and 1 molecule of biomarker #n.

Note that in the foregoing, a cleavable linker is included in barcoded binders (Panel A in FIG. 27A-C); barcode products are ligated together (Panel H, FIG. 30); and the cleavable linkers are subsequently released (Panel I, FIG. 31). The invention provides methods for linking and releasing oligos. Methods of cleaving and releasing are not limited to the examples shown in FIGS. 27-30, and may be used generally in methods of the invention.

FIG. 32A-C illustrates methods for linking and for releasing barcodes. FIG. 32, panel A, shows coupling barcodes by photoligation and releasing barcodes by photocleavage. FIG. 32, panel B, illustrates including restriction sites or binder-specific loops for cleavage enzymes for subsequent cleavage of barcodes (or for blocking of enzymes).

Barcodes with dPCR

The invention generally provides methods for labeling target material including providing copies of a construct that includes a unique N-mer and a functional N-mer. In some embodiments, constructs of the invention are further analyzed in combination with digital PCR.

For example, sticky-ended Barcodes containing dPCR optimized counter sequences can be provided for use in counting barcoded digital sandwich assays. The optimized multiplexing dPCR set can be used in conjunction with dELISA panels of any "plexity" including, for example, moderate-plex (e.g. 15-100 plex for just FAM/VIC probes) or higher-plex for any dELISA panel known in the art (e.g. cytokine panel; viral antigen panel; bacterial antigen panel).

In some embodiments, barcodes can be used with digital PCR for a copy-number variant (CNV) analysis. Methods include generating a sticky-ended barcode set that will hybridize to a set of targets that have disease-associated copy number variation. Using the non-amplified version of the priming universal barcode library on purified DNA will result in digitally countable (e.g. by optimized multiplex dPCR) CNV analysis. If a diverse collection of these sticky-ended barcoded priming probe pairs are provided in a droplet (i.e. each library droplet has the same barcode, but a mixture of targeting probes) this collection can be combined with genetic material (e.g., a genome, transcriptome, a chromosome, a target nucleic acid). The constructs are allowed to hybridize to the target, and then detected or counted according to the methods described herein. From these results, variations in copy number can be ascertained.

Barcoded Binders

Figure 33A:
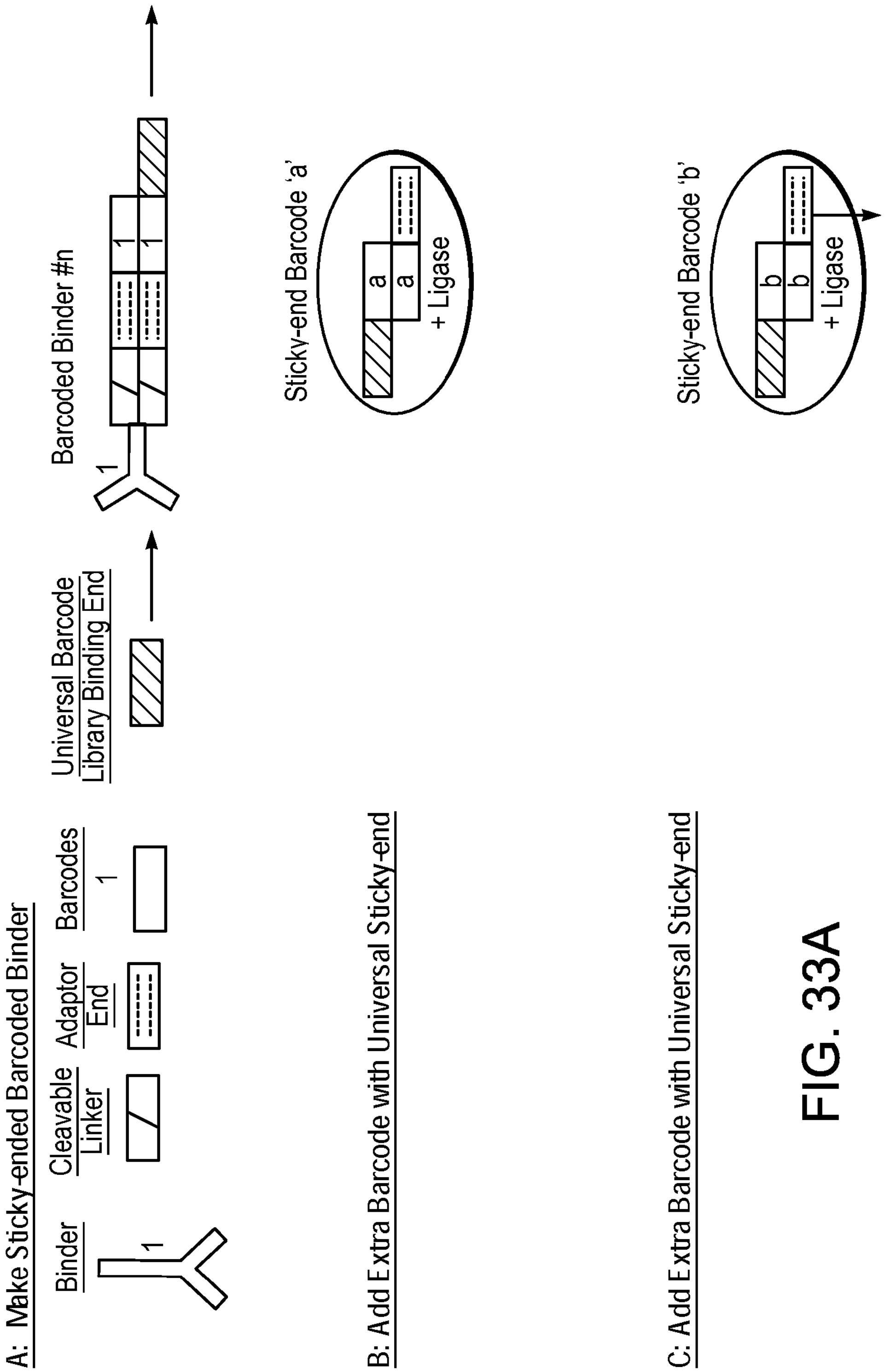
FIGS. 33A-B show a workflow for digital droplet proteomics using barcoded antibodies.
Figure 33B:
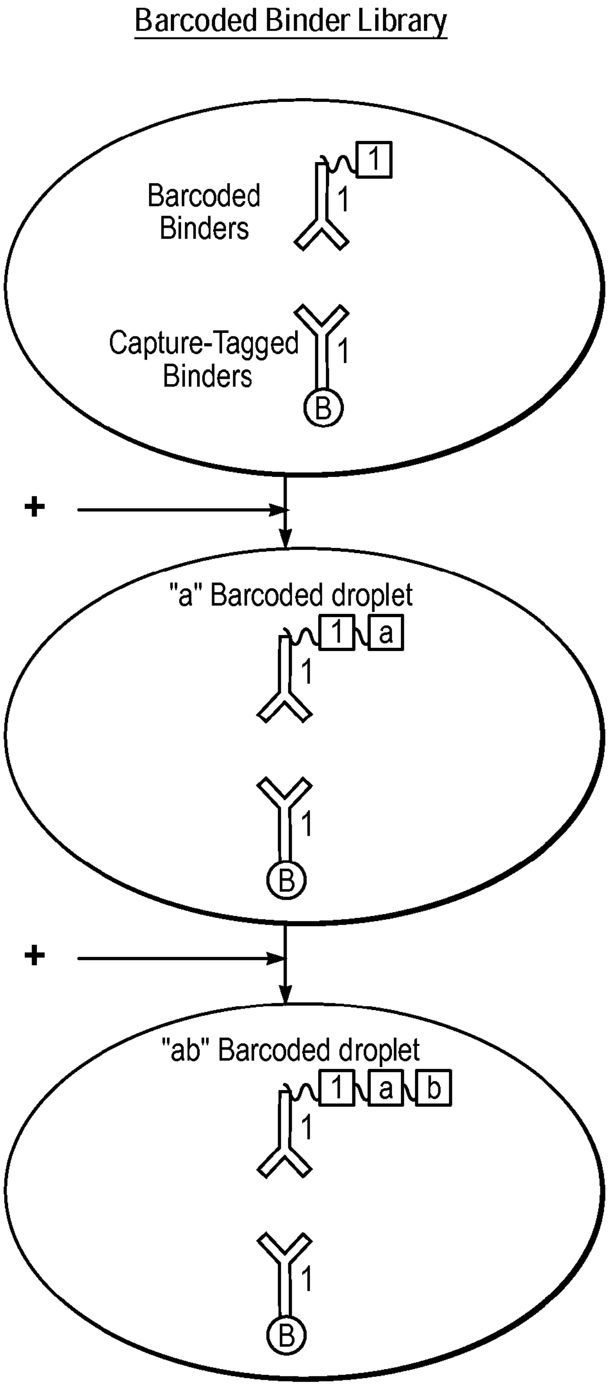

FIG. 33A-B depicts barcoding binders generally (e.g., for digital proteomics). Binders are shown in a form generally representing an antibody for purposes of illustration, but methods of barcoding binders are not labeled to antibodies and include any known binder. As shown in Panel A, a barcode is attached to a binder, optionally via a cleavable linker and adaptor end. The barcoded binder can be further functionalized by including an optional universal barcode library binding end. The binder shown in a droplet on the right side of Panel A can also be provided with a binder that is capture-tagged (for example, with biotin) for subsequent selective capture of target material.

Panel B illustrates an optional additional step for adding additional barcode information to the barcoded binder. A sticky-end barcode is merged into the droplet with ligase, the sticky ends hybridize, and the construct is ligated together. This produces a binder linked to a barcode including barcode information from two supplied barcodes.

As shown in Panel C, this step can optionally be repeated—any number of times—to produce barcodes of increasing complexity, or greater numbers of unique barcodes.

While additional barcodes are shown here being added with ligase, this is optional. Barcodes can be hybridized on without ligation. Additional barcodes can optionally be added with strand-displacement polymerase or transposase. Suitable binders include, without limit, antibodies, aptamers, nucleic acids, proteins, cofactors, and other binding molecules discussed elsewhere herein.

Figure 34A:
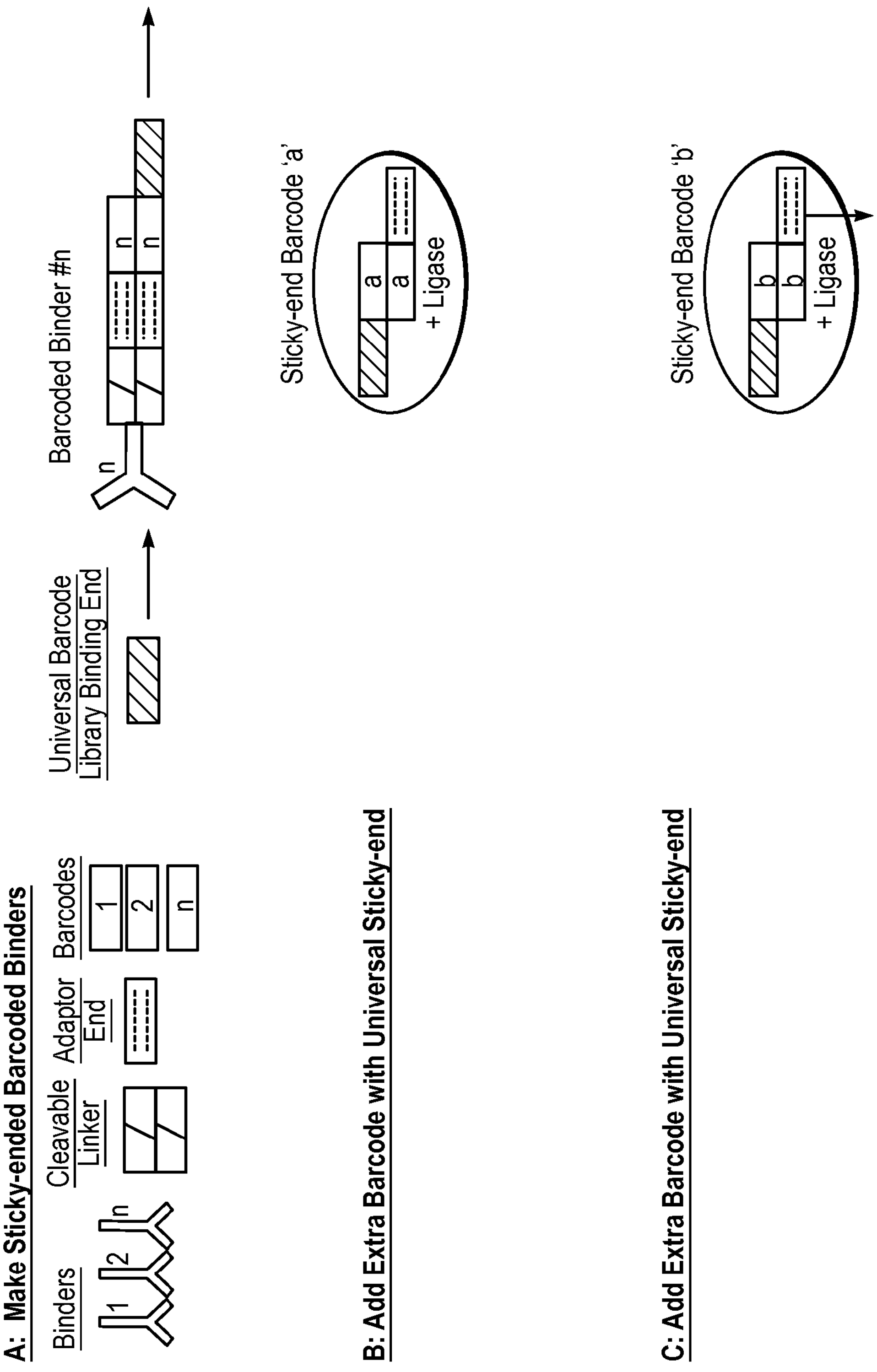
FIGS. 34A-B show barcoding a binder.
Figure 34B:
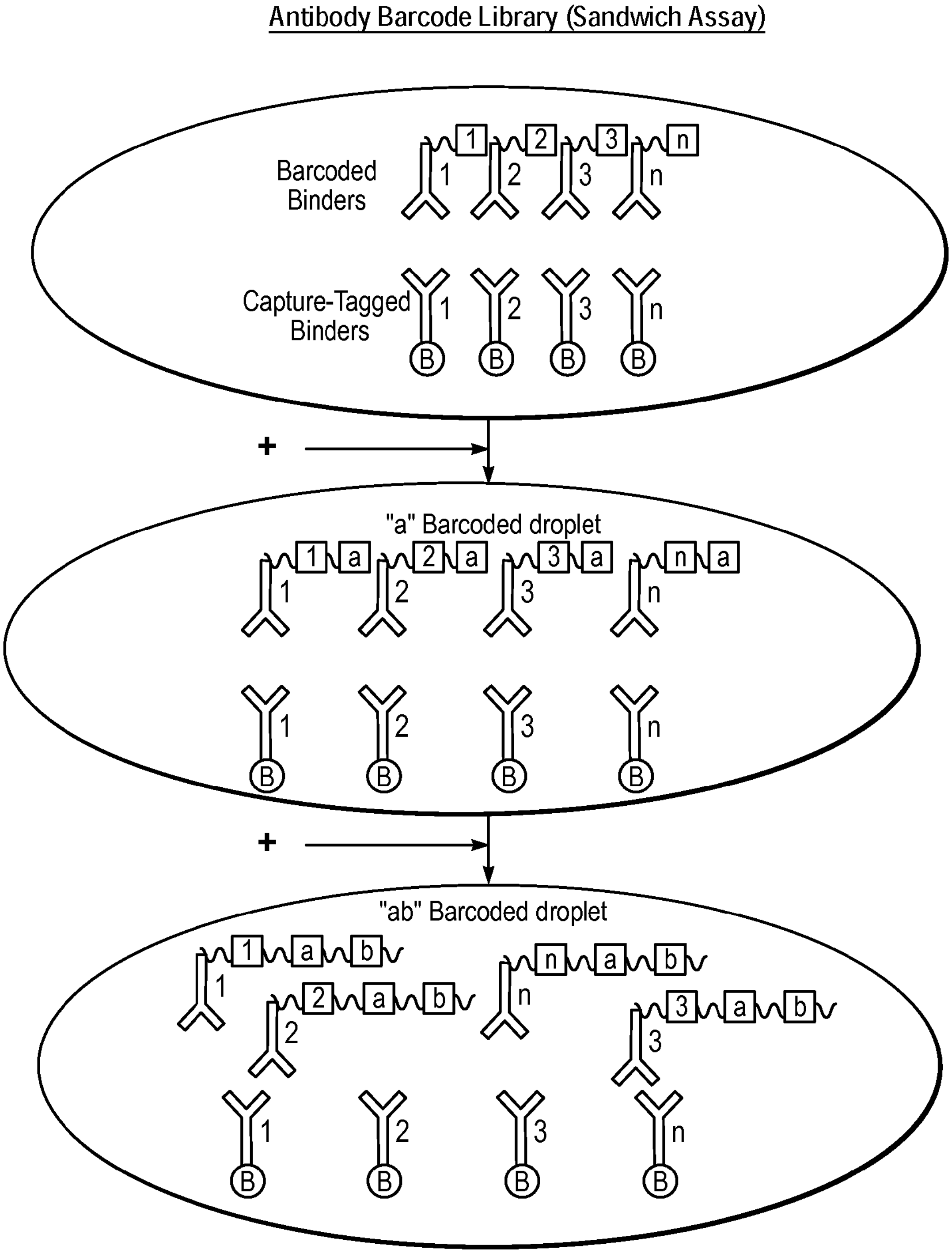

FIG. 34A-B shows an approach to high-plex barcoding of binders. Steps shown in FIG. 34A-B are generally followed, although multiple binders are provided. In a first step (e.g., Panel A of FIG. 34A-B), different binders are first individually barcoded. The second barcoding step (e.g., Panel B) then adds a droplet-specific barcode to the multiple binders.

Barcode Sandwich Assays

Figure 35A:
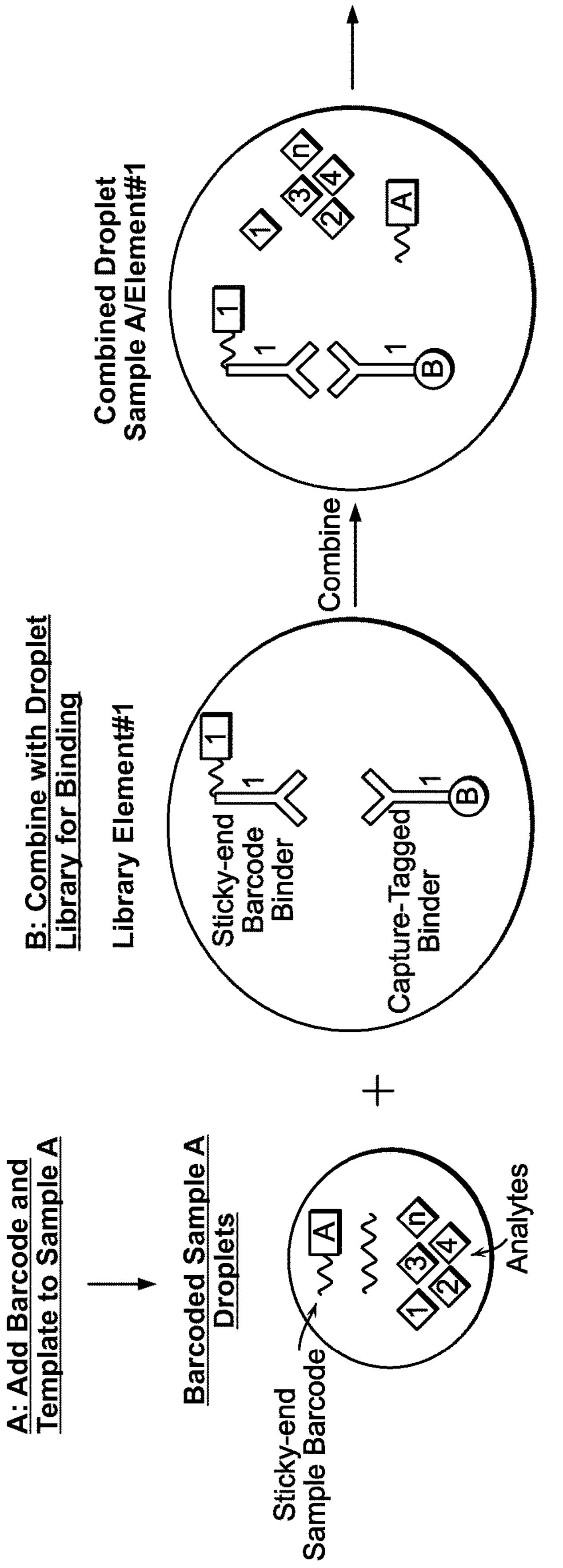
FIGS. 35A-B are a schematic depicting an exemplary workflow of a sandwich assay.
Figure 35B:
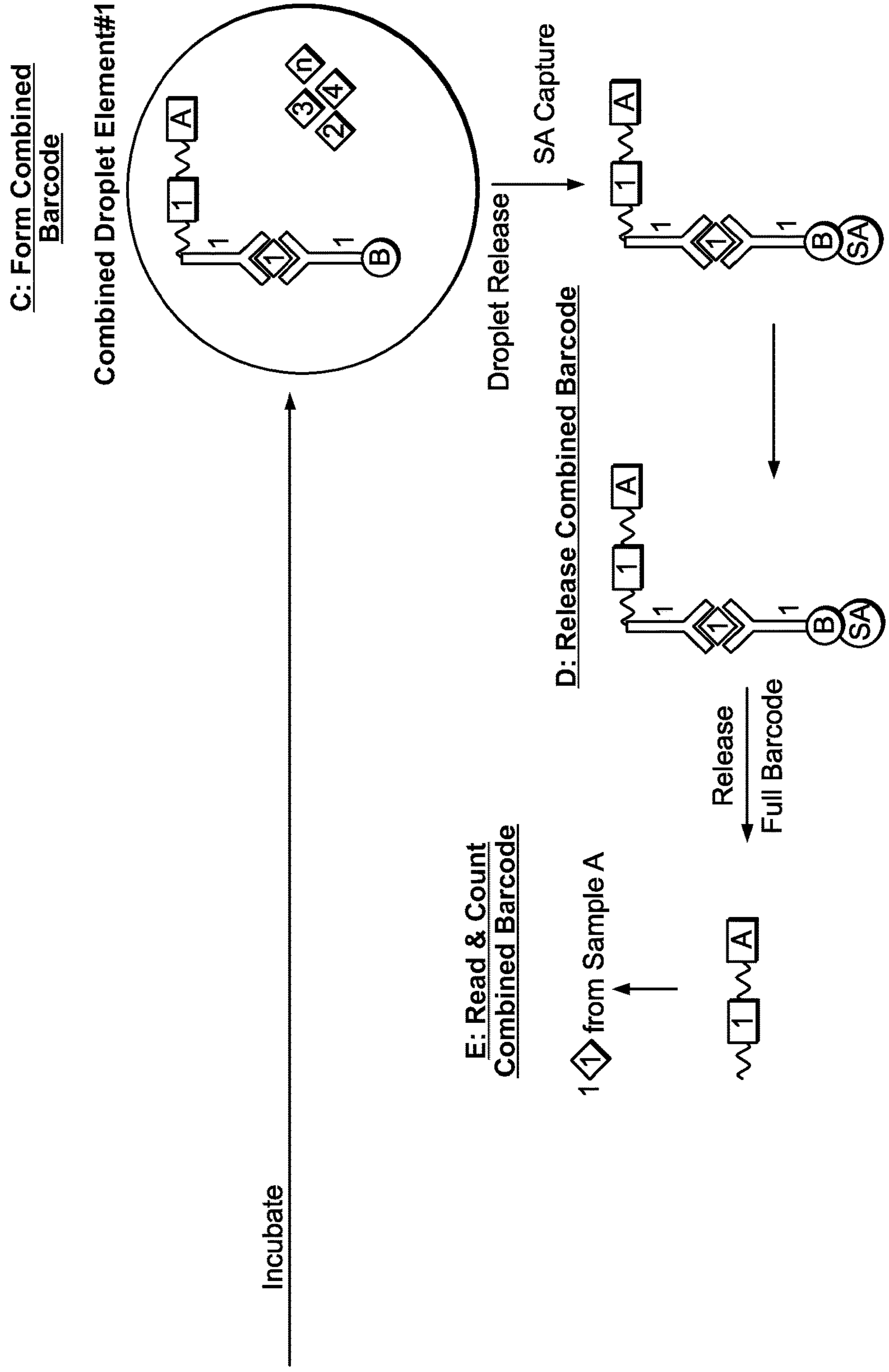

In certain embodiments, an ELISA sandwich can be formed, for example, by combining a serum droplet with a droplet containing ELISA reagents (e.g., with one antibody immobilized on a bead and the other in solution). FIG. 35A-B shows a general schematic for a sandwich assay using barcoded binders.

This aspect of the invention involves several components, such as creating tagged binding reagent droplet libraries consisting of individual members targeting single protein markers, with expandability to high levels of multiplexing (e.g. 1000 member library targets 1000 proteins/motifs); binding samples to the tagged detecting molecules in picoliter volume droplets in a highly parallel "single-plex" manner, performing pair-wise combination of droplet reagent libraries and sample droplets; digital counting of productive binding events after washing and release of a readable DNA sequence tag.

Although the instant invention can utilize any species suitable for binding to a protein or protein fragment (e.g. aptamers, affibodies), in one example provided herein, the binding species include antibody reagents. The sandwich principle will be identical (described for antibodies), using appropriate concentrations of two antibodies binding to different epitopes of the same target antigen for co-encapsulation in the reagent droplet. One of the antibodies can be biotinylated (available from many commercial sources, or can be made using a number of kits) and the other can be covalently tagged with a synthetic oligonucleotide. The oligonucleotide tags will be synthesized as amine-linked oligos by a commercial manufacturer (e.g. Sigma Genosys, IDT) and can include restriction enzyme motifs if desired. Well established methods for performing the oligo-tagging of antibodies are used.

Sandwich antibody pairs for many biologically and therapeutically relevant (e.g., cancer) targets are readily available. In one example, well characterized pairs are selected that bind proteins and protein motifs that are important in common cancer signaling pathways (using cell lysate samples), or which have been identified as relevant clinical biomarkers (using serum samples). Initial candidates for target proteins in cell lysate analysis include: Akt and phosphorylated AKT, EGFR and phosphorylated EGFR, Src and phosphorylated Src and TNFRI/II. Initial targets in serum include, but are not limited to: PSA, soluble TNFRI/II, soluble RANKL, CEA, AFP, CA125, beta2 microglobin.

Automated equipment for generation of primer droplet libraries is described above. This equipment can be used to generate a number of types of droplet libraries, including viral particles, antibodies, and beads. For the binding reagent library, a standard microtiter plate is prepared containing each mixed pair of sandwich reagents at the appropriate concentration as input to the library generation process.

Library reagent droplets of two types are prepared, with or without a streptavidin (SA) capture bead. The binding reagent droplet library is mixed and aliquoted for use in assay development. In preferred embodiments, a droplet library is stable and can be stored for longer than a year (e.g., 4° C.).

Figure 37A:
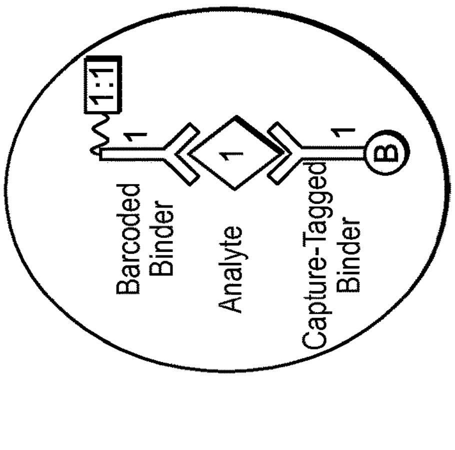
FIGS. 37A-J show types of sandwich assays.
Figure 37B:
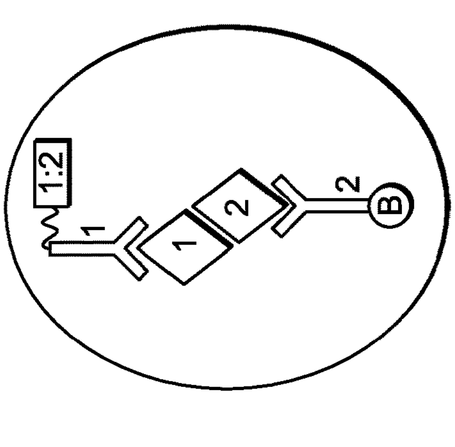
Figure 37C:
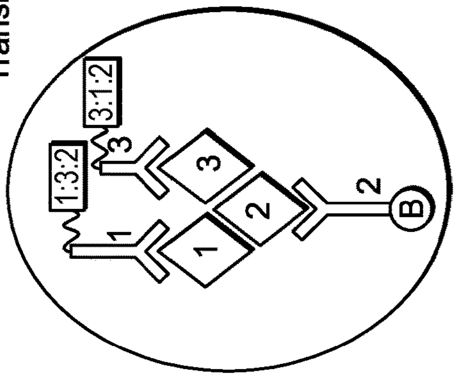
Figure 37D:
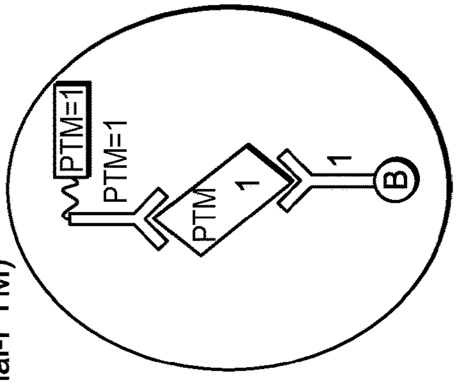
Figure 37E:
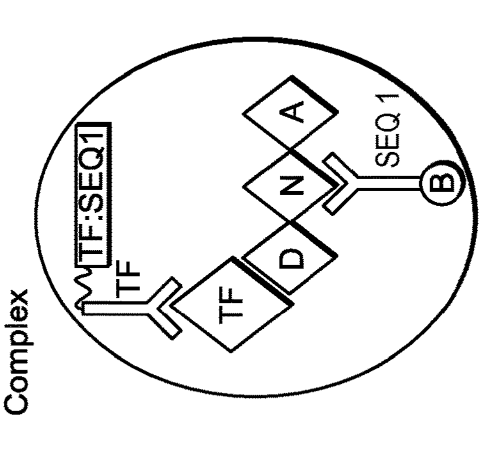
Figure 37F:
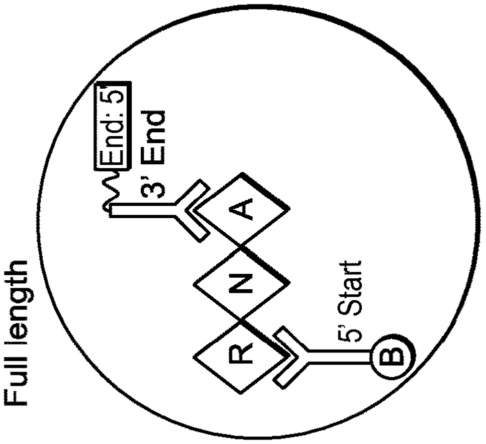
Figure 37G:
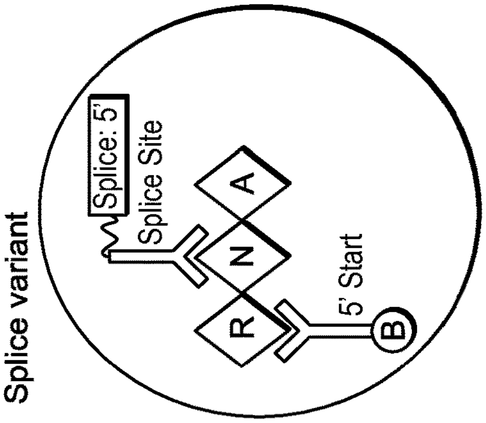
Figure 37H:
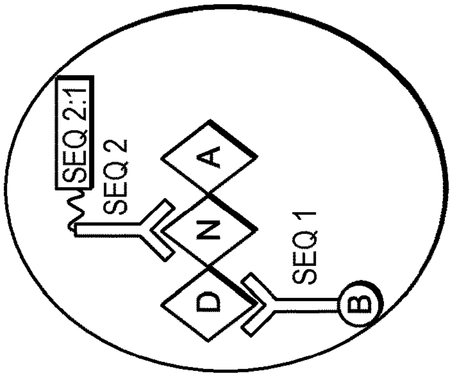
Figure 37I:
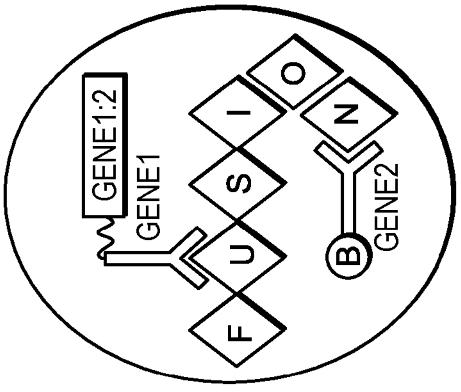
Figure 37J:
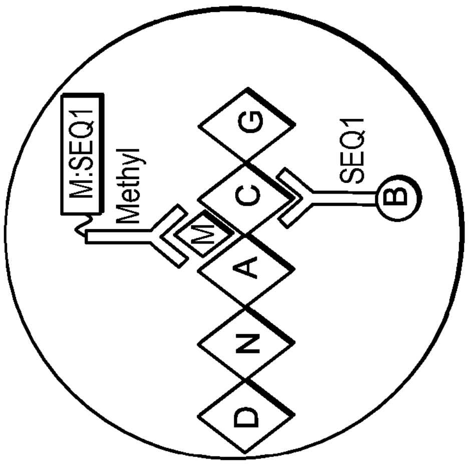
Figure 38A:
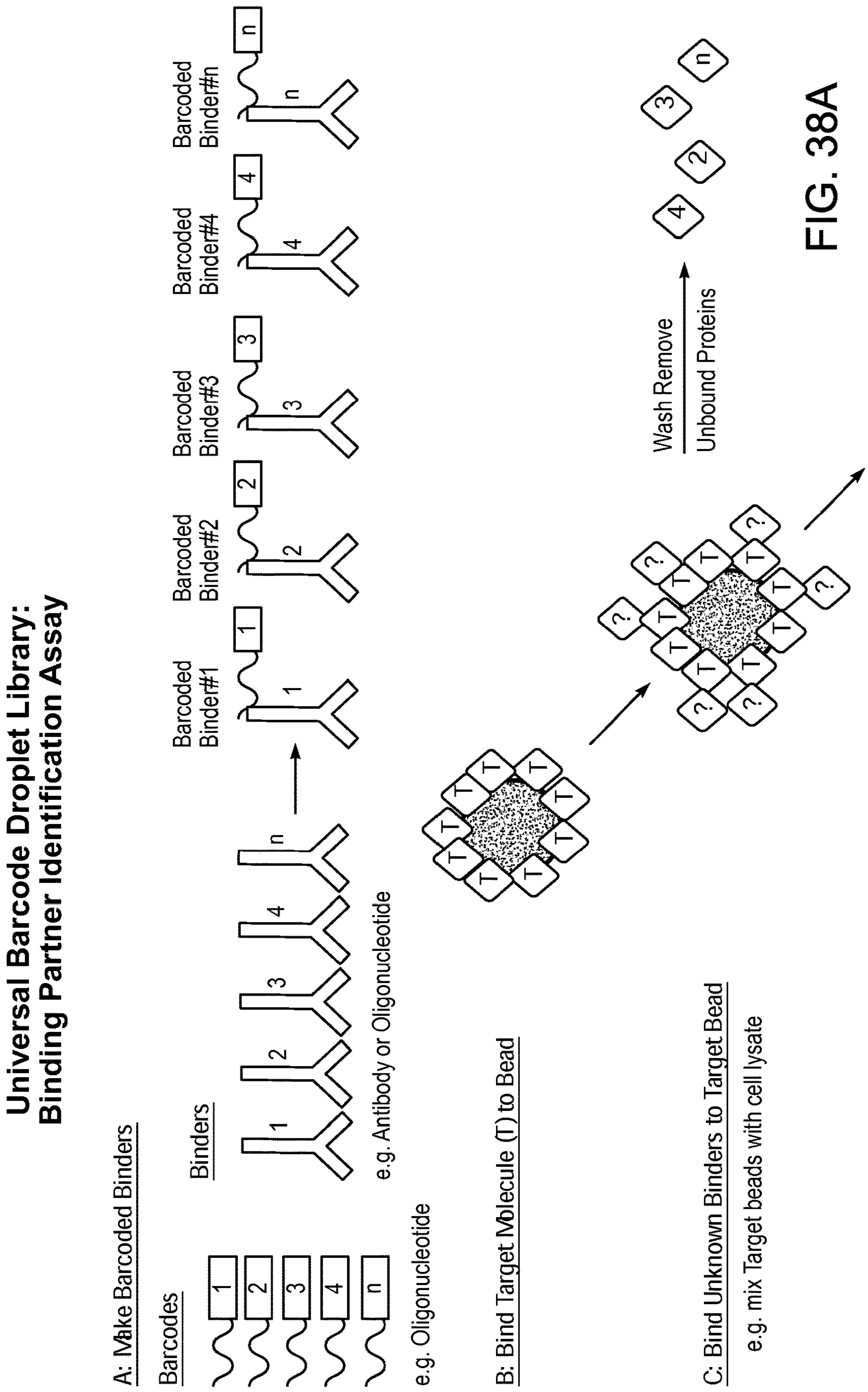
FIGS. 38A-B show use of universal barcodes in a binding partner identification assay.
Figure 38B:
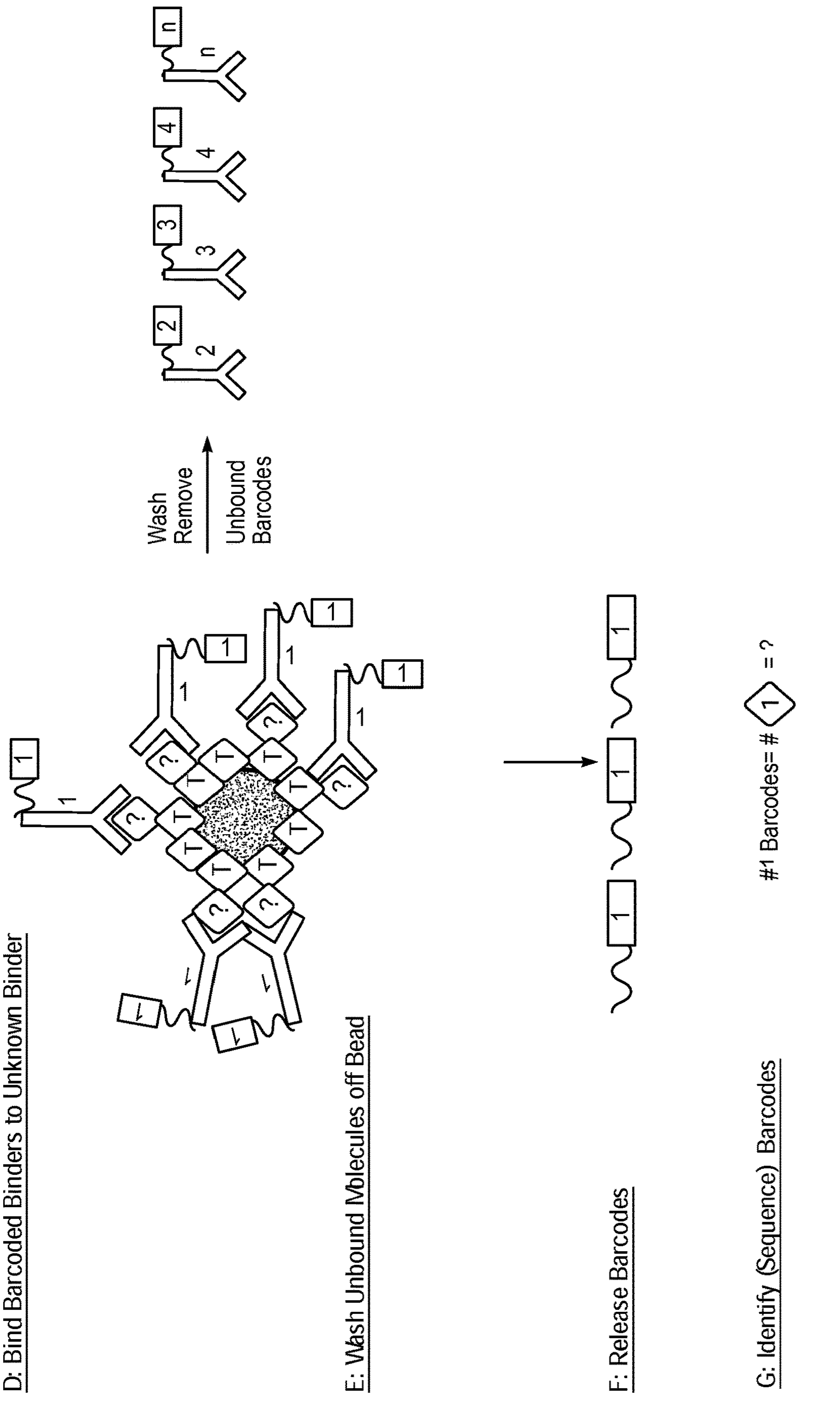
Figure 39A:
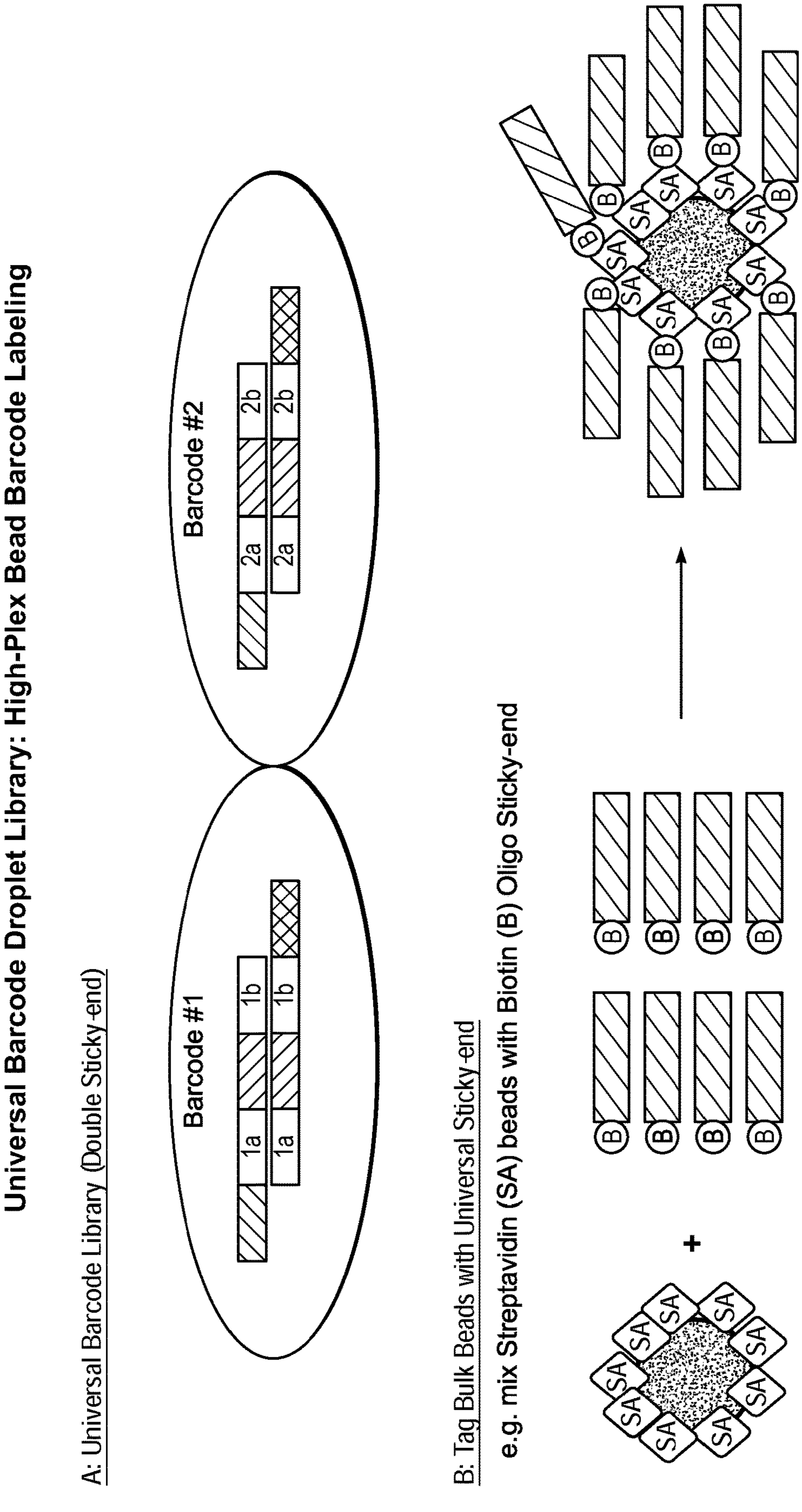
FIGS. 39A-B show barcodes for high-plex bead-based barcode labeling.
Figure 39B:
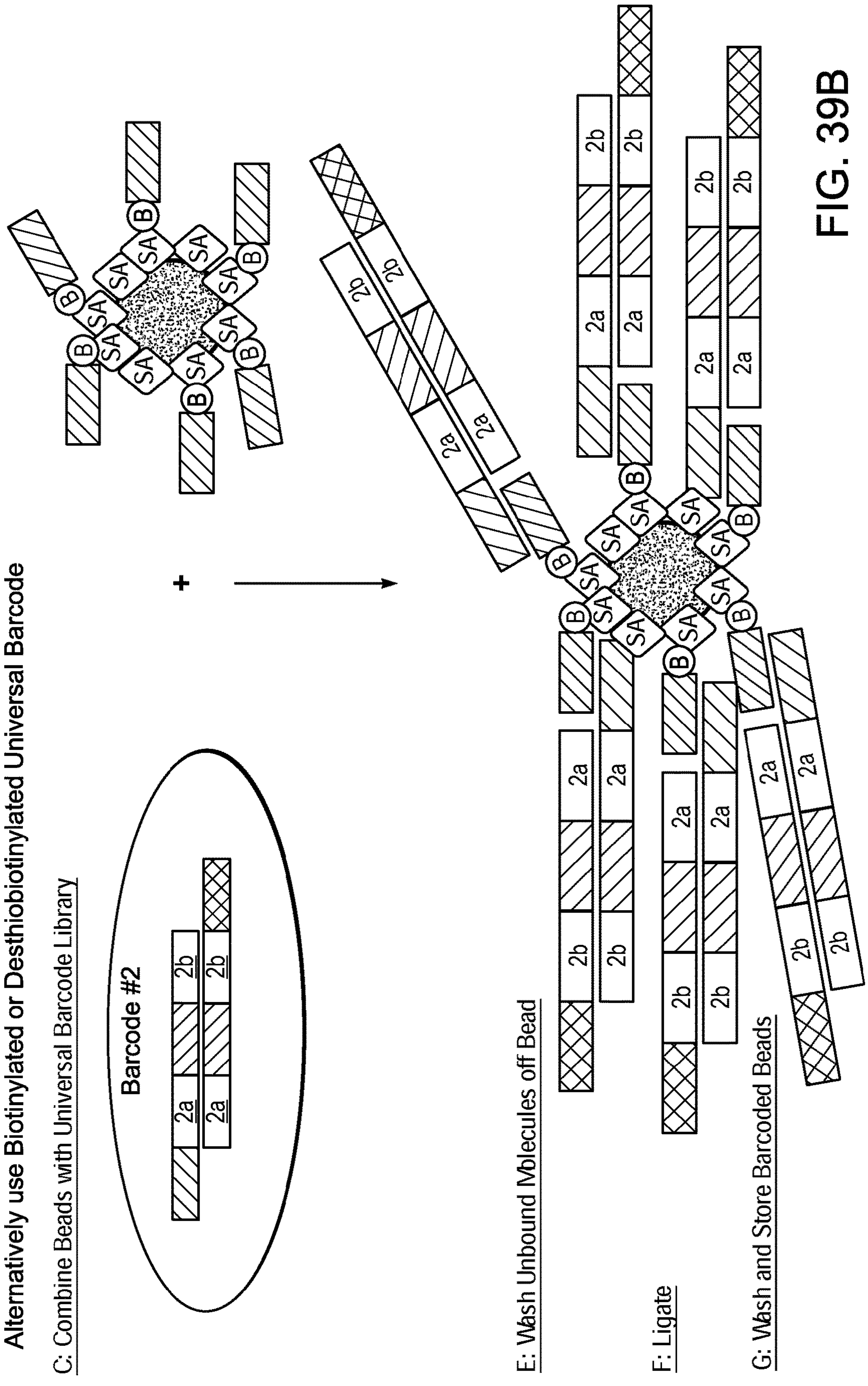

After pair-wise combination of the sample droplets and the tagged-antibody library droplets, and incubation (e.g., FIG. 37A), productive sandwiches containing all target molecules (and uncomplexed biotinylated antibody) bound to an immobilized streptavidin-containing surface (either SA beads co-encapsulated with the library reagents, or post release from the droplets). Washing the binding surface removes unbound material, including all background from non-targeted proteins. Finally, the remaining tags can be released by any means known in the art (e.g., by denaturation or restriction enzyme digestion) for digital quantification.

Any known method known in the art may be utilized to read the tags. Some examples include, quantitative PCR with standard equipment, digital PCR techniques or a tag readout scheme based on NextGen sequencing, including the use of barcoding strategies, and microarrays FIG. 35A-B shows the use of sticky-end barcodes with sticky-end barcoded binders for labeling a sample in a sandwich assay. To couple sample barcode information to a barcode sandwich assay as shown in FIG. 35A-B, a sticky-ended barcode is added to bulk Sample A, then made into droplets (Step A). In step B, sample droplets are combined with binders having sticky-ended barcodes and incubated to form a sandwich centered around an analyte. The binder barcode then anneals to the sample barcode. Ligation can be performed before or after release of sandwich from droplet. The droplet contents are released and the full sandwich on the capture surface is washed. The combined barcode is released (e.g. restriction digest) as shown in panel D. Then, reads for each barcode are counted (e.g. using sequencing).

Figure 36A:
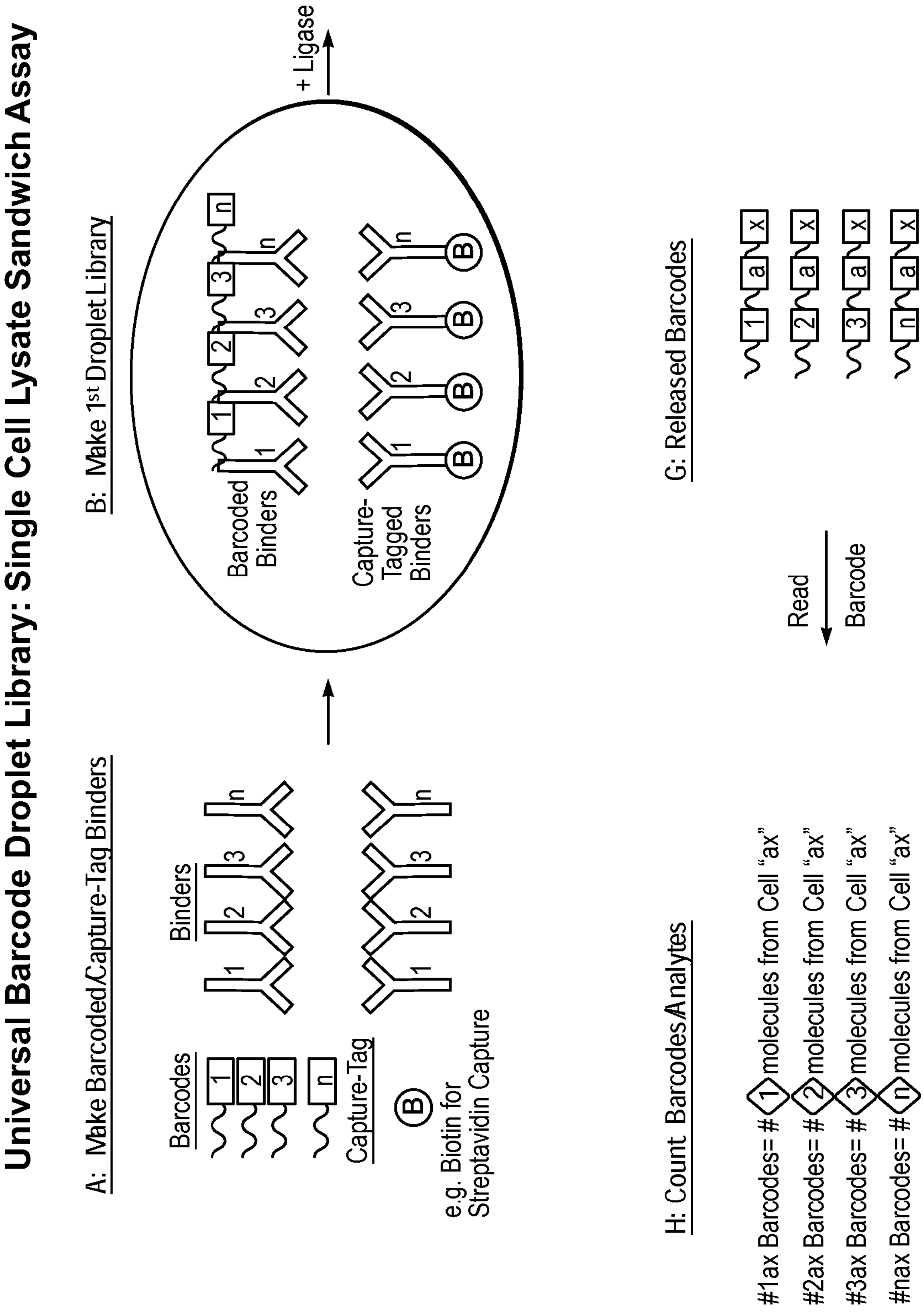
FIGS. 36A-B show use of a universal barcode library in a single cell lysate sandwich assay.
Figure 36B:
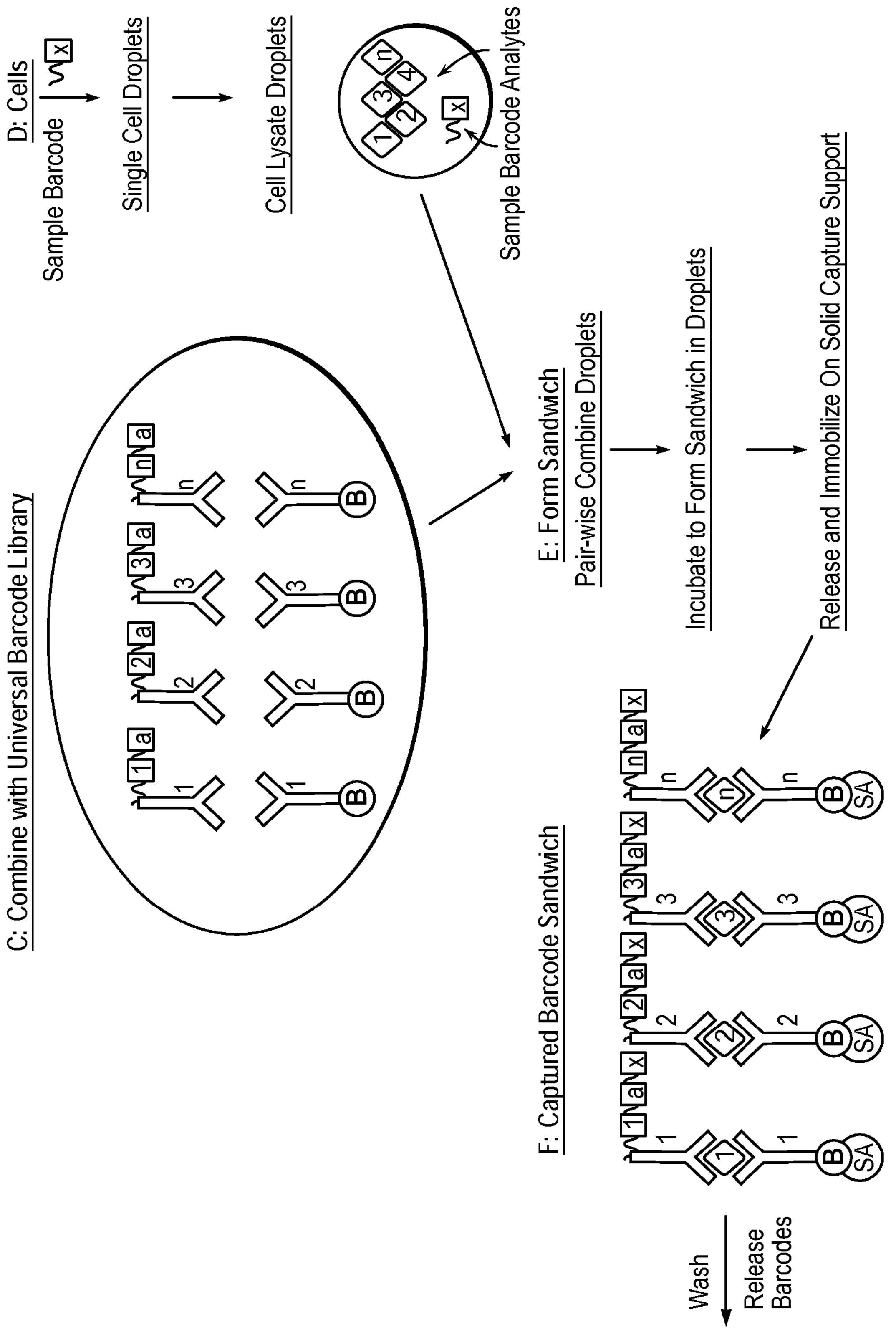

FIG. 36A-B shows the use of a universal barcode droplet library in a single-cell lysate sandwich assays. In the embodiment shown in FIG. 36A-B, a bind-and-ligate version of a library is generally illustrated. As shown in FIG. 36A-B, the universal barcoding droplet library can be combined with barcoded binders that are used in droplet-based sandwich assays, enabling very high-plex digital sandwich assays, including single cell lysate sandwich assays.

Cleavable sticky-ended barcoded binders are constructed (e.g., see FIG. 34A-B) and combined with matching binders that contain a 'capture-tag' (see FIG. 34A-B, right hand side) for use as paired binding and capture agents. Each binding pair targets one biomarker or complex, with each binder directed to a different epitope of the same biomarker or complex component. The Universal Barcode Droplet Library can be used to generate a very high number of uniquely barcoded binders, by successive addition of sticky-ended barcodes to the previously barcoded binders (two rounds of additional sticky-ended barcode addition are shown in FIG. 34A-B). By leaving a sticky-end available with the last barcode addition before use with a sample, a sticky-ended barcode that is provided along with the sample to be targeted by the binding pair can be annealed to the barcoded binder and subsequently ligated (see FIG. 36A-B). Association of the sample identifier with the barcoded binder pair identifier results in a combined barcode, that if captured and read, will identify both the binding agent pair and the sample source for the specific analyte targeted by the binding pair. As an example, in the case where the sample droplet contains a lysed single cell, the combination of the sample identifier and the unique binding pair barcode will allow determination of co-localization of the target molecules coming from the same cell lysate after the droplet contents are released, captured on a solid support and washed, and released and read (see FIG. 36A-B).

FIG. 36A-B shows an example workflow for quantifying analytes in a sample using barcoded binders in a sandwich assay. As shown in Panel A, two binding reagents types are constructed: barcoded binders and capture-tag binders. If the barcoded binder has a sticky-end, successive combination with a universal barcode droplet library enables building very high levels of barcode complexity, such that the number of barcodes exceeds the number of analytes or analyte droplets. Pairs of target-specific binders are made into a droplet library (Panel B), with each set of target binders in separate droplets. As shown in Panel C, a sticky-ended sample barcode identifier is added to the sample and sample droplets are generated, and (Panel D) combined with the library droplets to initiate highly parallel 'single-plex' binding reactions. After binding is complete, productive sandwiches are captured via the capture-tag (streptavidin (SA) biotin (B) interaction shown in Panel F), and washed to remove unbound material. The captured barcodes are released, recovered, and processed for reading as shown in Panel G. Reads for each barcode are counted (e.g. using sequencing).

FIG. 37A-J shows a number of examples of single or multiple target barcode sandwich assays. Panel A shows a binder pair targeting two different regions of the same analyte enable counting single target analytes. As shown in Panels B and C, binder pairs targeting different analytes in a complex enable identification and digital quantification of analyte complexes. Panel D shows a binder pair targeting two different regions of the same analyte, with one target being a specific modification (e.g. protein post-translational). Panel E shows cross-linked or stable complexes that can be analyzed (e.g. protein-nucleic acid). Panels F-J show the identification and counting of various nucleic acid molecules and motifs. Note that the binder barcode information includes details on which binders are in the library droplet (e.g. "3:1:2" in example C means Binder3 in the same droplet as Binder1 and Capture-Tag Binder2).

Sequencing Barcodes

Having labeled the DNA, RNA, or protein of cell-free material, a collection of cells, single cell, or portion thereof, using the methods described herein, the labeled (and possibly amplified) sample may be sequenced. Sequencing can be carried out using any suitable sequencing technique. A particularly useful method for nucleic acid sequencing is one wherein nucleotides are added successively to a free 3' hydroxyl group, resulting in synthesis of a polynucleotide chain in 5' to 3' direction. The nature of the nucleotide added may be determined after each nucleotide addition or at the end of the sequencing process. Sequencing techniques using sequencing by ligation, wherein not every contiguous base is sequenced, and techniques such as massively parallel signature sequencing (MPSS) where bases are removed from, rather than added to the strands on the surface are also within the scope of the invention.

The invention also encompasses methods of sequencing amplified nucleic acids generated by solid-phase amplification. Thus, the invention provides a method of nucleic acid sequencing comprising amplifying a pool of nucleic acid templates using solid-phase amplification and carrying out a nucleic acid sequencing reaction to determine the sequence of the whole or a part of at least one amplified nucleic acid strand produced in the solid-phase amplification reaction. The initiation point for the sequencing reaction may be provided by annealing of a sequencing primer to a product of a solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilized on the solid surface are so-called bridged structures formed by annealing of pairs of immobilized polynucleotide strands and immobilized complementary strands, both strands being attached to the solid support at the 5' end. Arrays comprised of such bridged structures provide inefficient templates for typical nucleic acid sequencing techniques, since hybridization of a conventional sequencing primer to one of the immobilized strands is not favored compared to annealing of this strand to its immobilized complementary strand under standard conditions for hybridization.

In order to provide more suitable templates for nucleic acid sequencing, it may be advantageous to remove or displace substantially all or at least a portion of one of the immobilized strands in the bridged structure in order to generate a template which is at least partially single-stranded. The portion of the template which is single-stranded will thus be available for hybridization to a sequencing primer. The process of removing all or a portion of one immobilized strand in a 'bridged' double-stranded nucleic acid structure may be referred to herein as linearization, and is described in further detail in U.S. Pub. 2009/0118128, the contents of which are incorporated herein by reference in their entirety.

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M5505S), or by exposure to heat or alkali, cleavage of ribonucleotides incorporated into amplification products otherwise comprised of deoxyribonucleotides, photochemical cleavage or cleavage of a peptide linker.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., supra; Ausubel et al. supra). Denaturation results in the production of a sequencing template which is partially or substantially single-stranded. A sequencing reaction may then be initiated by hybridization of a sequencing primer to the single-stranded portion of the template.

Thus, the invention encompasses methods wherein the nucleic acid sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One sequencing method which can be used in accordance with the invention relies on the use of modified nucleotides having removable 3' blocks, for example as described in WO04018497, US 2007/0166705A1 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, 3' block may be removed to allow addition of the next successive nucleotide. By ordering the products derived using these modified nucleotides, it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may be labeled (e.g., fluorescent label) for detection. Each nucleotide type may thus carry a different fluorescent label, for example, as described in U.S. Pub. 2010/0009353, the contents of which are incorporated herein by reference in their entirety. The detectable label need not, however, be a fluorescent label. Any label can be used which allows the detection of an incorporated nucleotide.

One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in WO07123744 and U.S. Pub. 2010/0111768, the contents of which are incorporated herein by reference in their entirety.

In all cases, regardless of the incorporation of molecular barcodes or the location of the barcodes in the event that they are incorporated, sequencing adaptors can be attached to the nucleic acid product in a bi-directional way such that in the same sequencing run there will be sequencing reads from both 5' and 3' end of the target sequence. In some cases it is advantage to use the location of the barcode on 5' or 3' end of the target sequence to indicate the direction of the read. It is well known to one skilled in the art how to attach the sequencing adaptors using techniques such as PCR or ligation.

The invention is not intended to be limited to use of the sequencing method outlined above, as essentially any sequencing methodology which relies on successive incorporation of nucleotides into a polynucleotide chain can be used. Suitable alternative techniques include, for example, the genome sequencers from Roche/454 Life Sciences (Margulies et al. (2005) Nature, 437:376-380; U.S. Pat. Nos. 6,274,320; 6,258,568; 6,210,891), the SOLID system from Life Technologies Applied Biosystems (Grand Island, NY), the HELISCOPE system from Helicos Biosciences (Cambridge, MA) (see, e.g., U.S. Pub. 2007/0070349), and the Ion sequencers from Life Technologies Ion Torrent, Ion Torrent Systems, Inc. (Guilford, CT).

High Accuracy NGS

Methods of the invention can be used for highly accurate nucleic acid sequencing, particularly by enabling the discrimination between true SNPs and sequencing errors. This is particularly valuable where an allele frequency may be much lower than 50% (e.g., 1%, 0.01%, etc.), for example, when testing for loss of heterzygosity in a tumor. The presence of low percentage mutants in cancer samples due to the heterogeneity of the tumor or the presence of normal cells can result in a mutant allele frequencies below 5%. Other applications such as the detection of cell free circulating tumor DNA from blood and the detection of minimal residual disease (MRD) in cancer are other applications requiring the correct identification of low percentage alleles in a mixture of other alleles. Detection of mutations in bacteria or virus that are at a low percentage, but which convey resistance to drug therapies, can alter treatment regiments if the potential for resistance is known ahead of time.

For the applications mentioned above as well as others, there is a need to accurately detect base changes at frequencies 5% or lower. However, this level can be below what is expected for the error rate encountered throughout the entire sequencing process. A method is provided that can distinguish between true base changes from those that were introduced through error. Methods of the invention include labeling each target molecule going into the process with a unique barcode that ends up in the sequencing read. This allows each sequencing read to be traced back to the original molecule in the sample. This enables the ability to distinguish between base errors and true base changes.

Figure 43:
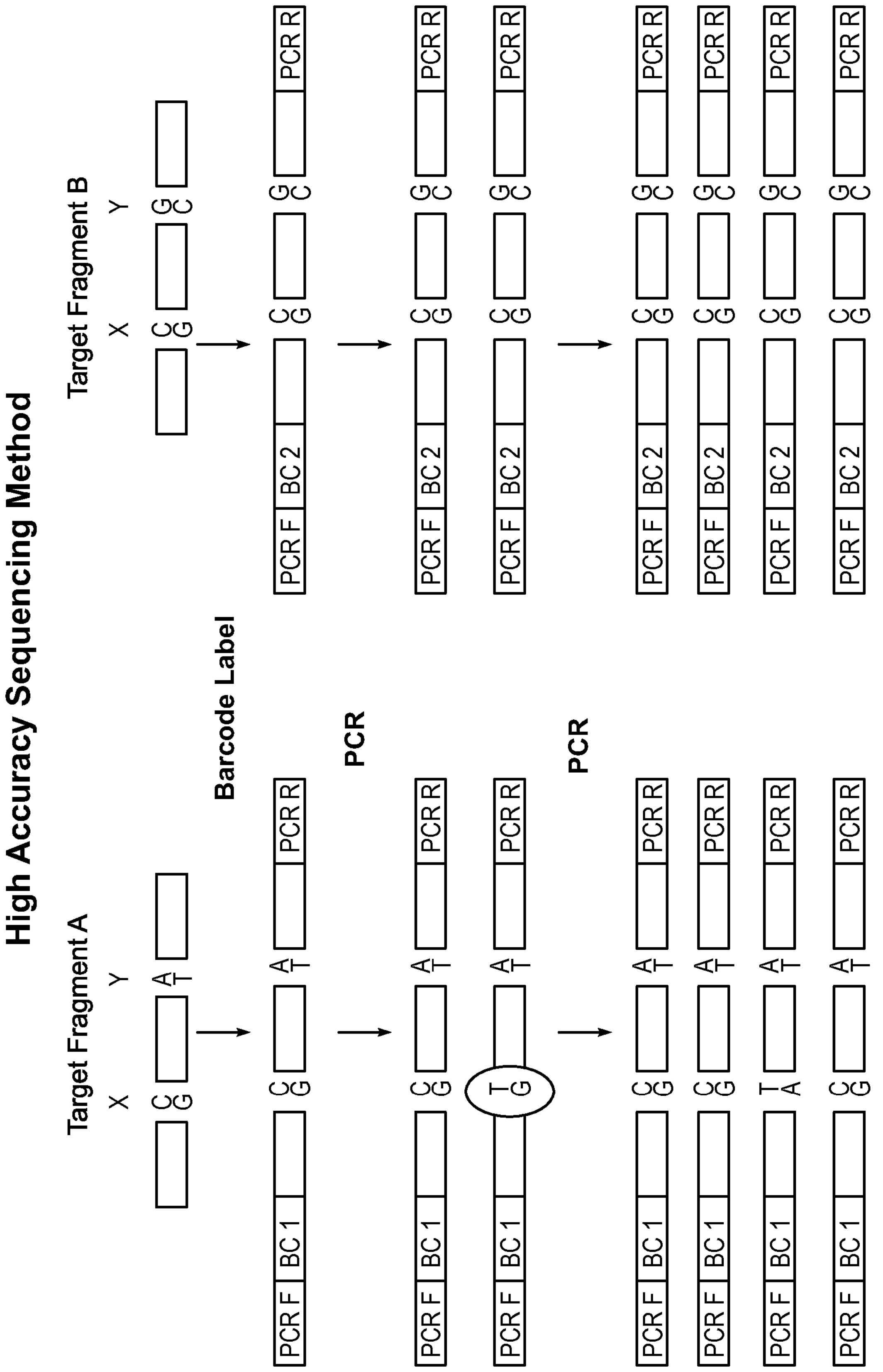
FIG. 43 shows high-accuracy next-generation sequencing (NGS).

In one illustrative example shown in FIG. 43, a sample has two fragments for the same target region of interest (Target Fragment A and Target Fragment B). In this target region there are two bases of interest (X and Y). The base at site X is the same in both fragments (C: G). The base at site Y is different, an A: T in Fragment A and a G: C in Fragment B. The first step is to label each fragment with a unique barcode. Fragment A is labeled with barcode 1 (BC1) and Fragment B is labeled with barcode 2 (BC2). In addition in this example sequence corresponding to PCR primers is also added to the fragment so that each of the fragments can be amplified by PCR (PCR F, PCR R). After barcode labeling, each of the fragments go through one cycle of PCR. Fragment B is replicated correctly, however, there is base change introduced into Fragment A at site X changing the C to a T in one of the strands (drawn-in oval in FIG. 43). The sample is subjected to another round of PCR generating four PCR products for each fragment. If this sample was sent out for sequencing at this point in which both the barcode and the target sequence were read and associated, BC1 in the results would reveal a sequencing error. This is shown in FIG. 44.

The barcoding allows a user to determine whether a detected base change is real or an artifact of some kind. In this case sequencing without a barcode would identify the base change at site X of a C to a T to be a true change present at 12.5% (1 out of 8 reads with a T). However, examining the associated barcode would identify that the there are two different bases (C and T) associated with the same barcode. This could only happen if the change happened after barcoding and thus is an artifact of the process. However, the base change at site Y is a true change because all the bases at site Y are the same for each barcode (BC1 all A, BC2 all G). The attachment of a barcode to DNA or RNA prior to processing allows a user to distinguish a real base change from a sequencing artifact even down to very low percentages.

Padlock Probe Library

In certain embodiments, the invention provides a gap-filling padlock probe library. A padlock barcode library can have sticky-ends, for example, to combine with universal barcode library building block.

Padlock probes can be hybridized to target (in either a sequence-specific manner, or with universal or random sequences), and polymerase plus ligase can be used to fill in the gap between probe ends. This can produce a circular DNA template including a (optionally barcoded) copy of a target template for downstream processing.

Restriction Barcoding

Figure 69A:
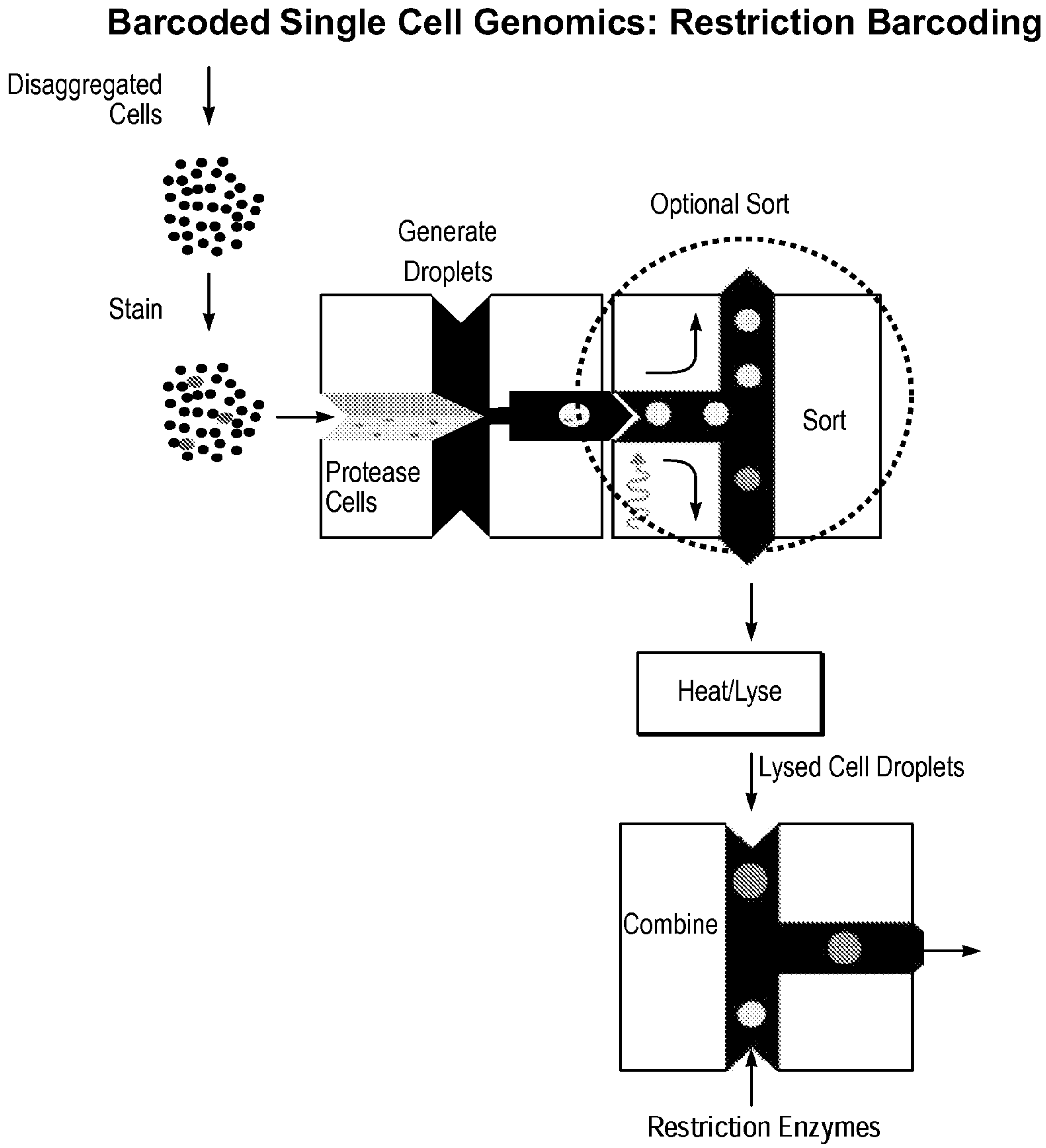
FIGS. 69A-B show a workflow for restriction barcoding.
Figure 69B:
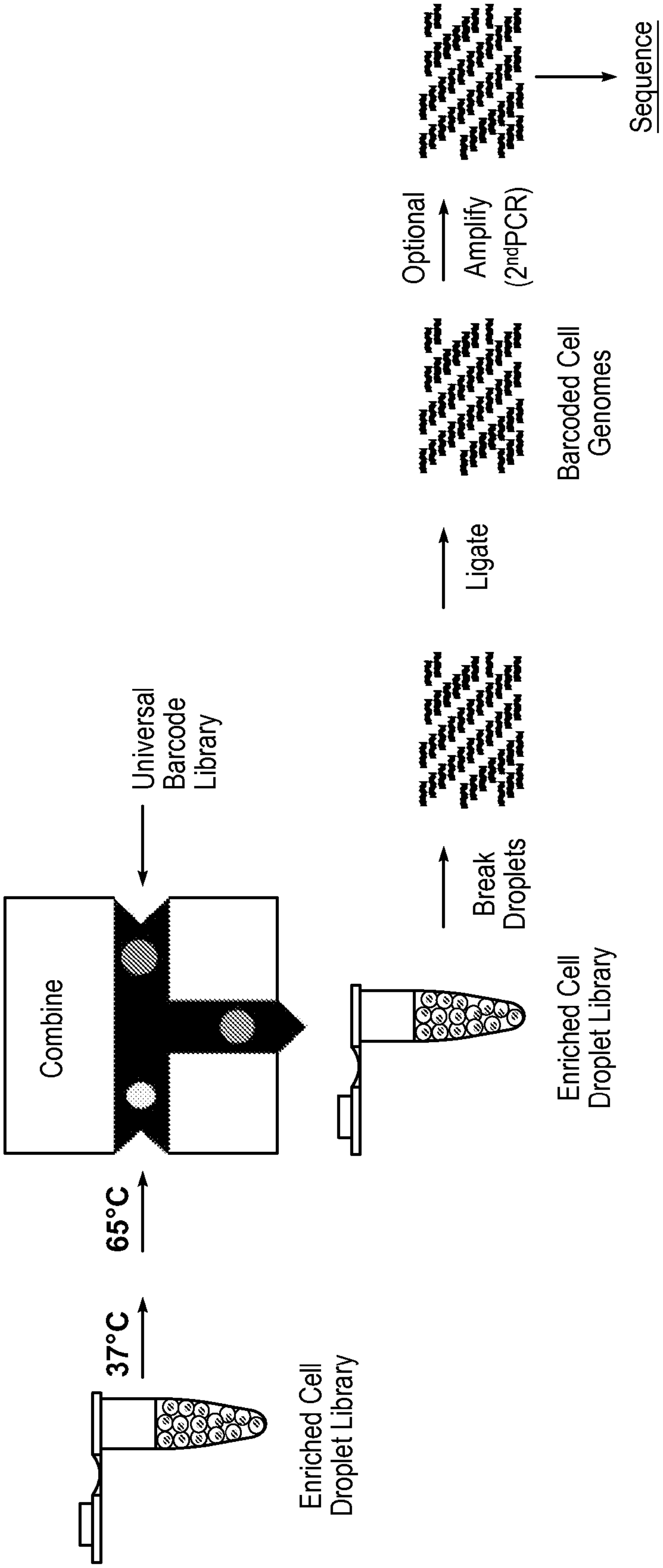

In certain embodiments, the invention includes restriction barcoding. FIG. 69A-B shows a workflow for restriction barcoding. Cells or nucleic acid are sequestered in droplets. If cells, these can be lysed. Any restriction enzyme or combination of restriction enzymes can be introduced into the cells.

Any nucleic acid can be provided (e.g., a barcode construct of the invention) having a restriction site. Nucleic acids can be provided sticky-ended, or can be exposed to restriction enzymes to expose sticky ends. Barcode sticky ends can be hybridized to target sticky ends, and optionally ligated.

In some embodiments, a barcode in provided with a restriction site or associated sticky end, and a capture tag or moiety such as a bead. After target is connected to the barcode via the sticky end, functional steps can exploit the bead or capture moiety (e.g., to isolate target). Then in subsequent downstream processing, for example, target can be released by subsequent restriction digestion.

Sticky-Ended Motif-Probes

In certain embodiments, the invention provides (amplified and non-amplified versions of) probes having sticky ends of a certain motif. General or specific motifs can be used and include transcription factor binding sites, TATA-box, telomeric sequences, known promoters, or any other known motif.

For example, a probe having a TATA-box can be provided (e.g. as a singlet, without a corresponding "downstream/3'" partner, or as part of a pair. A plurality of such probes can be hybridized to a target sample, and polymerase can synthesize a copy of the target from the probe-binding positions (e.g., the probe can provide a 3' free hydroxyl group to seed polymerization). This can proceed by primer extension (e.g., synthesizing a single copy of each target area) or via an amplification reaction.

In certain embodiments, a barcoded sticky-ended motif probe is bound to telomeres, and the count is correlated to telomere length.

III. Probe-Type Labels

In addition to barcode-based methods discussed above, labeled target material can be analyzed using digital PCR methods or by counting of fluorescent probe labels. Digital PCR is discussed below. Methods further include incorporating labels having a fluorescent or other colorimetric probe using the methods described herein. In some embodiments, labels are incorporated and amplified material is released from encapsulation and can be input into a digital PCR reaction to simultaneously screen for multiple genotypes and/or mutations for a plurality of target genes in the sample.

Ideally, the sensitivity of digital PCR is limited only by the number of independent amplifications that can be analyzed, which has motivated the development of several ultra-high throughput miniaturized methods allowing millions of single molecule PCR reactions to be performed in parallel (discussed in detail elsewhere). In a preferred embodiment of the invention, digital PCR is performed in aqueous droplets separated by oil using a microfluidics system. In another preferred embodiment, the oil is a fluorinated oil such as the Fluorinert oils (3M). In a still more preferred embodiment the fluorinated oil contains a surfactant, such as PFPE-PEG-PFPE triblock copolymer, to stabilize the droplets against coalescence during the amplification step or at any point where they contact each other. Microfluidic approaches allow the rapid generation of large numbers (e.g. 106 or greater) of very uniformly sized droplets that function as picoliter volume reaction vessels (see reviews of droplet-based microfluidics). But as will be described, the invention is not limited to dPCR performed in water-in-oil emulsions, but rather is general to all methods of reaction compartmentalization for dPCR. In the description that follows, the invention is described in terms of the use of droplets for compartmentalization, but it is understood that this choice of description is not limiting for the invention, and that all of the methods of the invention are compatible with all other methods of reaction compartmentalization for dPCR. In yet another embodiment, the labeled, amplified genetic mixture is analyzed using an array (e.g., microarray) readout.

Methods of the invention involve novel strategies for performing multiple different amplification reactions on the same sample simultaneously to quantify the abundance of multiple different DNA targets, commonly known to those familiar with the art as "multiplexing". Methods of the invention for multiplexing dPCR assays promise greater plexity—the number of simultaneous reactions—than possible with existing qPCR or dPCR techniques. It is based on the singular nature of amplifications at terminal or limiting dilution that arises because most often only a single target allele is ever present in any one droplet even when multiple primers/probes targeting different alleles are present. This alleviates the complications that otherwise plague simultaneous competing reactions, such as varying arrival time into the exponential stage and unintended interactions between primers.

In one aspect, the invention provides materials and methods for improving amplicon yield while maintaining the quality of droplet-based digital PCR. More specifically, the invention provides droplets containing a single nucleic acid template and multiplexed PCR primers and methods for detecting a plurality of targets in a biological sample by forming such droplets and amplifying the nucleic acid templates using droplet-based digital PCR.

Reactions within microfluidic droplets yield very uniform fluorescence intensity at the end point, and ultimately the intensity depends on the efficiency of probe hydrolysis. Thus, in another aspect of the methods of the invention, different reactions with different efficiencies can be discriminated on the basis of end point fluorescence intensity alone even if they have the same color. Furthermore, in another method of the invention, the efficiencies can be tuned simply by adjusting the probe concentration, resulting in an easy-to-use and general purpose method for multiplexing. In one demonstration of the invention, a 5 plex TaqMan® dPCR assay worked "right out of the box", in contrast to lengthy optimizations that typify qPCR multiplexing to this degree. In another aspect of the invention, adding multiple colors increases the number of possible reactions geometrically, rather than linearly as with qPCR, because individual reactions can be labeled with multiple fluorophores. As an example, two fluorophores (VIC and FAM) were used to distinguish five different reactions in one implementation of the invention.

Detection

In certain embodiments, after amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation—or in certain embodiments the droplets may be re-injected for read-out back into the original fluidic circuit used for droplet generation. The droplets may be individually analyzed and detected using any methods known in the art, such as detecting the presence or amount of a reporter.

Figure 47:
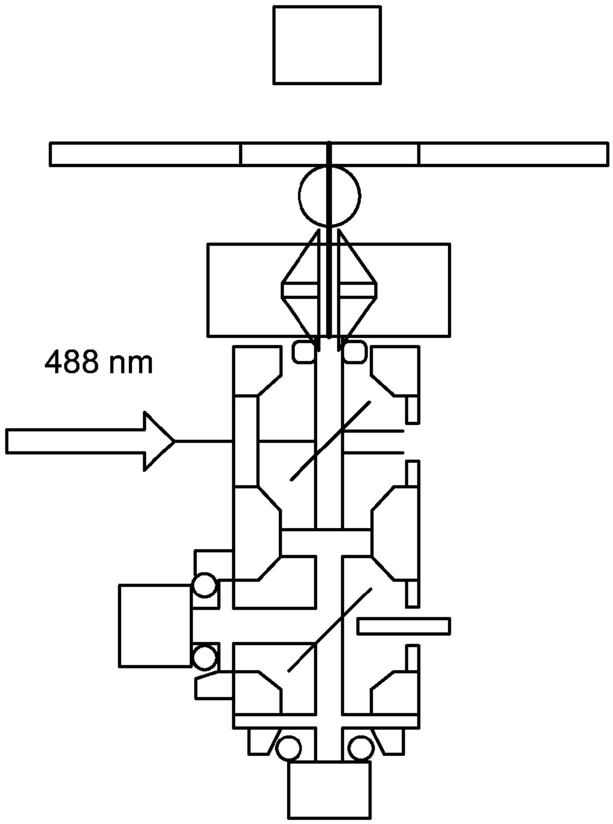
FIG. 47 shows a detection apparatus according to certain embodiments.

An apparatus can include optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. FIG. 47 shows a detection apparatus according to certain embodiments. Detecting labeled material in droplets is discussed in U.S. Pub. 2008/0014589; U.S. Pub. 2008/0003142, and U.S. Pub. 2010/0137163.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Optical Labels

In particular embodiments, the labels incorporated into the DNA or RNA of a single cell, or portion thereof, are optically labeled probes, such as fluorescently labeled probes that are attached to a primer (or N-mer) that hybridizes to a unique region of the target. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VIC™ (from Applied Biosystems). Labels other than fluorescent labels are contemplated by the invention, including other optically-detectable labels.

In a particular embodiment, the optical label can be conjugated to an antibody, an siRNA, an aptamer, or a ribozyme specific for target gene or region of interest on the target.

Labels can be used for identification of the library elements of the various types of droplet libraries. Libraries can be labeled for unique identification of each library element by any means known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label.

The label can be detected by any means known in the art. Preferably, the label is detected by fluorescence polarization, fluorescence intensity, fluorescence lifetime, fluorescence energy transfer, pH, ionic content, temperature or combinations thereof. Various labels and means for detection are described in greater detail herein.

Specifically, after a label is added to each of the various library elements, the elements are then encapsulated and each of the droplets contains a unique label so that the library elements may be identified. In one example, by using various combinations of labels and detection methods, it is possible to use two different colors with different intensities or to use a single color at a different intensity and different florescence anisotropy.

Quality Control

Optical labels are also utilized in quality control in order to ensure that the droplet libraries are well controlled, and that equal number of each library elements are contained within uniform volumes in each droplet library. After 120 minutes of mixing, using 8-labels in a 96-member library, the average number of droplets is 13,883 for each of the library elements.

In some quality control examples, 384-member libraries were prepared with eight optical labels; typically 5 to 20 micro-liters of each library element are emulsified into approximately 10 picoliter volume droplets so there are about 1 million droplets of each library element and 384 million droplets in the library.

The eight optical labels are a dye at concentrations that increase by a factor of c (where c ranges from about 1.2 to 1.4) from one optical label to the next so that the nth optical label has (c)(n−1) the dye concentration of the lowest concentration. Optical labels are used with concentrations between 10 nM and I uM. Typically, the range of optical label concentrations for one series of labels is 1 order of magnitude (e.g., 10 nM to 100 nM with a multiplier of 1.43 for each increasing label concentration). A larger range of droplet label concentrations can also be used. Further, multiplexed two-color labels can be used as well.

Plates are prepared with 384 separate library elements in separate wells of the 384-well plates; 8 of which have optical labels. The library elements are made into droplets, collected in a vial, (also known as a creaming tower) and mixed for several hours. The mixer works by flipping the vial over about once every 30 seconds and then allowing the droplets to rise. Multiple plates can be emulsified and pooled or collected sequentially into the same vial.

A small fraction of the droplets are taken out of the vial to verify 1) that the droplets are present in the correct predetermined ratio and 2) that the droplets are of uniform size. Typically, 1,000 to 10,000 droplets of each library element (0.384 to 3.84 million QC-droplets) are removed from the vial through a PEEK line in the center opening in the vial cap by positive displacement with a drive oil infused through the side opening in vial cap. The PEEK line takes the droplets into a port on a microfluidic chip at a rate of several thousand droplets/second; for 10 picoliter droplets at a rate of 3000 droplets/s corresponds to a typical infusion rate of roughly 110 micro-liters/hr. Once on chip the droplets are spaced out by adding oil before they are imaged and pass one droplet at a time through a laser excitation spot. Maximum fluorescence intensity data from individual droplets is collected for all of the QC-droplets and histograms are built to show the number of droplets within a given fluorescence intensity range. As expected, if eight of the library elements have optical labels, then there are eight peaks in the histograms. The increasing concentration factor c=1.38 results in uniformly separated peaks across one decade when plotted on a log scale. The relative number of droplets in each peak is used as a quality metric to validate that the libraries were prepared with the expected relative representation. In this example, the percent variation is determined to be only 2.7% demonstrating that all library elements have uniform representation.

Image analysis can be utilized to determine and monitor osmotic pressure within the droplets. Osmotic pressure (e.g., two member library prepared with a small difference in buffer concentration) can effect droplets. Specifically, droplets with a lower salt concentration shrink over time and droplets with higher salt concentration grow over time, until uniform salt concentrations are achieved.

Image analysis can also be utilized for quality control of the library reformatting process. After the various library elements are generated, pooled and mixed, optical labels can be used to verify uniform representation of all library elements. Additionally, image analysis is used to verify uniform volume for all droplets.

Further, image analysis can be used for shelf life testing by quantifying the materials performance. Droplets are stored in vials under a variety of conditions to test droplets stability against droplet-droplet coalescence events. Conditions tested include temperature, vibration, presence of air in vials, surfactant type, and surfactant concentration. A Quality Score of percent coalescence is calculated by image analysis. Shelf-life for the droplet libraries of the present invention exceed 90 days.

Droplet Digital PCR

In certain aspects, the invention provides methods and systems for droplet digital PCR including high plexity multiplexing.

Figure 48A:
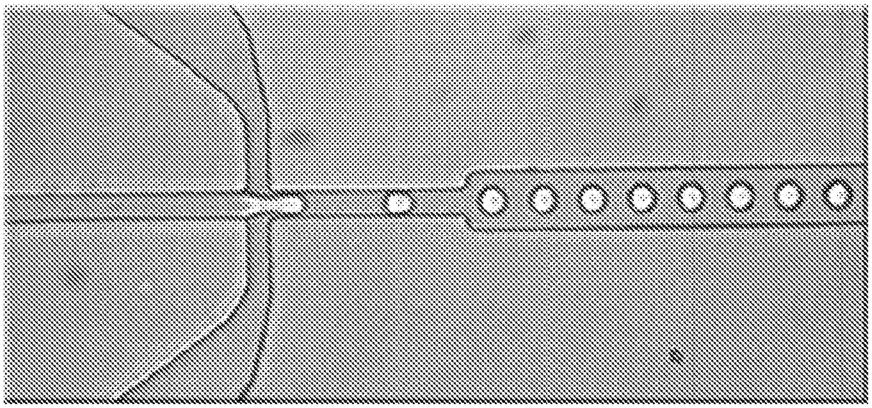
FIG. 48A shows a droplet generation chip.
Figure 48B:
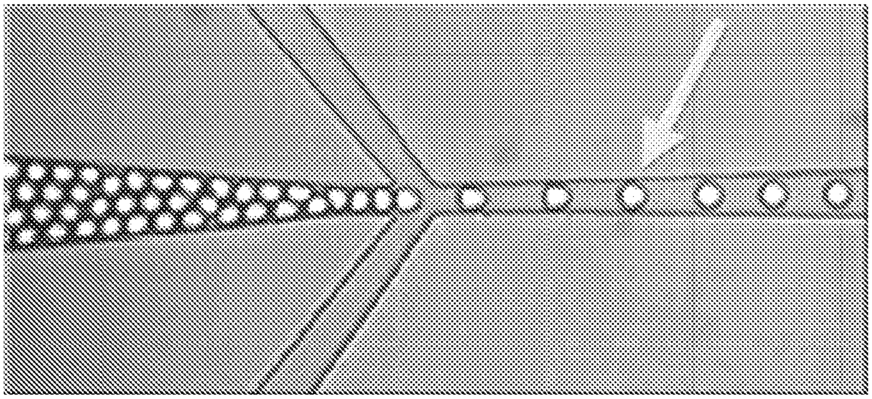
FIG. 48B depicts the droplet spacing for readout.
Figure 48C:
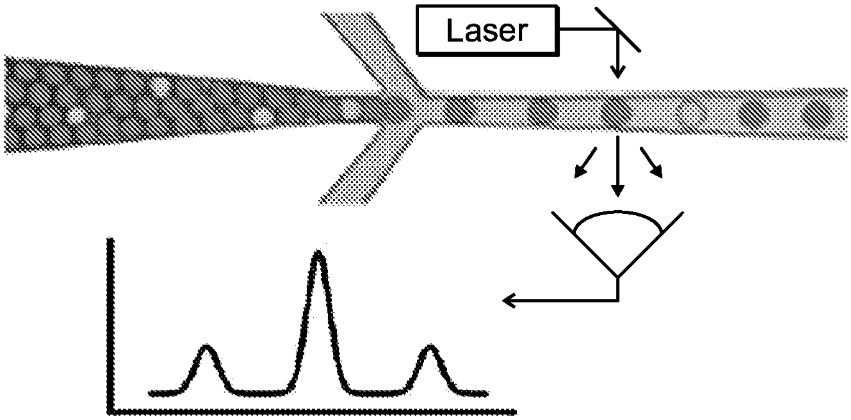
FIG. 48C depicts a cartoon of droplet readout by fluorescence.

An exemplary microfluidic system for droplet generation and readout is depicted in FIG. 48. The microfluidic system for droplet generation and readout. As shown in FIG. 48*a* (droplet generation chip), a continuous aqueous phase containing the PCR master mix, primers, and probes, and template DNA is flowed into the fluidic intersection from the left, and the carrier oil enters from the top and bottom. An emerging bolus of aqueous liquid is imaged inside the intersection just prior to snapping off into a discrete 4 pL droplet as the fluidic strain began to exceed the surface tension of the aqueous liquid. The steady train of droplets leaving the intersection toward the right is collected off chip as a stable emulsion for thermal cycling. FIG. 48*b* depicts the droplet spacing for readout. Flows are arranged as in FIG. 48*a*, except instead of a continuous phase, the emulsion from (a) is injected from the left into the intersection after thermal cycling. The oil drains from the emulsion during off-chip handling, hence the emulsion appears tightly packed in the image before the intersection. The oil introduced in the intersection separates the droplets and the fluorescence of each droplet is measured at the location marked by the arrow. FIG. 48*c* depicts a cartoon of droplet readout by fluorescence. The relatively infrequent PCR(+) droplets (light gray) flow along with the majority of PCR(−) droplets (dark gray) toward the detector. The droplets are interrogated sequentially by laser induced fluorescence while passing through the detection region.

In a serial dilution the average number of target DNA molecules per droplet-called the "occupancy" from this point forward-decreases in direct proportion to the DNA concentration. The occupancy is calculated from Poisson statistics using the following equation well known to those experienced in the art: occupancy=ln(P+N/N) (1)

where P and N are the numbers of PCR(+) and PCR(−) droplets respectively.

Digital PCR performance in the emulsion format is validated by measuring a serial dilution of a reference gene, branched chain keto acid dehydrogenase E1 (BCKDHA). Mixtures of the PCR master mix, 1× primers and probe for BCKDHA, and varying concentrations of a mixture of human genomic DNA (1:1 NA14091 and NA13705) are compartmentalized into over one million 5.3 pL droplets in a water-in-fluorinated oil emulsion using the droplet generation microfluidic chip. The emulsion is thermally cycled off-chip and afterwards the fluorescence of each droplet is analyzed by fluorescence in the readout chip (see FIG. 48).

Droplets are analyzed by fluorescence while flowing through the readout chip to count the numbers of PCR(+) and PCR(−) droplets (see FIG. 48*c*). As each droplet passes the detection zone (marked with an arrow in FIG. 48*b*), a burst of fluorescence is observed. To account for small run-to-run differences in the fluorescence intensity that can occur due to different chip positioning, etc., each set of data is scaled such that the average fluorescence intensity of the empty droplets is 0.1 V.

Figure 49A:
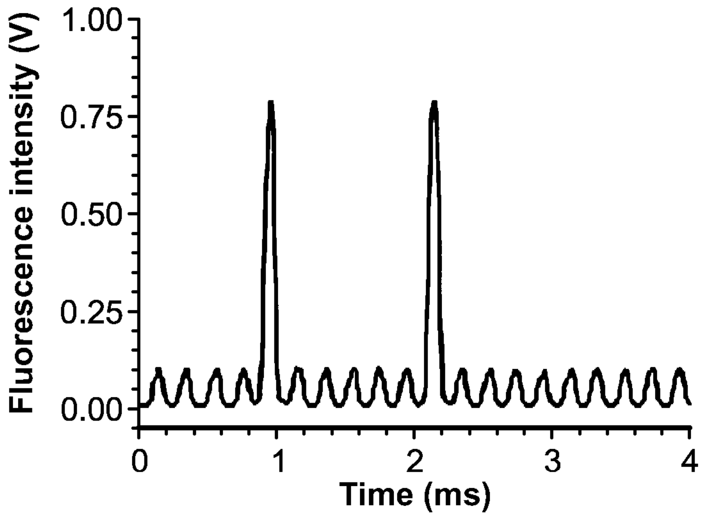
FIGS. 49A-49C depict the serial dilution of template DNA quantified by dPCR.
Figure 49B:
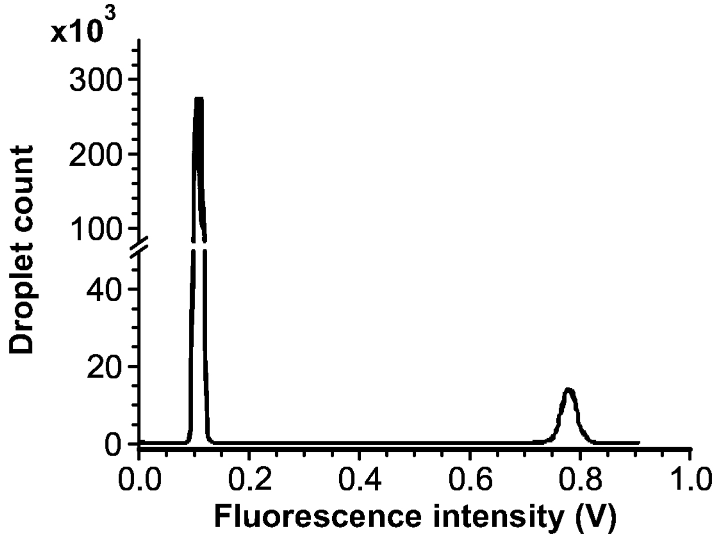
Figure 49C:
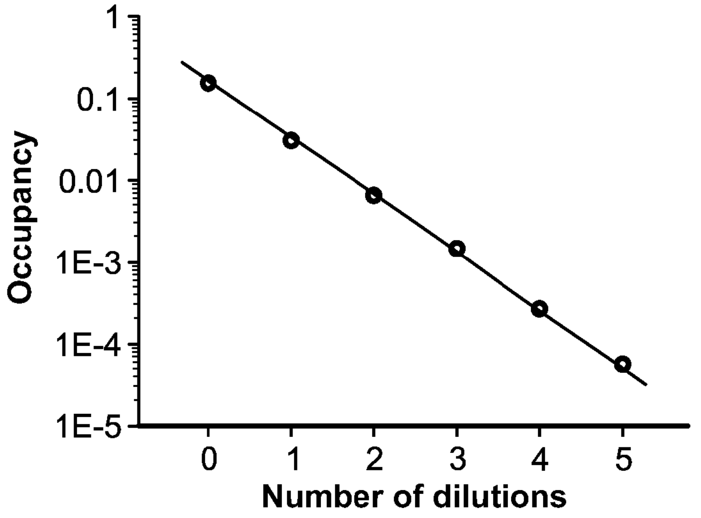

FIG. 49*a* shows droplet fluorescence during readout for the most concentrated sample. Each discrete burst of fluorescence corresponds to an individual droplet. Two different groups of droplets are evident: PCR(+) droplets peaking at ˜0.8 V and PCR(−) droplets at ˜0.1 V; FIG. 49*b* shows a histogram of the peak fluorescence intensities of droplets from the complete data trace in 6*a*. PCR(+) and PCR(−) droplets appear as two very distinct populations centered at 0.78 and 0.10 V, respectively; FIG. 49*c* shows the serial dilution of template DNA. Open circles: measured occupancies; solid line: the best fit to Eqn 2 (A=0.15, f=4.8, R^2-0.9999).

FIG. 49*a* shows a very short duration of a typical trace of fluorescence bursts from individual droplets for the sample with the highest DNA concentration in the series. PCR(+) and PCR(−) droplets are easily discriminated by fluorescence intensity. The two large bursts of fluorescence peaking at ˜0.8 V arose from the PCR(+) droplets, whereas the smaller bursts due to incomplete fluorescence quenching in the PCR(−) droplets peaked at ˜0.1 V. A histogram of peak intensities from the complete data set reveals two clear populations centered at 0.10 and 0.78 V (FIG. 49*b*), demonstrating that the trend evident in the short trace in FIG. 49*a* is stable over much longer periods of time. Integration over the two populations in FIG. 49*b* yields a total of 197,507 PCR(+) and 1,240,126 PCR(−) droplets. Hence the occupancy is 0.15 for this sample by Eqn. 1, corresponding to the expected occupancy of 0.18 based on the measured DNA concentration of 110 ng/μL. The occupancy is measured for each sample in the serial dilution and fit to the dilution equation: occuplancy(n)=A/f^n (2)

where n is the number of dilutions, A is the occupancy at the starting concentration (n=0), and f is the dilution factor. The linear fit is in excellent agreement with the data, with an R^2 value of 0.9999 and the fitted dilution factor of 4.8 in close agreement with the expected value of 5.0.

Multiplexing Primers in Digital PCR

Droplet-based digital PCR technology uses a single primer pair per droplet. This library droplet is merged with a template droplet which contains all the PCR reagents including genomic DNA except for the primers. After merging of the template and the primer library droplets the new droplet now contains all the reagents necessary to perform PCR. The droplet is then thermocycled to produce amplicons. In one embodiment, the template DNA is diluted in the template mix such that on average there is less than one haploid genome per droplet. Droplet-based digital PCR is described in U.S. Pat. No. 7,041,481; U.S. Pub. 2008/0014589; U.S. Pub. 2008/0003142; and U.S. Pub. 2010/0137163, the contents of each of which are incorporated by reference herein in their entireties.

Having only one haploid genome (i.e., one allele) per droplet gives droplet PCR advantages over standard singleplex or multiplex PCR in tubes or microwells. For example, in traditional PCR, both alleles are present in the reaction mix so if there is a difference in the PCR efficiency between alleles, the allele with the highest efficiency will be over represented. Additionally, there can be variances in the sequence to which the PCR primers hybridize, despite careful primer design. A variance in the primer hybridization sequence can cause that primer to have a lower efficiency for hybridization for the allele that has the variance compared to the allele that has the wild type sequence. This can also cause one allele to be amplified preferentially over the other allele if both alleles are present in the same reaction mix.

These issues are avoided in droplet-based PCR because there is only one template molecule per droplet, and thus one allele per droplet. Thus, even if primer variance exists that reduces the PCR efficiency for one allele, there is no competition between alleles because the alleles are separated and thus uniformly amplified.

Because droplet-based digital PCR utilizes only one template molecule per droplet, even if there are multiple PCR primer pairs present in the droplet, only one primer pair will be active. Since only one amplicon is being generated per droplet, there is no competition between amplicons, resulting in uniform amplicon yield between different amplicons.

A certain amount of DNA is required to generate either a specific quantity of DNA and/or a specific number of PCR positive droplets to achieve sufficient sequencing coverage per base. Because only a percentage of the droplets are PCR positive, approximately 1 in 3 in the standard procedure, it takes more DNA to achieve the equivalent PCR yield per template DNA molecule. The number of PCR positive droplets and thus the amplicon yield can be increased by adding more genomic DNA. For instance, increasing the amount of genomic DNA twofold while maintaining the number of droplets constant will double the amplicon yield. However there is a limit to the amount of genomic DNA that can be added before there is a significant chance of having both alleles for a gene in the same droplet, thereby eliminating the advantage of droplet PCR for overcoming allele specific PCR and resulting in allelic dropout.

One way to allow the input of more genomic DNA is by generating more droplets to keep the haploid molecules per droplet ratio constant. For instance doubling the amount of DNA and doubling the amount of droplets increases the amplicon yield by 2× while maintaining the same haploid genome per droplet ratio. However, while doubling the number of droplets isn't problematic, increasing the amount of DNA can be challenging to users that have a limited amount of DNA.

The multiplexing of PCR primers in droplets enables the simultaneous increase in the number of PCR droplets while keeping the amount of input DNA the same or lower to generate an equal or greater amplicon yield. This results in an overall increase in the amount of PCR positive droplets and amplicon yield without the consumption of more DNA.

By way of example, if there is an average of 1 haploid genome per every 4 droplets or ¼ of the haploid genome per droplet and one PCR primer pair per droplet, the chances of the correct template being present for the PCR primer in the droplet is 1 out of 4. However, if there are 2 PCR primer pairs per droplet, then there is double the chance that there will be the correct template present in the droplet. This results in 1 out of 2 droplets being PCR positive which doubles the amplicon yield without doubling the input DNA. If the number of droplets containing the 2× multiplexed primers is doubled and the DNA kept constant, then the number of PCR positive droplets drops back to 1 in 4, but the total number of PCR droplets remains the same because the number of droplets have been doubled. If the multiplexing level in each droplet is increased to 4× and the input DNA is the same, the chance of the correct template molecule being present in each droplet doubles. This results in the number of PCR positive droplets being increased to 1 in 2 which doubles the amount of amplicon yield without increasing the amount of input DNA. Thus, by increasing the multiplexing of PCR primers in each droplet and by increasing the number of droplets overall, the amplicon yield can be increased by 4-fold without increasing the amount of input DNA.

Alternatively, if the amplicon yield is already sufficient, by increasing the multiplexing level for the PCR primers in each droplet, the amount of input genomic DNA can be dropped without sacrificing amplicon yield. For example if the multiplexing level of the PCR primers goes from 1× to 2×, the amount of input genomic DNA can be decreased by 2× while still maintaining the same overall amplicon yield.

Even though the number of PCR primer pairs per droplet is greater than one, there is still only one template molecule per droplet and thus there is only one primer pair per droplet that is being utilized at one time. This means that the advantages of droplet PCR for eliminating bias from either allele specific PCR or competition between different amplicons is maintained.

An example demonstration of droplet-based amplification and detection of multiple target sequences in a single droplet is shown in FIG. 50. Multiple copies of 5 sets of primers (primers for TERT, RNaseP, E1a, SMN1 and SMN2) were encapsulated in a single droplet at various concentrations along with the template DNA and the PCR master mix.

Figure 50A:
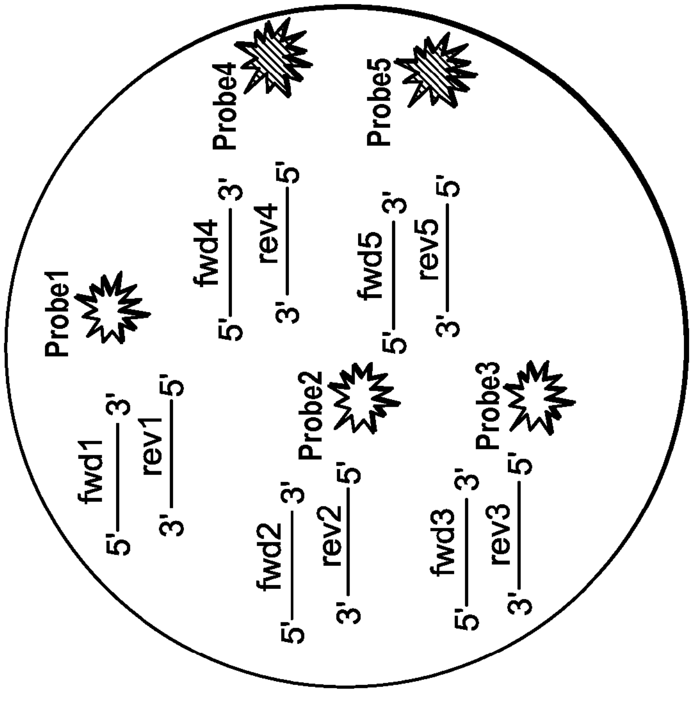
FIG. 50A is a schematic representation of a droplet having 5 sets of primers for PCR amplification of a template sequence and 5 probes, each labeled with a fluorescent dye, that binds specifically to the amplified sequences.
Figure 50B:
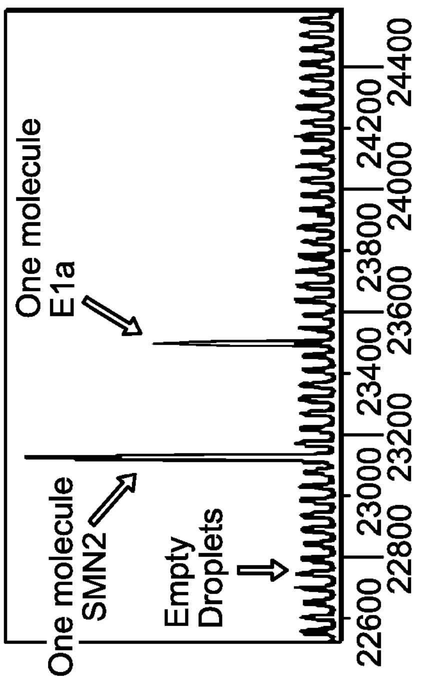
FIG. 50B is a time trace of fluorescence intensity detected from droplets.
Figure 50C:
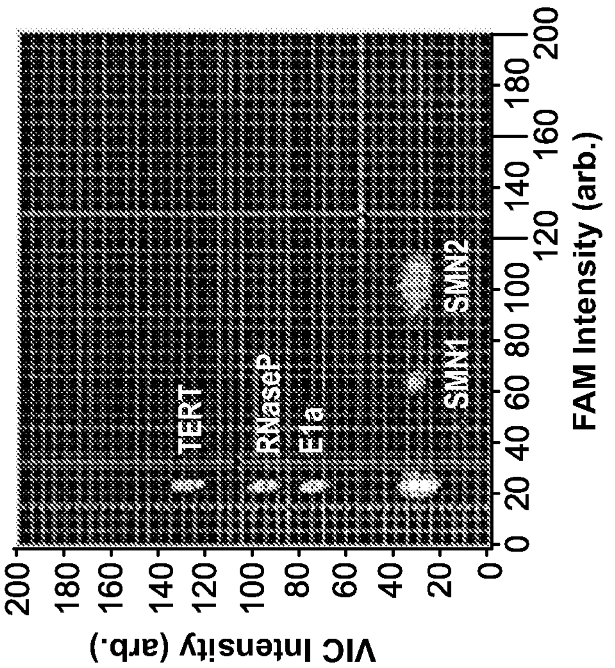
FIG. 50C is a scatter plot showing clusters corresponding to amplified sequences.
Figure 53A:
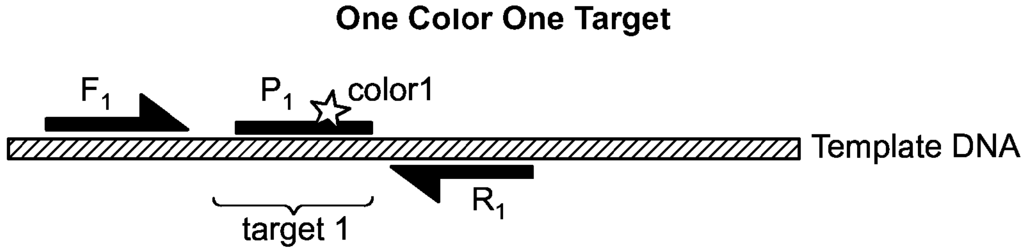
FIGS. 53A-E schematically depict one-color detection of a genetic sequence with a microfluidic device.
Figure 53B:
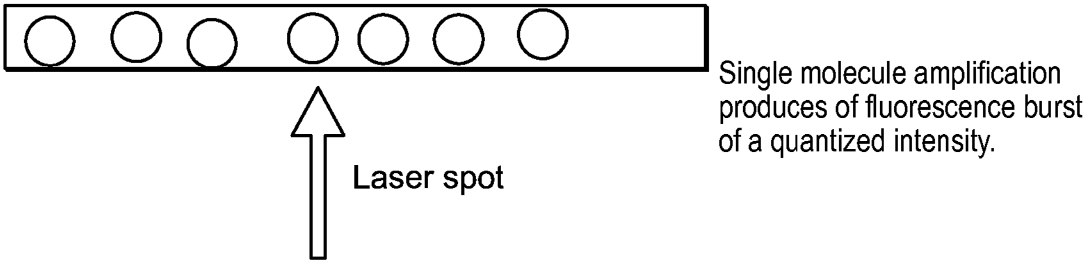
Figure 53C:
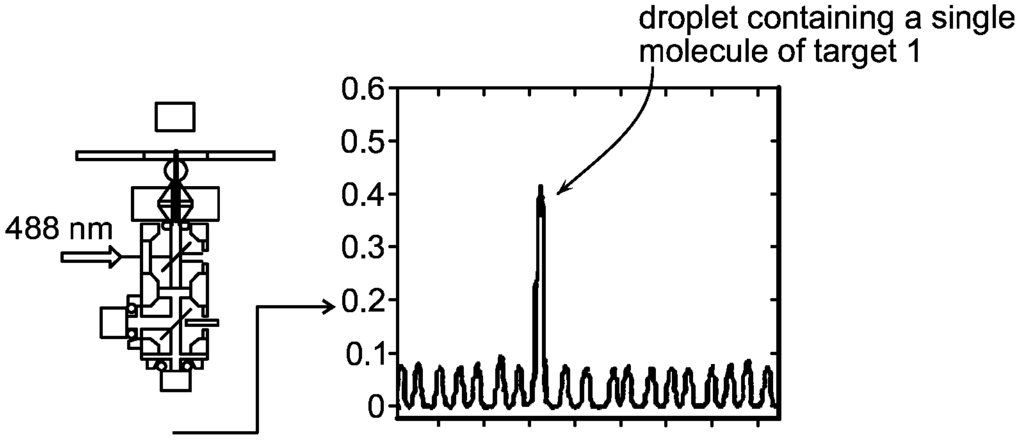
Figure 53E:
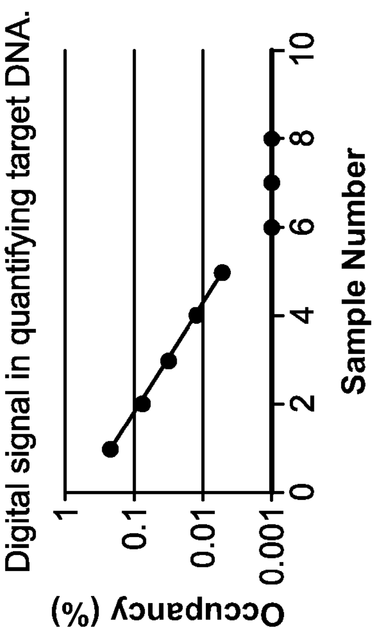
Figure 53D:
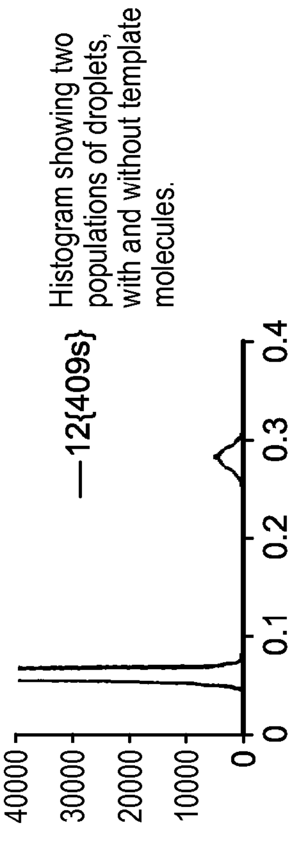
Figure 54A:
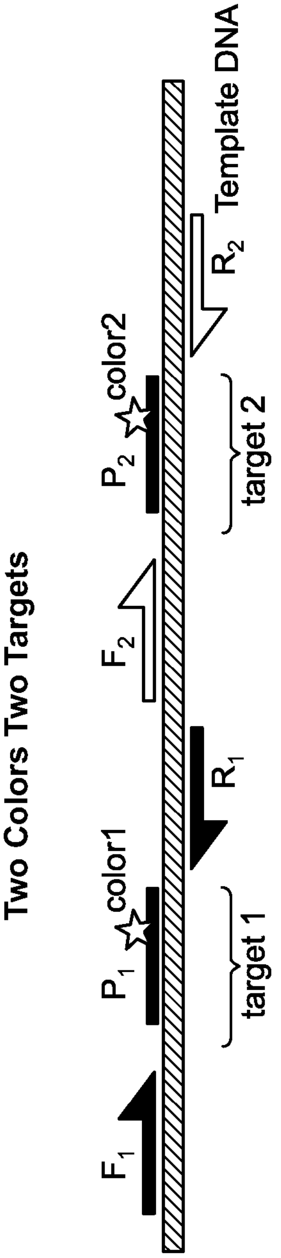
FIGS. 54A-D show detection of two genetic sequences with a microfluidic device.
Figure 54B:
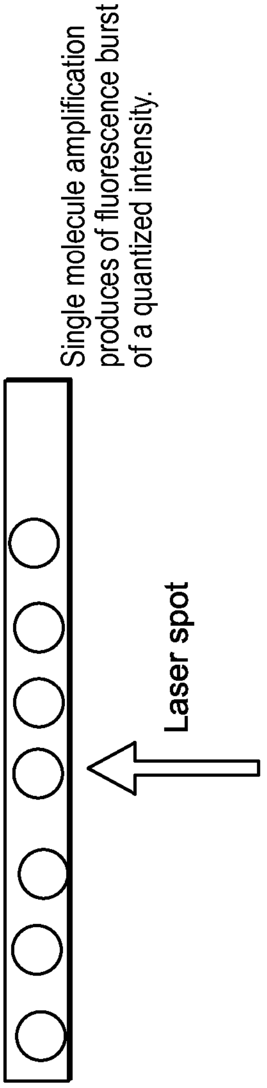
Figure 54C:
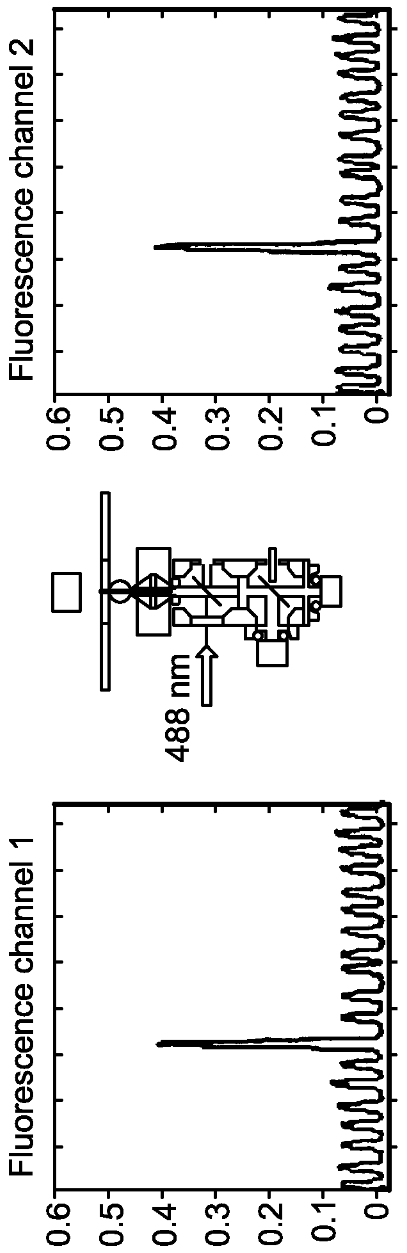
Figure 54D:
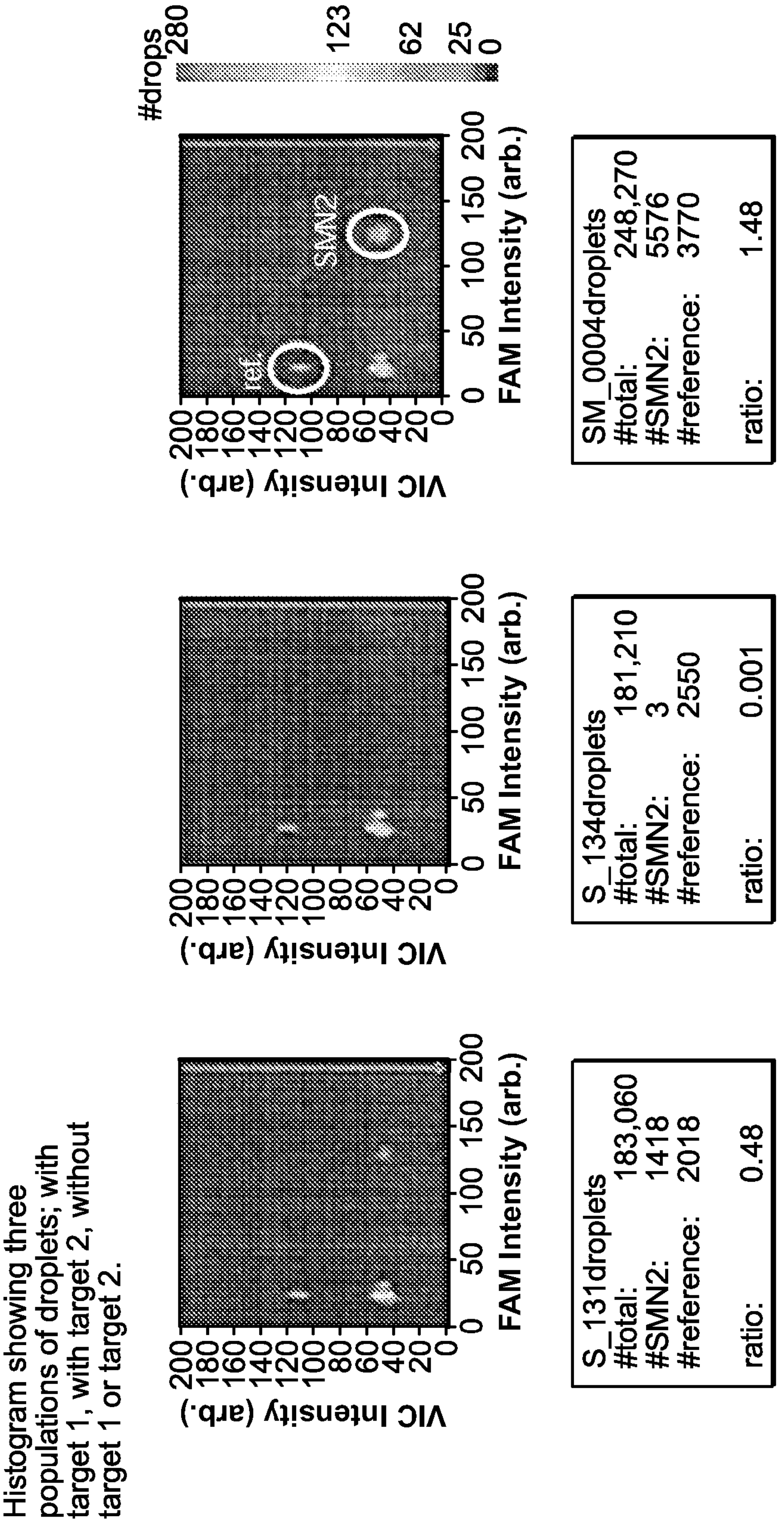
Figure 55A:
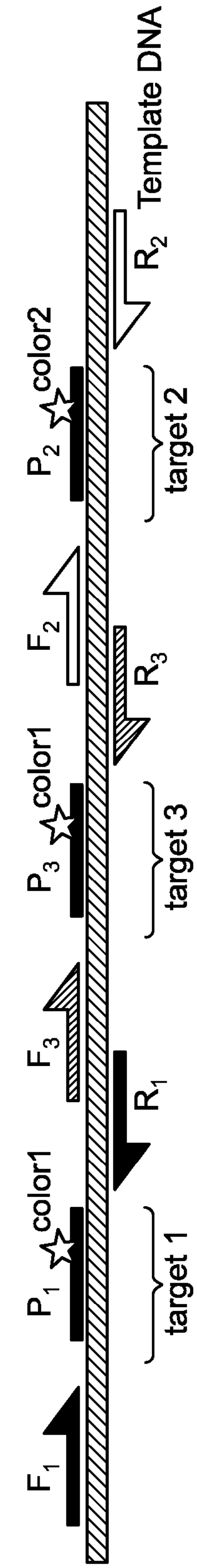
FIGS. 55A-D show detection of three genetic sequences with a microfluidic device.
Figure 55B:
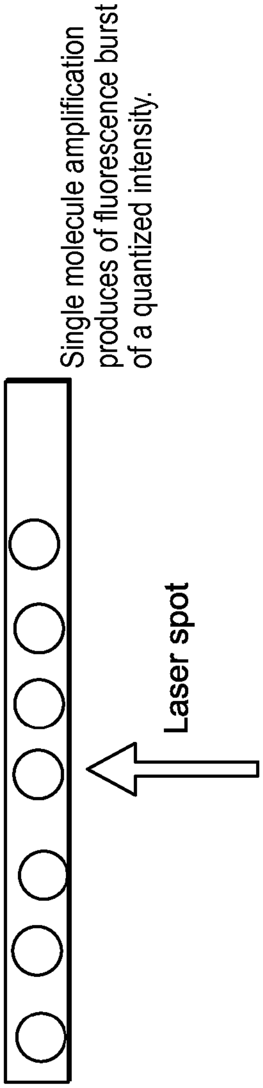
Figure 55C:
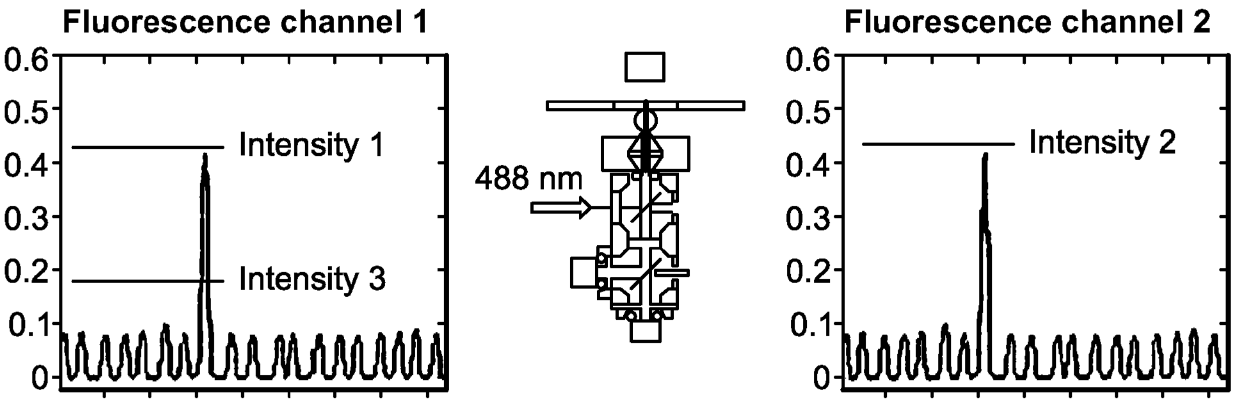
Figure 55D:
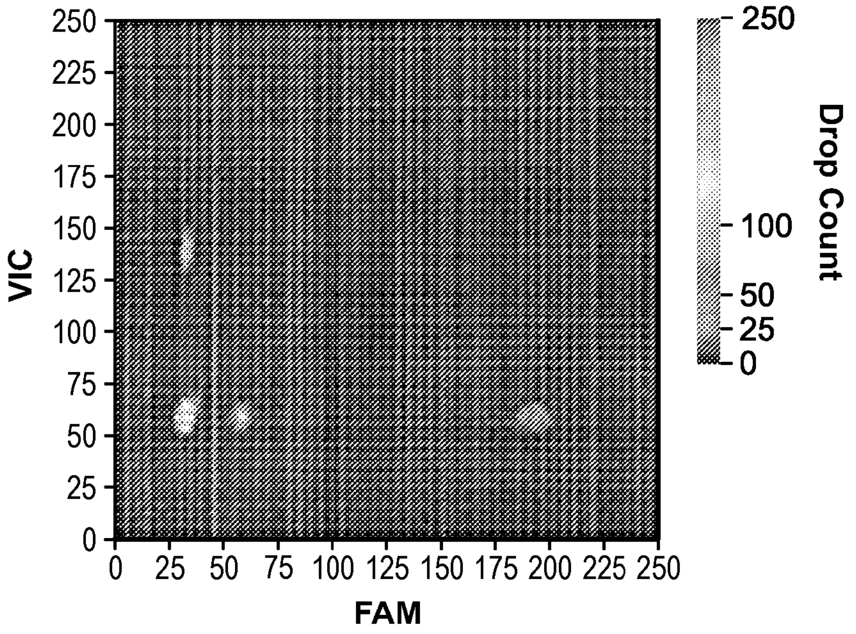

FIG. 50A is a schematic representation of a droplet having 5 sets of primers for PCR amplification of a template sequence and 5 probes, each labeled with a fluorescent dye, that binds specifically to the amplified sequences; FIG. 50B is a time trace of fluorescence intensity detected from droplets after PCR amplification; FIG. 50C is a scatter plot showing clusters representing droplets that contain specific amplified sequences (TERT, RNaseP, E1a, SMN1 and SMN2).

Probes that specifically bind to TERT, RNaseP, E1a, SMN1 or SMN2 were also encapsulated in the droplets containing the primers. Probes for TERT, RNaseP and Ela were labeled with the VIC dye and probes for SMN1 and SMN2 were labeled with the FAM dye. The sequences for TERT RNaseP, E1a, SMN1 and SMN2 were amplified by PCR. The PCR was conducted with a standard thermal cycling setting. For example:

95° C. for 10 min 31 cycles

92° C. for 15 s

60° C. for 60 s

At the end of the PCR, the fluorescence emission from each droplet was determined and plotted on a scattered plot based on its wavelength and intensity. Six clusters, each representing droplets having the corresponding fluorescence wavelength and intensity were shown. The TERT, RNaseP and Ela clusters showed the fluorescence of the VIC dye at three distinct intensities and SMN1 and SMN1 clusters showed the fluorescence of the FAM dye at two distinct intensities (FIG. 50C). The number of droplets, each having sequences selected from TERT, RNaseP, E1a, SMN1 and SMN2, can be determined from the scattered plot.

FIG. 51 and FIG. 52 show another demonstration of droplet-based amplification and detection of multiple target sequences in a single droplet. Here, five sets of primers (for TERT, RNaseP, E1a, 815A and 815G) were encapsulated in a single droplet at various concentrations along with the template DNA, the PCR master mix, and the probes. The five different probes TERT, RNaseP, E1a, 815A and 815G were also encapsulated in the droplets containing the primers. Probes for TERT and 815A were labeled with the VIC dye and probes for 815G were labeled with the FAM dye. For each of RNaseP and Ela, two probes, one labeled with the VIC dye and the other labeled with the FAM dye, were encapsulated.

The primer-plus-probe droplets were fused with template droplets. PCR reactions were conducted with the fused droplets to amplify the sequences for TERT, RNaseP, E1a, 815A and 815G. The PCR was conducted with a standard thermal cycling setting.

At the end of the PCR, the fluorescence emission from each fused droplet was determined and plotted on a scattered plot based on its wavelength and intensity. FIG. 52 shows six clusters, each representing droplets having the corresponding fluorescence wavelength and intensity. The TERT and 815A clusters showed the fluorescence of the VIC dye at two distinct intensities; the 815G clusters showed the fluorescence of the FAM dye; and the RNaseP and Ela clusters showed the fluorescence of both the FAM and the VIC dye at distinct intensities (FIG. 52). The number of droplets, each having one or more sequences selected from TERT, RNaseP, E1a, 815A and 815G, can be determined from the scattered plot. The copy number of RNaseP, E1a, 815A and 815G in the template were determined by the ratio between the number of droplets having the RNaseP, Ela, 815A and/or 815G sequences and the number of droplets having the TERT sequence (FIGS. 51-52). FIG. 52B is a table showing the copy number of specific sequences shown in FIG. 49B.

In yet another exemplary demonstration of multiplexed primer pairs in a droplet-based digital PCR reaction, two droplet libraries were generated: droplet library A was generated where each droplet contained only one primer pair; and droplet library B was generated where the primer pairs were multiplexed at 5× level in each droplet. HapMap sample NA18858 was processed in duplicate with droplet libraries A or B using standard procedures. Two μg sample DNA was used for droplet library A and one μg sample DNA was used for the 5× multiplex droplet library B. After PCR amplification, both droplet libraries were broken and purified over a Qiagen MinElute column and then run on an Agilent Bioanalyzer. Samples were sequenced by Illumina on the Illumina GAII with 50 nucleotide reads and the sequencing results were analyzed using the standard sequencing metrics. The results from the 5× multiplexed droplet library B were compared to the singleplex droplet library A as shown in FIG. 45.

The results obtained from the 5× multiplexed droplet library B were equivalent or better than what was obtained from droplet library A. The multiplexing of primers delivers the same sequencing results for base coverage, specificity and uniformity that the singleplexing does with the added advantage of reduced input DNA as shown in FIG. 45.

In FIG. 45, the following entries appear:

Total reads: total number of sequencing read found within the provided sample data.

Mapped reads (%): percentage of total reads that mapped to the human genome.

Specificity: percentage of mapped reads that include the target. The target includes all amplicon sequences with primer sequences excluded.

Mean base coverage: average base coverage within the target. The target includes all amplicon sequences with primer sequences excluded.

C1: % of target that has at least 1× base coverage. Note: non-unique sequencing reads are mapped randomly.

C20: % of target that has at least 20× base coverage.

C100: % of target that has at least 100× base coverage.

Base coverage (0.2× of mean): % of target that has at least 20% of mean base coverage.

Monochromatic Copy Number Assay

Traditional digital PCR methods involve the use of a single labeled probe specific for an individual target. FIG. 53A-E is a schematic depicting one-color detection of a target sequence using droplet-based digital PCR. As shown in Panel A of FIG. 53A-E, a template DNA is amplified with a forward primer (F1) and a reverse primer (R1). Probe (P1) labeled with a fluorophore of color 1 binds to the target genetic sequence (target 1). Droplets are made of diluted solution of template DNA under conditions of limiting or terminal dilution. Droplets containing the target sequence emit fluorescence and are detected by laser (Panels B and C). The number of microcapsules either containing or not containing the target sequence is shown in a histogram (D) and quantified (E).

FIG. 54A-D is a schematic depicting two-color detection of two genetic sequences with a microfluidic device. As shown in Panel A of FIG. 54A-D, a template DNA is amplified with two sets of primers: forward primer (F1) and a reverse primer (R1), and forward primer (F2) and a reverse primer (R2). Probe (P1) labeled with a fluorophore of color 1 binds to the target 1 and probe (P2) labeled with a fluorophore of color 2 binds to the target 2 (Panels B and C). Droplets are made of diluted solution of template DNA under conditions of limiting or terminal dilution. Droplets containing the target sequence 1 or 2 emit fluorescence of color 1 or 2 respectively and are optically detected by laser (Panels B and C). The number of microcapsules containing target 1 or 2 is shown by histogram in Panel D.

Methods of the invention involve performing accurate quantitation of multiple different DNA targets by dPCR using probes with the same fluorophore. FIG. 55A-D is a schematic depicting two-color detection of three genetic sequences with a microfluidic device. As shown in Panel A of FIG. 55A-D, a template DNA is amplified with three sets of primers: forward primers (F1, F2 and F3) and reverse primers (R1, R2 and R3). Probes (P1, P2 and P3) are labeled with fluorophores (color 1, color 2 and color 1) and bind to the target genetic sequences (target 1, target 2 and target 3) (Panels B and C). Droplets are made of diluted solution of template DNA under conditions of limiting or terminal dilution. Droplets containing target sequence 1 or 3 emit fluorescence of color 1 at two different intensities; and droplets containing target sequence 2 emit fluorescence of color 2. The number of droplets containing target 1, 2 or 3 is shown by histogram in Panel D.

Recent results from the droplet digital PCR (dPCR) shows that multiple independent PCR reactions can be run and separately quantified using the same fluorophore. Specifically, an SMN2 assay yields an unexpected population of droplets with slightly elevated signal in the FAM detection channel.

Figure 56:
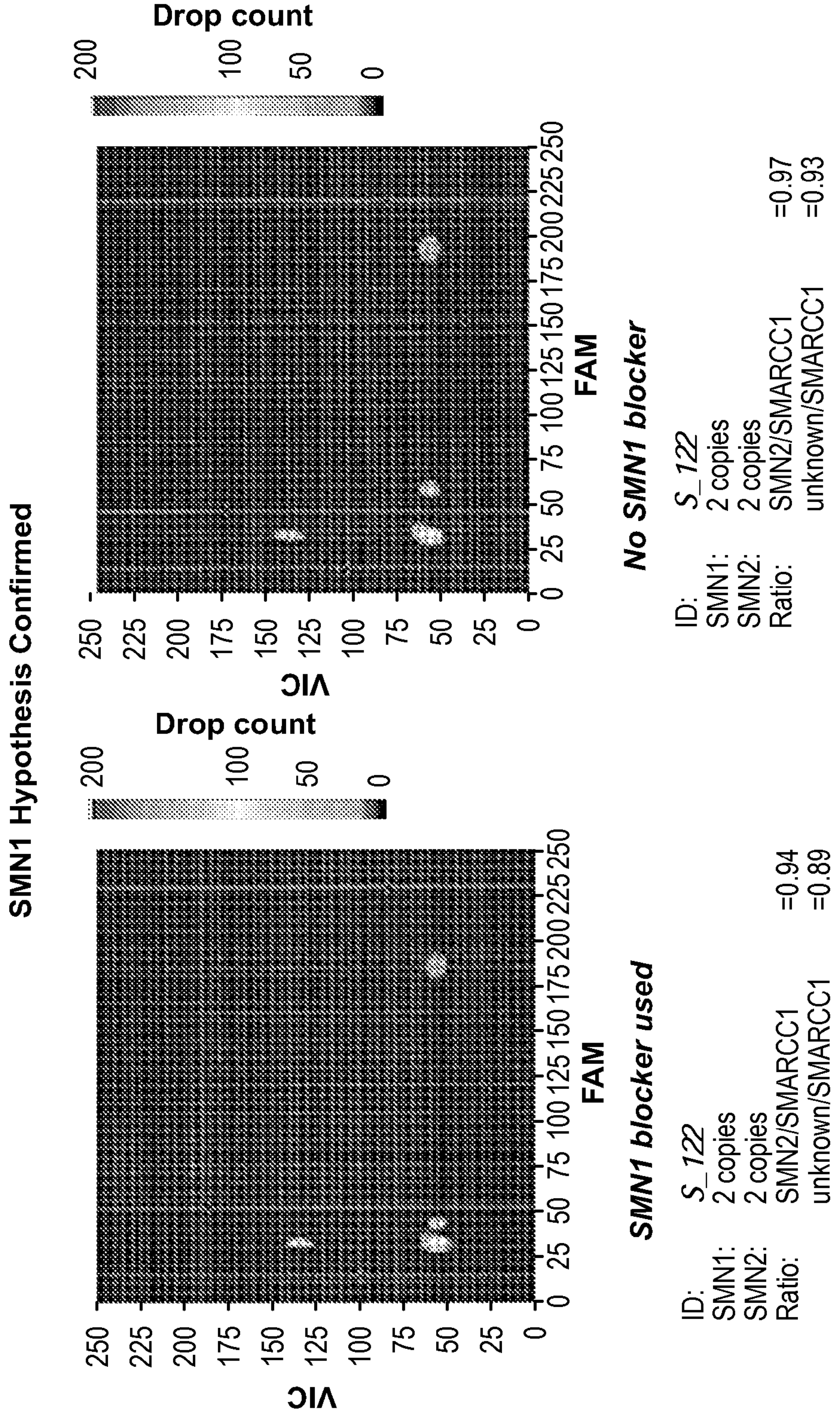
FIG. 56 shows dot plots depicting genetic sequences detected by fluorescence intensity.

The results are depicted in FIG. 56, which shows two dot plots depicting clusters of genetic sequences detected through fluorescence intensity. The left panel is a dot plot showing four clusters, where SMN1 blocker was present, each corresponding to droplet containing: top left—reference sequence (SMARCC1); bottom left—no sequence; bottom middle—SMN1; and bottom right—SMN2. Right panel is a dot plot showing four clusters. No block for SMN1 sequence was present. Top left: droplets containing the reference sequence (SMARCC1); bottom left: droplets not containing any sequence; bottom middle: droplets containing sequence for SMN1; and bottom right: droplets containing sequence for SMN2. The shift of the bottom middle cluster in right panel as compared to left panel confirms that fluorescence intensity provides a very sensitive measurement for the presence of a sequence.

Without intending to be bound by any theory, the simplest explanation is that the cluster arises from weak association of the SMN2 probe to the SMN1 gene despite the presence of a blocker to that gene (a non-fluorescent complementary probe to the SMN1 gene).

One confirmation of SMN1 as the source of the unexpected cluster was an observed dependence of the intensity of this feature on the presence of the SMN1 blocker. A shift toward higher FAM fluorescent intensities was observed in the absence of the blocker (FIG. 56). In another definitive confirmation the ratio of the SMN1 (putative) population size to the reference size of 0.96 in perfect agreement with expectation (two copies of each) (S_131 sample). Another sample, S_122, with the same number of SMN1 copies yielded a ratio of 0.88 in one run and 0.93 in another, also consistent with the proposed explanation of the unexpected cluster.

Without intending to be bound by any theory, these observations indicate that SMN2 probe binding to SMN1 DNA yields an elevated fluorescent signal. A simple kinetic model explaining this phenomenon assumes that the hybridization of the SMN2 probe to the SMN1 DNA achieves equilibrium at a faster rate than the polymerase fills in the complementary strand. The amount of probe fluorophore that is released in each thermal cycle is therefore proportional to (or even equal to) the number of bound probes. Thus the lower the binding affinity the fewer the number of probe fluorophores that are released. Due to SMN1 sequence mismatch(es) with the SMN2 probe, the affinity of the probe is certainly expected to be lower to SMN1 than SMN2. This model also explains the signal dependence on the sMN1 blocker: the blocker competitively inhibits the SMN2 probe hydrolysis by the polymerase exonuclease activity.

It may also be, however, that the probe hybridization does not reach equilibrium before exonuclease activity. In this case, the association rates would play a more dominant role. Similar logic applies. The binding rate to the matching site is likely to be faster than to the mismatch site, and the blocker would act to decelerate probe binding to the mismatch site. The binding of SMN2 probe to SMN1 DNA might be detectable by conventional bulk qPCR, especially in absence of SMN2, but highly quantitative results like those shown here are very unlikely. Definitely, there is no report of qPCR or any other technique quantifying two different DNA sequence motifs with the same color fluorophore. Sequestration of the individual reactions by single molecule amplification within droplets eliminates any confusion regarding mixed contributions to the signal.

The advantage of quantifying DNA with multiple probes of the same color fluorophore goes beyond two highly homologous sequences, as shown here. Rather, any plurality of sequences of any degree of similarity or dissimilarity can be quantified so long as the different probes have significantly different binding occupancies to their respective DNA binding sites.

Another advantage of dPCR for multiplexed reactions is that the different reactions do not compete with each other for reagents as they would in qPCR. However, the possibility for unintended cross-reactivity remains. A multiplexed assay can require a more dilute sample. For instance, at 10% occupancy a duplex reaction would have double occupancy 1% of the time. Hence 1 in 10 PCR+ droplets would be doubles, resulting in a final intensity at least as high and possibly higher than the brighter of the two probes. For a simple duplex system the contribution from each probe could be recovered. In this example the total number of PCR+ droplets for probe 1 would be (Probe 1)+ (Probe1+Probe2).

Higher degrees of multiplexing would require greater dilution. For example, for a 4-plex at 1% occupancy the probability of one probe overlapping any of the other 3 is ~3%, and that error may be too high for some applications. The need for large dilutions strongly favors the large number of dPCR reactions.

In another example of the invention, a single fluorophore (FAM) was used in a gene copy number assay for both the reference and the target DNA. A model system was used with varying concentrations of plasmid DNA to represent a change in the target gene copy number, relative to a reference gene, equivalent to 0-16 copies of the target gene per cell. BCKDHA and SMN2 plasmid DNA served as the reference and target with 1× and 0.5× primers and probes respectively. With a starting ratio of 8:1 SMN2 to BCKDHA, the sample was diluted serially by 2× into a solution of BCKDHA at the same concentration to vary just the amount of SMN2. The resultant samples were emulsified, thermally cycled, and over 105 droplets were analyzed for each sample as described in the previous section. The process was repeated in triplicate.

Figure 57A:
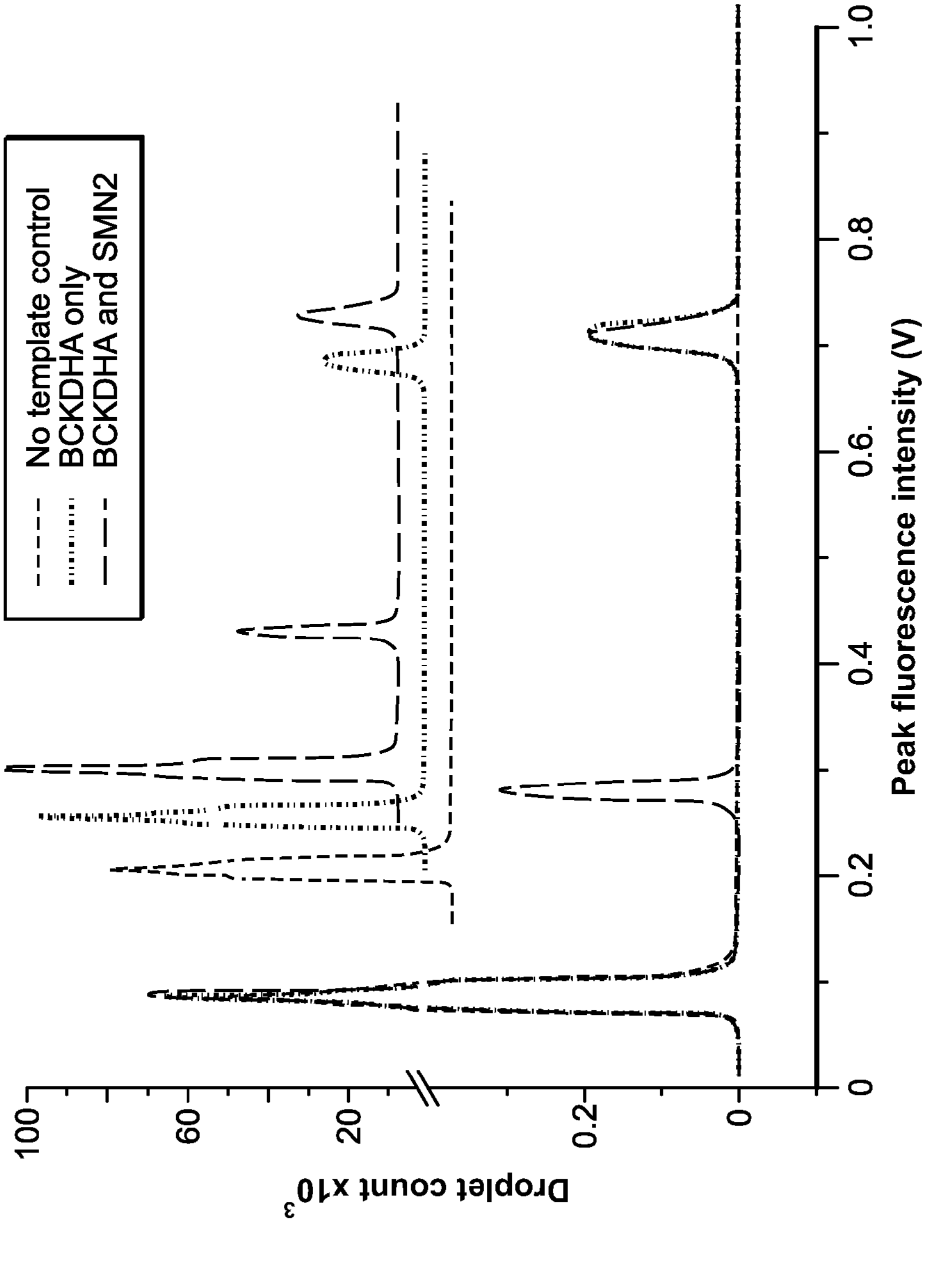
FIG. 57A depicts a histogram of droplet peak fluorescence intensities.
Figure 57B:
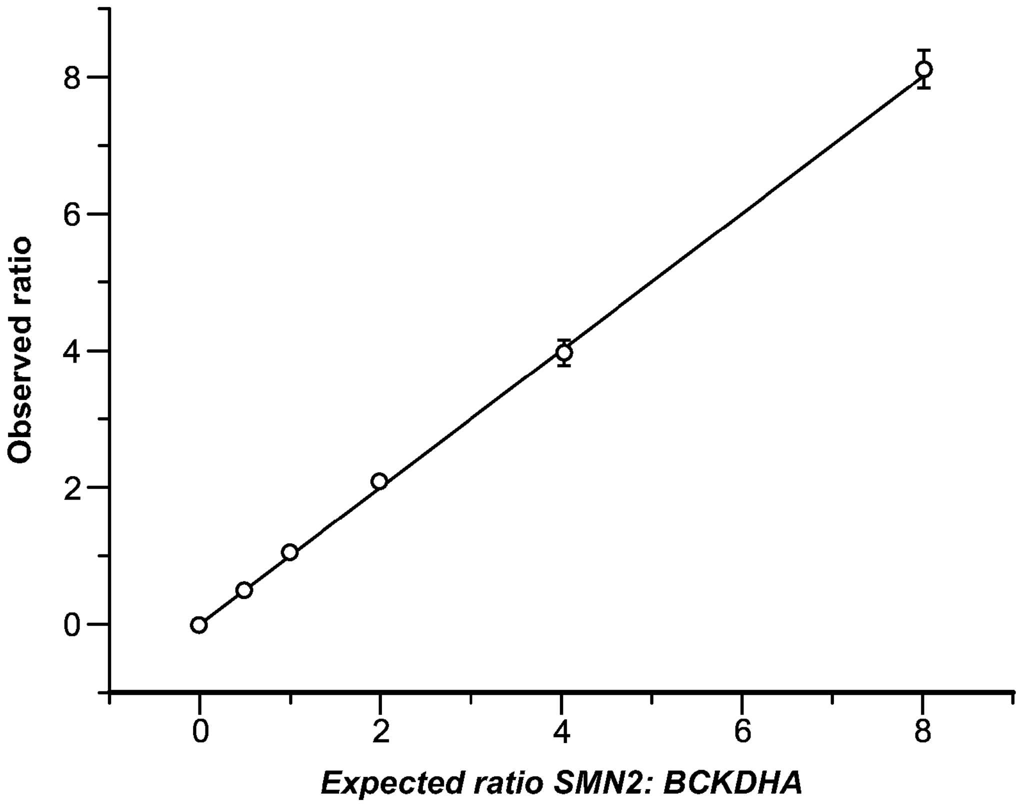
FIG. 57B shows a comparison of gene copy numbers by monochromatic dPCR.

Methods of the invention also include analytical techniques for identification of fluorescence signatures unique to each probe. FIGS. 57*a*-57*b* depict histograms of a duplex gene copy number assay using only one type of fluorophore by digital PCR.

In this example of the invention, histograms of the droplet fluorescence intensities are shown in FIG. 57*a* for three different template DNA samples: a no template control (dotted line), BCKDHA only (solid line), and 1:1 BCKDHA to SMN2 (dashed line). For clarity, the histograms are shown both overlapped to highlight the similarity for certain peaks, and offset from each other to reveal all of the features. In the case of 1:1 BCKDHA to SMN2, three populations were readily apparent: a dominant feature appeared at 0.08 V, and two smaller peaks were evident at 0.27 and 0.71 V. The dominant feature at 0.08 V was assigned to PCR(−) droplets since both small peaks disappeared, but the large one remained, in the no template control. The peak at 0.71 V was assigned to BCKDHA since it was the sole feature arising with the addition of just BCKDHA, and the peak at 0.27 V appeared on subsequent addition of SMN2, completing the assignments. A very small peak appeared at ~0.9 V, not visible on the scale of FIG. 57*a*, that corresponded to droplets occupied by both genes. As another method of the invention, once the different peaks are identified, droplets within each peak were counted corresponding to each possible state (PCR(+) for either BCKDHA or SMN2, or both, or PCR(−)), and the gene copy number was then determined from the ratio of occupancies. Gene copy numbers for each sample in the serial dilution are plotted in FIG. 57*b* against expected values (observed ratios of SMN2 to BCKDHA to expected ratios of SMN2 to BSKDHA), with an excellent linear fit (y=1.01x) across the full range (R2=0.9997, slope=1.01), demonstrating accurate and precise measurement of the equivalent of 0 to 16 copies of SMN2 per cell.

It is possible to determine if a heterogeneous sample contained components with different copy level numbers. If the copy number variants to be assayed were spaced close enough along the chromosome, the DNA from a sample could be fragmented and encapsulated in droplets at a level of one haploid genomic equivalent or less per droplet. The droplet would also contain a TaqMan assay specific for the copy number variant. The intensity of the signal in each droplet would depend on the number of copy number variants are present for the sample. Counting of the number of droplets of different intensities would indicate things like how many cells in a particular sample had what level of copy number variants.

Splice Variants

In certain embodiments, target material includes alternatively spliced transcripts, and the invention provides labels for detecting or counting the splice variant. TaqMan assays can be designed that are specific for each of the exons in an RNA transcript. After the RNA is turned into cDNA it can be encapsulated into a droplet at 1 copy or less per droplet. The droplet would also contain the multiplexed TaqMan assay for each of the exons. Each of the TaqMan assays would contain a different probe but all the probes would have the same fluorescent dye attached. The droplets would be thermocycled to generate signal for each of the TaqMan assays. If there are multiple splice variants in the sample they each will contain a different number of exons depending on the splicing events. The fluorescent intensity of each droplet would be different depending on the number of exons present. By counting the number of droplets with different intensities it would be possible to identify the presence and abundance of different splice variants in a sample.

Tuning Probe Intensity

Identifying probes by fluorescence intensity often requires adjusting the brightness of the probes, particularly for higher-plex assays with dense probe patterns. In the previous section the probes for the gene copy number assay yielded very well resolved peaks (FIG. 57*a*). Clearly room exists to accommodate one or multiple extra probes in the copy number assay within the resolution of the measurement, but a method for adjusting the fluorescence intensity of the new probes is required to avoid interference with the existing assay. One method of the invention involves varying the probe and primer concentrations together as a very simple technique to optimize relative intensities in higher-plex reactions.

FIG. 58A-C is a schematic for tuning the intensity of a detectable label to a particular target with a microfluidic device. As shown in Panel A of FIG. 58A-C, a template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to single base mismatch between P2 and target 2. As shown in Panel B, template DNA is amplified with two sets of primers: forward primers (F1 and F2) and reverse primers (R1 and R2) (Panel B). Fluorescence from target 2 is lower in intensity than that from target 1 due to the presence of a competing probe 2 that is not labeled with the fluorophore. As shown in Panel C, template DNA is amplified with two sets of primers: forward primers (F1 and F2) and reverse primers (R1 and R2). Probes (P1 and P2) are labeled with fluorophore of color 1 and bind to target 1 and target 2 respectively. Fluorescence from target 2 is lower in intensity than that from target 1 due to the presence of a competing probe 2 that is labeled with a different fluorophore.

Figure 59:
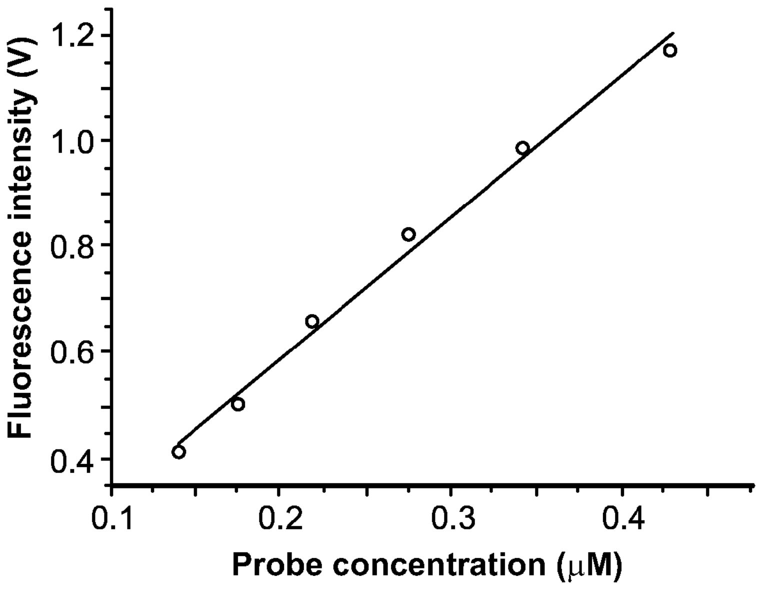
FIG. 59 is a line graph depicting the linear dependence of droplet fluorescence intensity on probe concentration (Line, best linear fit ($y=-0.092x+0.082$, $R2=0.995$).

FIG. 59 shows probe fluorescence intensities throughout a serial dilution of the probes and primers for a different reference gene, ribonuclease P (RNaseP), against a constant amount of genomic DNA from the Coriell cell line NA3814 at an occupancy of 0.02 target DNA molecules per droplet. The probe fluorescent intensities varied in direct proportion to probe concentration over a narrow concentration range spanning ~0.15 to 0.4 μM (R2=0.995)—roughly centered about the typical probe concentration of 0.2 μM—after compensation for dilution errors and other run-to-run differences such as optical realignments using the intensity of the PCR(−) droplets as a reference. In summary, probe intensities can be varied by dilution over a small but adequate range for the purpose of tuning multiplexed assays without affecting the amplification itself.

Although the example above for adjusting probe fluorescence intensities involves varying probe and primer concentrations together by the same factor, the invention is not limited to this method alone for varying probe intensity. Other methods include varying just the probe concentration; varying just the primer concentrations; varying just the forward primer concentration; varying just the reverse primer concentration; varying the probe, forward, and reverse primers concentrations in any way; varying the thermal cycling program; varying the PCR master mix; incorporating into the assay some fraction of probes that lack fluorophores; or incorporating into the assay any hybridization-based competitive inhibitors to probe binding, such as blocking oligomer nucleotides, peptide nucleic acids, and locked nucleic acids. The invention incorporates such methods by themselves or in any combination.

Higher-Plex Reactions

One method of the invention involves performing higher-plex assays with a single probe color (e.g., fluorophore). As described above, probe fluorescent intensities can be adjusted by a variety of means such that each intensity level uniquely identifies a DNA target. For example, targets T1, T2, T3, and T4 might be uniquely identified by intensity levels I1, I2, I3, and I4. Not intending to be bound by theory, the maximum number of intensity levels possible for unique identification of targets is related to the resolution of the different intensity levels—that is the spread of intensities for each particular probe compared to the separation between the average intensities of the probes—and it is also related to the intensity of the empty droplets that tends to grow with increasing numbers of probes. The number of intensity levels can be 0, 1, 2, 3, 4, 10, 20, 50, or any number (e.g., up to 100, or higher). In the examples show below, as many as three intensity levels are demonstrated.

Another method of the invention involves performing higher-plex assays using multiple different probe colors (i.e. fluorophores). As above for the monochromatic multiplexing assay, for each color probe, multiple targets can be identified based on intensity. Additionally, multiple colors that are spectrally separable can be used simultaneously. For example, a single droplet might contain four different probes for measuring four different targets. Two probes might be of color A with different intensities (say, A1 and A2), and the other two probes of color B with different intensities (say B1 and B2). The corresponding targets are T1, T2, T3, and T4 for A1, A2, B1, and B2 respectively. If a droplet shows an increase in fluoresce in color A, the droplet therefore contained either targets T1 or T2. Then, based on the fluorescence intensity of color A, the target could be identified as T1 or the target could be identified as T2. If, however, a droplet shows an increase in fluorescence in color B, the droplet therefore contained either targets T3 or T4. Then, based on the fluorescence intensity of color B, the target could be identified as T3 or the target could be identified as T4. Not intending to be bound by theory, the maximum number of different colors possible is limited by spectral overlap between fluorescence emission of the different fluorophores. The maximum number of colors can be 1, or 2, or 3, or 4, or up to 10, or up to 20. The maximum number of colors can be higher than 20. In the demonstrations that follow, the largest number of colors is two.

Another method of the invention involves performing higher-plex assays using multiple different probe colors (i.e. fluorophores), however unlike the strategy above where each target is identified by single type of probe with a unique color and intensity, instead in this method a single target may be identified by multiple probes that constitute a unique signature of both colors and intensities. For example, a single droplet might contain four different probes for measuring three different targets (say, T1, T2, and T3). Two probes might be of color A (say, A1, and A2), and two probes might be of color B (say, B1 and B2). T1 is measured by probe A1, T2 is measured by probe B1, but T3 is measured by both probes A2 and B2. Thus, when a droplet contains T1 only increased fluorescence appears in color A. When a droplet contains T2 only increased fluorescence appears in color B. However when a droplet contains T3, increased fluorescence appears in both colors A and B.

Generally, without wishing to be constrained by theory, the above three methods for higher-plex dPCR are simplest to implement under conditions of terminal dilution, that is when the probability of multiple different target molecules co-occupying the same droplet is very low compared to the probability of any single target occupying a droplet. With multiple occupancy arises the complexity of simultaneous assays competing within the same reaction droplet, and also complexity of assigning the resulting fluorescence intensity that involves a combination of fluorescence from two different reaction products that may or may not be equal to the sum of the two fluorescence intensities of the individual reaction products. However, methods of the invention can accommodate these complications arising from multiple occupancy.

Methods of the invention for higher-plex reactions also include methods for primer and probe pairing. In the simplest case targets are unlikely to reside on the same DNA fragments, such as when targets are from different cells; or when targets are from different chromosomes within a single cell type; or when targets are distant from each other within a single chromosome such that they become physically separated during DNA fragmentation; or when targets are very close to each other within a chromosome, but nevertheless become separated by targeted cleavage of the DNA, such as by restriction enzyme digestion; or for any other reason. In such cases each probe can be paired with a single set of primers (forward and reverse). However, in other cases the target regions might frequently reside on the same DNA fragments, for example when targets reside within the same codon, or for any other reason. In such cases, a single set of primers might serve for multiple probes (for an example, see Pekin et al.).

Figure 68:
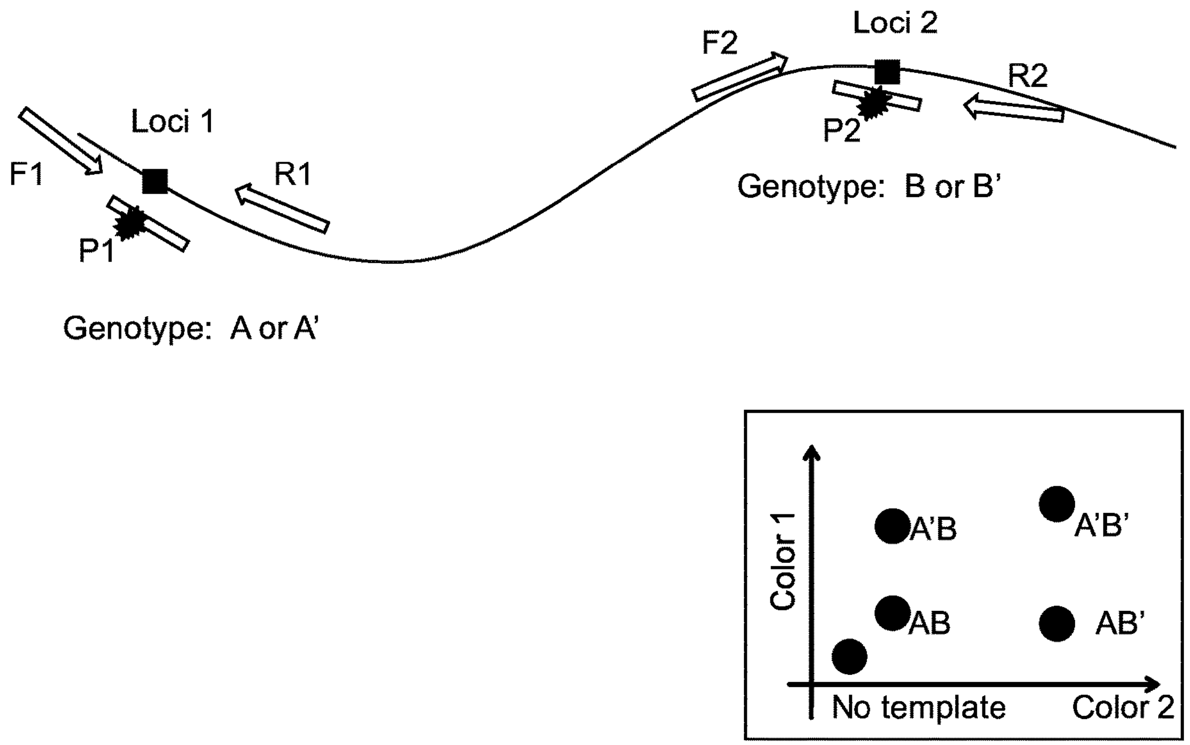
FIG. 68 is a schematic showing haplotype detection in droplets.

Higher multiplex reactions can be performed to distinguish the haplotypes of two SNPs. For example, assume that at position one there can be genotypes A or A' and at position two there can be genotypes of B or B'. In a diploid genome four unique haplotypes are possible (A,B; A,B';A',B; and A',B'). If for example A' and B' represent drug resistant mutations for infection, it is often the case that A'B and AB' are less severe and treated differently than A'B' which represents a significant drug resistance that must be treated with extreme care. Digital PCR with intensity discrimination is ideally suited for identifying low prevalence of A'B' in a background of mixtures of the other three haplotypes. Haplotyping information is also important for construction of haplotypes (e.g., human leukocyte antigen (HLA) haplotypes). One way that the present example can be constructed is by assay design such that color one is used for A and is of high or low intensity indicative of allele A or A' respectively and color two is used for B and is of high or low intensity respectively indicative of B or B'. Populations of [color1, color2] corresponding to [Low, Low] would be a measure of an allele of AB and [high, low] allele A'B and an allele of [A'B'] will be readily distinguishable as [high, high] even in a background that is predominately a mixture of A'B and AB'. See FIG. 68. In some cases it will be advantageous to start by encapsulating into the droplets long single molecules of nucleic acid that contain both A and B SNP location and in other cases it will be desirable to start by encapsulating single cells, bacteria or other organism within the droplets prior to releasing the nucleic acid from the organism. In still other embodiments the multiplex intensity detection of multiple simultaneous targets can be used as surrogate markers for multiple types of binding interactions or labeling of target materials. This technique is also not limited to single molecule detection and can be used for haplotype detection in single cells (e.g., bacteria, somatic cells, etc.). In single cell analysis, a sorting step may be applied prior to haplotyping.

5-Plex SMA Assay

The invention in general provides multiplex assays for genetic markers. Here is discussed a 5-plex assay for spinal muscular atrophy (SMA). The invention includes other "plex" levels and other genetic markers. SMA was selected for one example due to both its important clinical significance as well as its complicated genetics. It is the second-most prevalent fatal neurodegenerative disease and affects ~1 in 10,000 live births. SMA is most often caused by homozygous absence of exon 7 within the survival of motor neuron 1 gene (SMN1, reviewed by Wirth et al.), however the severity of the condition is modulated by the number of gene copies of SMN2 with prognosis ranging from lethal to asymptomatic over 1-5 copy numbers (reviewed by Elsheikh et al.). Hence accurate quantitation of SMN2 copy number is important for clinical prognosis and genetic counseling. Aside from large deletions of SMN1, a number of single point mutations or short deletions/duplications within the same gene also account for ~4% of cases of SMA. In a significant step toward a comprehensive SMA assay, the multiplexed dPCR assay demonstrated here contains both copy number assays (for SMN1 & 2) and an assay for one of the prevalent SNPs (c.815A>G).

One embodiment of the invention is a multi-plex assay for diagnostics. Here, a 5 plex assay quantifies common genetic variants impacting SMA including two copy number assays for the SMN1 and SMN2 genes with BCKDHA as a reference, and a SNP assay for the c.815A>G mutation. Two differently colored fluorophores, FAM and VIC, were used to uniquely identify each of the assays. The probes for SMN1 and SMN2 contained only FAM, and for c.815A only VIC. However, mixtures of VIC and FAM-labeled probes were used for BCKDHA and c.815G. The use of VIC and FAM fluorophores in this example does not limit the invention, rather the 5 plex assay can be used with any suitable hybridization-based probe chemistries. For validating the assay, a model chromosome was synthesized containing a single target region for each of the different primer/probe pairs. EcoRV restriction sites flanked each target, allowing separation of the fragments.

Figure 60A:
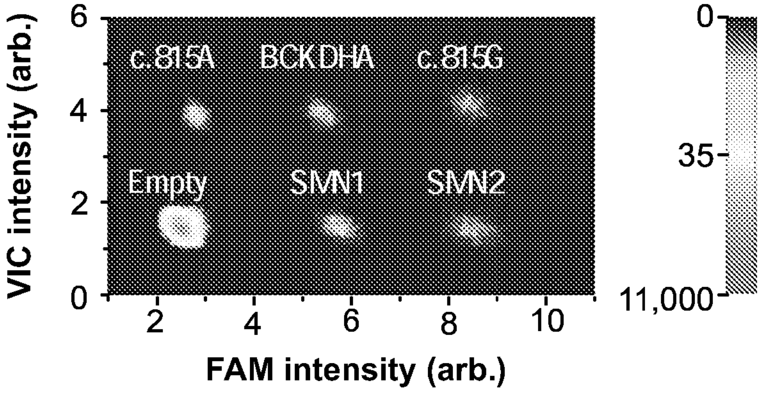
FIG. 60A is a 2-D histogram of droplet fluorescence intensities.

As another method of the invention, histogram-based data presentation and analysis is incorporated into the invention for identifying and characterizing statistically similar populations of droplets that arise from one probe signature (color and intensity), and for discriminating one population of droplets from the others. FIG. 60*a* shows a 2 dimensional histogram of droplet fluorescence intensities as a contoured heat map, with hotter colors representing higher occurrences. Standard techniques were used to compensate for spectral overlap of the FAM and VIC signals. Samples were run at 0.006 occupancy per target. Six populations were clearly evident, five for the assay and one for PCR(−) droplets. As one method of the invention, the populations were assigned by selective exclusion of assay components. For example, excluding the SMN2 primers and probe eliminated the population at the bottom right in the histogram, but otherwise the distribution remained unchanged.

Figure 60B:
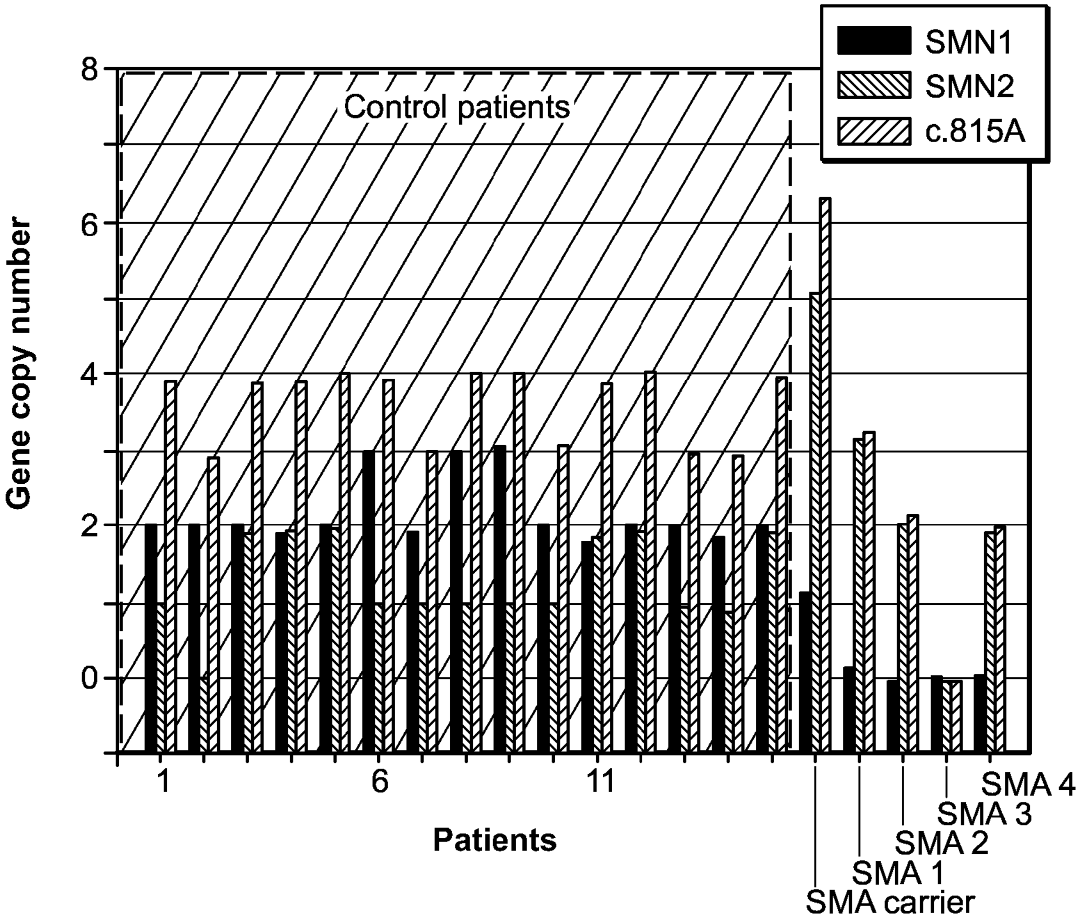
FIG. 60B shows the results of the SMA pilot study.

FIG. 60*a* is a 2-D histogram of droplet fluorescence intensities, shown as a heat map, for the 5 plex assay against the synthetic model chromosome for validation. The six well resolved droplet populations corresponded to the five individual assays plus the empty droplets; FIG. 60*b* shows the results of the SMA pilot study.

Assignments are labeled in FIG. 60*a*. As we have found to be generally true for this method of multiplexing, the assay worked immediately with well resolved or at least distinguishable populations for each target. As another method of the invention, the relative positions of the different populations in the histogram were then adjusted into a regularly spaced rectangular array by tuning the probe concentration as described in the previous section. Usually no more than two iterations are required for optimization.

In another method of the invention, the different populations were sufficiently well resolved to allow droplets within each population to be counted by integration across rectangular boundaries. The boundaries were positioned at midsections between neighboring peaks. The methods of the invention are not constrained to rectangular boundaries, or to specific boundary locations between peaks. Rather, any closed or unclosed boundary condition can suffice. Boundary conditions do not need to be "binary" either, in the sense that weighted integrations can also be performed across the boundaries to arrive at droplet counts. The peak position of each cluster varied by no more than 2% from run to run after normalization to the intensity of the empty droplets to account for variations in detection efficiency (data not shown). Hence, once identified, the same boundaries for integration could be reused between samples. The methods of the invention are not limited to fixed boundary positions. Dynamic population identification and boundary selection in between samples or studies is anticipated. Twenty different patient samples from the Coriell cell repositories were analyzed with this assay: 4 afflicted with SMA, 1 SMA carrier, and 15 negative controls. Assay results are shown in FIG. 60*b*. Gene copy number was calculated as before, as the ratio of occupancies derived from the number of target droplets vs. reference droplets. Like the copy number measurement in FIG. 57, each assay yielded ratios very close to the expected integer values, but when all of the patient data was plotted as actual ratio vs. expected integer ratio a small systematic deviation from the ideal slope of 1 was observed. Measured slopes were 0.92, 0.92, and 0.99 for SMN1, SMN2, and c.815A respectively. For clarity, the data in FIG. 60*b* was scaled to the ideal slope of 1.

The measured genotypes of the different patients were consistent with their disease conditions (unafflicted, carrier, or afflicted). The patients afflicted with SMA each had zero copies of SMN1 (numbers SMA 1-4 in FIG. 60*b*), the carrier had just one copy, and the negative controls all had two or three copies (numbers 1-15). Three unrelated individuals (numbers 6, 8, and 9) had three copies of SMN1, occurring at a rate of 20% which is similar to a previous report for healthy individuals. Variability in SMN1 copy number is not surprising since it lies within an unstable region of chromosome 5q13. A larger variety of SMN2 copy numbers was observed. One to two copies were most common in the control group, although one individual had zero copies, a distribution consistent with expectations for normal individuals. The SMA carrier and afflicted patients had elevated copy numbers of SMN2 on average: 5 for the carrier, two afflicted with 3 copies, and the others with 2 copies. The afflicted patients were all diagnosed as SMA Type I, the most severe form, based on clinical observations according to the Coriell repository. The strong genotype/phenotype correlation between SMN2 copy number and disease severity suggests that the two individuals with three copies of SMN2 might have an improved Type II prognosis, especially for the patient SMA 1 who had survived to three years at the time of sampling, much beyond the typical maximum life expectancy for SMA Type I of 2 years. However there remains reluctance to predict disease outcome based on SMN2 copies alone since other less well characterized or unknown modifying genes may impact prognosis and because not all SMN2 copies may be complete genes. Furthermore some Type I patients have begun surviving longer in newer clinical settings. Hence, with little clinical information regarding the patients available to us, we can conclude that our SMN2 assay results were consistent with broad expectations for disease severity.

The SNP assay revealed that all patients carried the normal c.815A genotype and no instances of c.815G were observed. The mutation is relatively rare and hence was not expected to appear in a small patient panel. Of interest, however, was the presence of an apparent extra gene fragment in two unrelated individuals that was uncovered with the SNP assay. The c.815A>G assay does not discriminate between SMN1 and SMN2 due to their high sequence similarity, and hence the total copies of c.815A and G should equal the sum of the copies of SMN1 and SMN2. This was true for all patients except for healthy patients number 1 and 2, both of whom had one extra copy of c.815A. c.815 lies on exon 6, and the SNP that discriminates between the SMN1 and SMN2 genes lies on exon 7, hence the extra genes may be fragments of SMN1 lacking exon 7. This seems reasonable because the deletion of exon 7 is the common mutation causing 95% of cases of SMA (reviewed by Wirth et al.) and it is carried by 1/40 to 1/60 adults. Thus these patients might have been typical carriers of SMA but for the acquisition of at least one compensating healthy copy of SMN1 on the same chromosome.

9 Plex SMA Assay

Figure 61:
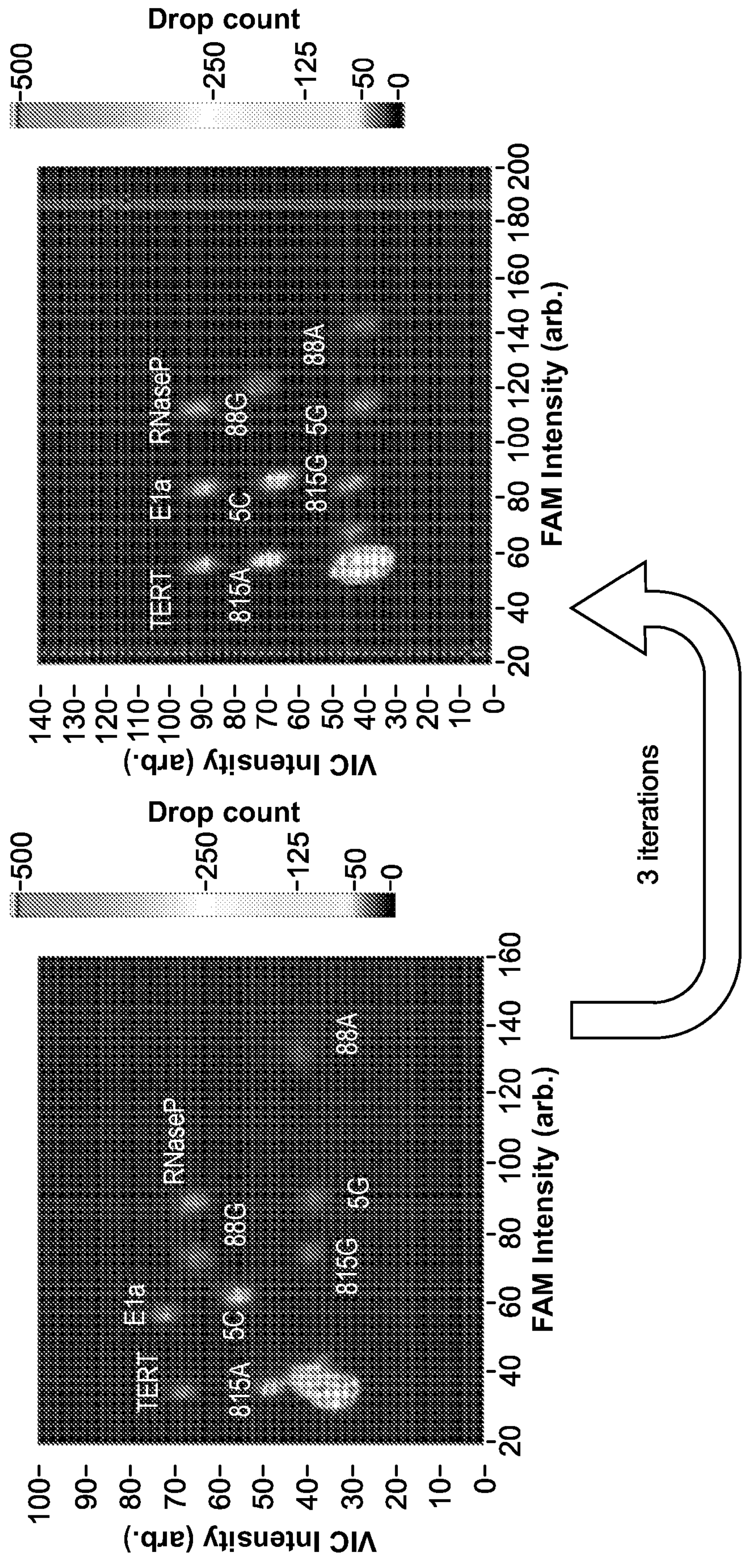
FIG. 61 depicts a 9 plex dPCR assay for spinal muscular atrophy with only two fluorophores, showing the process of optimizing droplet intensities.

A 9 plex assay for certain SMA related targets was also demonstrated with just two colors (probes containing FAM and VIC fluorophores). Aside from the optimized primer and probe concentrations, assay conditions and experimental procedures were identical to the 5 plex assay above. FIG. 61*a* shows the various droplet populations in 2 D histograms before optimization of probe concentrations. The identity of the different targets is shown on the figure itself. As one method of the invention, the identification of the different populations was made as before, by selective exclusion and/or addition of one or more assays. Most of the populations were already well resolved, with the exception of the probe for the c.815A genotype that was in close proximity with the cluster corresponding to empty droplets. After three iterations of optimization of probe concentrations, all of the target populations were well resolved from each other, and well resolved from the empty droplets (FIG. 61*b*). Three methods of the invention were highlighted in this demonstration: (1) nine DNA targets were uniquely identified in a two-dimensional histogram, far beyond the capabilities of conventional qPCR; (2) target DNA molecules were distinguished on the basis of some combination of both color and intensity arising from one or multiple probes against the same target; and (3) the relative positions of the target molecules within the histogram were adjusted by varying the probe concentrations to optimize the pattern of colors and intensities for increased resolution amongst the various droplet populations.

As one method of the invention, different droplet populations were identified by selective addition or exclusion of assays in the examples above. However the invention is not limited to this method alone. Rather, any method for population assignments known to those in the art are considered. Methods of the invention include any method that can cause an identifiable displacement, appearance, or disappearance of one or more populations within the histograms including changing the probe and primer concentrations together, either by the same factor or by different factors; changing the probe concentration alone; changing the primer concentrations alone; changing the thermal cycling conditions; and changing the master mix composition. Another method of the invention takes advantage of prior knowledge of the position of an assay within a histogram to assist assignment.

Multiplexing Capacity

The level of multiplexing demonstrated in the preceding SMA example was 9×, significantly exceeding the maximum practicable number with qPCR. Without wishing to be constrained by theory, the two main limitations are the resolution between assays and the increasing fluorescence intensity of empty droplets with higher loading of probes. A method of the invention involves optimizing the pattern of colors and intensities of the different probes for maximum multiplexing while still achieving adequate specificity for each individual reaction. Although rectangular arrays of droplet populations were demonstrated for the 5 and 9 plex reactions, another desirable pattern is the tight-packed hexagonal array. However the invention is not constrained to any particular array strategy.

Adding extra colors would increase the capability even further, however with some diminishing returns because the fluorescence of the empty droplets would continue to rise. The capacity could be yet further increased with better probes yielding larger differential signals, such as hybrid 5' nuclease/molecular beacon probes that reduce background by contact quenching yet exhibit the bright signals typical of free unquenched fluorophores. With such improvements multiplexing capacity exceeding 50× can be envisioned.

Multiplexing with Optical Labeling

Using droplet-based microfluidics, multiple targets can also be measured simultaneously by a different method. According to the alternative method, primers and probes can be loaded individually into droplets along with an optical label to uniquely identify the assay. Typically the optical label is a fluorophore, or a combination of different fluorophores, that are spectrally distinct from the probe fluorophore. Various different types of droplets, each containing different assays that are uniquely identified by different optical labels, can be mixed into a "library" of droplets. Then, according to methods of the invention above, library droplets are merged one-to-one with droplets containing template DNA. After thermal cycling, some droplets that contain template DNA will exhibit brighter fluorescence at the emission wavelengths of the probes. The specific target DNA molecules giving rise to these PCR(+) signals are subsequently identified by the optical probes. In one study, the six common mutations in KRAS codon 12 were screened in parallel in a single experiment by one-to-one fusion of droplets containing genomic DNA with any one of seven different types of droplets (a seven-member library), each containing a TaqMan® probe specific for a different KRAS mutation, or wild-type KRAS, and an optical code.

In one method of the invention, optical labeling can be combined with the various methods for multiplexing dPCR already incorporated into this invention. For example, a single optical label might code for the entire 5 plex SMA assay, above, instead of just a single assay as in the KRAS example above. In this manner, other optical labels might code for different screening assays for newborn infants. According to other methods of the invention, above, a single DNA sample from an infant could then be analyzed with all of the assays simultaneously by merging droplets containing the DNA one-to-one with library droplets containing the optically encoded assays.

Figure 62:
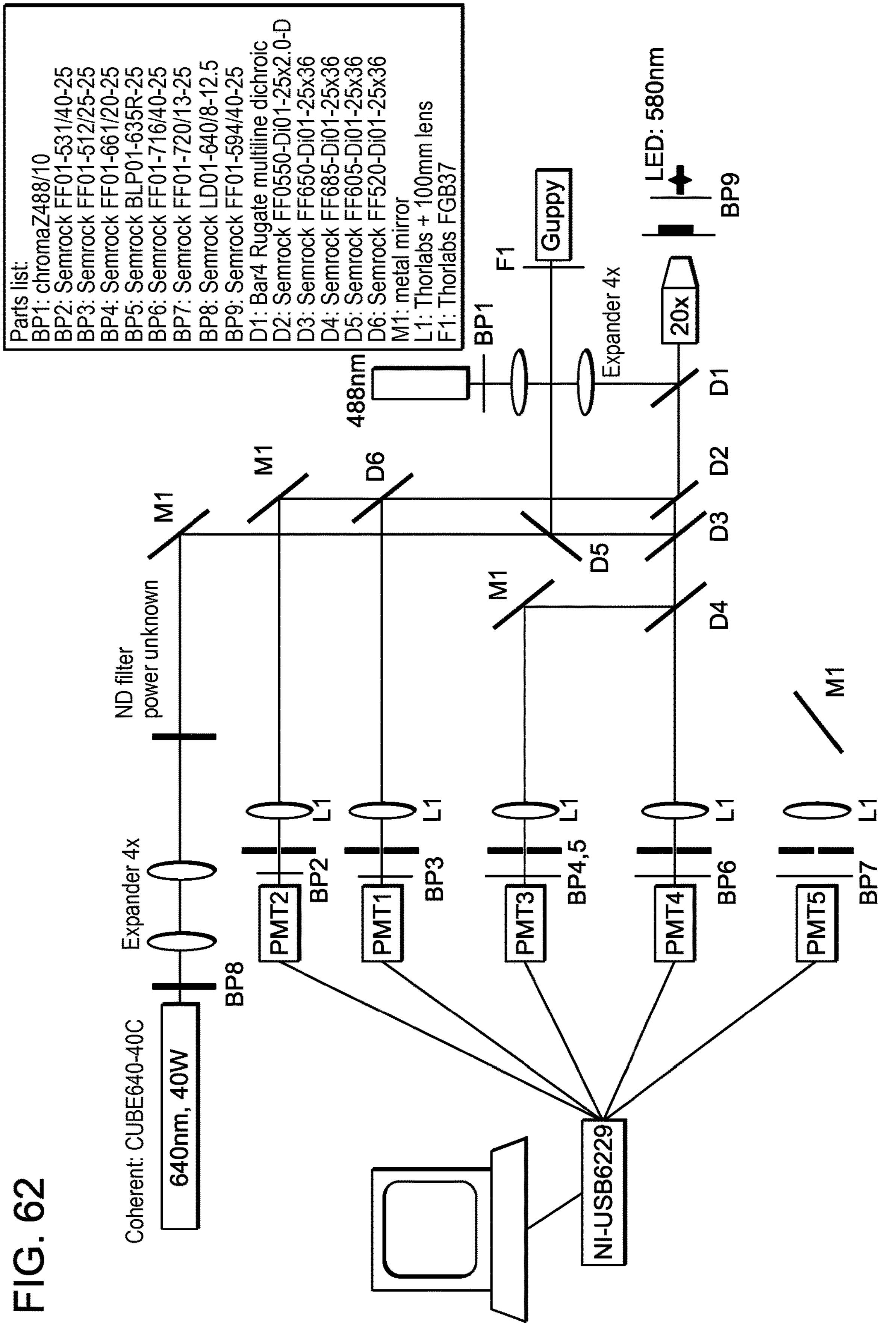
FIG. 62 depicts an optical schematic for combining optical labels with multiplexing.

As an example of combining multiplexing with optical labels, a so called 3×3×3 combination multiplex reaction with optical labeling was demonstrated (3×3 optical labeling with two fluorophores, each encoding a triplex assay, for a total of 27 plex). Two fluorophores were employed for optical labeling, Alexa633 and CF680 (excited by a 640 nm laser), with three intensity levels each producing nine total optical labels. As before with the 5 and 9 plex assays for SMA, TaqMan assays were used with FAM and VIC fluorophores (excited by a 488 nm laser). The fluorescence from the FAM and VIC fluorophores were recorded simultaneously with the fluorescence from the optical labels, requiring modifications to the optical layout of the instrumentation described for the SMA assay (the optical schematic for two-laser excitation and 4-color detection is shown in entirety in FIG. 62). Also, co-flow microfluidics were used in this example (the use of co-flow based microfluidics for this application is one of the methods of the invention described above). In this case, the template DNA was introduced into the chip in one flow, and the PCR master mix, the primers and probes for one triplex assay, and the unique composition of fluorophores for the optical label were introduced into the chip in another flow simultaneously. The two flow streams converged in a fluidic intersection upstream from the droplet forming module, and thus each droplet formed contained the contents of both flow streams. Methods to implement co-flow microfluidics are well known to those in the art. The droplets were collected, and then the procedure was repeated with the next triplex assay and optical label. The procedure was repeated a total of nine times, once for each pair of assays and optical labels. All of the droplets were collected into a single PCR tube and thermally cycled off chip. The mixture of thermally cycled droplets was reinjected into the same read-out chip as used for the SMA assay, above, and the fluorescence intensities of the assays from all four fluorophores was recorded.

Figure 63:
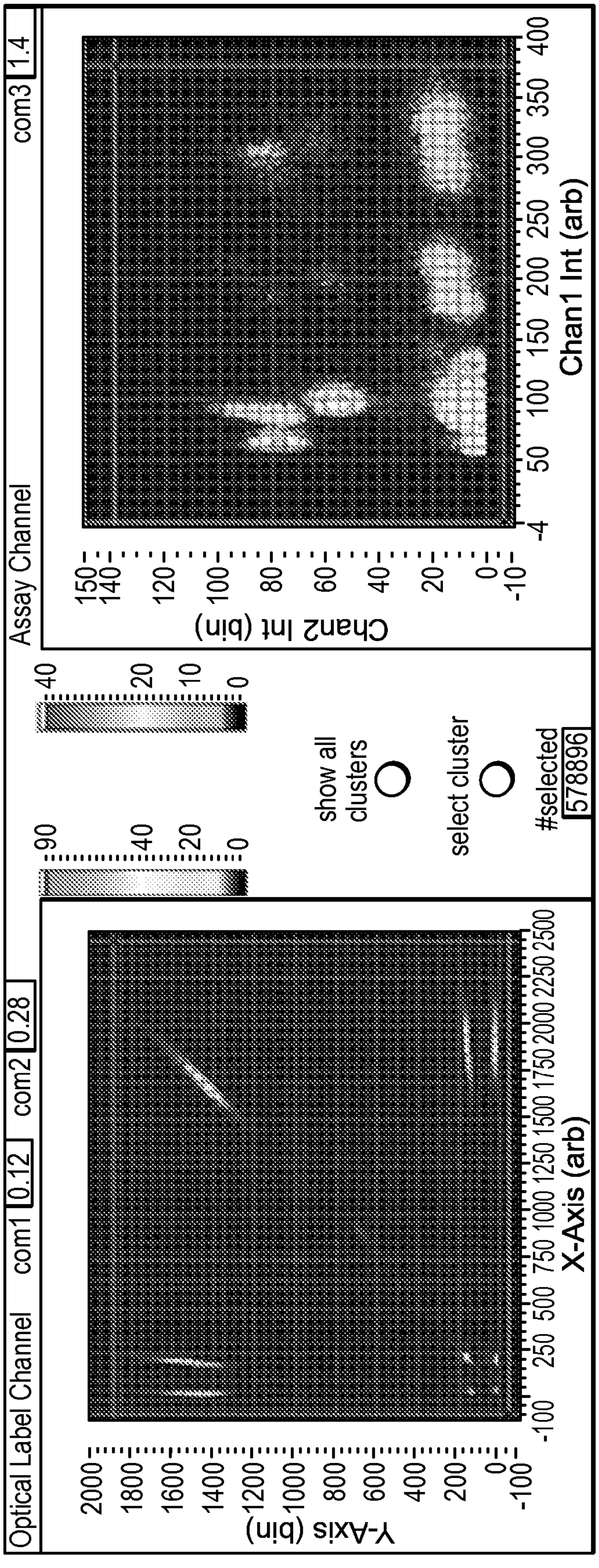
FIG. 63 depicts a dPCR assay combining multiplexing with optical labels using co-flow microfluidics.

FIG. 63 shows the cumulative results from all droplets in the 3×3×3 assay using co-flow microfluidics. The figure shows two 2 D histograms of droplet fluorescence intensities, the histogram on the left from all of the optical labels, and the histogram on the right from the assays. The contributions from all droplets are shown, that is, from three different triplex assays. (Both panels) 2 D histograms shown as heat maps with hotter colors representing higher droplet counts. (Left panel) histogram of optical labels, i.e. fluorescence intensities of droplets measured at wavelengths for the two fluorophores comprising the optical labels. (Right panel) assay histogram, i.e. fluorescence intensities of droplets measured at wavelengths suitable for FAM detection (x axis), and VIC detection (y axis). Both histograms were compensated for spectral overlap by standard techniques.

Standard methods were used to compensate for spectral overlap. The histograms if FIG. 63 are shown as a heat maps, with hotter colors designating larger numbers of droplets. Nine different clusters of droplets were clearly evident in the histogram of the optical labels, corresponding to each of the nine different optical labels: there is a small group of four clusters at the bottom left corner of the histogram, corresponding to optical labels with the lowest fluorescent intensities; and there are five clusters appearing as linear streaks at the higher intensities. The droplet clusters were less distinct in the histogram, but this was as expected because the droplets shown contained all of the triplex assays. The individual assays became clearly distinct once a single type of assay was selected by using the optical labels, as follows.

Methods of the invention involve selecting individual populations of droplets all containing the same optical labels, or groups of optical labels. In some methods of the invention, boundaries of fluorescence intensity were used to specify populations. In the example shown here, a rectangular boundary was used specifying the minimum and maximum fluorescence intensities for each fluorophore. However the methods of the invention are not restricted to rectangular boundaries. Any boundary, closed or unclosed, can be employed. Furthermore, according to methods of the invention, selections of droplet populations can be made by any method, and is not restricted to threshold-based methods such as boundary selection.

Figure 64A:
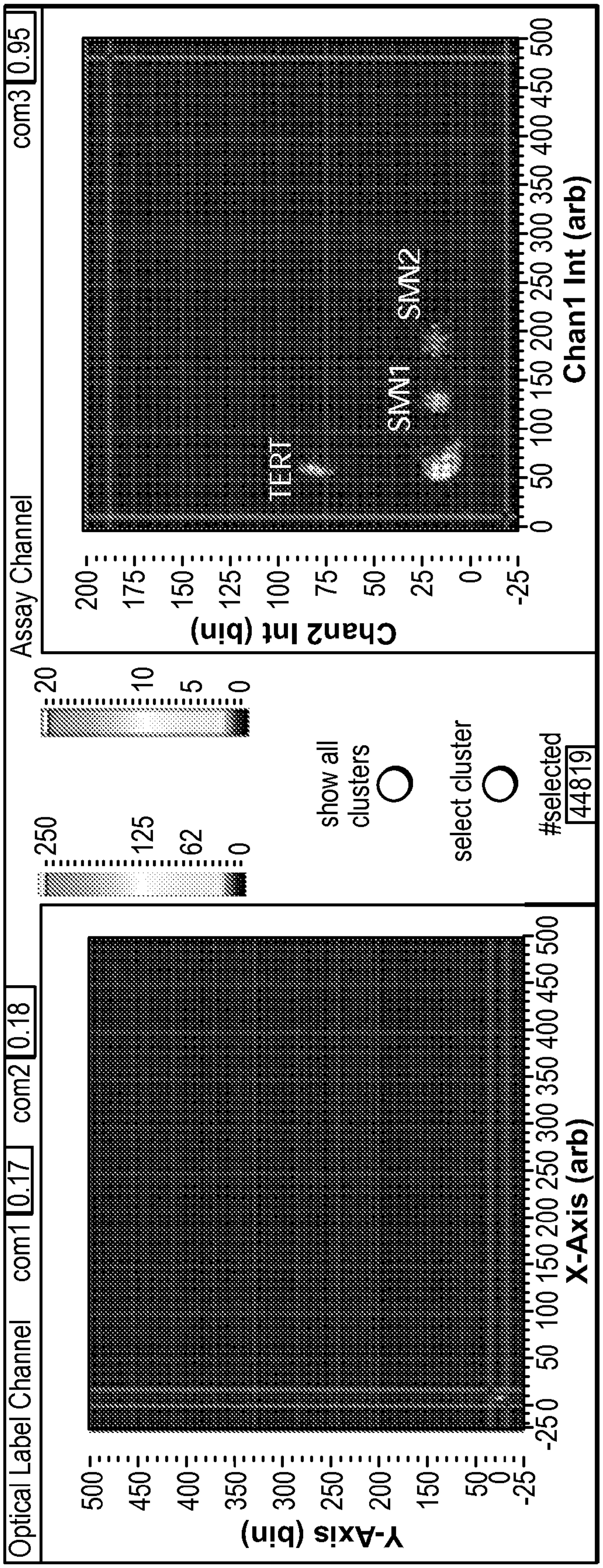
FIGS. 64A-C show single assay selections using optical labels.
Figure 64B:
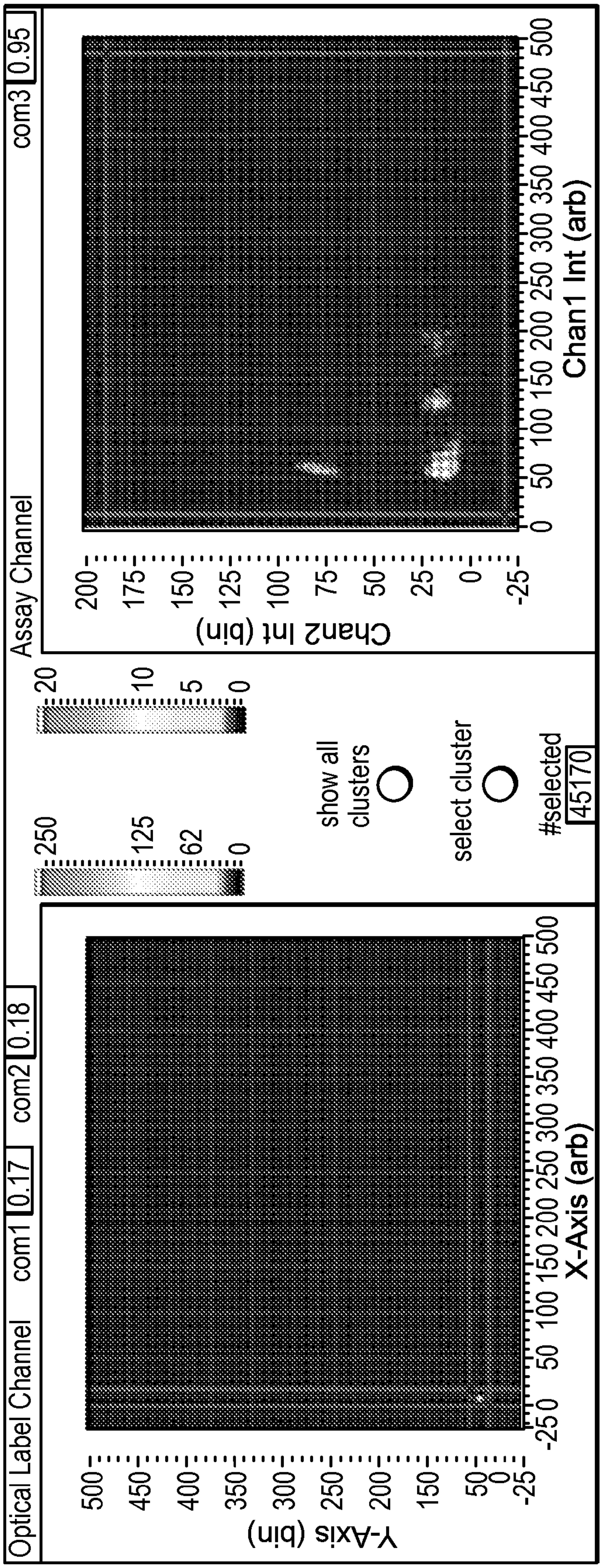
Figure 64C:
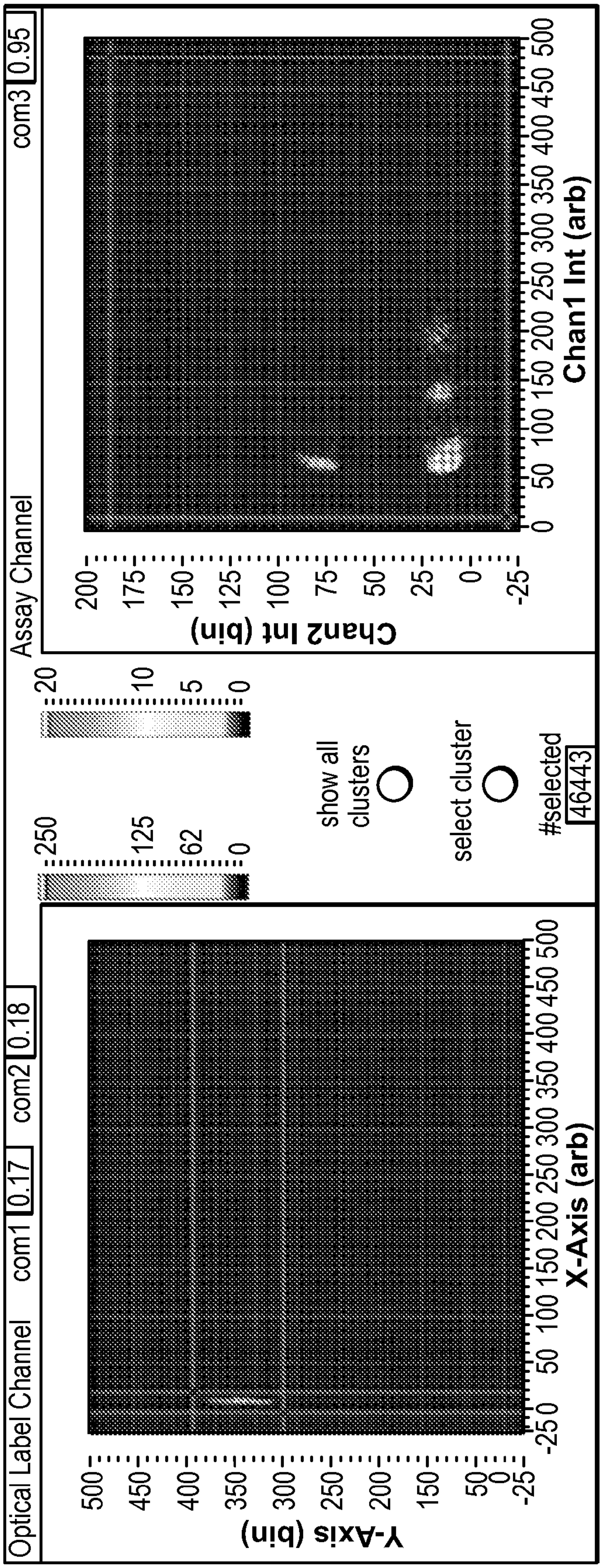

FIG. 64A shows the droplet fluorescence intensities for the assay (right histogram) when only one optical label was selected (left histogram). Selections were taken from all of the droplets from FIG. 64A-C. Each of the three different selections in panels A-C were for optical labels encoding the same assay (TERT, SMN1, and SMN2). Histograms are as described in FIG. 63. (Left histograms, optical labels) Superimposed lines demark the bounding box for selecting a single optical label. (Right histograms, assay) Only droplets containing the selected optical label are displayed.

The lines overlaid on the histogram of the optical labels identify the rectangular boundary used to select just the optical label with the lowest fluorescence for both fluorophores. Both histograms showed only the droplets that were selected. After selection, four distinct clusters of droplets appeared in the assay histogram, three for the different assays (in this case, assays for SMN1, SMN2, and TERT, where TERT is another common reference gene) and one for the empty droplets. The copy numbers for SMN1 and SMN2 were measured by the same methods of the invention as described above for the 5 plex SMA assay, with values of 1.8 and 0.94 close to the expected values of 2 and 1, respectively. The same assay was encoded with two other optical labels, and their selections are shown in FIGS. 20B and C. Similar results were achieved, with an overall measurement of 1.9±0.1 and 0.9±0.1 copies of SMN1 and SMN2 respectively, showing the measurement to be accurate within experimental uncertainty.

Figure 65A:
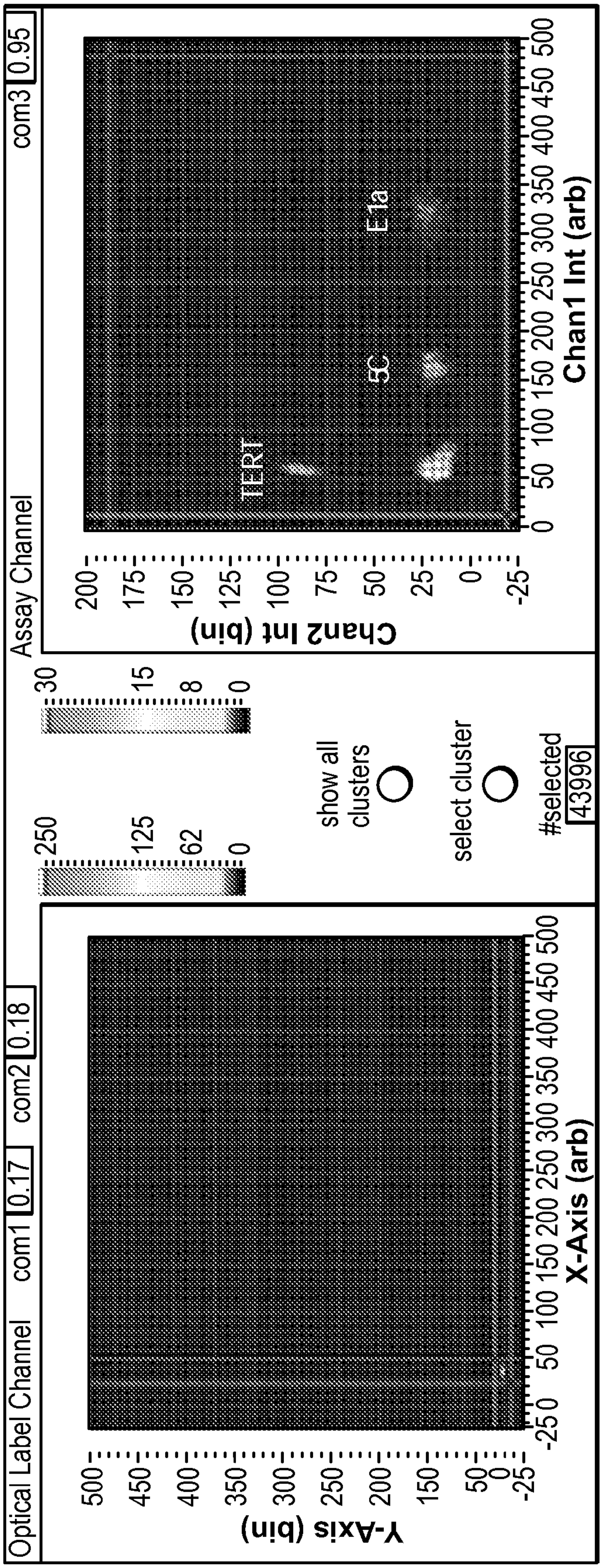
FIGS. 65A-C show single assay selections using optical labels.

FIGS. 65A, B, and C show optical label selections for a different assay (TERT, c.5C in the SMN1 gene, and BCKDHA (labeled Ela in the figure)). Selections were taken from all of the droplets from FIG. 19. Each of the three different selections in panels A-C were for optical labels encoding the same assay (TERT, c.5C from SMN1, and BCKDHA). Histograms are as described in FIG. 63. (Left histograms, optical labels) Superimposed lines demark the bounding box for selecting a single optical label. (Right histograms, assay) Only droplets containing the selected optical label are displayed.

Figure 65B:
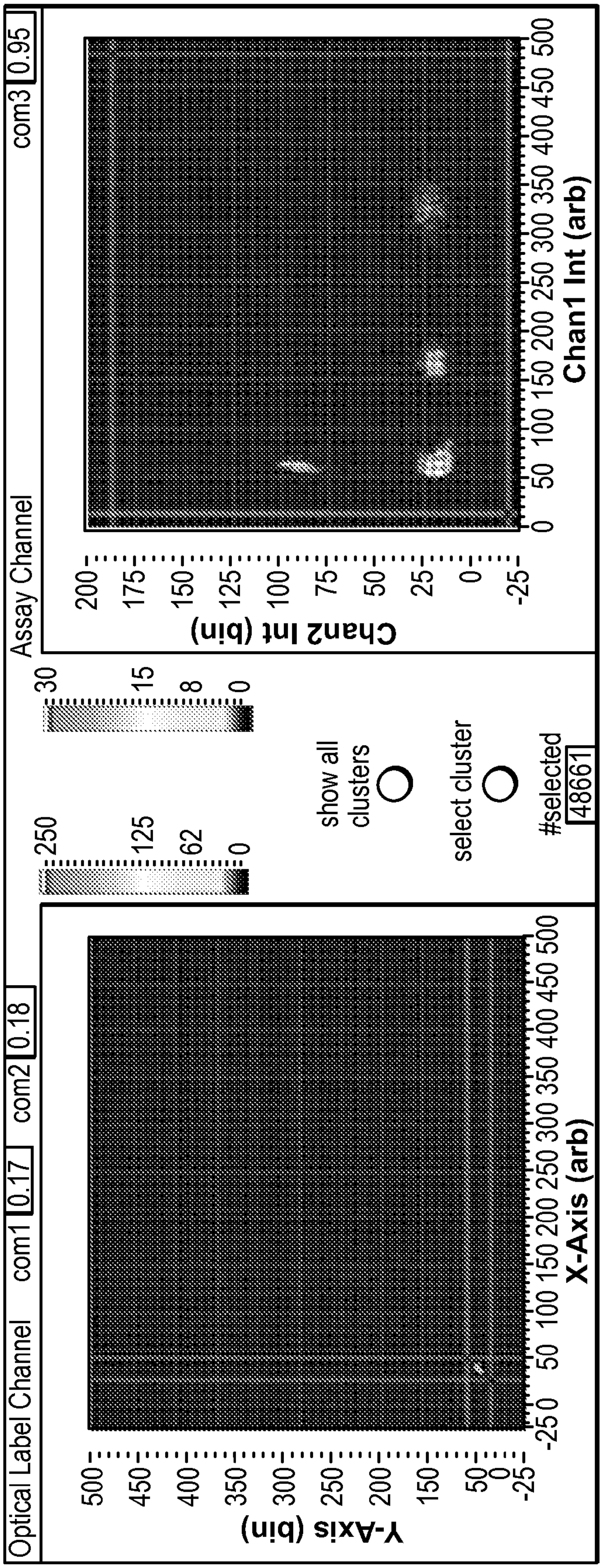
Figure 65C:
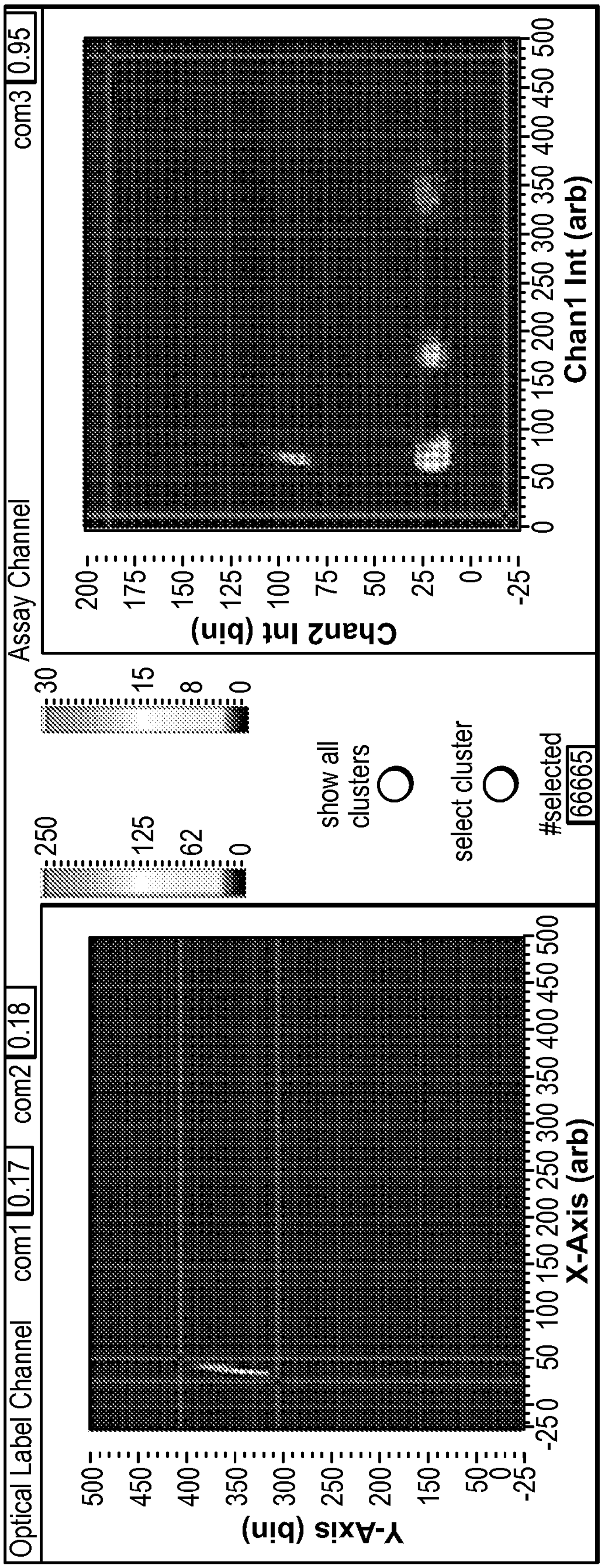

In each case shown in FIG. 65A-C four distinct clusters also appeared, and accurate measurements of gene copy number were made for c.5C and BCKDHA, referenced to TERT, of 2.9±0.1 and 2.0±0.2 compared to 3 and 2, respectively.

Figure 66A:
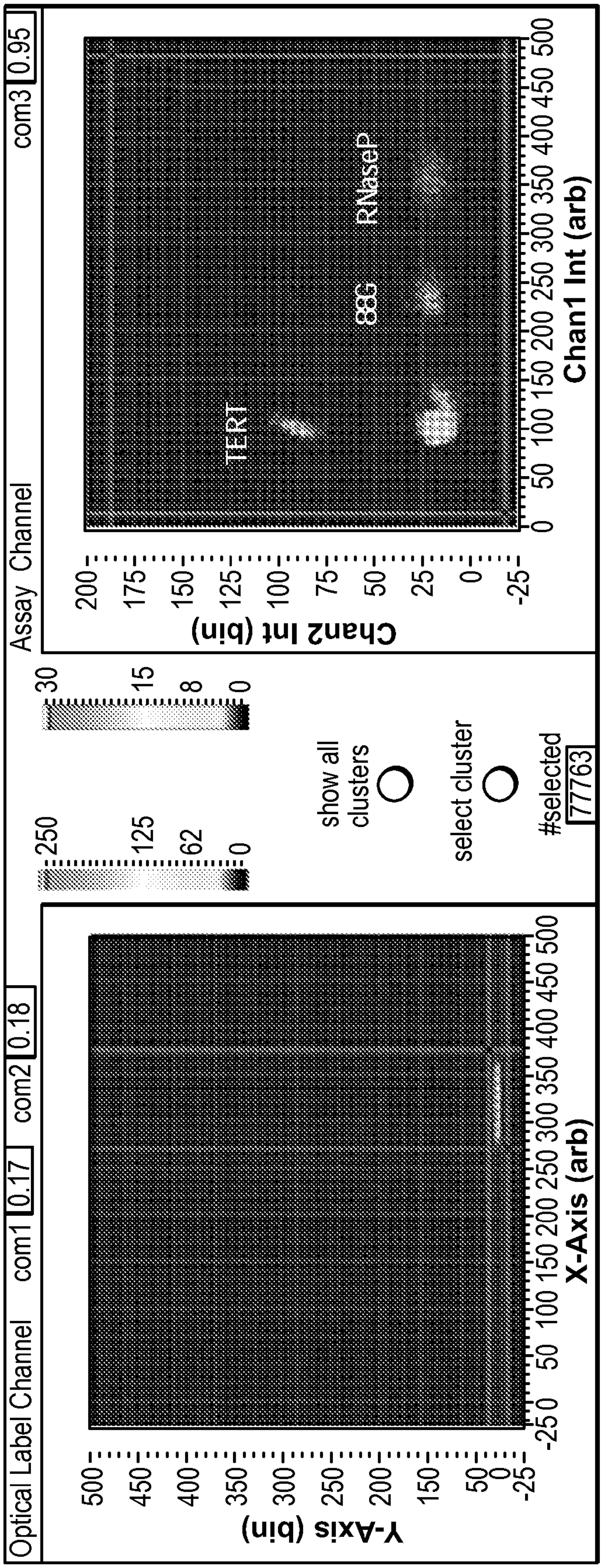
FIGS. 66A-C show single assay selections using optical labels.
Figure 66B:
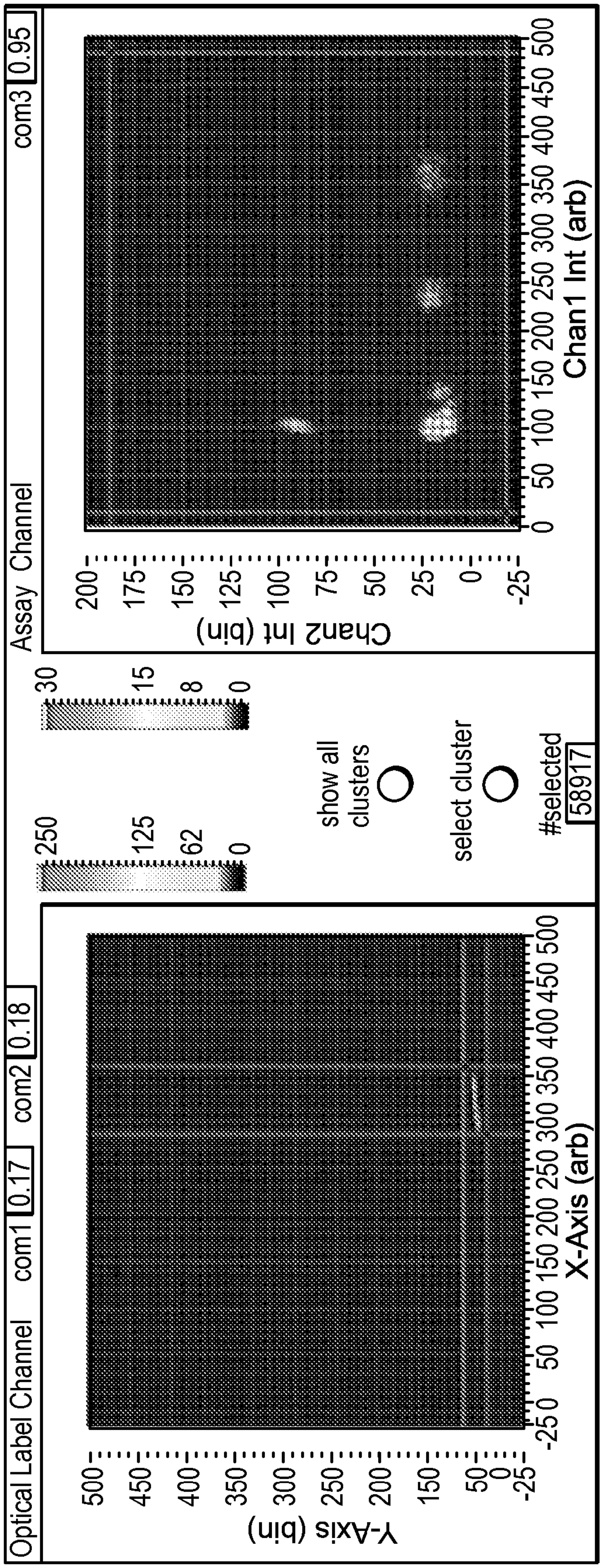
Figure 66C:
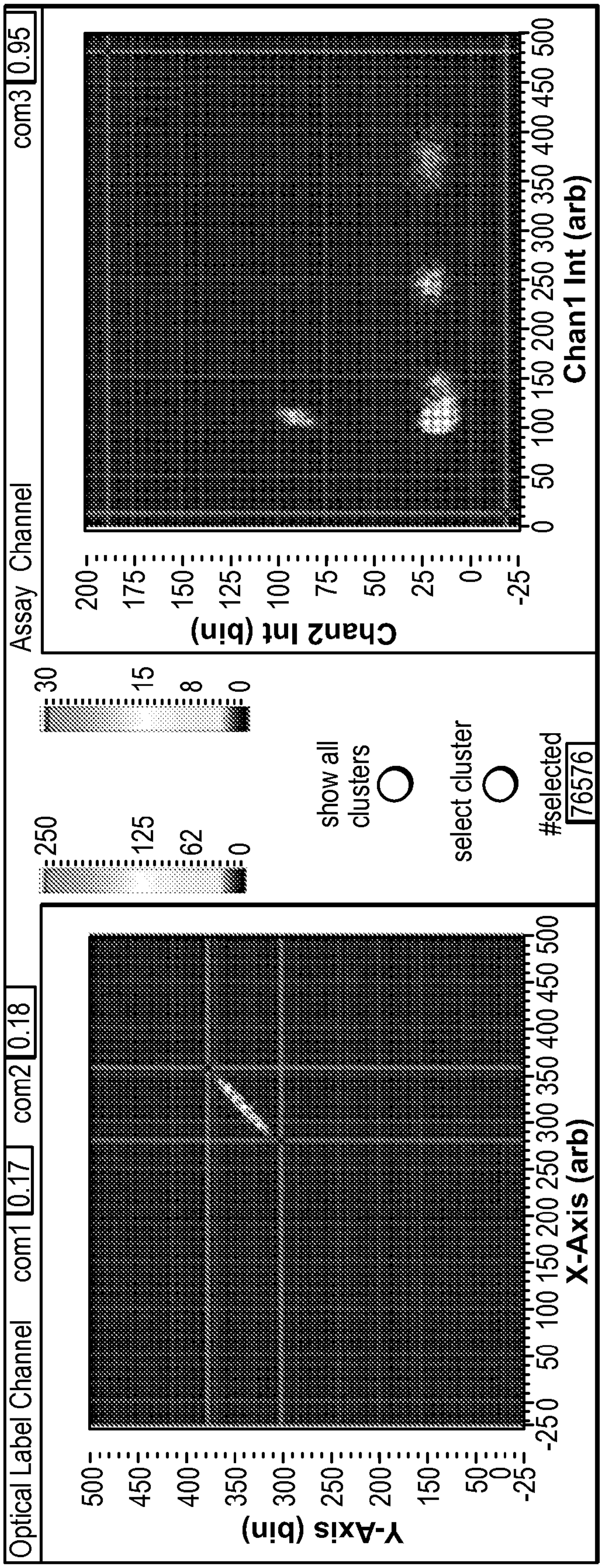
Figure 67A:
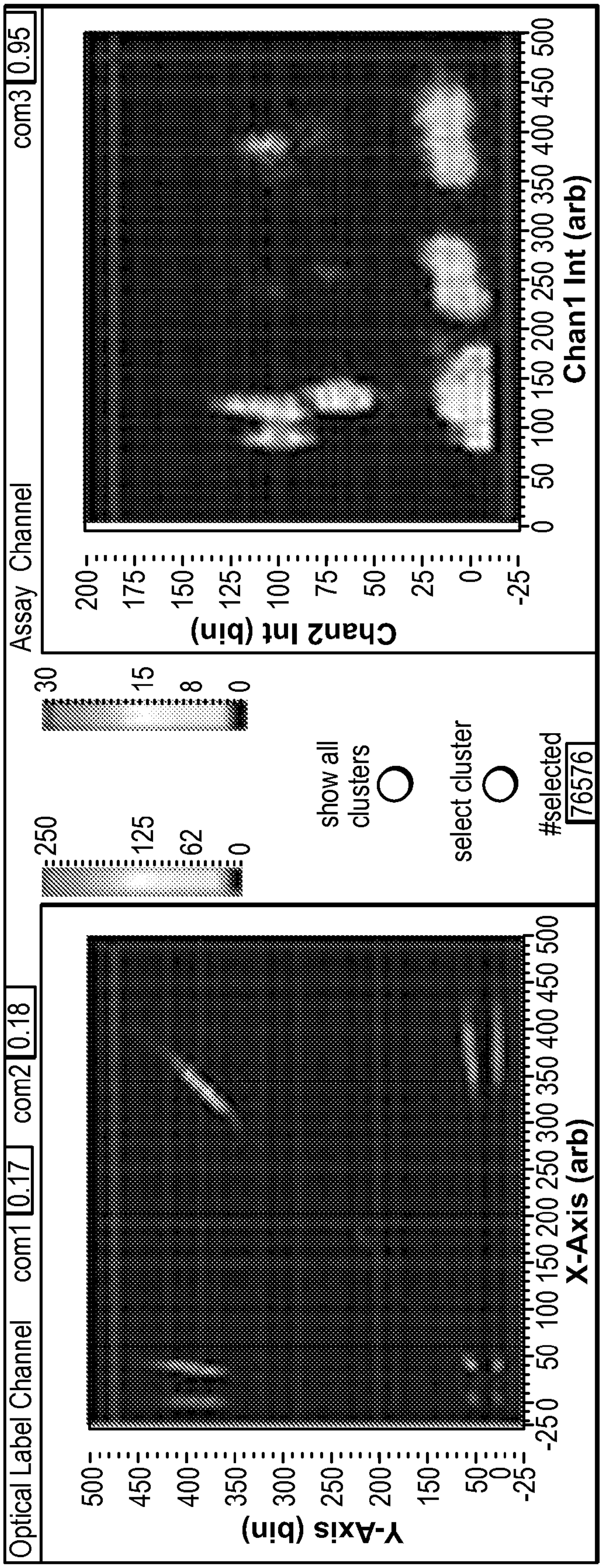
FIGS. 67A-J depict a dPCR assay combining multiplexing with optical labels.
Figure 67B:
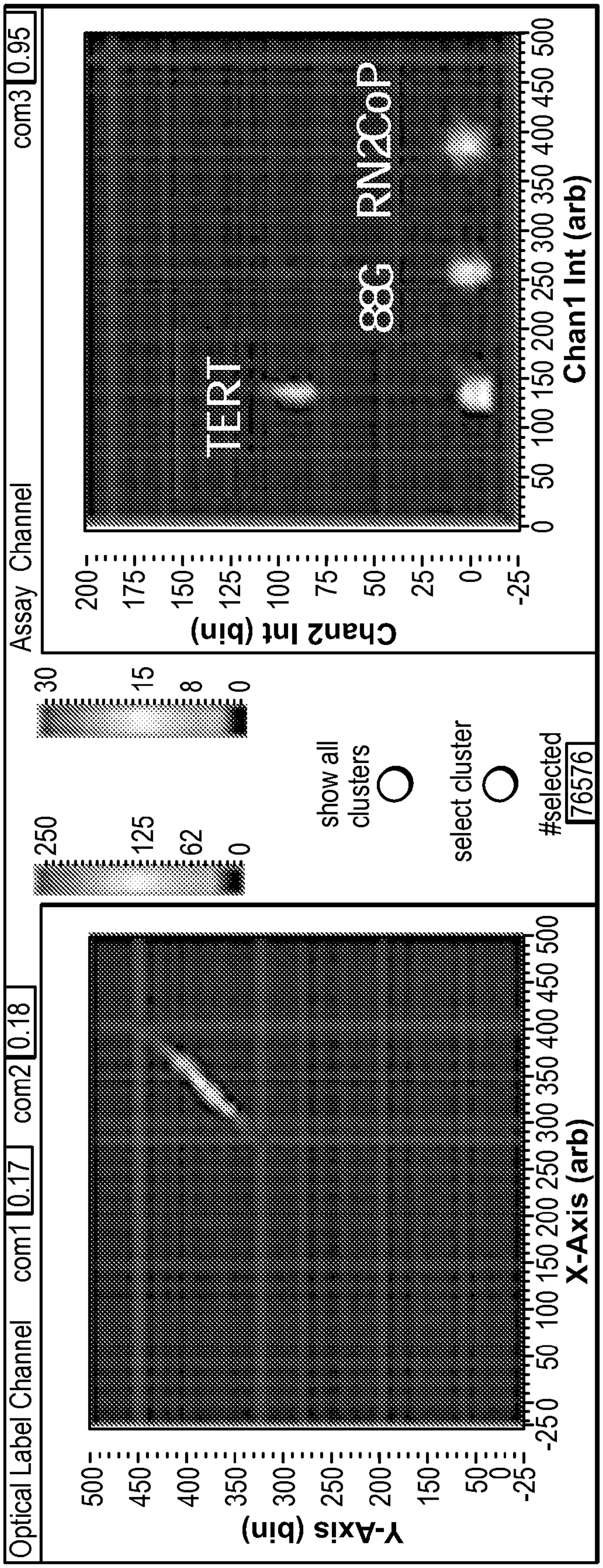
Figure 67C:
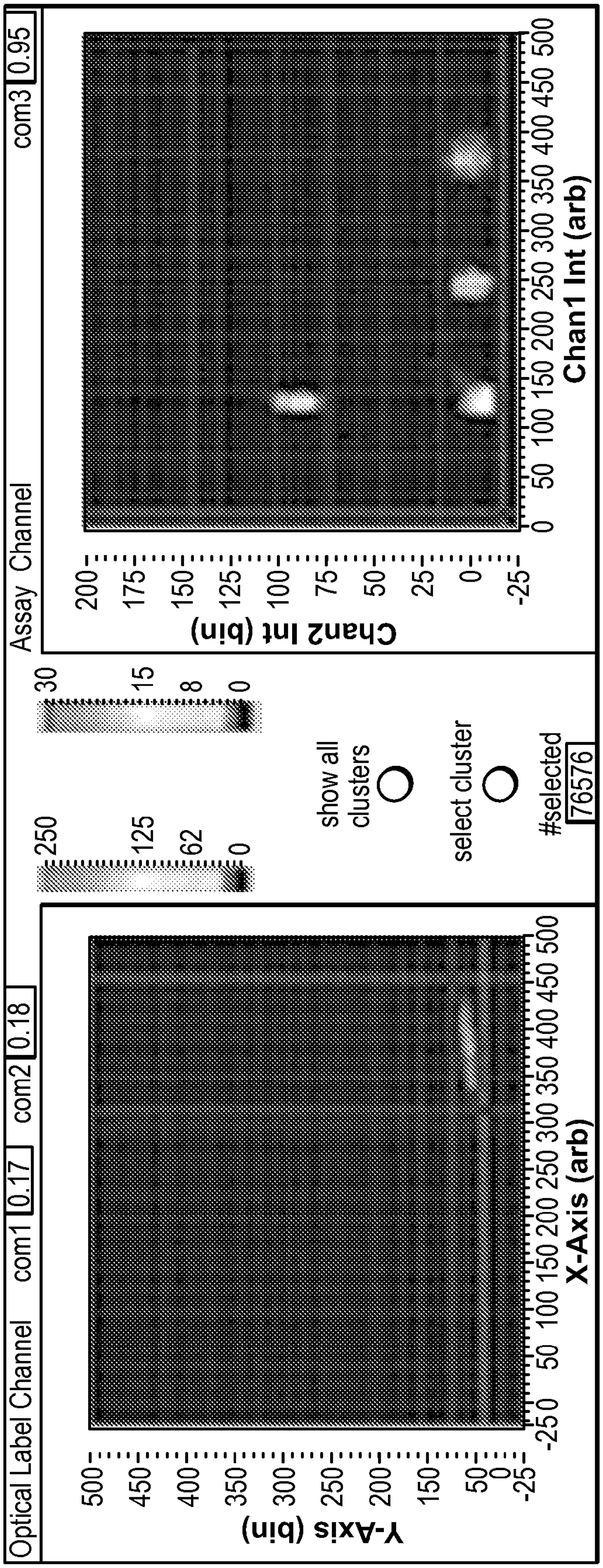
Figure 67D:
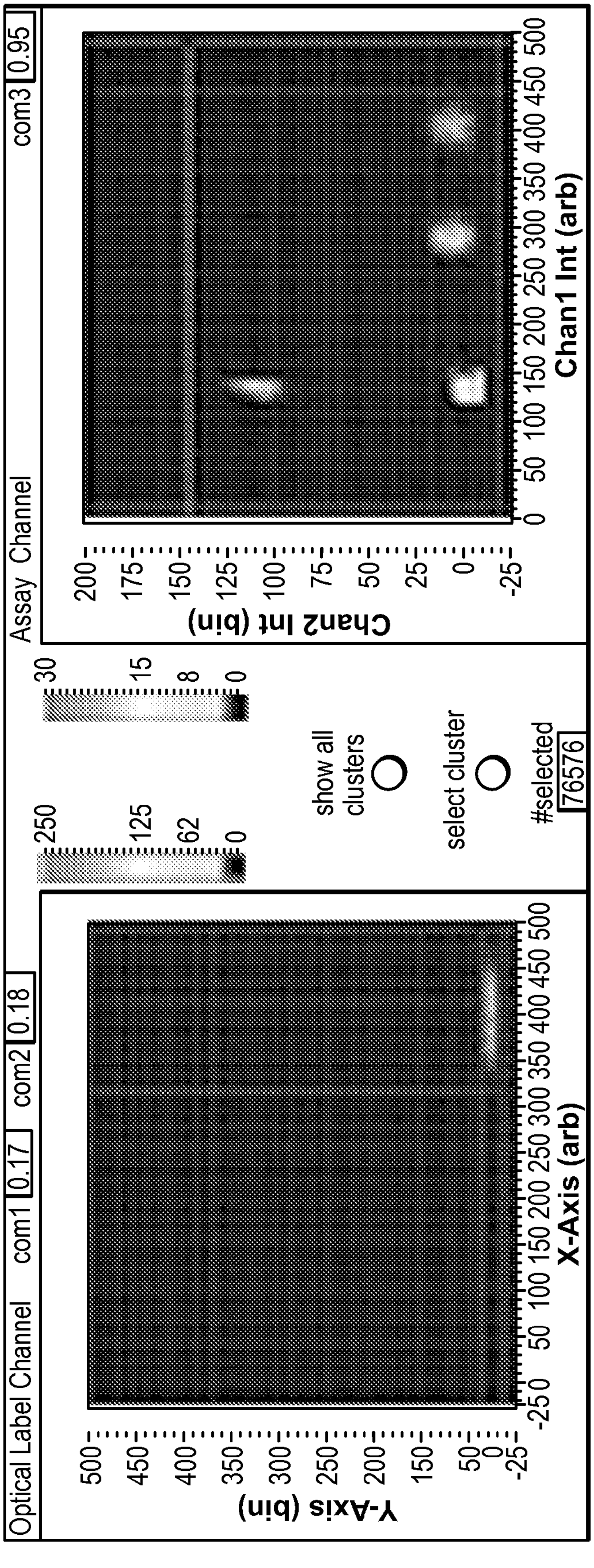
Figure 67E:
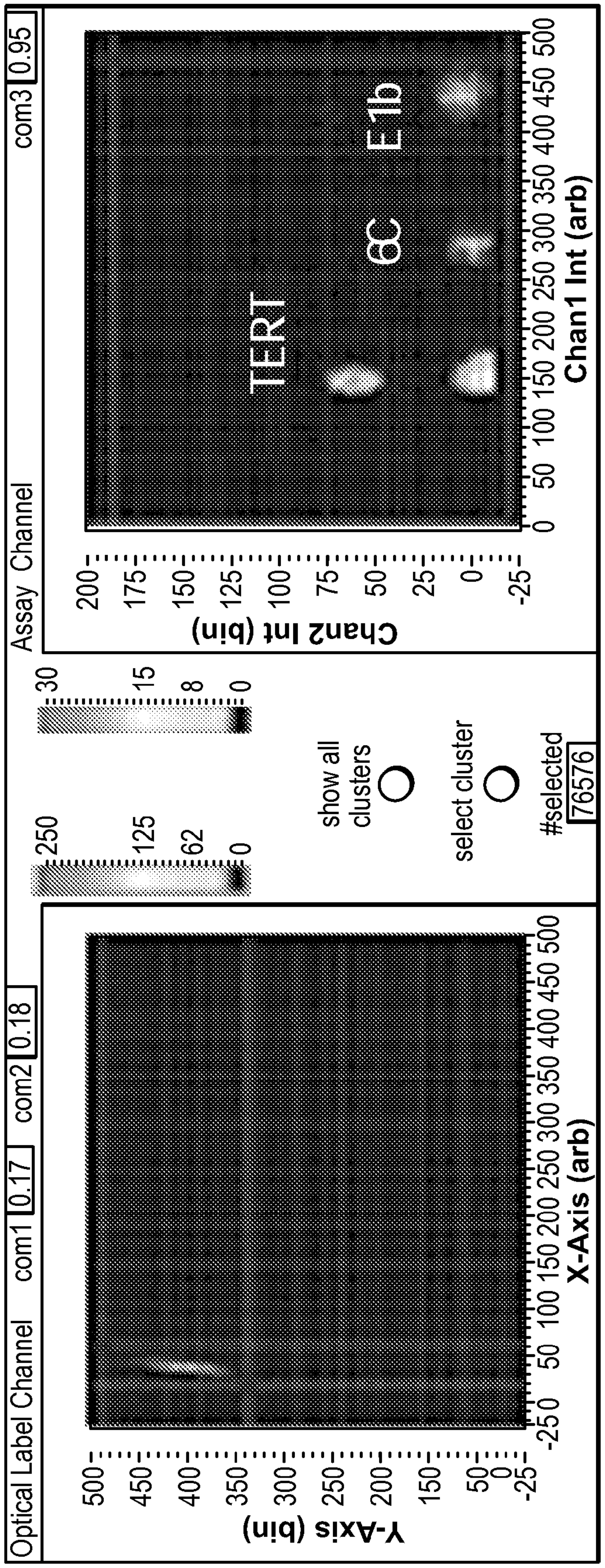
Figure 67F:
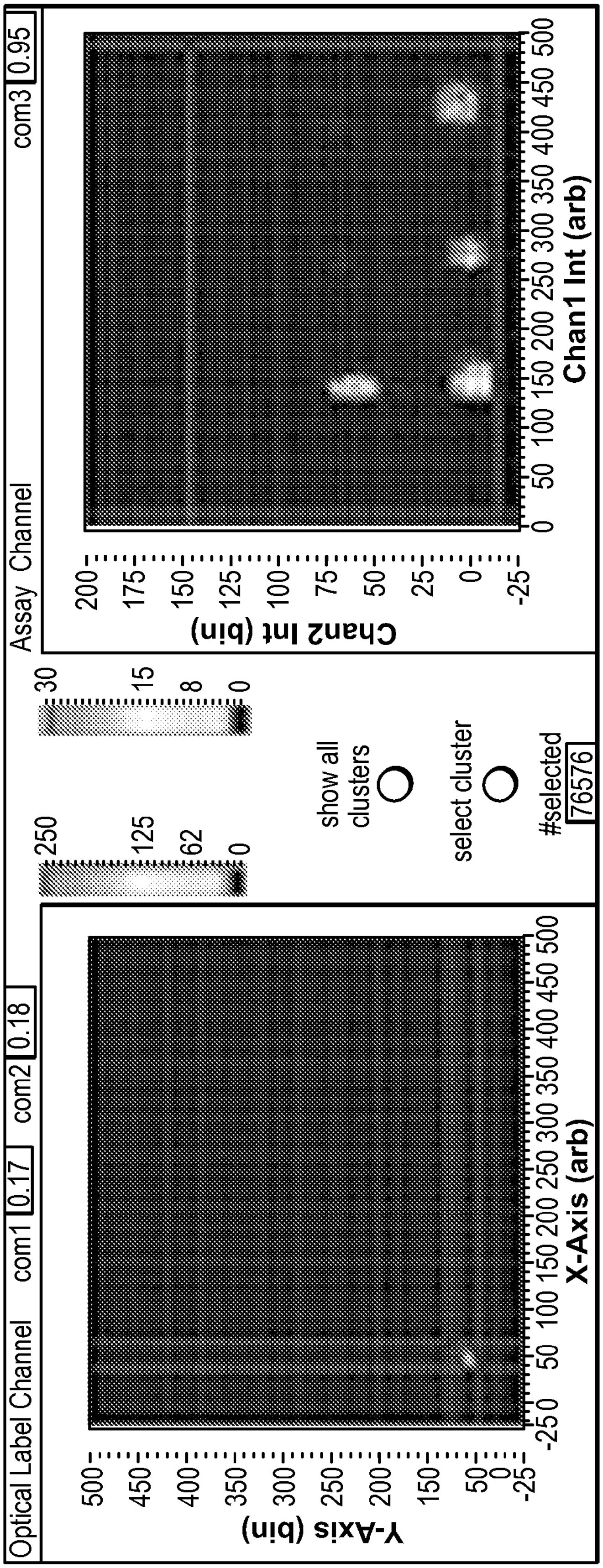
Figure 67G:
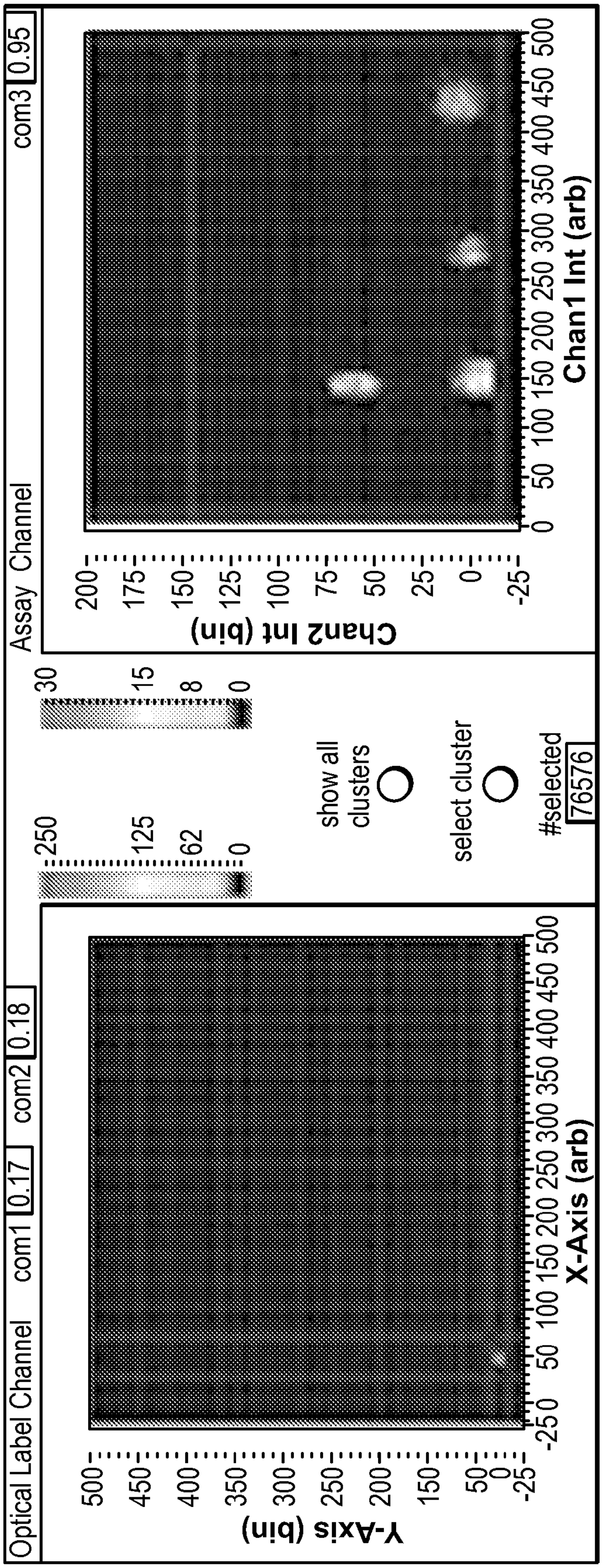
Figure 67H:
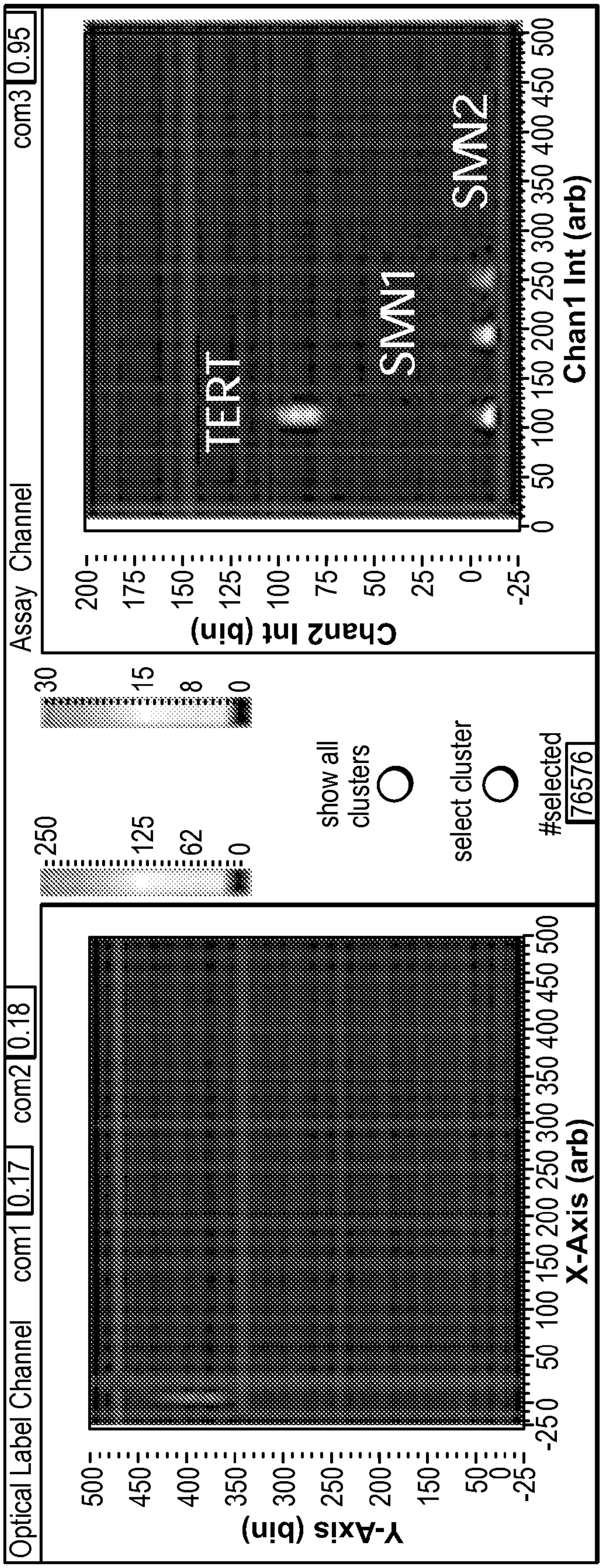
Figure 67I:
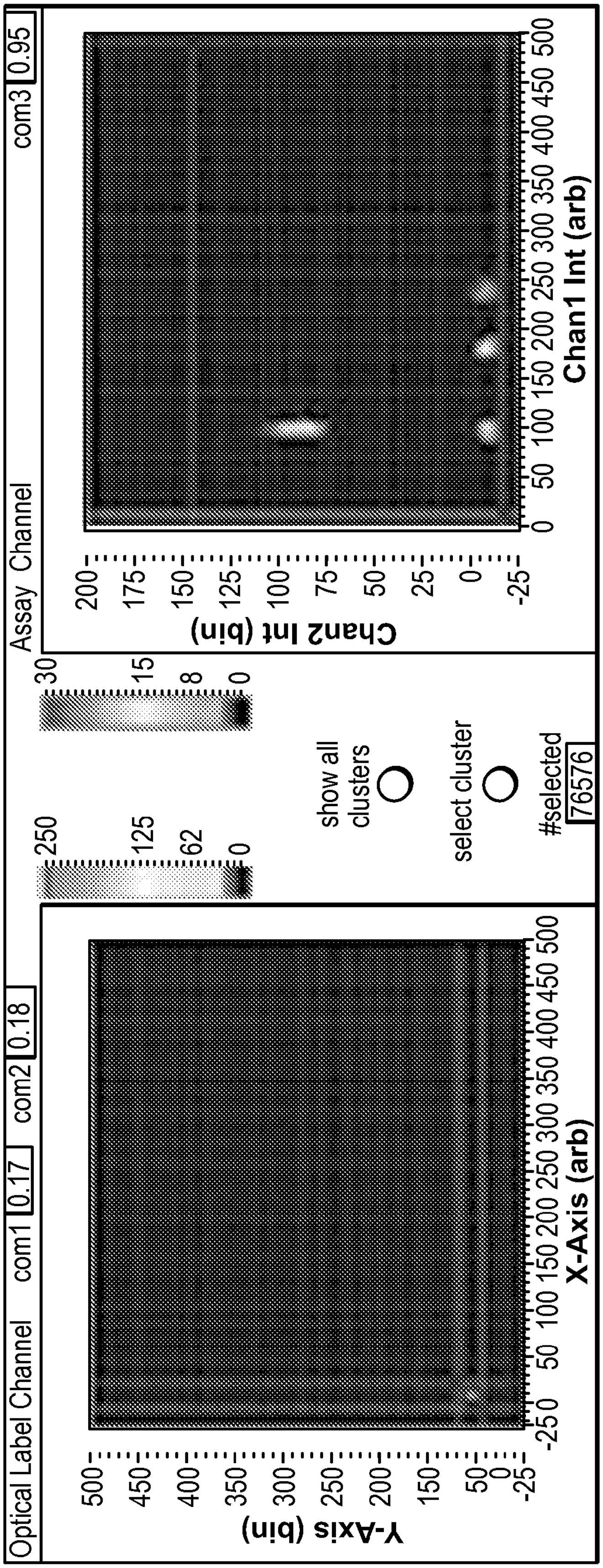
Figure 67J:
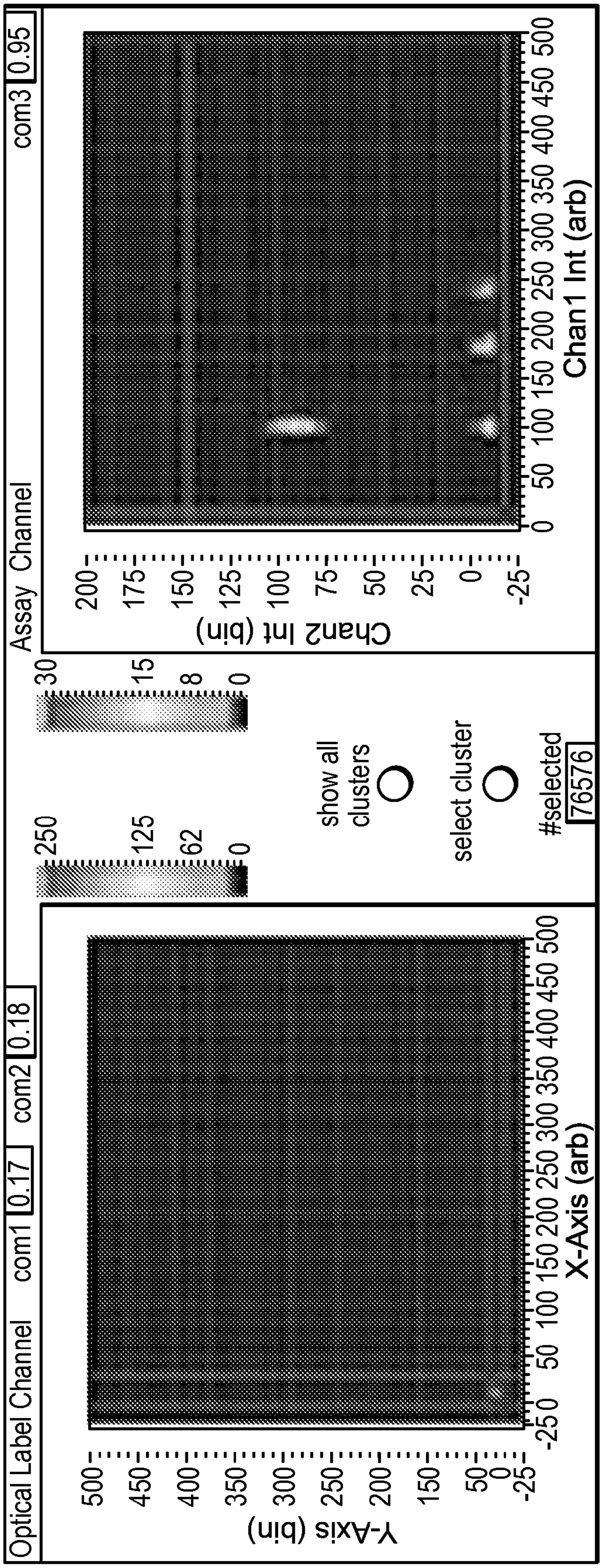

FIGS. 66, B, and C show optical label selections for a third assay (TERT, c.88G in the SMN1 gene, and RNaseP, where RNaseP is a common reference gene). Selections were taken from all of the droplets from FIG. 63. Each of the three different selections in panels A-C were for optical labels encoding the same assay (TERT, c.88G from SMN1, and BCKDHA). Histograms are as described in FIG. 63. (Left histograms, optical labels) Superimposed lines demark the bounding box for selecting a single optical label. (Right histograms, assay) Only droplets containing the selected optical label are displayed. Accurate gene copy numbers of 2.1±0.1 were measured for both c.88G and RNaseP, referenced to TERT, compared to the expected value of 2.

In summary, the demonstration here shows use of nine different optical labels to enable independent measurement of three triplex assays in a single experiment. Although some of the optical labels encoded for redundant assays in this example (there were only three different assays despite having nine optical labels), the invention is not constrained to any particular formatting of assays and optical labels. Embodiments of the invention include formats where all of the assays are the same across all of the optical labels; where none of the assays are the same across all of the optical labels; where some of the assays are the same across all of the optical labels; where some of the assays have greater plexity than others across all of the optical labels; where all of the assays have the same plexity across all of the optical labels; and any other arrangements of assays across all of the optical labels are considered.

Although two different fluorophores were used to create the optical labels in this example, the invention is not constrained to any particular number of fluorophores comprising the optical labels. Embodiments of the invention include optical labels comprised of 1 fluorophore, or 2 fluorophores, or 3 fluorophores, or 4 fluorophores, or up to 10 fluorophores, or up to 20 fluorophores. Optical labels can also comprise more than 20 fluorophores.

Although solely triplex assays were used in the example demonstration here, the invention is not constrained to use of triplex assays with optical labels. Embodiments of the invention include plexities of the following amounts when used with optical labels: single plex, duplex, triplex, 4 plex, up to 10 plex, up to 20 plex, up to 50 plex, and up to 100 plex. Embodiments of the invention also include plexities exceeding 100 when used with optical labels.

Another method of the invention involves the use of droplet merging, instead of co-flow, for combining multiplexing with optical labels. A demonstration using droplet merging was performed with the same 3×3×3 assay as in the preceding example with co-flow. The assays (probes and primers) combined with their unique optical labels were first encapsulated into droplets along with the PCR master mix. Subsequently, according to methods of the invention described above, a library containing a mixture of droplets from all nine optically labeled assays was merged one-to-one with droplets containing template DNA from the same patient as in the preceding example. As another method of the invention, the droplet merge was performed using a lambda-injector style merge module, as described in U.S. Provisional Application, Ser. No. 61/441,985, incorporated by reference herein. Aside from the differences between co-flow and merge, the assays and experimental procedures were identical to those above for the co-flow experiment. FIG. 67A-J shows 2 D histograms of droplet fluorescence intensity for the optical labels and the assays that are similar to those in FIGS. 63-66. FIG. 67A-J depicts a dPCR assay combining multiplexing with optical labels using droplet merging. As in the case for co-flow, upon selection of droplets containing individual optical labels, the expected distinct clusters of droplets corresponding to each assay were clearly evident. Furthermore for each assay the measured gene copy number matched or very nearly matched the expected values within experimental uncertainty (See FIG. 46).

Although methods of the invention include using either microfluidics with co-flow or droplet merging, the invention is not limited in this regard. Any fluidic method capable of generating optically labeled droplets that also contain fluorogenic DNA hybridization probes are considered. For example, other embodiments well known in the art are mixing optical labels and assays in the macrofluidic environment before injection into a droplet generating chip; and mixing optical labels and assays thoroughly upstream from the droplet forming module in dedicated mixing modules, such as with a serpentine mixer.

Data Analysis

One method of the invention involves histogram-based data presentation and analysis for identifying and characterizing populations of statistically similar droplets that arise from unique probe signatures (color and intensity), and for discriminating one population of droplets from the others. Another method of the invention involves histogram-based data presentation and analysis for identifying and selecting populations of droplets based on unique signatures from optical labels. Examples of one and two-dimensional histograms have been provided for these methods, but the invention is not limited in this regard. As described above, it is anticipated that greater numbers of colors will be used for both multiplexing and for optical labels. Hence, embodiments of the invention include histograms of dimensionality greater than two, such as 3, or 4, or up to 10, or up to 20. Histograms of dimensionality greater than 20 are also incorporated into the invention.

Another method of the invention involves the selection of droplets within histograms, either for counting, or for assay selection as in the use of optical labels, or for any other purpose. Methods of the invention include selections by boundaries, either closed or unclosed, of any possible shape and dimension. Methods of the invention also include selections of droplets that exhibit fluorescence from single types of fluorophores, or from multiple types of fluorophores, such as arising from multiple probes against a common DNA target.

EXAMPLES

The following examples, including the experiments conducted and results achieved are provided for illustrative purposes only and are not to be construed as limiting upon the present invention.

Example 1: Oligonucleotide Labeling of Single Cell Genomes

Figure 40A:
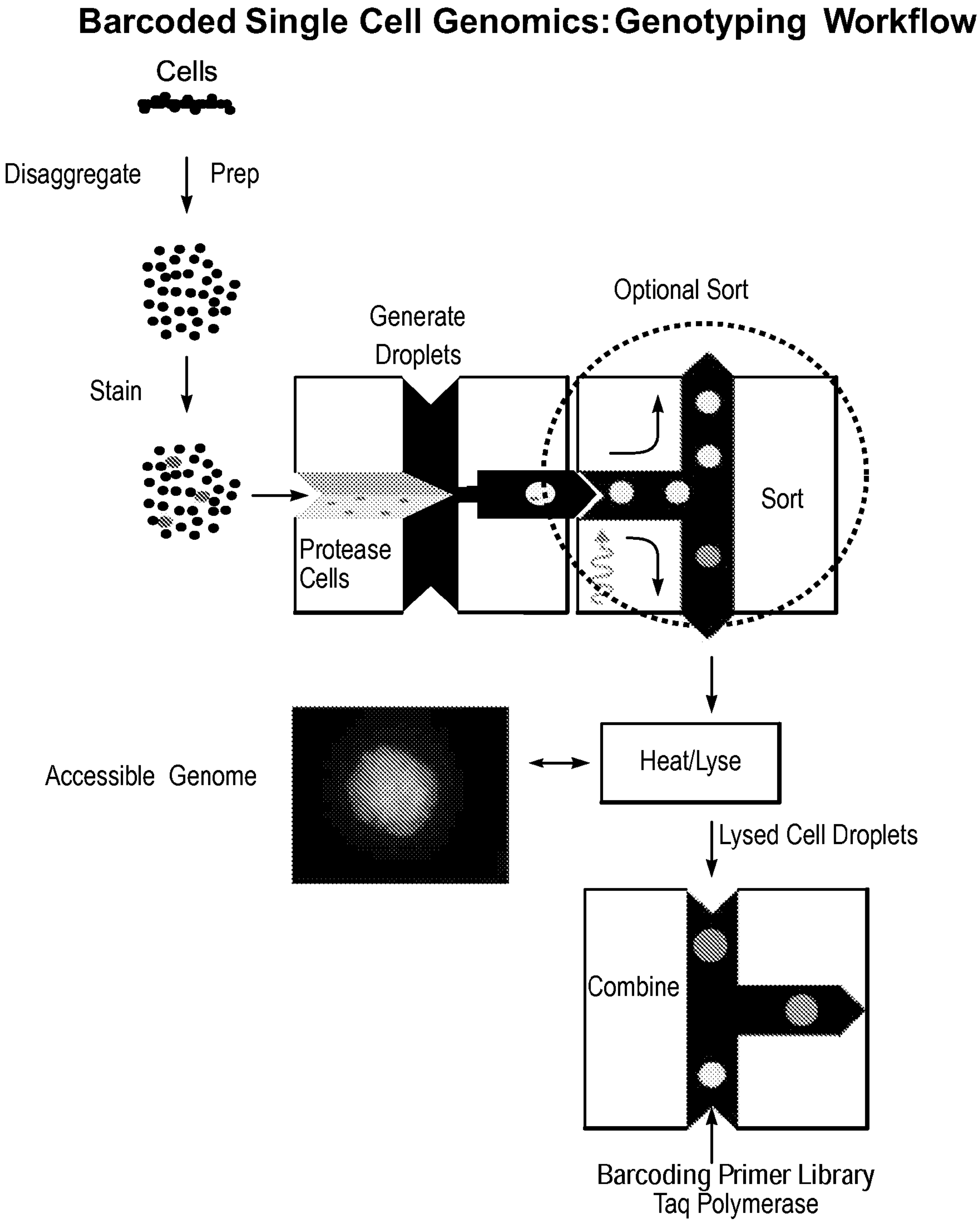
FIG. 40A-B depict a flowchart depicting the steps associated with isolation, encapsulation, molecular labeling, sorting and analysis of single cell genomes using fluidic droplets.
Figure 40B:
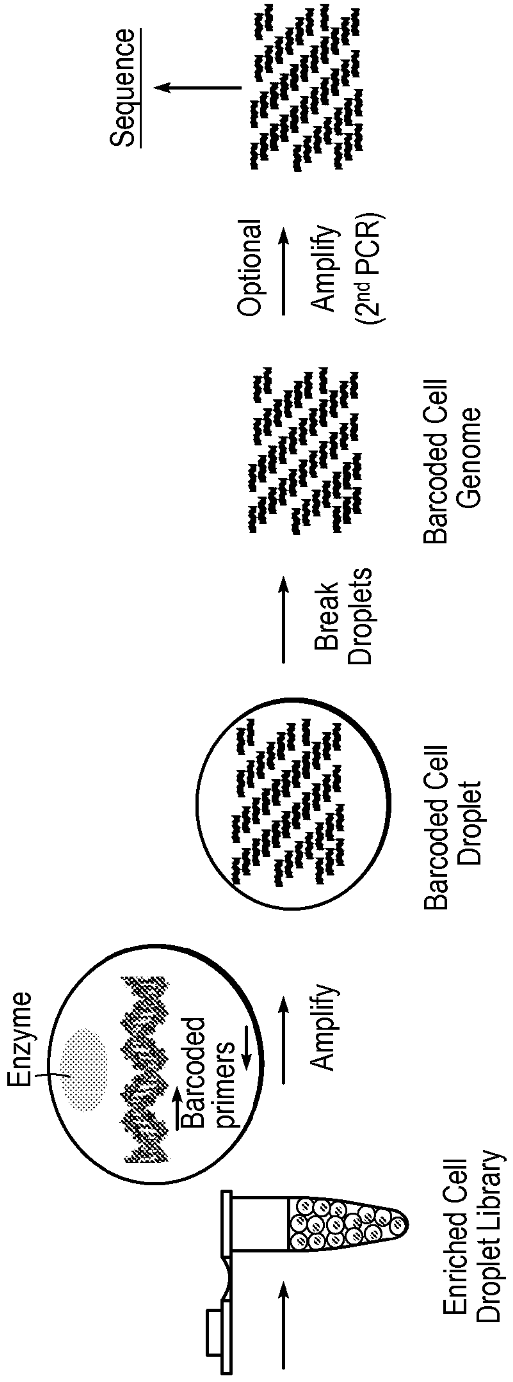
Figure 41:
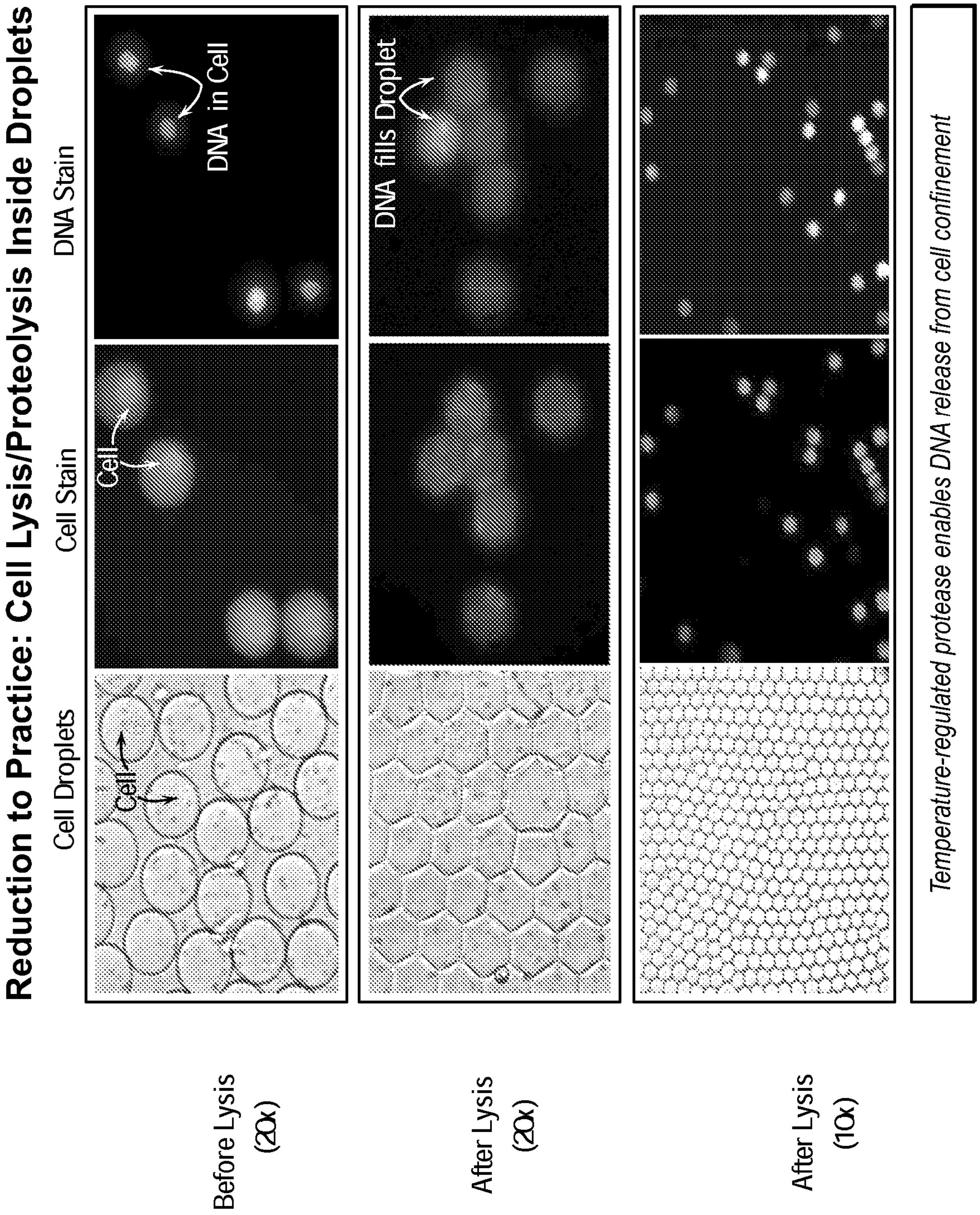
FIG. 41 depicts lysis/proteolysis of cells (before and after) inside fluidic droplets.
Figure 42:
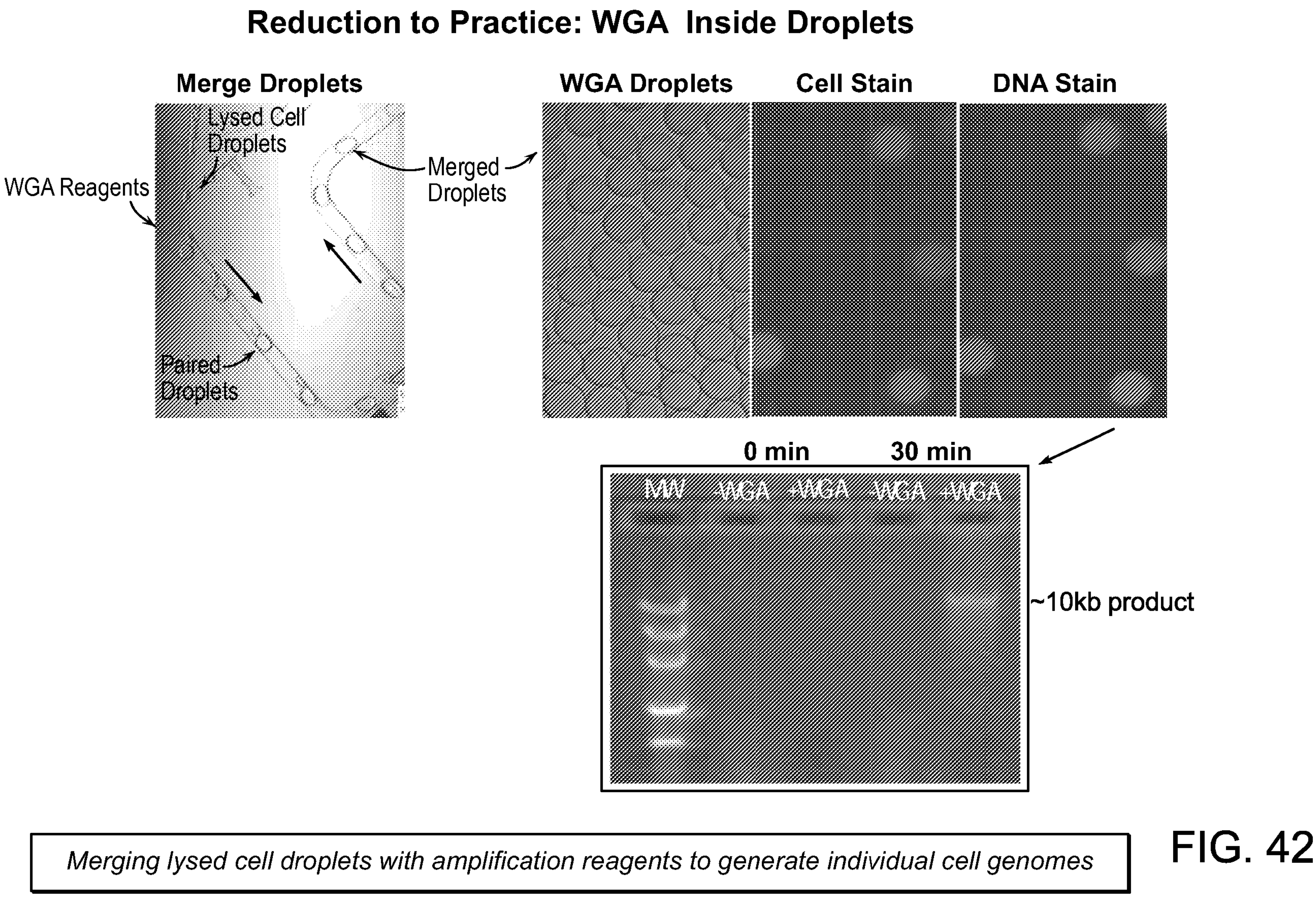
FIG. 42 are images depicting the merger of droplets containing lysed cells and droplets containing reagents for WGA, and subsequent whole genome amplification (WGA) in the merged fluidic droplets.

Barcoding of single cell genomes is performed following encapsulation, cell lysis, and temperature-sensitive proteolysis of single cells in droplets (see FIG. 40A-B for overall workflow). Single cell droplets are generated using a limited dilution regime loading of a dispersed cell suspension into a microfluidic droplet generation device (as previously described). Additional droplet manipulations can also be performed (e.g. droplet sorting) in advance of the step where the droplets are combined with the labeling droplet library. After combining the single genome-containing droplets with barcoded droplet libraries, and either multiple displacement amplification (MDA) enzymes for whole genome amplification (WGA) (e.g. using the enzyme phi29 (see FIG. 21)), transposase enzymes (see FIG. 22)), or other amplification enzymes and reagents, each cell's genome becomes labeled with a barcode that will identify the amplified genomic loci as coming from a unique genome during subsequent sequencing and analysis. In the example scheme shown in FIG. 21 for MDA WGA, the 'tailed barcoded primer' labeling reagent is tri-partite, with a universal tail portion (e.g., oligonucleotide sequences for use in sequencing library construction) immediately 5' to a barcode sequence, followed by one of a set of random hexamer bases that enable priming from multiple places in the genome. In the example scheme for using a transposase (FIG. 22), the 'tailed barcoded primer' labeling reagent is bi-partite, with a universal tail portion immediately 5' to a barcode sequence. The labeling enzyme and any required buffer or co-reaction component can either be included in the primer droplet library or added subsequently via droplet fusion methods. Data regarding the cell lysis and temperature-responsive proteolysis steps are shown in FIG. 41. Data regarding whole genome amplification using phi29 in droplets is shown in FIG. 42.

Example 2: Oligonucleotide Labeling of Single Chromosomes

Barcoding of single chromosomes can be performed following encapsulation of individual chromosomes in droplets (see FIG. 43 for overall workflow). First cells are treated (e.g. nocadazole) to cause metaphase arrest (synchronizing the cell cycle and condensing the chromosomes) and the cell membranes are lysed (e.g. osmotic pressure) to release the condensed chromosomes. Limited proteolysis separates the chromosome pairs into individual chromatids. Single-chromosome droplets are generated using a limited dilution regime loading of a dispersed chromatid suspension into a microfluidic droplet generation device (previously described). Additional droplet manipulations can also be performed (e.g. droplet sorting, additional proteolysis using a thermo-responsive protease) in advance of the step where the droplets are combined with the labeling droplet library. After combining the single chromosome-containing droplets with barcoded droplet libraries, and either MDA enzymes for WGA (e.g. phi29) (see FIG. 21) or transposase enzymes (see FIG. 22), each chromosome becomes labeled with a barcode that will identify the amplified genomic locus as coming from a unique chromosome during subsequent sequencing and post-process analysis.

Example 3: Oligonucleotide Labeling of Single Cell RNAs

Barcoding of single cell RNAs can be performed following encapsulation and lysis of single cells in droplets (see FIG. 23A-B for overall workflow). Single cell droplets are first generated using limited dilution regime loading of a dispersed cell suspension into a microfluidic droplet generation device (previously described). Additional droplet manipulations can also be performed (e.g. droplet sorting) in advance of the step where the droplets are combined with the labeling droplet library. One can choose to label and recover several types of RNA collections: polyA-tailed mRNA (using poly dT affinity reagents), sequence-selected subsets of RNA species using sequence-specific primers, or other subsets (e.g. using random hexamer primers). The example scheme described here (and shown in FIG. 23A-FIG. 26B) is for recovering and labeling the entire polyA+ mRNA compliment of a cell, i.e. the transcriptome. For this example (FIG. 23A-B), the 'biotinylated tailed barcoded primer' labeling reagent is tri-partite, with a biotinylated universal tail portion (including a 5' biotinylated oligonucleotide sequence that will be used for both capture onto streptavidin beads and for use in subsequent amplification) immediately 5' to a barcode sequence, followed by a string of T's (poly dT) ending in an 'anchoring' sequence (NV; with V degenerate for the 3 bases other than T, and N degenerate for all bases). Example workflows are shown in FIG. 23A-B (Flow Chart), FIG. 24 (including optional upfront sorting, and cell lysis within droplets using a temperature-inducible protease), FIG. 40A-B (including optional upfront sorting, and cell lysis within droplets using a detergent and heat), and FIG. 26A-B (capture beads are included in the droplet library). Following combination of the lysed cell droplet with the barcoded mRNA capture primer library, the droplets are incubated for a time sufficient for binding the mRNA to the primer library, and the resulting hybrids are subsequently released from the droplet emulsion by addition of a droplet destabilizing reagent. The aqueous phase containing the mRNA hybridized to the biotinylated capture primers is incubated with immobilized streptavidin (or a workflow is used that includes capture beads in the primer droplet library, see FIG. 40A-B), and the bound complexes are washed in preparation for reverse transcription using the universal tail primer. The resulting material from these procedures is barcoded first strand cDNA, with all of the mRNA from each individual cell encoded with the same barcode. Standard steps for processing cDNA for sequencing are performed, and sequencing of this collection will provide a digital count of each captured mRNA assigned to a barcode that is unique for each cell. The above process can be conducted on selected RNAs from the transcriptome using the procedure outline above or using sequence-specific capture primers.

Example 4: Oligonucleotide Labeling of Single DNA Molecules

Haplotype-like information about variation in DNA sequence along a contiguous stretch of DNA is challenging to acquire using current sample prep and sequencing technologies. In particular, there is a need for determining 'haplotype phasing' of long stretches of genomic sequence data derived from 'short read' sequencing platforms. Individual single nucleotide polymorphism (SNP) and collections of SNPs can be determined, but the assignment of a series of SNPs to either of the 2 alleles present in a diploid genome cannot be performed beyond the 'read-length' of the sequencing platform (unless individual chromosomes are isolated for sequencing). By including barcodes in multiplexed tiled PCR reactions within droplets, this aspect of the invention enables 'haplotype phase' assignments to be made using current short-read sequencing platforms, and allows this haplotype information to be correlated with patient's disease propensity, and ultimately to be used as a genomic biomarker for disease propensity and therapeutic treatment.

As an example, the Illumina sequencing platform generates sequence data with a read length of 125 bp per amplicon. If paired-end reads are used, one can potentially generate high quality reads 125 bp from both ends of a 250 bp amplicon. As each 250 bp amplicon is generated from a single molecule of target DNA, any number of SNPs identified along this amplicon are unambiguously 'in phase' with each other, allowing a 'haplotype' to be defined for this 250 bp region. However, it is not currently possible to get phased haplotype information across a longer target DNA stretch using 'tiled' amplicons, as sequence from adjacent 250 bp amplicons could come from either allele in the sample, and one would need to know that the tiled amplicons were all generated from the same DNA template strand.

Several aspects of the invention are combined to enable assignment of a series of SNPs to target DNA stretches longer than the read-length of the sequencing platform, such as a PCR primer library that contains primers with a large number of barcodes, multiplexed PCR primers that will not cross-hybridize with each other and which will uniquely amplify the target DNA locus, and droplet based amplification. The overall workflow example is shown in FIG. 35A-B. Optionally, the target locus can be pre-amplified using a single pair of PCR primers that flanks the entire locus, before appropriate loading of the sample into droplets for amplification and barcoding (not depicted in the workflow in FIG. 35A-B).

In an exemplary embodiment, the 'tailed barcoded primer' labeling reagent is tri-partite, with a universal tail portion (for use in subsequent amplification) immediately 5' to a barcode sequence followed by the sequence-specific targeting primer bases. A primer droplet library 'member' includes a droplet that contains all of the targeted primers sufficient for covering the target bases, each with the same barcode that will enable post-sequencing correlation to the target strand. The number of library members is determined by the ratio of barcode number to the number of target alleles to be analyzed. By way of example, without limitation, FIG. 35A-B shows 100 cells as input, with 4000 barcodes giving a 1/10 chance of duplicate barcodes for any allele. In this example, the DNA from 100 cells provides 400 target alleles, which is loaded (together with polymerase, buffer, and nucleotides) into one million droplets and combined with the barcoding primer library to generate a PCR-competent droplet emulsion. As an example for a 3 kb target region, 13 tiled primer pairs can be used to cover all of the target bases. Fewer primer pairs can be used if only subsets of the target bases need to be phased. After thermocycling, the amplified products are released into a single bulk aqueous phase (e.g., using a droplet de-stabilizing reagent), and a subsequent PCR reaction is performed using the universal primer tail and any sequencing platform-specific adaptor (and additional barcodes) needed before sequencing. Examples of the PCR inputs and outputs are shown in FIG. 11A-C. Using a yield threshold of ~150 sequencing reads as being more than sufficient for high confidence SNP calling, the total number of PCR cycles (droplet PCR plus bulk PCR) can be limited to 10 cycles (sufficient to generate 150 copies).

Figure 70A:
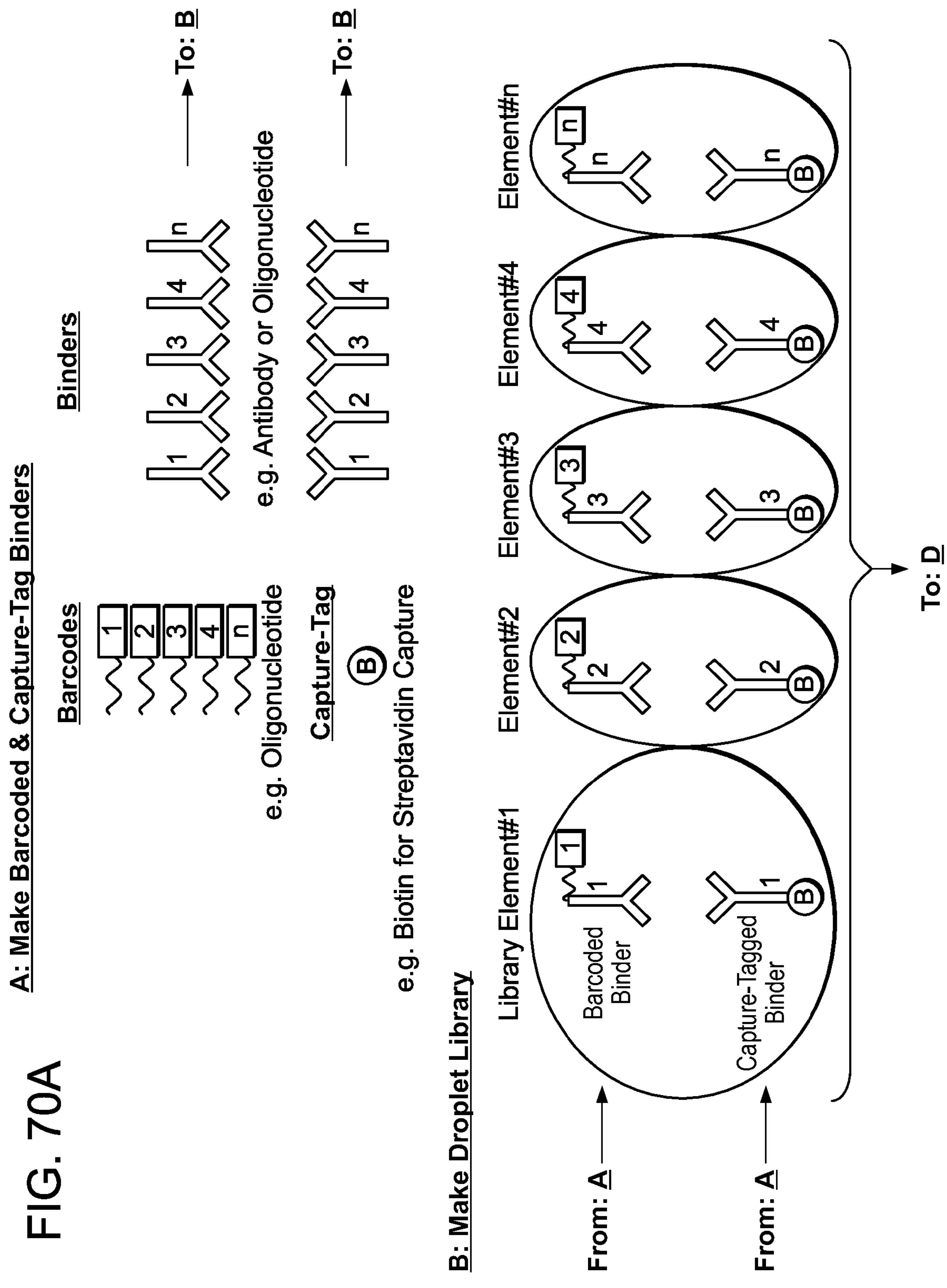
FIGS. 70A-B shows a workflow for barcoding sandwich assays for dPCR readout.
Figure 70B:
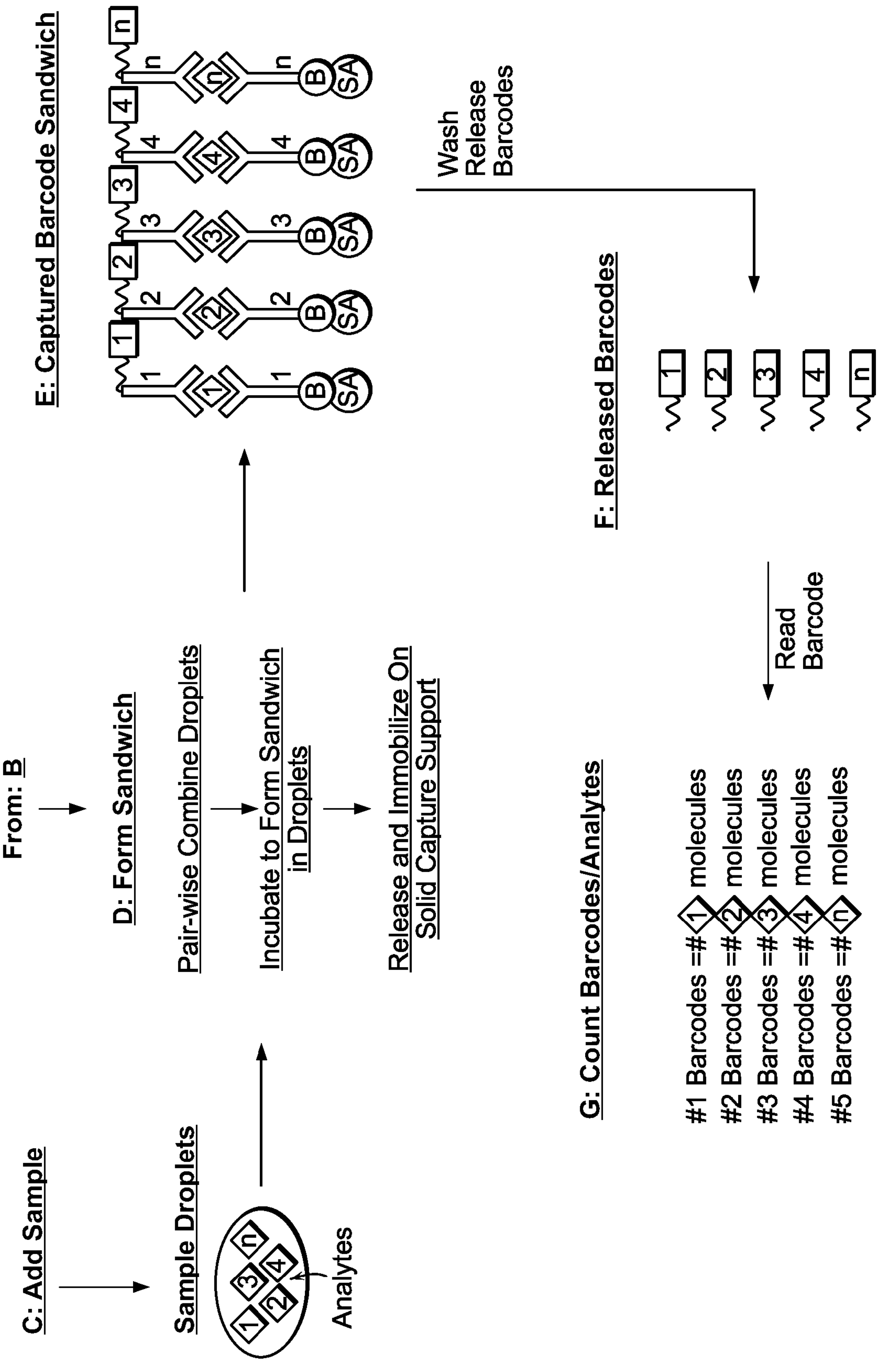
Figure 71B:
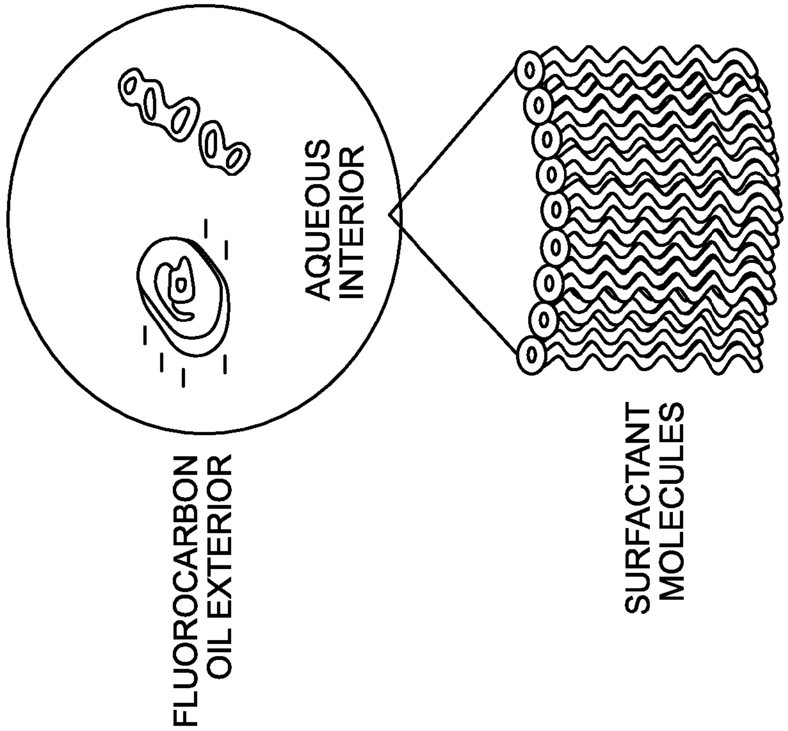
FIGS. 71A-D shows droplet generation, merging, and combining
Figure 71A:
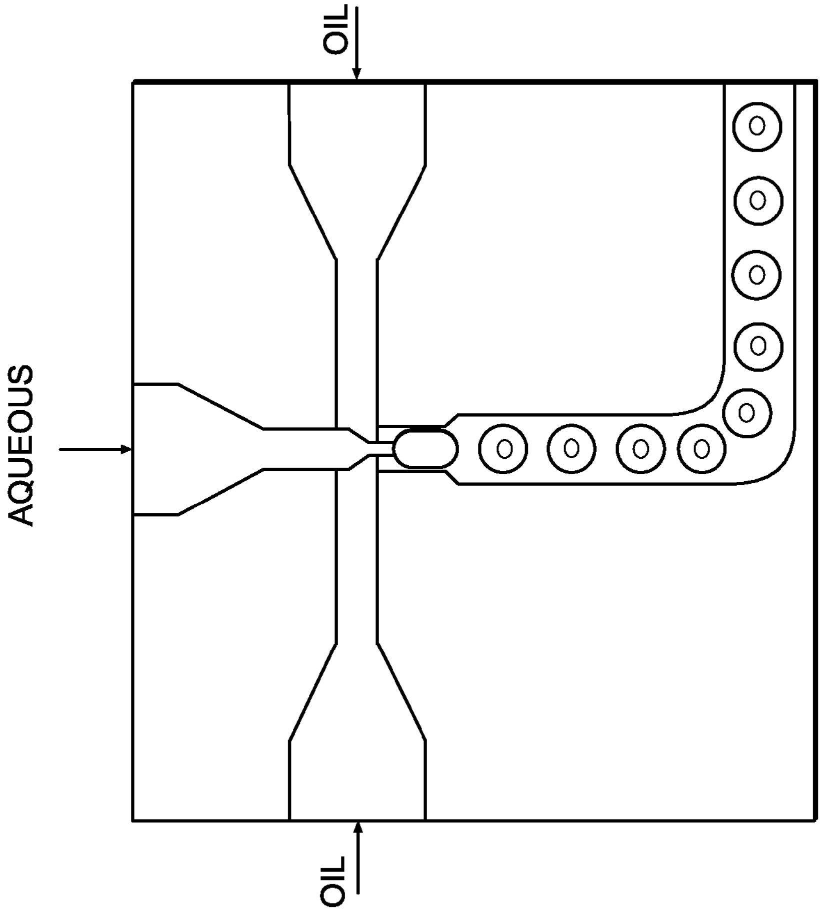
Figure 71C:
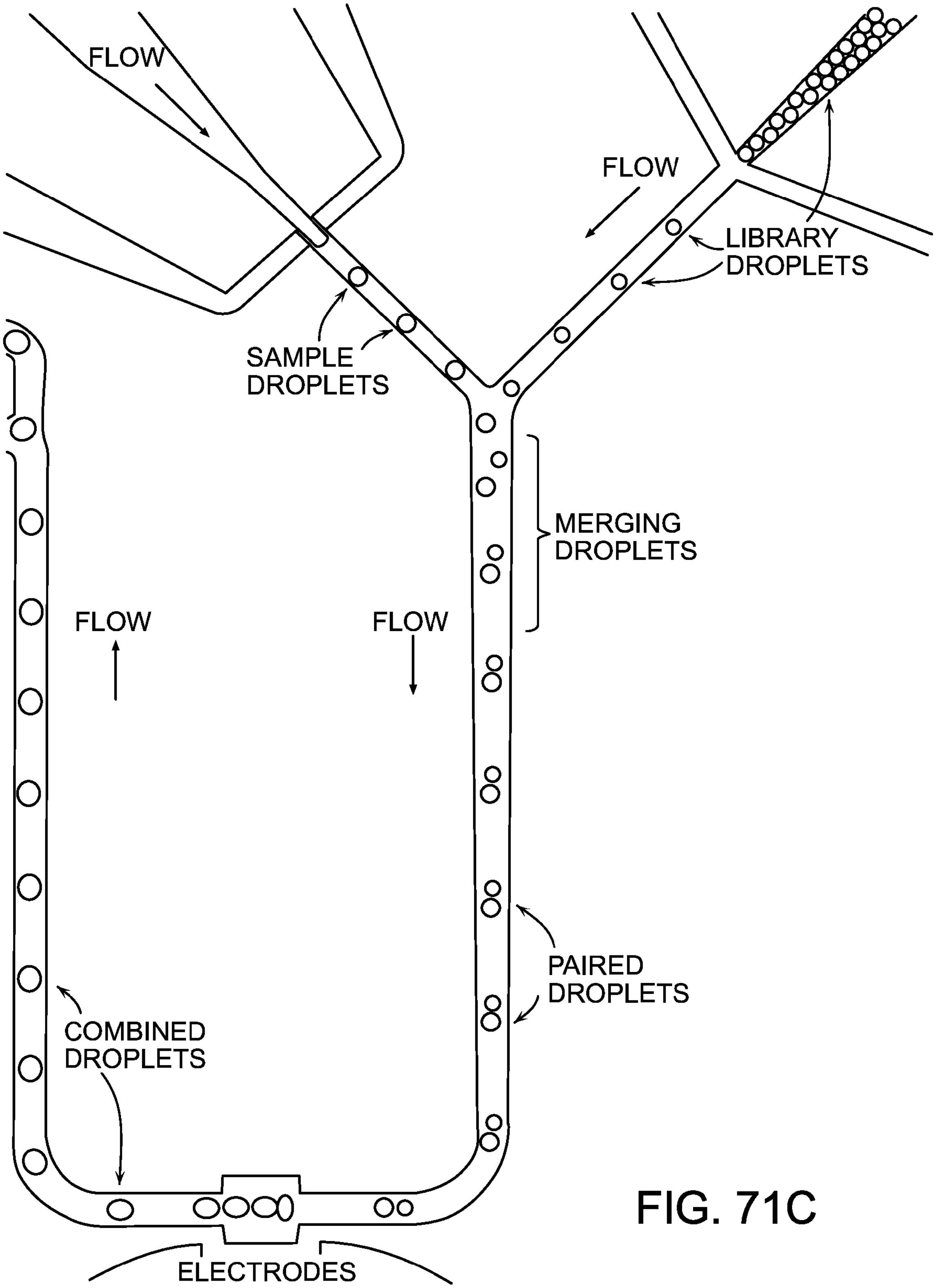
Figure 71D:
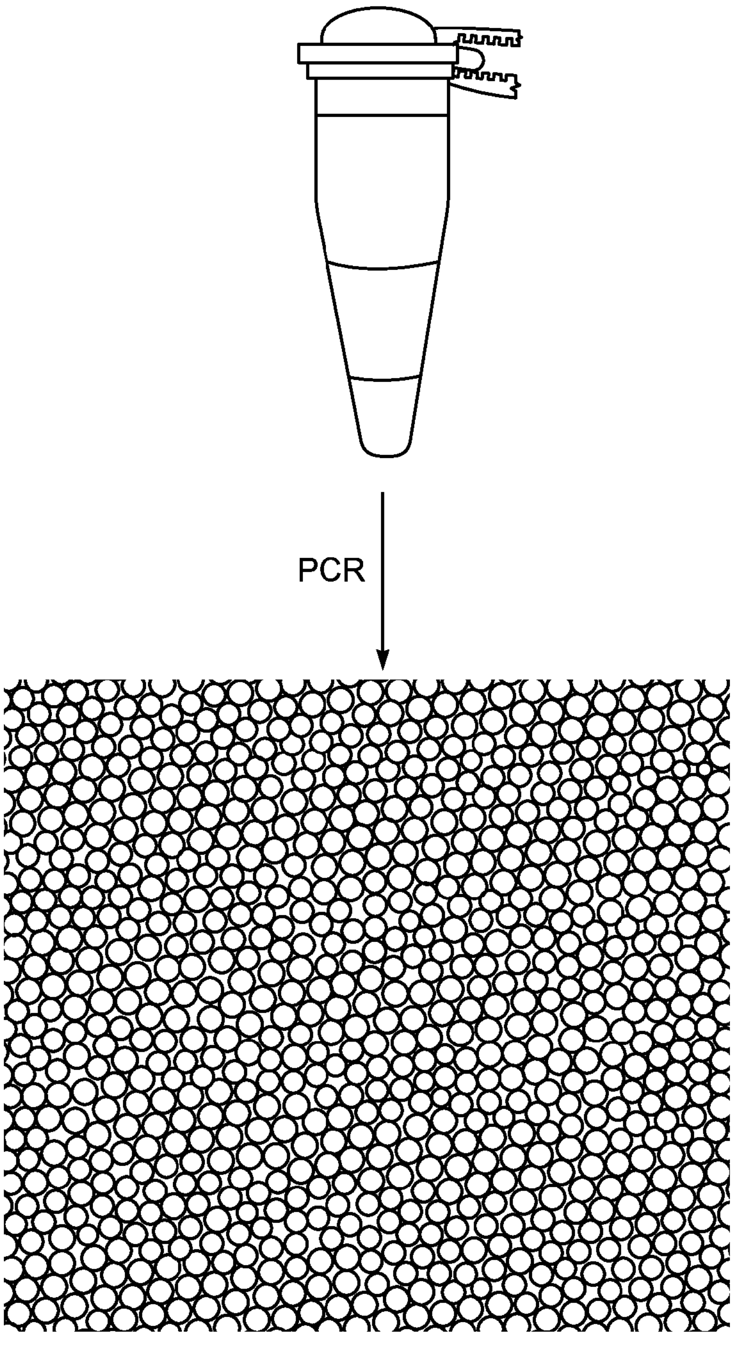
Figure 72A:
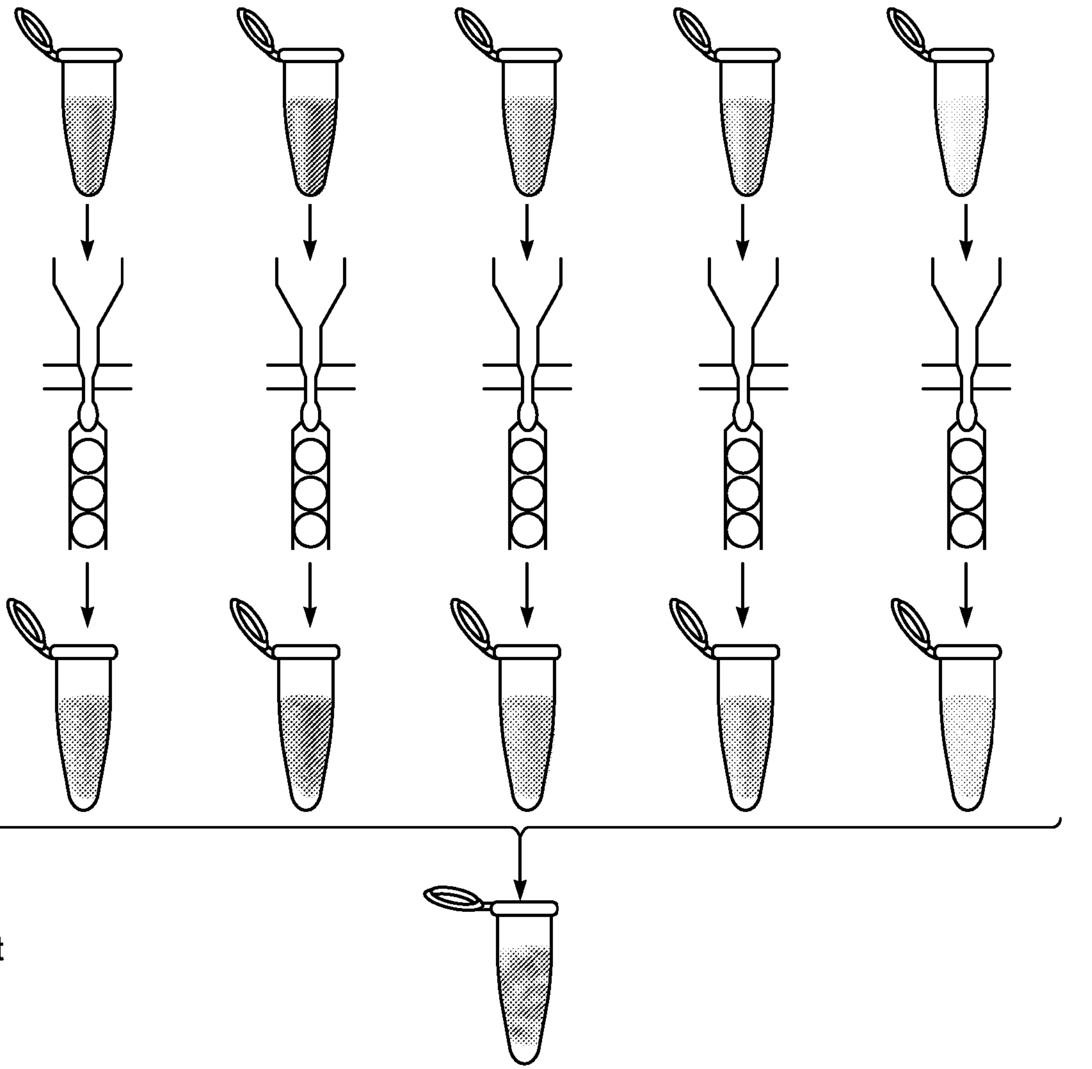
FIGS. 72A-D show droplet library generation and use in binding assays.
Figure 72B:
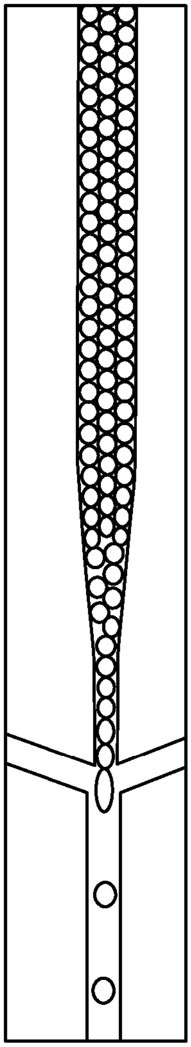
Figure 72D:
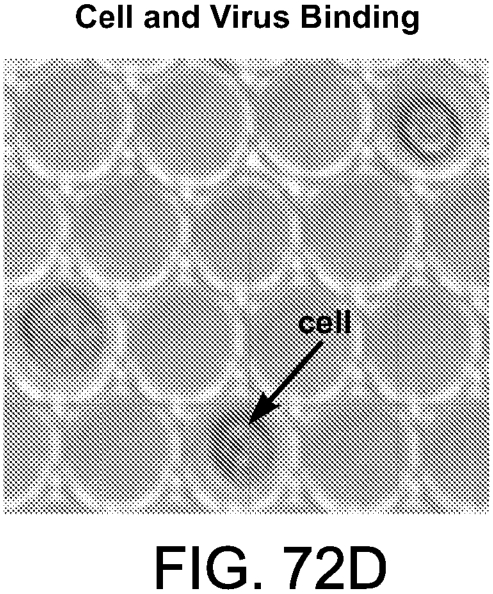
Figure 72C:
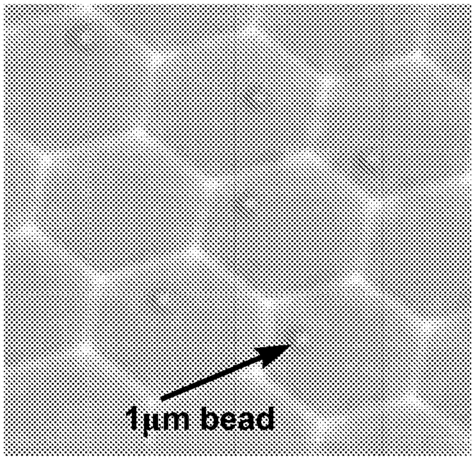

Example 5: Oligonucleotide Labeling of Digital Sandwich Assays with dPCR Readout Barcoding of digital sandwich assays is performed using barcoded binders and capture tagged-binders (e.g. antibody ELISA pair) constructed in a similar manner as shown in FIG. 33A-B or FIG. 37A-J, constituting a sandwich assay barcoded binder library. The overall workflow for the droplet barcoded sandwich assay is shown in FIG. 70A-B: A) Two binding reagents types are constructed: Barcoded Binders and Capture-Tag Binders; B) Pairs of target-specific binders are made into a droplet library, with each set of target binders in separate droplets; C) The sample is made into sample droplets, and D) combined with the library droplets to initiate highly parallel 'single-plex' binding reactions. After binding is complete, productive sandwiches are E) captured via the capture-tag (e.g. streptavidin (SA) biotin (B) interaction shown), and washed to remove unbound material; F) The captured barcodes are released, recovered, and processed for reading; G) Reads for each barcode are counted.

In this example the barcodes added to the barcoded binders are constituted such that they are targets for dPCR analysis, with optimized barcode sequences that enable optically resolved multiplex dPCR analysis. For example, if an optimized set of 15 barcode targets is constructed for identification of 15 different target proteins, then counting the number of each barcode type using the optimized dPCR readout will enable a 15-plex sandwich assay (e.g. 15 different cytokines can be quantified from a blood sample after combination with the Sandwich Assay Barcoded Binder Library and readout using a 16-plex optimized dPCR scheme with 4 concentrations of FAM and 4 concentrations of VIC TaqMan probes).

In addition, the dPCR optimized barcodes can be sticky-ended, enabling additional barcoding information to be added (e.g. a sticky-ended barcode present in the sample droplet can be ligated to the barcoded binder, such that the final released barcode has an additional motif that can include a fluorescent moiety that is optically resolved from FAM and VIC, enabling higher-plex analysis).

EQUIVALENTS

The invention may be embodied in other specific forms without departing from the spirit or essential characteristics thereof. The foregoing embodiments are therefore to be considered in all respects illustrative rather than limiting on the invention described herein.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

The invention claimed is:

1. A method for detecting target molecules, the method comprising:

incubating a cell comprising one or more target molecules with a plurality of antibodies that are conjugated to an epitope barcode oligonucleotide, thereby allowing antibodies of the plurality of antibodies to bind to the one or more target molecules;

combining one or more epitope barcode oligonucleotides with cell barcodes comprising a sequence identifying the cell to form one or more composite epitope-cell barcode oligonucleotides;

capturing mRNA of the cell with poly-T capture oligonucleotides, the poly-T capture oligonucleotides comprising transcript barcodes; and extending the poly-T capture oligonucleotides to yield cDNA comprising the transcript barcodes, wherein sequence identity and counts of the one or more composite epitope-cell barcode oligonucleotides and the cDNA provide a quantitative measure of the one or more target molecules.

2. The method of claim 1, wherein the incubating step yields one or more antibodies bound to one or more target molecules of the cell.

3. The method of claim 1, wherein the one or more target molecules comprise one or more biomarkers.

4. The method of claim 1, wherein the one or more target molecules comprise one or more proteins.

5. The method of claim 4, wherein the one or more proteins comprise one or more cell surface proteins.

6. The method of claim 4, wherein the one or more proteins comprise one or more intracellular proteins.

7. The method of claim 1, further comprising, after the incubating step, separating the cell from antibodies that have not bound to the one or more target molecules.

8. The method of claim 7, wherein the separating step comprises washing to remove the antibodies that have not bound to the one or more target molecules.

9. The method of claim 1, wherein the cell barcodes comprise a cell barcode sequence and a capture sequence that hybridizes to a sequence in the one or more epitope barcode oligonucleotides.

10. The method of claim 1, wherein the combining step comprises forming the one or more composite epitope-cell barcode oligonucleotides by hybridization, ligation, or hybridization and extension.

11. The method of claim 1, further comprising sequencing the one or more composite epitope-cell barcode oligonucleotides or amplicons thereof released from the antibodies and the cDNA or amplicons thereof to generate sequence reads and mapping the sequence reads to identify at least a target molecule of the cell.

12. The method of claim 1, wherein each of the transcript barcodes includes a unique N-mer.

13. The method of claim 12, wherein the transcript barcodes are used to quantify the mRNA of the cell.

14. The method of claim 12, wherein each of the poly-T capture oligonucleotides and the epitope barcode oligonucleotides comprises a poly-T capture sequence.

15. The method of claim 1, further comprising sequencing the one or more composite epitope-cell barcode oligonucleotides or amplicons thereof and/or the cDNA or amplicons thereof to yield sequence data.

16. The method of claim 15, wherein the sequencing step includes: amplifying the composite epitope-cell barcode oligonucleotides released from the antibodies to produce target amplicons; amplifying the cDNA to produce cDNA amplicons; and sequencing the target amplicons and the cDNA amplicons to yield sequence data.

17. The method of claim 15, further comprising mapping the sequence data to determine transcriptome and proteome information for the cell.

18. The method of claim 1, wherein the epitope barcode oligonucleotide conjugated to an antibody of the plurality of antibodies identifies the identity of the antibody to which it is conjugated.

* * * * *